United States Patent
Lancaster et al.

(10) Patent No.: US 10,052,337 B2
(45) Date of Patent: Aug. 21, 2018

(54) COMPOSITIONS OF OBETICHOLIC ACID AND METHODS OF USE

(71) Applicants: Intercept Pharmaceuticals, Inc., New York, NY (US); Sumitomo Dainippon Pharma Co., Ltd., Osaki-shi, Osaka (JP)

(72) Inventors: Richard Gail Lancaster, San Diego, CA (US); Kay K. Olmstead, Escondido, CA (US); Masashi Kagihiro, Suita (JP); Mitsuhiro Matono, Sett-sushi (JP); Ikuko Taoka, Toyonaka (JP); Mark Pruzanski, New York, NY (US); David Shapiro, Rancho Sante Fe, CA (US); Roya Hooshmand-Rad, San Diego, CA (US); Richard Pencek, San Diego, CA (US); Cathi Sciacca, San Diego, CA (US); Lise Eliot, San Diego, CA (US); Jeffrey Edwards, San Diego, CA (US); Leigh A. MacConell, Encinitas, CA (US); Tonya K. Marmon, San Diego, CA (US)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/139,138

(22) Filed: Apr. 26, 2016

(65) Prior Publication Data
US 2017/0035784 A1 Feb. 9, 2017

Related U.S. Application Data

(60) Provisional application No. 62/153,040, filed on Apr. 27, 2015, provisional application No. 62/317,933, filed on Apr. 4, 2016.

(51) Int. Cl.
*A61K 9/16* (2006.01)
*A61K 31/575* (2006.01)
(Continued)

(52) U.S. Cl.
CPC .............. *A61K 31/575* (2013.01); *A61K 9/14* (2013.01); *A61K 9/1617* (2013.01);
(Continued)

(58) Field of Classification Search
CPC .... A61K 45/06; A61K 31/575; A61K 9/2059; A61K 9/2054; A61K 9/2072; A61K 9/14; A61K 9/1617; C07J 9/005
See application file for complete search history.

(56) References Cited

U.S. PATENT DOCUMENTS 7,078,376 B1  7/2006 Thomson
7,138,390 B2  11/2006 Pellicciari
(Continued)

FOREIGN PATENT DOCUMENTS

WO      2015036442 A1 *  3/2015
WO  WO 2015/036442 A1    3/2015

OTHER PUBLICATIONS

Corpechot, C. et al. "Biochemical Response to Ursodeoxycholic Acid and Long-Term Prognosis in Primary Biliary Cirrhosis", *Hepatology*, 2008, vol. 48 p. 871-877.
(Continued)

*Primary Examiner* — Carlos A Azpuru

(57) ABSTRACT

The disclosure relates to obeticholic acid formulations with improved stability, dissolution, and/or solubility, methods of preparing the same for use and methods of treating various diseases and conditions.

19 Claims, 37 Drawing Sheets

(51) Int. Cl.
    *A61K 47/50*     (2017.01)
    *A61K 9/14*     (2006.01)
    *C07J 9/00*     (2006.01)
    *A61K 9/20*     (2006.01)
    *A61K 45/06*     (2006.01)

(52) U.S. Cl.
    CPC .......... *A61K 9/2054* (2013.01); *A61K 9/2059* (2013.01); *A61K 9/2072* (2013.01); *A61K 45/06* (2013.01); *A61K 47/50* (2017.08); *C07J 9/005* (2013.01)

(56) References Cited

U.S. PATENT DOCUMENTS

| | | |
|---|---|---|
| 2005/0101565 A1 | 5/2005 | Dasseux |
| 2012/0071451 A1 | 3/2012 | Spenard et al. |
| 2012/0160944 A1 | 6/2012 | Dodd et al. |
| 2013/0345188 A1 | 12/2013 | Steiner et al. |

OTHER PUBLICATIONS

Corpechot, C. et al. "Early primary biliary cirrhosis: Biochemical response to treatment and prediction of long-term outcome", *Journal of Hepatology*, 2011, vol. 55, p. 1361-1367.

Kuiper, E. et al. "Improved Prognosis of Patients with Primary Biliary Cirrhosis That Have a Biochemical Response to Ursodeoxycholic Acid", *Gastroenterology*, 2009, vol. 136, p. 1281-1287.

Kumagi, T. et al. "Baseline Ductopenia and Treatment Response Predict Long-Term Histological Progression in Primary Biliary Cirrhosis", *The American Journal of Gastroenterology*, 2010, vol. 105, p. 2186-2194.

Momah, N. et al. "Optimizing biochemical markers as endpoints for clinical trials in primary biliary cirrhosis", *Liver International*, 2012, vol. 32, p. 790-795.

\* cited by examiner

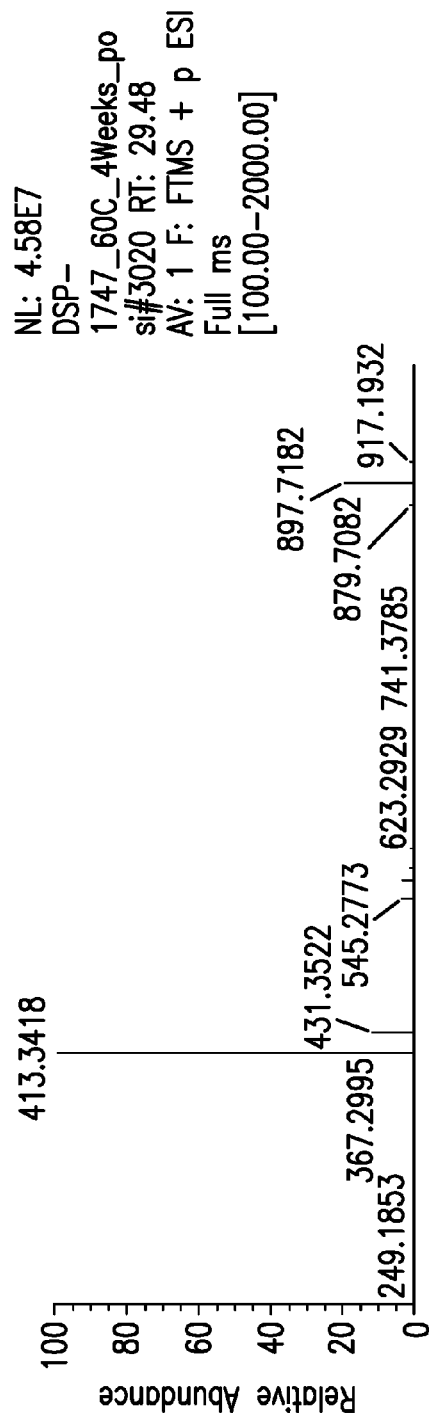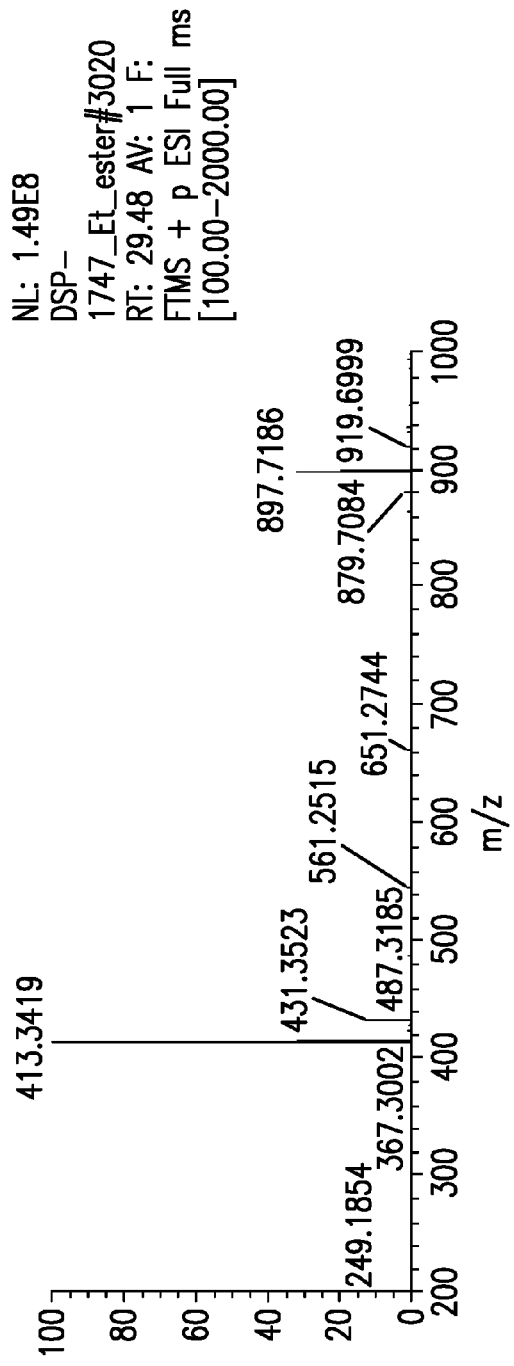
FIG. 7B

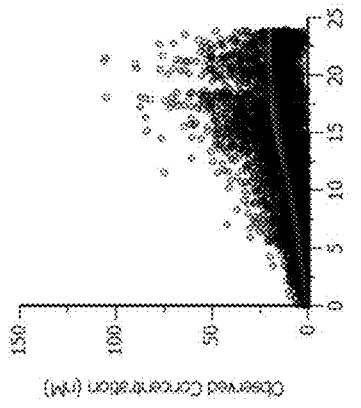
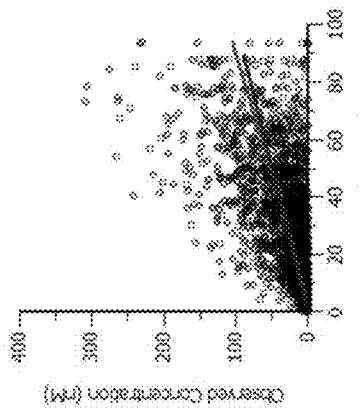
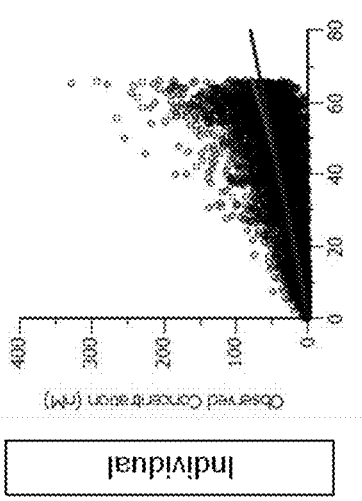
FIG. 18A  FIG. 18B  FIG. 18C
FIG. 18D  FIG. 18E  FIG. 18F
Black circles represent individual data points. Solid blue line is the line of unity. Solid red line is a loess fit of the relationship between predicted and observed.

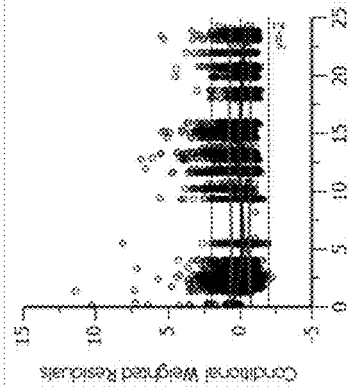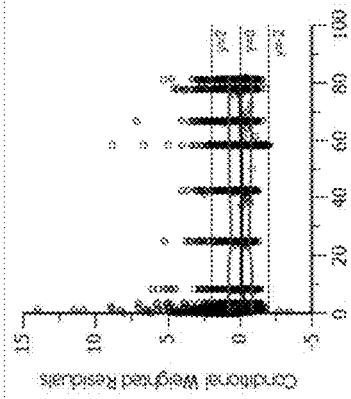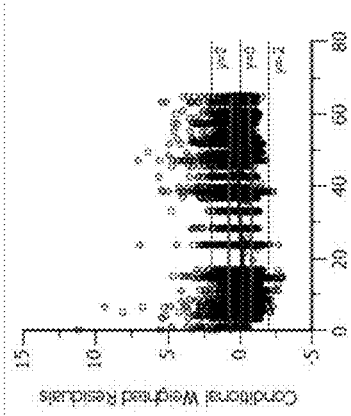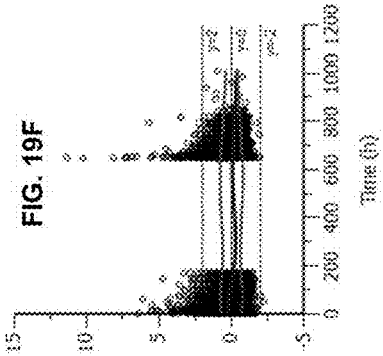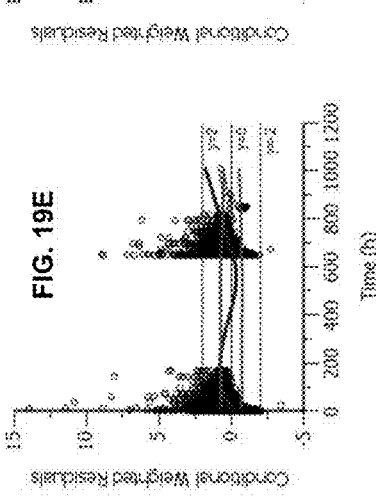
FIG. 19A Glyco-OCA  FIG. 19B Unconjugated OCA  FIG. 19C Tauro-OCA
FIG. 19D  FIG. 19E  FIG. 19F
Black circles represent individual conditional weighted residuals. Solid blue line is a loess fit of the conditional weighted residuals. Solid red lines are loess fits of the absolute values of the conditional weighted residuals.

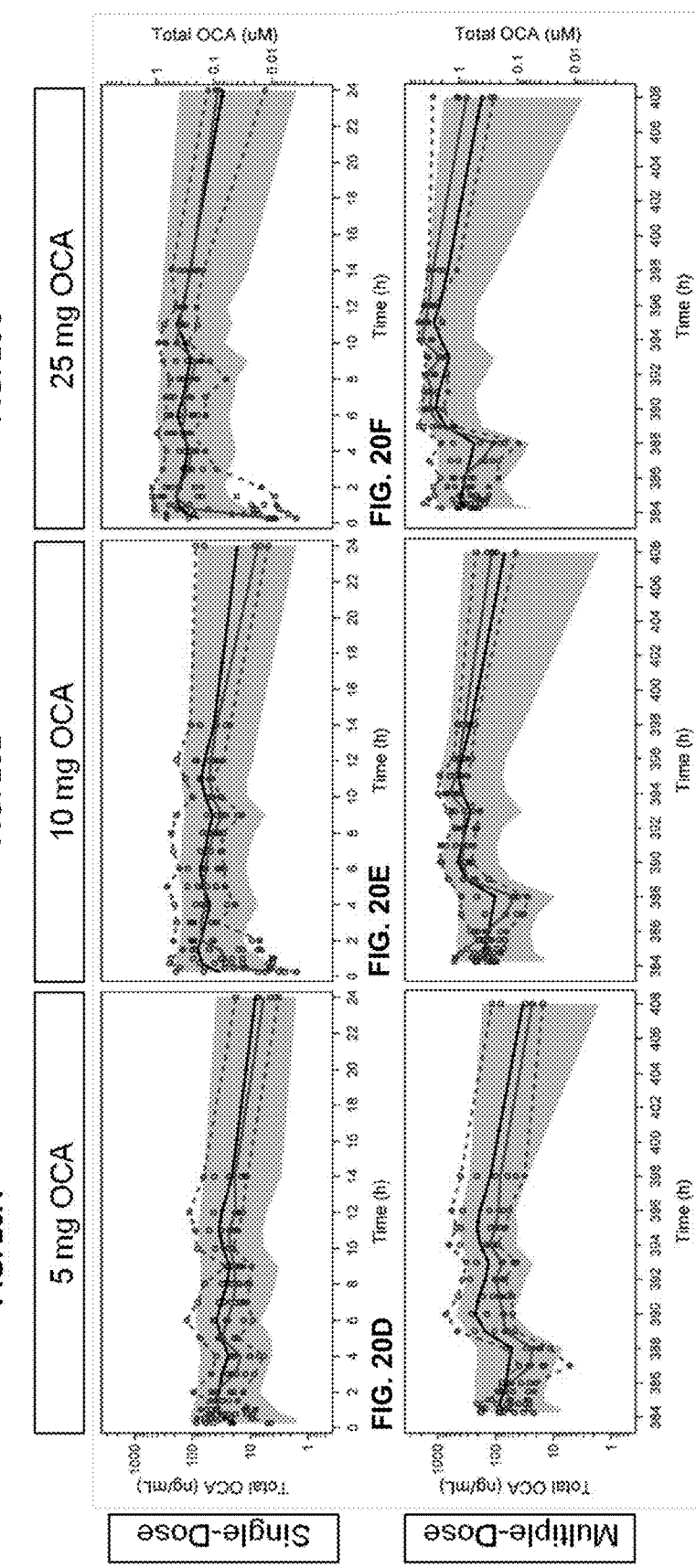

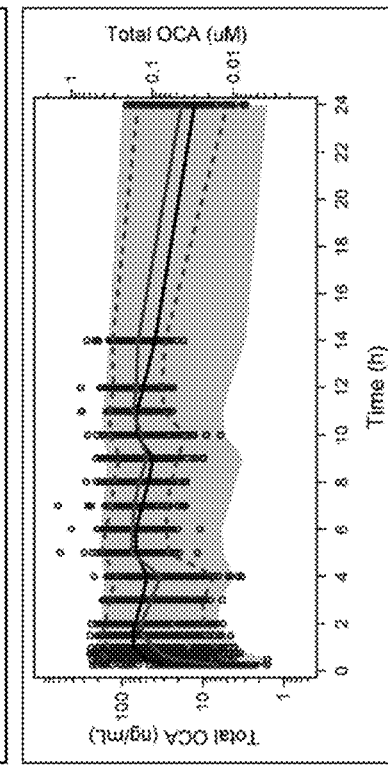
FIG. 21B
FIG. 21A
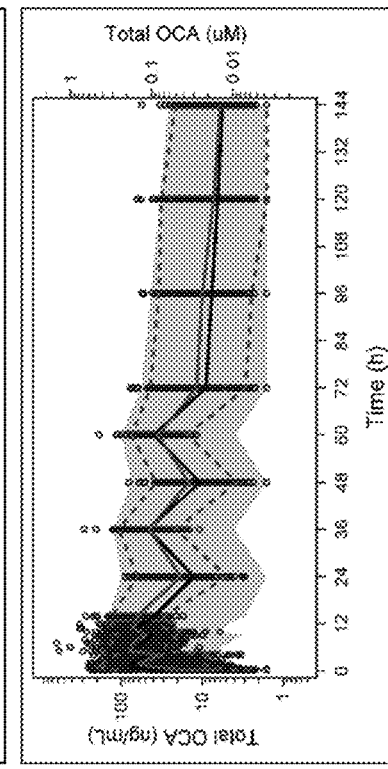
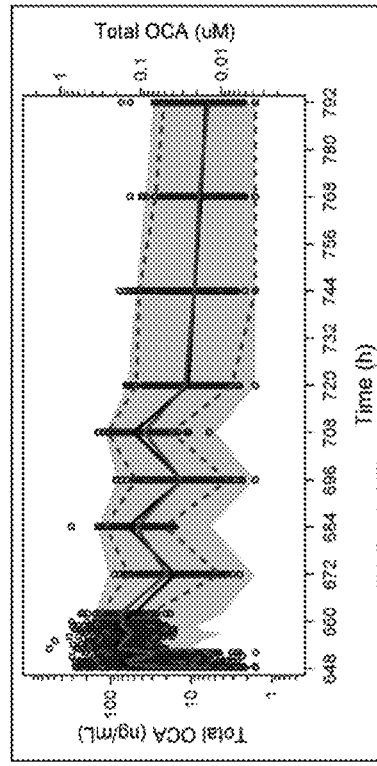
FIG. 21D
FIG. 21C
Blue circles represent observed data points. Solid red line represents median of observed data. Dashed red lines represent the 5th and 95th percentiles of observed data. Solid black line represents predicted median. Gray band represents the 90% prediction interval.

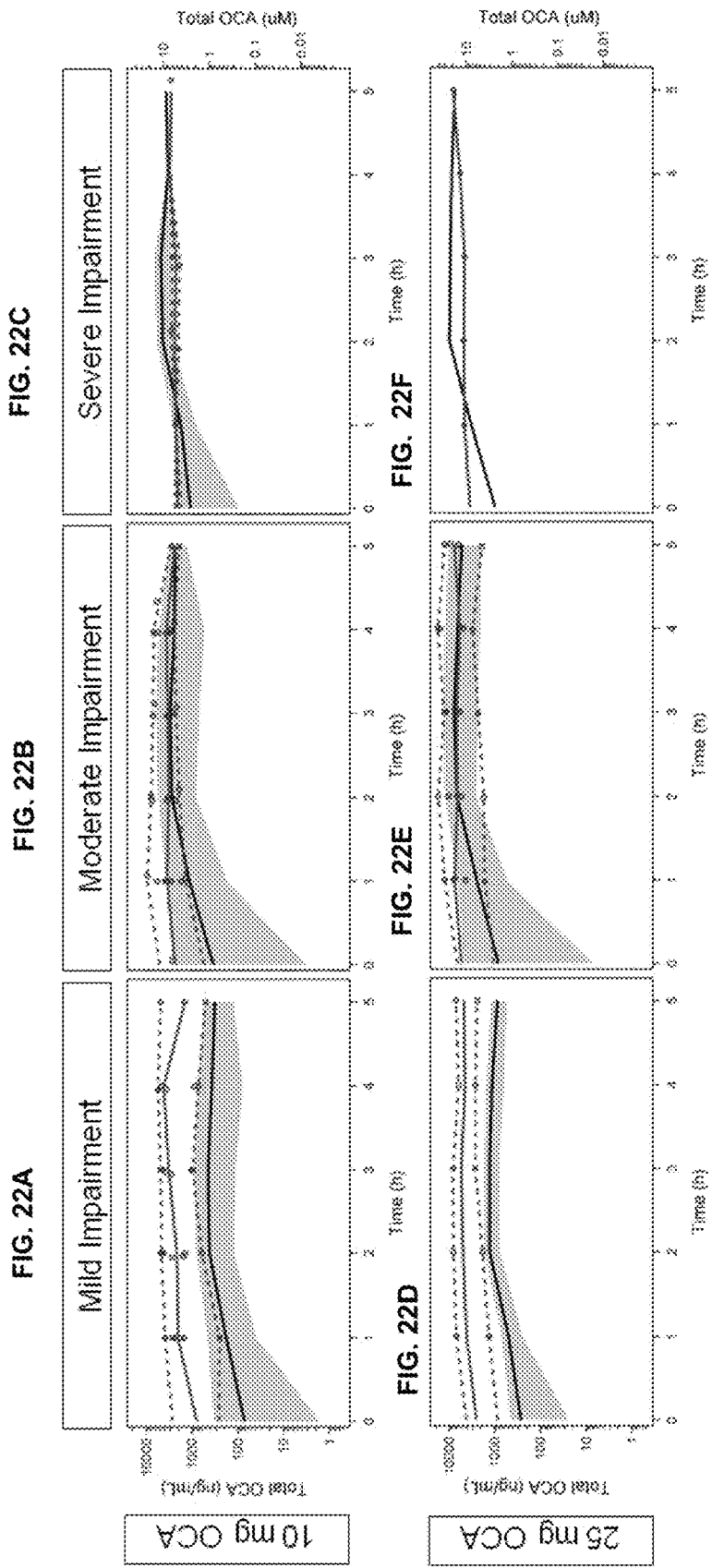

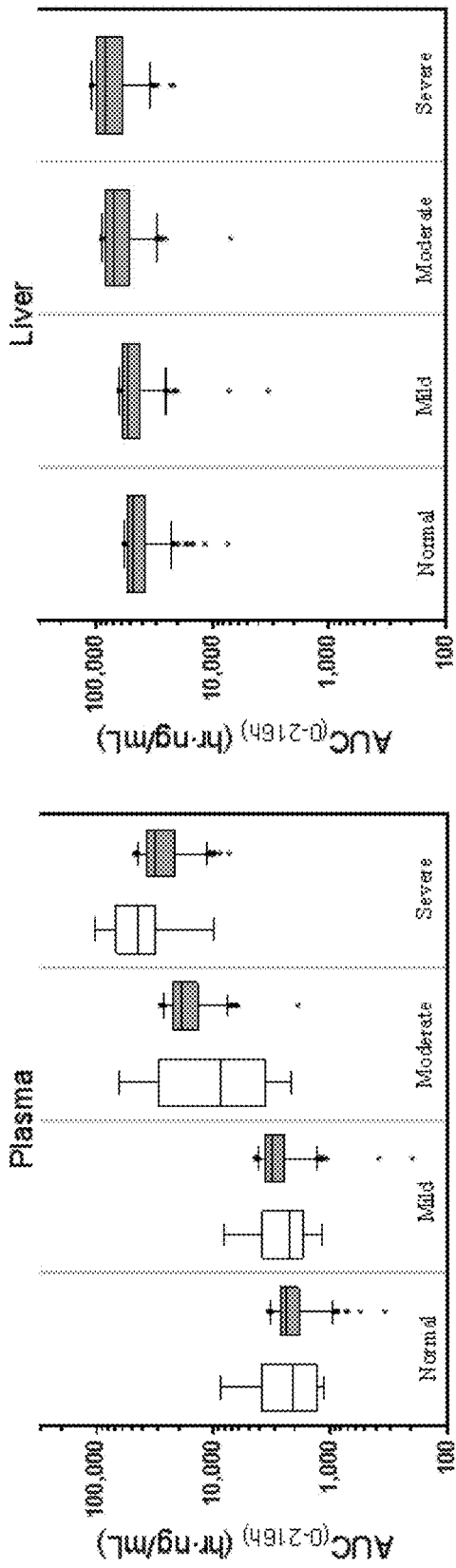

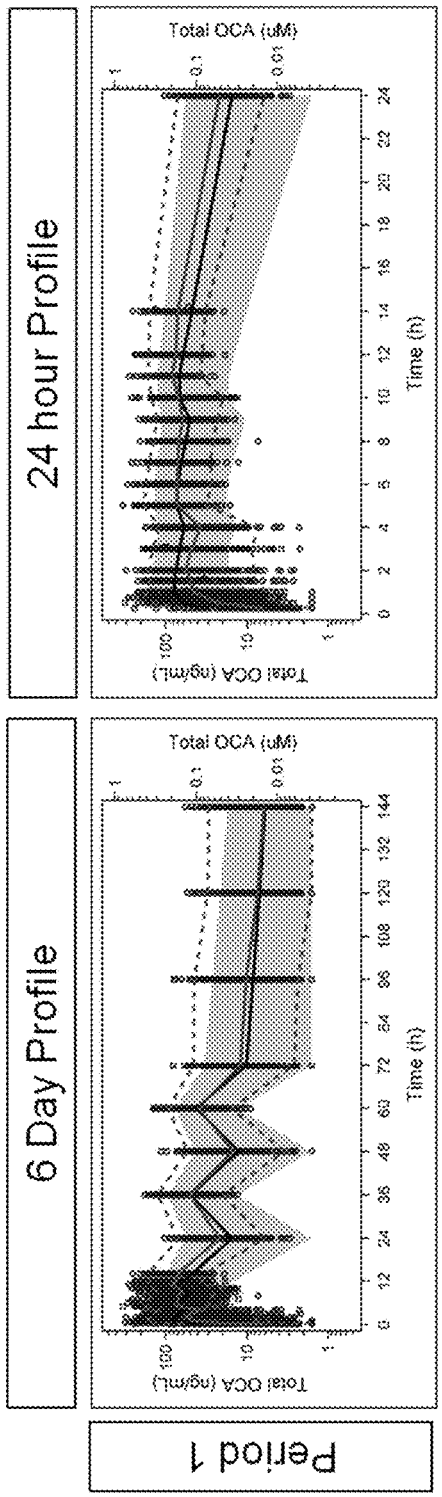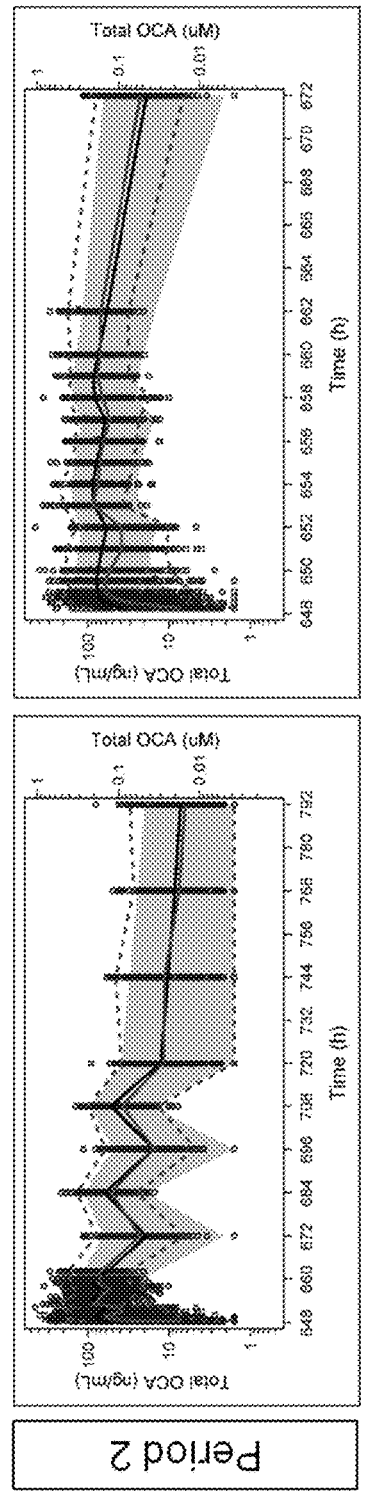

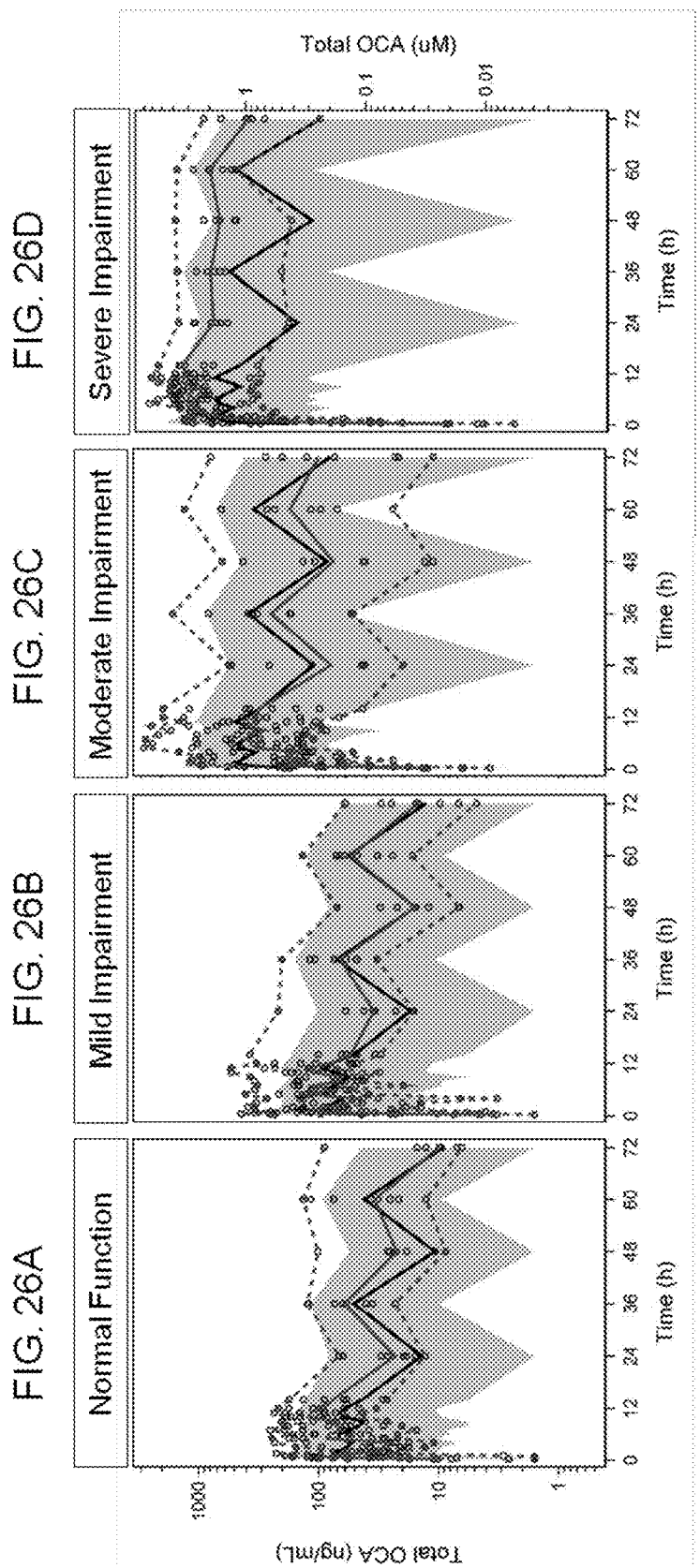

COMPOSITIONS OF OBETICHOLIC ACID AND METHODS OF USE

BACKGROUND

The farnesoid X receptor (FXR), also known as the bile acid receptor (BAR) or NR1H4, is a member of the nuclear receptor superfamily of ligand-activated transcription factors. FXR forms with retinoid X receptor (RXR) a heterodimer receptor crucial for bile acid homeostasis. FXR is expressed in various tissues including the liver, kidney, intestine, colon, ovary, and adrenal gland, and is activated by a variety of naturally occurring bile acids, including the primary bile acid chenodeoxycholic acid (CDCA) and its taurine and glycine conjugates. Upon activation, the FXR-RXR heterodimer binds the promoter region of target genes and regulates their expression.

6-Ethyl-chenodeoxycholic acid (6-ECDCA, or obeticholic acid, or OCA), a bile acid derivative, shows a potent FXR activating activity, and accordingly offers great promise for the treatment of FXR-mediated diseases or conditions. Thus, there is a need to develop obeticholic acid compositions having desirable dissolution profile and solubility, and possessing advantageous storage stability.

SUMMARY

The present disclosure relates to novel formulations of obeticholic acid, an FXR agonist, with improved stability, dissolution, and solubility, methods of preparing the same and methods of using the novel formulations for treating a disease or condition. In certain instances, the disease or condition is primary biliary cirrhosis (PBC), also known as primary biliary cholangitis. In other instances, the disease or condition is primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, or liver fibrosis. In another instance, the disease is NASH. In still other instances, the disease or condition is solid-tumor cancer such as, for example, hepatocellular carcinoma (HCC), colorectal cancer, gastric cancer, liver cancer, breast cancer, kidney cancer, or pancreatic cancer. Further provided herein are novel dosing regimens for administration of obeticholic acid for treatment of the diseases or conditions described herein.

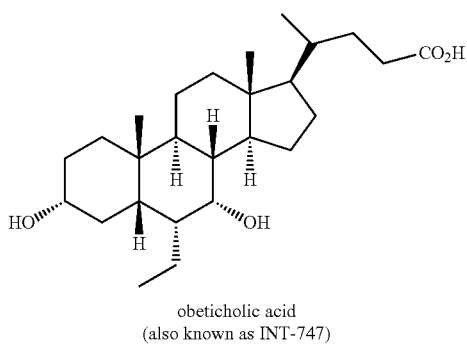

obeticholic acid
(also known as INT-747)

A first aspect of the disclosure relates to a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of less than 200 μm. Such compositions include all those described herein.

Another aspect of the disclosure relates to treating a disease or condition described herein in a patient in need thereof by administering a composition that includes obeticholic acid, or a pharmaceutically acceptable salt, ester, or amino acid conjugate thereof, where the obeticholic acid or a pharmaceutically acceptable salt, ester, or amino acid conjugate thereof is in the form of particles.

Another aspect of the disclosure relates to treating a disease or condition described herein in a patient in need thereof by administering a composition that includes obeticholic acid, or a pharmaceutically acceptable salt, ester, or amino acid conjugate thereof, where the obeticholic acid or a pharmaceutically acceptable salt, ester, or amino acid conjugate thereof is in the form of particles, and wherein at least 50% of the particles have a diameter of 200 μm or less.

Another aspect of the disclosure relates to treating primary biliary cirrhosis (PBC) in a patient in need thereof by administering a composition that includes obeticholic acid, or a pharmaceutically acceptable salt, ester, or amino acid conjugate thereof, optionally in a titration period, where the obeticholic acid or a pharmaceutically acceptable salt, ester, or amino acid conjugate thereof is in the form of particles, and wherein at least 50% of the particles have a diameter of 200 μm or less.

In still another aspect of the disclosure is a method of treating primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, or liver fibrosis in a patient in need thereof by administering a composition that includes obeticholic acid, or a pharmaceutically acceptable salt, ester, or amino acid conjugate thereof, optionally in a titration period, where the obeticholic acid or a pharmaceutically acceptable salt, ester, or amino acid conjugate thereof is in the form of particles. In one example, at least 50% of the particles have a diameter of 200 μm or less.

In yet another aspect of the disclosure is a method of treating a solid-tumor cancer in a patient in need thereof by administering a composition that includes obeticholic acid, or a pharmaceutically acceptable salt, ester, or amino acid conjugate thereof, optionally in a titration period, where the obeticholic acid or a pharmaceutically acceptable salt, ester, or amino acid conjugate thereof is in the form of particles. In one example, at least 50% of the particles have a diameter of 200 μm or less.

In another aspect of the disclosure is a method of treating an autoimmune disease in a patient in need thereof by administering a composition that obeticholic acid, or a pharmaceutically acceptable salt, ester, or amino acid conjugate thereof, optionally in a titration period, where the obeticholic acid or a pharmaceutically acceptable salt, ester, or amino acid conjugate thereof is in the form of particles. In one example, at least 50% of the particles have a diameter of 200 μm or less.

In another aspect of the disclosure are methods of treating a disease or condition described herein by administering a obeticholic acid composition described herein where the obeticholic acid composition is administered as part of a treatment regimen that includes a titration period and a starting dose of the obeticholic acid composition at an amount of about 5 mg or 10 mg. In particular instances, such methods include daily (QD) administration of an obeticholic acid described herein during the titration period. In particular instances, such methods also include administration of an adjusted dose of an obeticholic acid composition described herein after the titration period.

Another aspect of the disclosure relates to a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of less than 200 μm. Another aspect of the disclosure relates to a composition comprising obeticholic acid, or a pharmaceutically acceptable salt, ester, or amino acid conjugate thereof, and a pharmaceutically acceptable excipient (e.g., sodium starch glycolate) having a low alcohol (e.g., ethanol or methanol) content (e.g., less than 5% (wt/wt)).

In another aspect, the disclosure relates to a pharmaceutical composition, comprising a therapeutically effective amount of obeticholic acid, or a pharmaceutically acceptable salt, ester, or amino acid conjugate thereof, in the form of particles, and a pharmaceutically acceptable excipient (e.g., sodium starch glycolate) having a low alcohol (e.g., ethanol or methanol) content (e.g., less than 5% (wt/wt)), wherein at least 50% of the particles have a diameter of less than 200 μm.

Another aspect of the disclosure relates to a pharmaceutical composition, comprising obeticholic acid, or a pharmaceutically acceptable salt, ester, or amino acid conjugate thereof, in the form of particles, wherein at least 50% of the particles have a diameter of less than 200 μm, at about 1% to about 6% by weight, sodium starch glycolate at about 2% to about 8% by weight having a low alcohol (e.g., ethanol or methanol) content (e.g., less than 5% (wt/wt)), a lubricant (e.g., magnesium stearate) at about 0.1% to about 2.0% by weight, and a diluent (e.g., microcrystalline cellulose) at about 85% to about 95% by weight.

In another aspect, the disclosure relates to a method for preparing a composition comprising obeticholic acid, or a pharmaceutically acceptable salt, ester, or amino acid conjugate thereof, in the form of particles, wherein at least 50% of the particles have a diameter of less than 200 μm, comprising forming the particles through jet-milling.

Another aspect of the disclosure relates to a tablet comprising an intra-granular portion and an extra-granular portion, the intra-granular portion comprising obeticholic acid, or a pharmaceutically acceptable salt, ester, or amino acid conjugate thereof, microcrystalline cellulose, and one or more additional pharmaceutical excipients, and the extra-granular portion comprising one or more pharmaceutical excipients.

Another aspect of the disclosure relates to a tablet comprising an intra-granular portion and an extra-granular portion, the intra-granular portion comprising obeticholic acid, or a pharmaceutically acceptable salt, ester, or amino acid conjugate thereof, microcrystalline cellulose, and one or more additional pharmaceutical excipients, and the extra-granular portion comprising microcrystalline cellulose and one or more additional pharmaceutical excipients.

In another aspect, the disclosure relates to methods for treating or preventing an FXR mediated disease or condition or a disease or condition in which elevated concentrations of circulating lipid compounds or glucose in the blood, or decreased insulin level, or increased insulin resistance is involved, or inhibiting or reversing fibrosis, comprising administering a therapeutically effective amount of a composition of the present disclosure to a subject in need thereof.

Another aspect of the disclosure relates to use of a composition of the present disclosure for treating or preventing an FXR mediated disease or condition or a disease or condition in which elevated concentrations of circulating lipid compounds or glucose in the blood, or decreased insulin level, or increased insulin resistance is involved, or for inhibiting or reversing fibrosis.

In another aspect, the disclosure relates to use of a composition of the present disclosure in the manufacture of a medicament for treating or preventing an FXR mediated disease or condition or a disease or condition in which elevated concentrations of circulating lipid compounds or glucose in the blood, or decreased insulin level, or increased insulin resistance is involved, or for inhibiting or reversing fibrosis.

The compositions and methods of the present disclosure address unmet needs in the treatment or prevention of an FXR mediated disease or a disease or disorder in which elevated concentrations of circulating lipid compounds in the blood such as cholesterol and triglycerides or glucose are involved.

The compositions and methods of the present disclosure address unmet needs in the treatment of diseases and conditions described herein, including for example, PBC, PSC, NAFLD, NASH, cancer, and autoimmune diseases described herein.

BRIEF DESCRIPTION OF THE DRAWINGS

FIG. 7B shows the mass spectrum in the positive mode of a sample of obeticholic acid OCA and the synthesized ethyl ester of obeticholic acid OCA.

FIGS. 18A-F illustrate the Goodness of Fit: Observed Concentrations vs Predicted Concentrations of OCA. FIG. 18A shows the individual glyco-OCA group, FIG. 18B shows the individual unconjugated OCA group, FIG. 18C shows individual tauro-OCA group, FIG. 18D shows the population glyco-OCA group, FIG. 18E shows the population unconjugated OCA group, and FIG. 18F shows the population tauro-OCA group.

FIGS. 19A-F illustrate the Goodness of Fit: Residuals. FIG. 19A shows the glyco-OCA group vs. concentration, FIG. 19B shows the unconjugated OCA group vs. concentration, FIG. 19C shows the tauro-OCA group vs. concentration, FIG. 19D shows the glyco-OCA group vs. time, FIG. 19E shows the unconjugated OCA group vs. time, and FIG. 19F shows the tauro-OCA group vs. time.

FIGS. 20A-F illustrate External Validation of Model in Subjects with Normal Hepatic Function. FIG. 20A shows the single dose of 5 mg OCA, FIG. 20B shows the single dose of 10 mg OCA, FIG. 20C shows the single dose of 25 mg OCA, FIG. 20D shows the multiple dose of 5 mg OCA, FIG. 20E shows the multiple dose of 10 mg OCA, and FIG. 20F shows the multiple dose of 25 mg OCA.

FIGS. 21A-D illustrate External Validation of Model in Subjects with Normal Hepatic Function. FIG. 21A shows the 6 day profile in Period 1, FIG. 21B shows the 24-hour profile in Period 1, FIG. 21C shows the 6 day profile in Period 2, and FIG. 21D shows the 24-hour profile in Period 2.

FIGS. 22A-F illustrate External Validation of Model in Patients with Impaired Hepatic Function. FIG. 22A shows the effect of 10 mg OCA in mild impairment, FIG. 20B shows the effect of 10 mg OCA in moderate impairment, FIG. 22C shows the effect of 10 mg OCA in severe impairment, FIG. 22D shows the effect of 25 mg OCA in mild impairment, FIG. 22E shows the effect of 25 mg OCA in moderate impairment, and FIG. 22F shows the effect of 25 mg OCA in severe impairment.

FIG. 23A and FIG. 23B illustrates plasma OCA Concentrations are a Poor Surrogate for Liver OCA Concentrations.

FIGS. 25A-D illustrate a Visual Predictive Check of PK Model in Subjects with Normal Hepatic Function where FIG. 25A shows a 6-day profile, FIG. 25B shows a 24-hour profile, FIG. 25C shows a 6-day profile over period 2 and FIG. 25D shows a 24-hour profile over period 2.

FIGS. 26A-D show Visual Predictive Check of PK model in Patients with Normal and Impaired Hepatic Function where FIG. 26A shows normal function, FIG. 26B shows mild impairment, FIG. 26C shows moderate impairment and FIG. 26D shows severe impairment.

FIG. 27A shows a single dose of OCA 5 mg, FIG. 27B shows a single dose of OCA 10 mg, FIG. 27C shows a single dose of OCA 25 mg, FIG. 27D shows a multiple dose of OCA 5 mg, FIG. 27E shows a multiple dose of OCA 10 mg, and FIG. 27F shows a multiple dose of OCA 25 mg.

FIG. 28A shows mild impairment of OCA 10 mg, FIG. 28B shows moderate impairment of OCA 10 mg, FIG. 28C shows severe impairment of OCA 10 mg, FIG. 28D shows mild impairment of OCA 25 mg, FIG. 28E shows moderate impairment of OCA 25 mg, and FIG. 28F shows severe impairment of OCA 25 mg.

DETAILED DESCRIPTION

Figure 1:
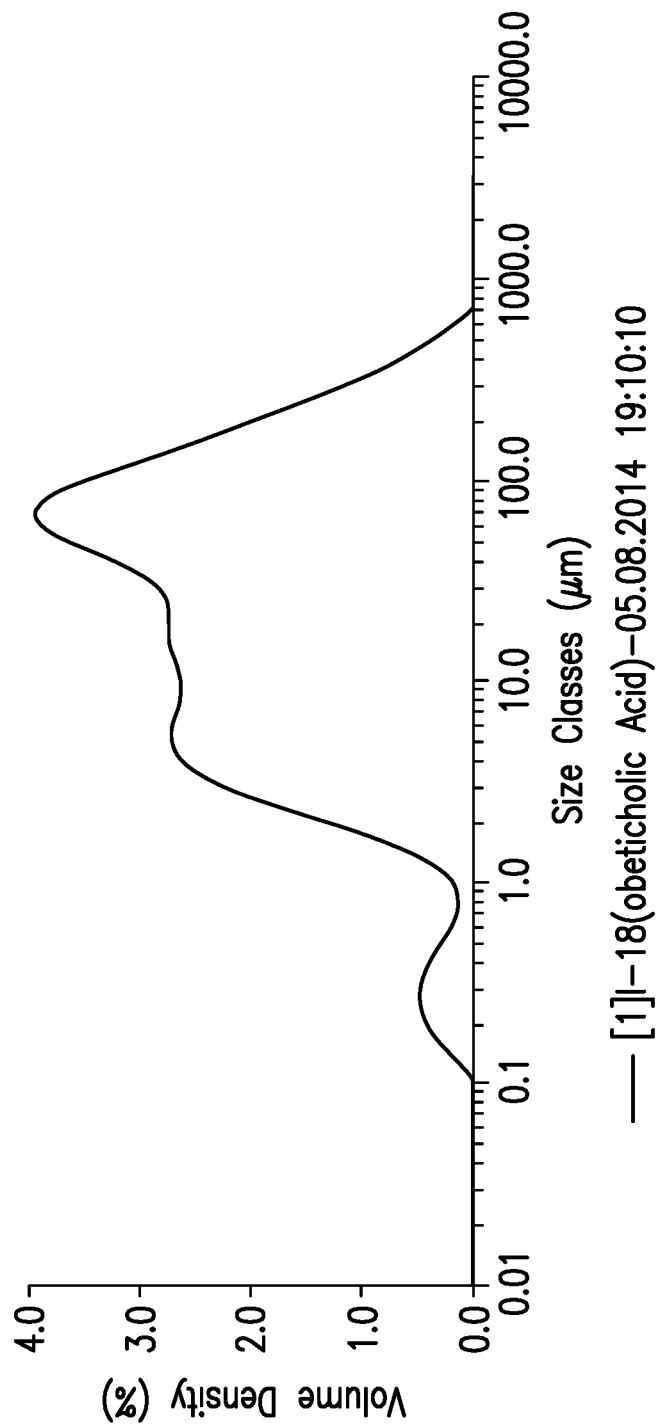
FIG. 1 is a particle size distribution histogram of obeticholic acid before jet-milling.

Pharmaceutical preparations containing a poorly water-soluble drug require some tools for improving the dissolution property of the drug, for example, adding a surfactant or other additive, or amorphizing the drug. However, the addition of the surfactant or other additive can chemically destabilize the drug, and methods of amorphizing the drug may require changing the crystal form.

When compositions containing a high concentration of a poorly water-soluble drug are produced, usually, powders are tableted by direct compression or granules are produced by dry or wet granulation methods and tableted. However, tableting by direct compression and granulation are largely affected by the physical properties of the drug and often have great weight variations and poor content uniformity at the time of tableting, resulting in poor manufacturability in consideration of productivity. Moreover, these approaches can provide a drug product with poor dissolution.

The present application is directed to compositions and formulations of obeticholic acid, a pharmaceutically active ingredient (also known as INT-747) having the chemical structure:

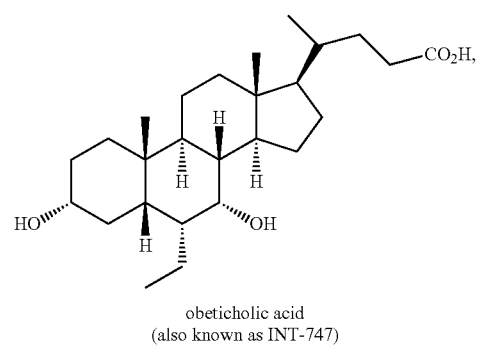

obeticholic acid
(also known as INT-747)

or a pharmaceutically acceptable salt, ester, or amino acid conjugate (such as, e.g., glycine, taurine or sarcosine conjugate) thereof having improved dissolution, solubility, and stability for the treatment of a disease or condition described herein.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present specification will control. All patents and publications cited in this specification are incorporated herein by reference in their entireties.

All percentages and ratios used herein, unless otherwise indicated, are by weight.

The term "viscosity enhancer," as used herein, refers to an agent or a mixture of agents that increases the thickness of a liquid thereby keeping the active ingredient suspended to allow accurate dosing. Viscosity enhancers include, but are not limited to, xantham gum, guar gum, acacia, alginic acid, sodium alginate, propylene glycol alginate, povidone, carbomer, salts of carboxymethylcellulose, methylcellulose, ethylcellulose, hydroxyethyl cellulose, hydroxypropyl cellulose, hydroxypropyl methylcellulose, bentonite, polydextrose, carrageenan, sucrose, sorbitol, xylitol, dextrose, fructose, malitol, gelatin, tragacanth, a polyvinyl alcohol, cetearyl alcohol, colloidal silicon dioxide and mixtures thereof. In one embodiment, the viscosity enhancer can be any viscosity enhancer known in the art.

The term "flavoring agent," as used herein, refers to an agent or a mixture of agents that adds flavor to a mixture. Flavoring agents include, but are not limited to, artificial strawberry flavor, art banana flavor and artificial cream flavor. In one embodiment, the flavoring agent can be any flavoring agent known in the art.

The term "preservative," as used herein, refers to an agent or mixture of agents that is used to protect a composition against antimicrobial (e.g., yeast, mold, bacteria) activity. Preservatives include, but are not limited to, sodium benzoate, benzoic acid, ethylenediaminetetraacetic acid, sorbic acid, benzethonium chloride, benzalkonium chloride, bronopol, butyl paraben, methyl paraben, ethylparaben, propyl paraben, thiomerosol, sodium propionate, chlorhexidine, chlorobutanol, chlorocresol, cresol, imidurea, phenol, phenylmercuric salts, potassium sorbate, propylene glycol, and mixtures thereof. In one embodiment, the preservative can be any preservative known in the art.

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

As used herein the term "6-ethyl chenodeoxycholic acid", "6-ECDCA", "obeticholic acid" or "OCA" refers to a compound having the chemical structure:

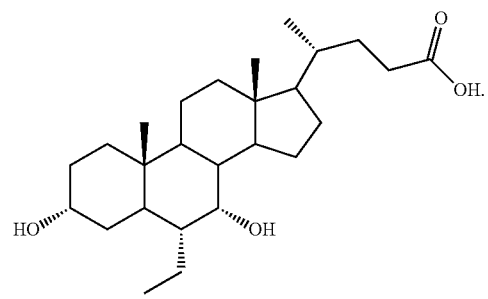 [SMILES: CC[C@@H]1C2C[C@H](O)CC[C@]2(C)C2CC[C@@]3(C)C(CCC3[C@H](C)CCC(=O)O)C2[C@@H]1O]

Other chemical names for obeticholic acid include: 3α,7α-dihydroxy-6α-ethyl-5β-cholan-24-oic acid, 6α-ethyl-chenodeoxycholic acid, 6-ethyl-CDCA, 6ECDCA, cholan-24-oic acid, 6-ethyl-3,7-dihydroxy-(3α,5β,6α,7α)- and INT-747. The CAS registry number for obeticholic acid is 459789-99-2. This term refers to all forms of obeticholic acid, e.g., non-crystalline, crystalline and substantially pure.

An "obeticholic acid composition" described herein refers to obeticholic acid administered to a patient in any form described herein including as a component of a pharmaceutical composition.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the term "purity" refers to a chemical analysis of a compound obtained from, e.g., HPLC. In one embodiment, the purity of a compound is compared to the purity of the reference standard, e.g., obeticholic acid, via the area under their respective peak for comparisons. In one embodiment, purity accounts for the organic impurities in a sample.

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

The term "regimen" refers to a protocol for dosing and/or timing the administration of one or more therapies (e.g., an obeticholic acid composition described herein or another active agent such as for example UDCA) for treating a disease, disorder, or condition described herein. A regimen can include periods of active administration and periods of rest as known in the art. Active administration periods include administration of the obeticholic acid compositions described herein in a defined course of time, including, for example, the number of and timing of dosages of the compositions. In some regimens, one or more rest periods can be included where no compound is actively administered, and in certain instances, includes time periods where the efficacy of such compounds can be minimal.

The term "enhance" refers to an increase or improvement in the function or activity of a protein or cell after administration or contacting with a combination described herein compared to the protein or cell prior to such administration or contact.

"Preventing" the disease state includes causing the clinical symptoms of the disease state not to develop in a subject that may be exposed to or predisposed to the disease state, but does not yet experience or display symptoms of the disease state.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

"Disease state" means any disease, disorder, condition, symptom, or indication.

The term "effective amount" as used herein refers to an amount of obeticholic acid (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of obeticholic acid that, when administered to a mammal for treating a disease, is sufficient to effect such treatment for the disease. The "therapeutically effective amount" will vary depending on obeticholic acid, the disease and its severity and the age, weight, etc., of the mammal to be treated. A therapeutically effective amount can refer to a starting dose or adjusted dose as set forth herein.

A therapeutically effective amount of obeticholic acid can be formulated with a pharmaceutically acceptable carrier for administration to a human or an animal. Accordingly, obeticholic acid or its formulations can be administered, for example, via oral, parenteral, or topical routes, to provide an effective amount of the compound. In alternative embodiments, obeticholic acid prepared in accordance with the present disclosure can be used to coat or impregnate a medical device, e.g., a stent.

For any compound, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

A "starting dose" as used herein refers to an initial dose provided to a patient to provide a clinical effect while minimizing onset or occurrence of an adverse effect. A starting dose can, in certain instances, be less than an amount typically administered to a patient. A starting dose is provided in an amount that is titrated or gradually increased over the course of a titration period or during the course of treatment with an obeticholic acid composition described herein.

A "titration period" refers to a length of time for which a starting dose is administered to a patient. A titration period continues for a specified length of time, where the patient is often monitored for liver function and/or liver biochemistry as described herein. In one embodiment a titration period concludes when a patient tolerates an obeticholic acid composition described herein but has a decreased or minimal reduction in alkaline phosphatase.

An "adjusted dose" as used herein refers to a dose of an obeticholic acid composition described herein administered after the termination of a titration period. An adjusted dose is often increased compared to a starting dose but, as provided herein, patient tolerance and other factors described herein determine the dosage amount of an adjusted dose. A "re-adjusted dose" as used herein refers to any changed dosage amount or dose frequency of an adjusted dose in a patient.

"Hepatic impairment" is used in accordance with its standard meaning(s) in the art and can, in certain embodiments herein refer to scoring based upon the Child-Pugh Score of A, B, and C.

The term "administering" refers to the act of delivering an obeticholic acid composition described herein into a subject by such routes as oral, mucosal, topical, suppository, intravenous, parenteral, intraperitoneal, intramuscular, intralesional, intrathecal, intranasal or subcutaneous administration. Parenteral administration includes intravenous, intramuscular, intra-arterial, intradermal, subcutaneous, intraperitoneal, intraventricular, and intracranial administration. The term can also refer to the frequency (e.g., daily, weekly, monthly, etc.) of providing an obeticholic acid composition described herein to a patient. Administration generally occurs after the onset of the disease, disorder, or condition, or its symptoms but, in certain instances, can occur before the onset of the disease, disorder, or condition, or its symptoms (e.g., administration for patients prone to such a disease, disorder, or condition). In certain embodiments, administration as used herein refers to oral administration.

The term "co-administration" refers to administration of two or more agents (e.g., an obeticholic acid composition described herein and another active agent such as UDCA or an anti-cancer agent described herein). The timing of co-administration depends in part of the combination and the compositions administered and can include administration at the same time, prior to, or after the administration of one or more additional therapies. An obeticholic acid composition of the instant invention can be administered alone or can be coadministered to the patient. Co-administration is meant to include simultaneous or sequential administration of an obeticholic acid composition individually or in combination (more than one compound or agent). Thus, the preparations can also be combined, when desired, with other active substances (e.g., to reduce metabolic degradation). The obeticholic acid compositions described herein can be used in combination with each other (i.e., two different obeticholic acid compositions), with other active agents known to be useful in treating a disease, or with adjunctive agents that are not effective alone, but can contribute to or enhance the efficacy of the active agent.

The term "anti-cancer agent" is used in accordance with its plain ordinary meaning and refers to a composition having anti-neoplastic properties or the ability to inhibit the growth or proliferation of cells. In embodiments, an anti-cancer agent is a chemotherapeutic agent. In embodiments, an anti-cancer agent is an agent identified herein having utility in methods of treating cancer. In embodiments, an anti-cancer agent is an agent approved by the FDA or similar regulatory agency of a country other than the USA, for treating cancer.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Solvates" means solvent addition forms that contain either stoichiometric or non-stoichiometric amounts of solvent. Obeticholic acid may have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Tautomers" refers to compounds whose structures differ markedly in arrangement of atoms, but which exist in easy and rapid equilibrium. It is to be understood that obeticholic acid may be depicted as different tautomers. It should also be understood that when obeticholic acid and synthetic intermediates of the disclosure have tautomeric forms, all tautomeric forms are intended to be within the scope of the disclosure, and the naming of obeticholic acid does not exclude any tautomer form. obeticholic acid and synthetic intermediates of the disclosure can exist in several tautomeric forms, including the keto-enol. For example, in keto-enol tautomerism a simultaneous shift of electrons and a hydrogen atom occurs. Tautomers exist as mixtures of a tautomeric set in solution. In solid form, usually one tautomer predominates. Even though one tautomer may be described, the present disclosure includes all tautomers of the present compounds.

It is to be understood accordingly that the isomers arising from asymmetric carbon atoms (e.g., all enantiomers and diastereomers) are included within the scope of the disclosure, unless indicated otherwise. Such isomers can be obtained in substantially pure form by classical separation techniques and by stereochemically controlled synthesis.

Furthermore, the structures and other compounds and moieties discussed in this application also include all tautomers thereof. Alkenes can include either the E- or Z-geometry, where appropriate. Obeticholic acid and synthetic intermediates may exist in stereoisomeric form, and therefore can be produced as individual stereoisomers or as mixtures.

A "pharmaceutical composition" is a formulation containing obeticholic acid in a form suitable for administration to a subject. In one embodiment, the pharmaceutical composition is in bulk or in unit dosage form. It is can be advantageous to formulate compositions in dosage unit form for ease of administration and uniformity of dosage. Dosage unit form, as used herein, refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the disclosure are dictated by and directly dependent on the unique characteristics of the active reagent and the particular therapeutic effect to be achieved, and the limitations inherent in the art of compounding such an active agent for the treatment of individuals.

The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The unit dosage form is any of a variety of forms, including, for example, a capsule, an IV bag, a tablet, a single pump on an aerosol inhaler, or a vial. The quantity obeticholic acid (e.g., a formulation of obeticholic acid, or a pharmaceutically acceptable salt, solvate, or amino acid conjugate thereof) in a unit dose of composition is an effective amount and is varied according to the particular treatment involved. One skilled in the art will appreciate that it is sometimes necessary to make routine variations to the dosage, depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, obeticholic acid is mixed under sterile conditions with a pharmaceutically acceptable carrier, and with any preservatives, buffers, or propellants that are required.

The term "flash dose" refers to obeticholic acid formulations that are rapidly dispersing dosage forms.

The term "immediate release" is defined as a release of obeticholic acid from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of obeticholic acid from a dosage form over a prolonged period.

A "subject" or "patient" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the patient is human. In one embodiment, the subject is human child (e.g., between about 30 kg to about 70 kg). In one embodiment, the human child has had a Kasai procedure, where the Kasai procedure effectively gives them a functional bile duct when they are born either without a bile duct or a bile duct that is completely blocked at birth.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

"Process of the disclosure" refers to a method for preparing obeticholic acid as described herein, wherein the method comprises preparing a crystalline form of obeticholic acid.

A "control" as used herein refers to a baseline level determined on a patient-by-patient basis, an amount or level considered by those skilled in the art as a normal value, or any level or measure of a condition or biomarker described herein taken from a patient or population of patients at any given time for a given condition.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what an abnormally elevated blood level is for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

In one aspect, the disclosure provides a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of less than 200 μm. The composition of the disclosure possesses advantageous properties, including improved dissolution profile and solubility.

In one embodiment, 90% of the particles have a diameter of 400 μm or less, 300 μm or less, 200 μm or less, 100 μm or less, 90 μm or less, 80 μm or less, 70 μm or less, 60 μm or less, 50 μm or less, 25 μm or less. In a further embodiment, 90% of the particles have a diameter of 300 μm or less, such as 200 μm or less, 100 μm or less, 90 μm or less, 80 μm or less, 70 μm or less, 60 μm or less, 50 μm or less, 25 μm or less. In a further embodiment, 90% of the particles have a diameter of 100 μm or less, such as 90 μm or less, 80 μm or less, 70 μm or less, more preferably 60 μm or less, more preferably 50 μm or less, 25 μm or less. In a further embodiment, 90% of the particles have a diameter of 90 μm or less, such as 80 μm or less, 70 μm or less, 60 μm or less, 50 μm or less, 25 μm or less. In a further embodiment, 90% of the particles have a diameter of 50 μm or less, such as 25 μm or less. In a further embodiment, 90% of the particles have a diameter of 25 μm or less.

In one embodiment, 50% of the particles have a diameter of 200 μm or less, such as 150 μm or less, 100 μm or less, 80 μm or less, 60 μm or less, 40 μm or less, 20 μm or less, 15 μm or less, 10 μm or less, 5 μm or less. In a further embodiment, 50% of the particles have a diameter of 100 μm or less, such as 80 μm or less, 60 μm or less, 40 μm or less, 20 μm or less, 15 μm or less, more preferably 10 μm or less, 5 μm or less. In a further embodiment, 50% of the particles have a diameter of 20 μm or less, such as 15 μm or less, 10 μm or less, 5 μm or less. In a further embodiment, 50% of the particles have a diameter of 10 μm or less, such as 5 μm or less. In a further embodiment, 50% of the particles have a diameter of 5 μm or less.

In one embodiment, 10% of the particles have a diameter of 5 μm or less, such as 4 μm or less, 3 μm or less, 2 μm or less, 1 μm or less. In a further embodiment, 10% of the particles have a diameter of 3 μm or less, 2 μm or less, or 1 μm or less. In a further embodiment, 10% of the particles have a diameter of 2 μm or less, such as, e.g., 1 μm or less. In a further embodiment, 10% of the particles have a diameter of 1 μm or less.

In one embodiment, 90% of the particles have a diameter of 400 μm or less, 50% of the particles have a diameter of 200 μm or less, and 10% of the particles have a diameter of 5 μm or less. In a further embodiment, 90% of the particles have a diameter of 300 μm or less, 50% of the particles have a diameter of 150 μm or less, and 10% of the particles have a diameter of 5 μm or less. In another embodiment, 90% of the particles have a diameter of 100 μm or less, 50% of the particles have a diameter of 50 μm or less, and 10% of the particles have a diameter of 5 μm or less. In another embodiment, 90% of the particles have a diameter of 100 μm or less, 50% of the particles have a diameter of 20 μm or less, and 10% of the particles have a diameter of 5 μm or less.

In yet another embodiment, 90% of the particles have a diameter of 100 μm or less, 50% of the particles have a diameter of 10 μm or less, and 10% of the particles have a diameter of 5 μm or less. In yet another embodiment, 90% of the particles have a diameter of 90 μm or less, 50% of the particles have a diameter of 10 μm or less, and 10% of the particles have a diameter of 5 μm or less. In another embodiment, 90% of the particles have a diameter of 50 μm or less, 50% of the particles have a diameter of 10 μm or less, and 10% of the particles have a diameter of 5 μm or less. In a further embodiment, 90% of the particles have a diameter of 50 μm or less, 50% of the particles have a diameter of 5 μm or less, and 10% of the particles have a diameter of 1 μm or less. In a further embodiment, 90% of the particles have a diameter of 25 μm or less, 50% of the particles have a diameter of 5 μm or less, and 10% of the particles have a diameter of 1 μm or less.

In one embodiment, 99% of the particles have a diameter of 200 μm or less, such as 1 μm to 100 μm, and 1 μm to 80 μm; 90% of the particles have a diameter of 200 μm or less, such as 2 μm to 100 μm, and 2 μm to 80 μm; and 50% of the particles have a diameter of 200 μm or less, such as 7 μm to 100 μm, 8 μm to 100 μm, and 9 μm to 80 μm. Furthermore preferably 90% of the particles have a diameter of 100 μm or less, and 50% of the particles have a diameter of 90 μm or less.

In one embodiment, 50% of the particles have a diameter of 100 μm or less, such as 5 μm to 100 μm, and 5 μm to 50 μm; 90% of the particles have a diameter of 200 μm or less, such as 3 μm to 200 μm, and 3 μm to 150 μm; and 99% of the particles have a diameter of 300 μm or less, such as 1 μm to 300 μm, and 1 μm to 200 μm. In a further embodiment, 90% of the particles have a diameter of 150 μm or less, such as 3 μm to 150 μm, and 3 μm to 100 μm; and 99% of the particles have a diameter of 200 μm or less, such as 1 μm to 200 μm, and 1 μm to 150 μm. In a further embodiment, 99% of the particles have a diameter of 150 μm or less, preferably 2 μm to 150 μm, and more preferably 2 μm to 100 μm.

In the present disclosure, the "particle size reduction" is carried out for the purpose of crushing solid particles by the application of mechanical force such as impact, shearing, or friction thereto to reduce the particle sizes, thereby facilitating the formation of a homogeneous mixed state and improving the dissolution rate and bioavailability of the drug owing to the increased surface area (which refers to as specific surface area, or "SSA") of the drug. Known particle size reduction methods include, but are not limited to: high-speed rotating impact mills (hammer mills and impact mills), which reduce particle size by means of the impact force of a high-speed rotating hammer or pin in a chamber; carrier mills (ball mills or vibration mills) which reduce particle size powder by means of impact force or friction force in a rotating cylinder in which the powder and magnetic balls are placed; and fluid energy mills (jet mills), which reduce particle size by jetting compressed air and raw material particles from a nozzle and colliding the particles accelerated by the jet of air with swirling particles in a chamber. In one embodiment, the particle size of obeticholic acid is reduced using a jet mill. "Micronization," as defined herein, is a reduction of particle size of an active ingredient, i.e., obeticholic acid, to a diameter that is less than about 200 μm, such as less than about 100 μm, less than about 50 μm, and less than 25 μm.

In some examples, obeticholic acid has a particle size distribution with a $D_{50}$ of not more than 100 μm. In specific embodiments, the $D_{50}$ is not more than 50 μm, not more than 20 μm, or not more than 10 μm. In other examples, the $D_{90}$ is not more than 200 μm, or not more than 100 μm. In still other examples, the $D_{10}$ is not more than 20 μm, not more than 10 μm, or not more than 5 μm.

Particle size analysis can be carried out via different methods. Non-limiting examples of the methods include, but are not limited to, sieve technique, wet dispersion method with laser diffraction analysis, dry dispersion method with laser diffraction analysis, or a combination thereof. Particle size analysis is not limited to the methods described herein and can be carried out using any method known to one skilled in the art. In one embodiment, particle size analysis can be performed via a sieve technique. In another embodiment, particle size analysis can be performed using a wet dispersion method (e.g., water as the dispersing agent, and analysis by laser diffraction using, e.g., Sympatec equipment). In yet another embodiment, particle size analysis can be performed using a dry dispersion method and analyzed by laser diffraction using, e.g., Sympatec equipment.

In one embodiment, particle size distribution (% volume at each particle size) is measured via a Sympatec laser diffraction analyzer (e.g., Helos/KF-Magic F71000 with Rodos Dispersing Unit, Vibri sampling unit with Sniffer rotation, Nilfisk exhaustion, or equivalent). In another embodiment, particle size distribution (% volume at each particle size) is measured via a Malvern laser diffraction analyzer.

For example, particles can be measured using the following:

Particle diameter distribution measurement apparatus: HELOS (KF-Magic F71000) & RODOS System (manufactured by Sympatec GmbH);

Measurement range of laser diffraction apparatus: 0.5/0.9 to 175 μm;

Calculation mode of laser diffraction apparatus: Fraunhofer HRLD (v3.2 Rel. 2);

Disperser: RODOS, dry dispersion system;

Dispersive pressure: 1.0 bar.

The composition of the present disclosure comprising obeticholic acid or a pharmaceutically acceptable salt, ester, or amino acid conjugate thereof, in the form of particles, offers improved dissolution and solubility.

Without any intent to be bound by theory, obeticholic acid (OCA) ($pK_a$=4.82) exhibits a pH-solubility profile consistent with that of a weak acid. Solutions of OCA at pH 6.8 to 10 produce clear solutions. However, recovery of OCA steadily diminishes at pH higher than 8.0, indicating basic decomposition of OCA. Despite the solubility observed at pH 6.8 to 10, the particle size distribution of OCA is believed to impact its dissolution rate.

In one embodiment, in vitro dissolution rates or profiles of the entire active ingredient of the pharmaceutical composition are measured from the entire pharmaceutical composition according to the steps and conditions in Example 3. The dissolution rate can be measured in a variety of buffers, which optionally contains one or more surfactants. Non-limiting examples of buffers include acetate buffer, phosphate buffers, and alkaline borate buffers, or a combination thereof. Non-limiting examples of surfactants include, polysorbate 80 (Tween 80®), potassium laurate, sodium laurate, triethanol ammonium laurate, potassium myristate, sodium myristate, triethanol ammonium myristate, sodium lauryl sulfate, polyoxyethylene alkyl ether sodium sulfate, sodium alkyl β-alanine, sodium sulfosuccinate, acylmethyl taurine, sodium alkylethane suifonate, polyoxyethylene alkyl ether sodium carboxylate, trimethyl ammonium chloride, benzalkonium chloride, lauryl amine oxide, amide propyl betaine coconut fatty add, amide propyl betaine laurate, amide propyl betaine myristate, sorbitan monolaurate, sorbitan monopalmitate, sorbitan sesquioleate, polyoxyethylene sorbitan monolaurate, polyethylene glycol monooleate, polyoxyethylene alkyl ether, polyglycol diester, lauroyl diethanol amide, fatty acid isopropanol amide, maltitol hydroxy fatty acid alkyl ether, alkylated polysaccharide, alkyl glucoside, and sucrose fatty acid ester or a combination thereof. In one embodiment, the dissolution rate is measured in Disodium Hydrogen Phosphate Buffer ($Na_2HPO_4$). In another embodiment, the dissolution rate is measured in a buffer containing a surfactant (e.g., 0.01-0.1% wt/wt). In one embodiment, the surfactant is polysorbate 80 (Tween 80®).

In one embodiment, in vitro dissolution rates or profiles are measured by using a using USP II paddle apparatus in Disodium Hydrogen Phosphate Buffer ($Na_2HPO_4$) at a temperature of about 37±0.5° C. and paddles rotation between about 50 rpm to about 100 rpm. In another embodiment, in vitro dissolution rates or profiles are measured by using a using USP II paddle apparatus in Disodium Hydrogen Phosphate Buffer ($Na_2HPO_4$) containing polysorbate 80 (Tween 80®) (e.g., 0.01-0.1% wt/wt) at a temperature of about 37±0.5° C. and paddles rotation between about 50 rpm to about 100 rpm. The entire pharmaceutical composition includes the entire active ingredient and if the pharmaceutical composition contains a capsule shell, carrier, excipient, diluent, disintegrating agent, lubricant, binder or any additional agent described in the Pharmaceutical Composition Section below, the measurement is performed with those components.

In one embodiment, in vitro dissolution is conducted at about 75 rpm using Disodium Hydrogen Phosphate Buffer ($Na_2HPO_4$). In another embodiment, in vitro dissolution is conducted at 75 rpm using about 900 mL of a Disodium Hydrogen Phosphate Buffer ($Na_2HPO_4$). Solutions are collected at 15 minutes, 30 minutes, 45 minutes, 60 minutes, and 75 minutes after the start of the dissolution. The dissolution rate of the compound is measured by high-performance liquid chromatography (HPLC) with Corona Charged Aerosol Detection (CAD).

In one embodiment, the concentration for OCA (e.g., in a Disodium Hydrogen Phosphate Buffer, optionally containing a surfactant, such as polysorbate 80 (Tween 80®)), after dissolution is between about 0.001 mg/mL to about 0.01 mg/mL, or between about 0.001 mg/mL to about 0.03 mg/mL. Above pH 6.8, the solubility of OCA is well above 0.01 mg/mL.

In one embodiment, the concentration for dissolved 5 mg tablets of OCA is between about 0.001 mg/mL to about 0.02 mg/mL. In another embodiment, the concentration for dissolved 5 mg tablets of OCA is between about 0.003 mg/mL to about 0.01 mg/mL. In yet another embodiment, the concentration for dissolved 5 mg tablets of OCA is between about 0.004 mg/mL to about 0.009 mg/mL. In another embodiment, the concentration for dissolved 5 mg tablets of OCA is between about 0.005 mg/mL to about 0.008 mg/mL. In yet another embodiment, the concentration for dissolved 5 mg tablets of OCA is between about 0.006 mg/mL to about 0.007 mg/mL. In another embodiment, the concentration for dissolved 5 mg tablets of OCA is about 0.006 mg/mL. In yet another embodiment, the concentration for dissolved 5 mg tablets of OCA is about 0.0056 mg/mL.

In one embodiment, the concentration for dissolved 10 mg tablets of OCA is between about 0.001 mg/mL to about 0.03 mg/mL. In another embodiment, the concentration for dissolved 10 mg tablets of OCA is between about 0.005 mg/mL to about 0.025 mg/mL. In yet another embodiment, the concentration for dissolved 10 mg tablets of OCA is between about 0.008 mg/mL to about 0.02 mg/mL. In another embodiment, the concentration for dissolved 10 mg tablets of OCA is between about 0.009 mg/mL to about 0.015 mg/mL. In yet another embodiment, the concentration for dissolved 10 mg tablets of OCA is about 0.011 mg/mL. In another embodiment, the concentration for dissolved 10 mg tablets of OCA is about 0.010 mg/mL.

In one embodiment, the concentration for dissolved 25 mg tablets of OCA is between about 0.001 mg/mL to about 0.05 mg/mL. In another embodiment, the concentration for dissolved 25 mg tablets of OCA is between about 0.01 mg/mL to about 0.08 mg/mL. In yet another embodiment, the concentration for dissolved 25 mg tablets of OCA is between about 0.02 mg/mL to about 0.06 mg/mL. In another embodiment, the concentration for dissolved 25 mg tablets of OCA is between about 0.025 mg/mL to about 0.04 mg/mL. In yet another embodiment, the concentration for dissolved 25 mg tablets of OCA is about 0.026 mg/mL to about 0.03 mg/mL. In another embodiment, the concentration for dissolved 25 mg tablets of OCA is about 0.028 mg/mL.

In one embodiment, the composition of the present disclosure comprising obeticholic acid or a pharmaceutically acceptable salt, ester, or amino acid conjugate thereof, in the form of particles, provides improved dissolution of obeticholic acid or a pharmaceutically acceptable salt, ester, or amino acid conjugate thereof. For example, obeticholic acid or a pharmaceutically acceptable salt, ester, or amino acid conjugate thereof in the particle composition of the present disclosure dissolves (e.g., in a Disodium Hydrogen Phosphate Buffer) at a rate that is at least 2%, 3%, 4%, 5%, 6%, 7%, 8%, 9%, 10%, 15%, 20%, 30%, 40%, 50%, 80%, or 100% faster than the dissolution rate when obeticholic acid or a pharmaceutically acceptable salt, ester, or amino acid conjugate thereof is not present in the particle composition of the present disclosure.

For example, about 55% to about 95% of obeticholic acid or a pharmaceutically acceptable salt, ester, or amino acid conjugate thereof in the particle composition of the present disclosure is dissolved within about 15 minutes, or about 65% to about 95% is dissolved within about 30 minutes, or about 80% to about 95% is dissolved within about 45 minutes, or about 87% to about 97% is dissolved within about 60 minutes, or about 87% to about 99% is dissolved within about 75 minutes. For example, about 60% to about 84% of obeticholic acid or a pharmaceutically acceptable salt, ester, or amino acid conjugate thereof in the particle composition of the present disclosure is dissolved within about 15 minutes, or about 75% to about 91% is dissolved within about 30 minutes, or about 85% to about 93% is dissolved within about 45 minutes, or about 90% to about 96% is dissolved within about 60 minutes, or about 90% to about 97% is dissolved within about 75 minutes. For example, about 62% to about 83% of obeticholic acid or a pharmaceutically acceptable salt, ester, or amino acid conjugate thereof in the particle composition of the present disclosure is dissolved within about 15 minutes, or about 80% to about 90% is dissolved within about 30 minutes, or about 87% to about 94% is dissolved within about 45 minutes, or about 92% to about 96% is dissolved within about 60 minutes, or about 91% to about 97% is dissolved within about 75 minutes. For example, about 60% to about 84% obeticholic acid or a pharmaceutically acceptable salt, ester, or amino acid conjugate thereof in the particle composition of the present disclosure is dissolved within about 15 minutes, or about 70% to about 90% is dissolved within about 30 minutes, or about 85% to about 92% is dissolved within about 45 minutes, or about 89% to about 96% is dissolved within about 60 minutes, or about 90% to about 96% is dissolved within about 75 minutes. For example, at least about 60% obeticholic acid or a pharmaceutically acceptable salt, ester, or amino acid conjugate thereof in the particle composition of the present disclosure is dissolved within about 15 minutes, or at least about 90% is dissolved within about 60 minutes. For example, obeticholic acid or a pharmaceutically acceptable salt, ester, or amino acid conjugate thereof in the particle composition of the present disclosure has an in vitro dissolution profile of about 51% dissolved within about 15 minutes, or about 66% dissolved within about 30 minutes, or about 79% dissolved within about 45 minutes, or about 85% dissolved within about 60 minutes.

In one embodiment, the composition of the present disclosure comprising obeticholic acid or a pharmaceutically acceptable salt, ester, or amino acid conjugate thereof, in the form of particles, provides improved solubility of obeticholic acid or a pharmaceutically acceptable salt, ester, or amino acid conjugate thereof. For example, obeticholic acid or a pharmaceutically acceptable salt, ester, or amino acid conjugate thereof in the particle composition of the present disclosure has a solubility (e.g., in a Disodium Hydrogen Phosphate Buffer) that is at least 2%, 3%, 4%, 5%, 6%, 7%, 8%, 9%, 10%, 15%, 20%, 30%, 40%, 50%, 80%, or 100% higher than the solubility when obeticholic acid or a pharmaceutically acceptable salt, ester, or amino acid conjugate thereof is not present in the particle composition of the present disclosure. For example, obeticholic acid or a pharmaceutically acceptable salt, ester, or amino acid conjugate thereof in the particle composition of the present disclosure has a solubility (e.g., in a Disodium Hydrogen Phosphate Buffer) that is at least 2%, 3%, 4%, 5%, 6%, 7%, 8%, 9%, 10%, 15%, or 20% higher than the solubility when obeticholic acid or a pharmaceutically acceptable salt, ester, or amino acid conjugate thereof is not present in the particle composition of the present disclosure at a pH (e.g., pH 6.8) at which obeticholic acid has the highest solubility (e.g., freely soluble) when not present in the particle composition of the present disclosure.

In one embodiment, obeticholic acid, or a pharmaceutically acceptable salt, ester, or amino acid conjugate thereof, and/or particles of obeticholic acid, or a pharmaceutically acceptable salt, ester, or amino acid conjugate thereof, has a solubility of about 0.001 to about 0.600 mg/mL. In another embodiment, obeticholic acid, or a pharmaceutically acceptable salt, ester, or amino acid conjugate thereof, and/or particles of obeticholic acid, or a pharmaceutically acceptable salt, ester, or amino acid conjugate thereof, has a solubility of about 0.02 to about 0.500 mg/mL. In yet another embodiment, obeticholic acid, or a pharmaceutically acceptable salt, ester, or amino acid conjugate thereof, and/or particles of obeticholic acid, or a pharmaceutically acceptable salt, ester, or amino acid conjugate thereof, has a solubility of about 0.03 to about 0.48 mg/mL. In another embodiment, obeticholic acid, or a pharmaceutically acceptable salt, ester, or amino acid conjugate thereof, and/or particles of obeticholic acid, or a pharmaceutically acceptable salt, ester, or amino acid conjugate thereof, has a solubility of about 0.05 to about 0.46 mg/mL. In yet another embodiment, obeticholic acid, or a pharmaceutically acceptable salt, ester, or amino acid conjugate thereof, and/or particles of obeticholic acid, or a pharmaceutically acceptable salt, ester, or amino acid conjugate thereof, has a solubility of about 0.1 to about 0.5 mg/mL. In another embodiment, obeticholic acid, or a pharmaceutically acceptable salt, ester, or amino acid conjugate thereof, and/or particles of obeticholic acid, or a pharmaceutically acceptable salt, ester, or amino acid conjugate thereof, has a solubility of about 0.2 to about 0.6 mg/mL.

The disclosure also comprehends isotopically-labeled obeticholic acid, or pharmaceutically acceptable salts, solvate, or amino acid conjugates thereof, which are identical to those recited in formulae of the disclosure and following, but for the fact that one or more atoms are replaced by an atom having an atomic mass or mass number different from the atomic mass or mass number most commonly found in nature. Examples of isotopes that can be incorporated into obeticholic acid, or pharmaceutically acceptable salts, solvate, or amino acid conjugates thereof include isotopes of hydrogen, carbon, nitrogen, fluorine, such as $^3$H, $^{11}$C, $^{14}$C and $^{18}$F.

Obeticholic acid, or pharmaceutically acceptable salts, solvates, or amino acid conjugates thereof that contain the aforementioned isotopes and/or other isotopes of other atoms are within the scope of the present disclosure. Isotopically-labeled obeticholic acid, or pharmaceutically acceptable salts, solvates, or amino acid conjugates thereof, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled obeticholic acid, or pharmaceutically acceptable salts, solvates, or amino acid conjugates thereof can generally be prepared by carrying out the procedures disclosed in the Schemes and/or in the Examples of the disclosure, by substituting a readily available isotopically labeled reagent for a non-isotopically labeled reagent. In one embodiment, obeticholic acid, or pharmaceutically acceptable salts, solvates, or amino acid conjugates thereof are not isotopically labeled. In one embodiment, deuterated obeticholic acid is useful for bioanalytical assays. In another embodiment, obeticholic acid, or pharmaceutically acceptable salts, solvates, or amino acid conjugates thereof are radiolabeled.

In another aspect, the disclosure provides a composition comprising obeticholic acid, or a pharmaceutically acceptable salt, ester, or amino acid conjugate thereof, and a pharmaceutically acceptable excipient having a low alcohol (e.g., an impurity having at least one primary OH group, such as ethanol or methanol) content. In one embodiment, the alcohol is a primary alcohol. As defined herein "primary alcohol" is an alcohol which has a hydroxy group connected to a primary carbon atom. The composition of the disclosure possesses advantageous properties, including improved stability of obeticholic acid in the composition.

The excipient can be any excipient present in the composition comprising obeticholic acid, or a pharmaceutically acceptable salt, ester, or amino acid conjugate thereof. Examples of excipients include, but are not limited to, calcium phosphate, microcrystalline cellulose, sodium starch glycolate and magnesium stearate, or a combination thereof. In one embodiment, the excipient can be any excipient known in the art. In another embodiment, the excipient is selected from calcium phosphate, microcrystalline cellulose, sodium starch glycolate and magnesium stearate. In yet another embodiment, the excipient is selected from microcrystalline cellulose, sodium starch glycolate and magnesium stearate. In another embodiment, the excipient is the excipient is magnesium stearate. In yet another embodiment, the excipient is microcrystalline cellulose. In a further embodiment, the excipient is sodium starch glycolate.

In one embodiment, the excipient has an impurity having a primary alcohol group. In another embodiment, the impurity in the excipient is ethanol, methanol, polyvinyl alcohol, polyethylene glycol, or a substance having at least one primary OH moiety.

In one embodiment, the total alcohol (e.g., the impurity having at least one primary OH group) content in the excipient is less than 6%, 5%, 4.5%, 4%, 3.5%, 3%, 2.5%, 2%, 1.5%, 1%, or 0.5% (wt/wt). In one embodiment, the alcohol is a substance having at least one primary OH moiety. In one embodiment, the alcohol is ethanol, methanol, polyvinyl alcohol, polyethylene glycol, or a combination thereof. In one embodiment, the total content of ethanol, methanol, polyvinyl alcohol, polyethylene glycol, or a combination thereof in the excipient is less than 6%, 5%, 4.5%, 4%, 3.5%, 3%, 2.5%, 2%, 1.5%, 1%, or 0.5% (wt/wt).

In one embodiment, the alcohol is ethanol. In one embodiment, the total ethanol content in the excipient is less than 6%, 5%, 4.5%, 4%, 3.5%, 3%, 2.5%, 2%, 1.5%, 1%, or 0.5% (wt/wt). In another embodiment, the excipient is sodium starch glycolate. In one embodiment, the sodium starch glycolate comprises less than 6%, 5%, 4.5%, 4%, 3.5%, 3%, 2.5%, 2%, 1.5%, 1%, or 0.5% (wt/wt) ethanol.

In one embodiment, the alcohol is methanol. In one embodiment, the total methanol content in the excipient is less than 6%, 5%, 4.5%, 4%, 3.5%, 3%, 2.5%, 2%, 1.5%, 1%, or 0.5% (wt/wt).

In another embodiment, the alcohol is a substance having at least one primary OH moiety. In one embodiment, the total content of the substance having at least one primary OH moiety in the excipient is less than 6%, 5%, 4.5%, 4%, 3.5%, 3%, 2.5%, 2%, 1.5%, 1%, or 0.5% (wt/wt).

In one embodiment, the alcohol is polyvinyl alcohol. In one embodiment, the total polyvinyl alcohol content in the excipient is less than 6%, 5%, 4.5%, 4%, 3.5%, 3%, 2.5%, 2%, 1.5%, 1%, or 0.5% (wt/wt). In one embodiment, the excipient is sodium starch glycolate. In one embodiment, the sodium starch glycolate comprises less than 6%, 5%, 4.5%, 4%, 3.5%, 3%, 2.5%, 2%, 1.5%, 1%, or 0.5% (wt/wt) polyvinyl alcohol.

In one embodiment, the alcohol is polyethylene glycol. In one embodiment, the total polyethylene glycol content in the excipient is less than 6%, 5%, 4.5%, 4%, 3.5%, 3%, 2.5%, 2%, 1.5%, 1%, or 0.5% (wt/wt). In one embodiment, the excipient is sodium starch glycolate. In one embodiment, the sodium starch glycolate comprises less than 6%, 5%, 4.5%, 4%, 3.5%, 3%, 2.5%, 2%, 1.5%, 1%, or 0.5% (wt/wt) polyethylene glycol.

The composition comprising obeticholic acid, or a pharmaceutically acceptable salt, ester, or amino acid conjugate thereof, and a pharmaceutically acceptable excipient having low alcohol content offers advantageous stability of obeticholic acid upon storage under various conditions.

In one embodiment, the composition comprising obeticholic acid, or a pharmaceutically acceptable salt, ester, or amino acid conjugate thereof, and a pharmaceutically acceptable excipient having a low primary alcohol content comprises a decreased amount of impurities, as compared to an obeticholic acid composition comprising an excipient having a high alcohol (e.g., greater than or equal to 6% (wt/wt) content).

In one embodiment, the impurity is an ester of obeticholic acid. In one embodiment, the amount of the ester of obeticholic acid is decreased by at least 10%, 20%, 30%, 40%, 50%, 60%, 70%, 80%, 90%, 95%, or 99%. In one embodiment, the amount of the ester of obeticholic acid is decreased by at least 50%, 60%, 70%, 80%, 90%, 95%, or 99%.

In one embodiment, the impurity is an ethyl ester of obeticholic acid. In one embodiment, the amount of the ethyl ester of obeticholic acid is decreased by at least 10%, 20%, 30%, 40%, 50%, 60%, 70%, 80%, 90%, 95%, or 99%. In one embodiment, the amount of the ethyl ester of obeticholic acid is decreased by at least 50%, 60%, 70%, 80%, 90%, 95%, or 99%. In another embodiment, the amount of the ethyl ester of obeticholic acid is less than 0.5%, 0.4%, 0.3%, 0.2%, 0.1%, 0.09%, 0.08%, 0.07%, 0.06%, 0.05%, 0.04%, 0.03%, 0.02%, or 0.01% (wt/wt). In a further embodiment, the amount of the ethyl ester of obeticholic acid is less than 0.5%, 0.4%, 0.3%, 0.2%, 0.1%, 0.09%, 0.08%, 0.07%, 0.06%, 0.05%, 0.04%, 0.03%, 0.02%, or 0.01% (wt/wt) at the storage condition of 40° C., 75% RH for 4 weeks. In a further embodiment, the amount of the ethyl ester of obeticholic acid is less than 0.2%, 0.1%, 0.09%, 0.08%, 0.07%, 0.06%, 0.05%, 0.04%, 0.03%, 0.02%, or 0.01% (wt/wt) at the storage condition of 40° C., 75% RH for 4 weeks.

In one embodiment, the impurity is a methyl ester of obeticholic acid. In one embodiment, the amount of the methyl ester of obeticholic acid is decreased by at least 10%, 20%, 30%, 40%, 50%, 60%, 70%, 80%, 90%, 95%, or 99%. In one embodiment, the amount of the methyl ester of obeticholic acid is decreased by at least 50%, 60%, 70%, 80%, 90%, 95%, or 99%. In another embodiment, the amount of the methyl ester of obeticholic acid is less than 0.5%, 0.4%, 0.3%, 0.2%, 0.1%, 0.09%, 0.08%, 0.07%, 0.06%, 0.05%, 0.04%, 0.03%, 0.02%, or 0.01% (wt/wt).

An analysis of the impurities in an obeticholic acid composition (e.g., the obeticholic acid composition of the present disclosure) can be conducted with methods known to one skilled in the art, for example, with LC/HRMS using LTQ-Orbitrap. The identities of various impurities can be confirmed through various techniques available in the art. For example, to determine whether an ethyl ester of obeticholic acid is an impurity, obeticholic acid can be dissolved in ethanol, and treated with concentrated acid and heated to synthesize the ethyl ester. The retention time and mass spectrometry of the impurity can be compared with those of the synthesized ethyl ester of obeticholic acid. The excipients were analyzed for ethanol content and excipients containing higher ethanol content were substituted with a low ethanol content excipient.

The composition comprising obeticholic acid, or a pharmaceutically acceptable salt, ester, or amino acid conjugate thereof, in the form of particles, or the composition comprising obeticholic acid, or a pharmaceutically acceptable salt, ester, or amino acid conjugate thereof, and a pharmaceutically acceptable excipient having a low alcohol content, as disclosed herein, can be incorporated into a pharmaceutical composition suitable for administration (e.g., oral administration).

Thus, in another aspect, the present disclosure provides a pharmaceutical composition, comprising a therapeutically effective amount of obeticholic acid, or a pharmaceutically acceptable salt, ester, or amino acid conjugate thereof, and a pharmaceutically acceptable excipient having a low alcohol content. In one embodiment, the pharmaceutical composition has a low alcohol content as described herein. In another embodiment, the pharmaceutical composition comprises sodium starch glycolate comprising less than 5% alcohol (e.g., ethanol).

In another embodiment, the pharmaceutical composition comprises a therapeutically effective amount of obeticholic acid, or a pharmaceutically acceptable salt, ester, or amino acid conjugate thereof, and a pharmaceutically acceptable excipient having a low alcohol content, wherein obeticholic acid is in the form of particles. In one embodiment, the particles have a size distribution as described herein.

In one embodiment, the pharmaceutical composition further comprises one or more pharmaceutical excipients. The excipient can be one or more selected from the group consisting of diluents, sweeteners, viscosity enhancing agents, dispersing agents, preservatives, flavoring agents and the like. One excipient can perform more than one function. In one embodiment, the one or more pharmaceutical excipients include a lubricant and/or a diluent.

Non-limiting examples of sweeteners include natural sweeteners such as sugars, e.g., fructose, glucose, sucrose, sugar alcohols such as mannitol, sorbitol or mixtures thereof and artificial sweeteners such as sodium saccharine, sodium cyclamate and aspartame. In one embodiment, the sweetener can be any sweetener known in the art. In another embodiment, the sweetener is selected from fructose, glucose, sucrose, mannitol, and sorbitol, or a combination thereof.

Dispersing agents include, but are not limited to, colloidal silicon dioxide and surfactants, wherein the surfactant is used alone or as an admixture with one or more surfactant. In one embodiment, the dispersing agent can be any dispersing agent known in the art. Combinations of colloidal silicon dioxide with one or more surfactants can also be used.

In one embodiment, the lubricant can be any lubricant known in the art. Non-limiting examples of lubricants include magnesium stearate, calcium stearate, stearic acid, glyceryl behenate, hydrogenated vegetable oil, and glycerine fumarate, and/or a combination thereof. In another embodiment, the lubricant is selected from magnesium stearate, calcium stearate, stearic acid, glyceryl behenate, hydrogenated vegetable oil, and glycerine fumarate. In another embodiment, the lubricant is calcium stearate. In yet another embodiment, the lubricant is stearic acid. In further embodiment, the lubricant is magnesium stearate.

In one embodiment, the diluent can be any diluent known in the art. Non-limiting examples of diluents include starch, pregelatinized starch, microcrystalline cellulose, calcium carbonate, dibasic calcium phosphate, tribasic calcium phosphate, calcium phosphate, lactose, dextrose, fructose, lactitol, lactose, magnesium carbonate, magnesium oxide, maltitol, maltodextrin, maltose, simethicone, sodium chloride, talc, xylitol, sorbitol, mannitol, and sucrose, and/or a combination thereof. In another embodiment, the diluent is selected from starch, pregelatinized starch, microcrystalline cellulose, calcium phosphate, lactose, sorbitol, mannitol, and sucrose. In another embodiment, the diluent is calcium phosphate. In yet another embodiment, the diluent is mannitol. In further embodiment, the diluent is microcrystalline cellulose.

In one embodiment, the pharmaceutical composition may further comprise a coating agent such as sugar-based coating agents, water-soluble film coating agents, enteric coating agents and delayed release coating agents or a coating composition comprising any combination thereof. In another embodiment, the coating agent can be any coating agent known in the art. Examples of coating agents include, but are not limited to, saccharose used alone or together with any of the agents such as talc, calcium carbonate, calcium phosphate, calcium sulphate, gelatine, gum arabic, polyvinylpyrrolidone and pullulan or any combination thereof; cellulose derivatives such as hydroxypropyl cellulose, hydroxypropyl methyl cellulose, hydroxyethyl cellulose, methyl hydroxyethyl cellulose and sodium carboxymethyl cellulose; synthetic polymers such as polyvinyl acetal diethyl amino acetate, aminoalkyl methacrylate copolymers and polyvinylpyrrolidone; polysaccharides such as pullulan; hydroxypropyl methyl cellulose phthalate; hydroxypropyl methyl cellulose acetate succinate; carboxymethyl ethyl cellulose; cellulose acetate phthalate; acrylic acid derivatives such as methacrylic acid copolymer L, methacrylic acid copolymer LD and methacrylic acid copolymer S; natural substances such as shellac; titanium dioxide; polyvinyl alcohol (e.g., Opadry®); polyethylene glycol; talc; lecithin; and/or combinations thereof. In one embodiment, the coating agent is selected from hydroxypropyl cellulose, hydroxypropyl methyl cellulose, hydroxyethyl cellulose, methyl hydroxyethyl cellulose, sodium carboxymethyl cellulose, polyvinyl acetal diethyl amino acetate, polyvinyl alcohol, polyethylene glycol, and lecithin, or a combination thereof. In another embodiment, the coating agent is Opadry® II (e.g., Opadry® II green, white, yellow, etc.).

In one embodiment, the pharmaceutical composition comprising obeticholic acid, or a pharmaceutically acceptable salt, ester, or amino acid conjugate thereof, in the form of particles, at about 1% to about 6% by weight, sodium starch glycolate at about 2% to about 8% by weight having a low alcohol content, a lubricant (e.g., magnesium stearate) at about 0.1% to about 2.0% by weight, and a diluent (e.g., microcrystalline cellulose) at about 85% to about 95% by weight. In one embodiment, the sodium starch glycolate comprises less than 6% (wt/wt) ethanol.

In one embodiment, the pharmaceutically composition is in solid particle form. Any inert excipient that is commonly used as a carrier or diluent may be used in the pharmaceutical composition of the present disclosure, such as for example, a gum, a starch, a sugar, a cellulosic material, a glycolate, an acrylate, or mixtures thereof. In one embodiment, the filler/diluent is microcrystalline cellulose. The pharmaceutical composition may further comprise a disintegrating agent (e.g., sodium starch glycolate) and/or a lubricant (e.g., magnesium stearate). Also, the pharmaceutical composition may comprise one or more additives selected from a buffer, a surfactant, a solubilizing agent, a plasticizer, an emulsifier, a stabilizing agent, a viscosity increasing agent, a sweetener, a film forming agent, or any combination thereof. Furthermore, the pharmaceutical composition of the present disclosure may be in the form of controlled release of immediate release formulations.

The percentage of the active ingredient (i.e., obeticholic acid, or a pharmaceutically acceptable salt, ester, or amino acid conjugate thereof) and various excipients in the pharmaceutical composition of the present disclosure may vary. For example, the composition may comprise between about 0.1 and about 99%, between about 1-50%, between about 1-25%, or about 1-6% by weight of active ingredient. Furthermore, the composition may comprise between about 20-99%, between about 45-97%, between about 65-96%, or between about 85-95% by weight microcrystalline cellulose as a filler or diluent. Furthermore, the composition may comprise between about 1-30%, between about 1-20%, or between about 2-8% by weight sodium starch glycolate as a disintegrant. Furthermore, the composition may comprise between about 0.1-5% or about 0.5-2.0% by weight magnesium stearate as a lubricant.

In one embodiment, the pharmaceutical composition of the present disclosure is about 0.1% to about 10% by weight of active ingredient (i.e., obeticholic acid, or a pharmaceutically acceptable salt, ester, or amino acid conjugate thereof), about 0.1% to about 20% by weight of sodium starch glycolate, about 0.01% to about 8.0% by weight of magnesium stearate, and about 65% to about 99% by weight of microcrystalline cellulose. In another embodiment, the pharmaceutical composition of the present disclosure is about 0.5% to about 8% by weight of active ingredient, about 1% to about 10% by weight of sodium starch glycolate, about 0.05% to about 4.0% by weight of magnesium stearate, and about 75% to about 97% by weight of microcrystalline cellulose. In yet another embodiment, the pharmaceutical composition of the present disclosure is about 1% to about 6% by weight of active ingredient, about 2% to about 8% by weight of sodium starch glycolate, about 0.1% to about 2.0% by weight of magnesium stearate, and about 85% to about 95% by weight of microcrystalline cellulose. In one embodiment, obeticholic acid, or a pharmaceutically acceptable salt, ester, or amino acid conjugate thereof, in the pharmaceutical composition is in the form of particles, as described herein.

In another aspect, the present disclosure provides a pharmaceutical composition, comprising a therapeutically effective amount of obeticholic acid, or a pharmaceutically acceptable salt, ester, or amino acid conjugate thereof, in the form of particles, and a pharmaceutically acceptable excipient having a low alcohol content. In one embodiment, the obeticholic acid particle composition is an obeticholic acid particle composition described herein. In one embodiment, the pharmaceutical composition has a low alcohol content as described herein. In one embodiment, the pharmaceutical composition comprises sodium starch glycolate comprising less than 6% alcohol (e.g., ethanol).

In another aspect, the present disclosure provides a method for preparing a pharmaceutical composition containing a therapeutically effective amount of obeticholic acid, or a pharmaceutically acceptable salt, ester, or amino acid conjugate thereof, in the form of particles, comprising i) micronizing obeticholic acid acceptable salt, ester, or amino acid conjugate thereof until at least 90% of the particles have a diameter of less than 100 μm, such as less than 90 μm, less than 50 μm, less than 25 μm, less than 20 μm, less than 15 μm, less than 10 μm, less than 5 μm, or less than 1 μm, and ii) combining the micronized obeticholic acid particles with at least one pharmaceutically acceptable excipient. In one embodiment, the micronizing is carried out using a jet-mill.

In another aspect, the present disclosure provides a method for preparing a pharmaceutical composition containing a therapeutically effective amount of obeticholic acid, or a pharmaceutically acceptable salt, ester, or amino acid conjugate thereof, in the form of particles, comprising i) micronizing obeticholic acid acceptable salt, ester, or amino acid conjugate thereof until at least 50% of the particles have a diameter of less than 10 μm, i.e., less than 5 μm, and ii) combining the micronized obeticholic acid particles with at least one pharmaceutically acceptable excipient. In one embodiment, the micronizing is carried out using a jet-mill.

In another aspect, the present disclosure provides a method for preparing a pharmaceutical composition containing a therapeutically effective amount of obeticholic acid, or a pharmaceutically acceptable salt, ester, or amino acid conjugate thereof, in the form of particles, comprising i) micronizing obeticholic acid acceptable salt, ester, or amino acid conjugate thereof until at least 10% of the particles have a diameter of less than 5 μm, i.e., less than 1 μm, and ii) combining the micronized obeticholic acid particles with at least one pharmaceutically acceptable excipient. In one embodiment, the micronizing is carried out using a jet-mill.

In another aspect, the present disclosure provides a method for preparing a pharmaceutical composition containing a therapeutically effective amount of obeticholic acid, or a pharmaceutically acceptable salt, ester, or amino acid conjugate thereof, in the form of particles, comprising i) micronizing obeticholic acid acceptable salt, ester, or amino acid conjugate thereof until at least 90% of the particles have a diameter of less than 100 μm, preferably less than 90 μm, less than 50 μm, less than 25 μm, less than 20 μm, less than 15 μm, less than 10 μm, less than 5 μm, less than 1 μm; at least 50% of the particles have a diameter of less than 10 μm, less than 5 μm, less than 1 μm; and at least 10% of the particles have a diameter of less than 5 μm, or less than 1 μm, and ii) combining the micronized obeticholic acid particles with at least one pharmaceutically acceptable excipient. In one embodiment, the micronizing is carried out using a jet-mill.

In another aspect, the present disclosure provides a method for preparing a pharmaceutical composition containing a therapeutically effective amount of obeticholic acid, or a pharmaceutically acceptable salt, ester, or amino acid conjugate thereof, in the form of particles, comprising i) micronizing obeticholic acid acceptable salt, ester, or amino acid conjugate thereof until at least 90% of the particles have a diameter of less than 100 μm, at least 50% of the particles have a diameter of less than 10 μm, and at least 10% of the particles have a diameter of less than 5 μm, and ii) combining the micronized obeticholic acid particles with at least one pharmaceutically acceptable excipient. In one embodiment, the micronizing is carried out using a jet-mill.

In another aspect, the present disclosure provides a method for preparing a pharmaceutical composition containing a therapeutically effective amount of obeticholic acid, or a pharmaceutically acceptable salt, ester, or amino acid conjugate thereof, in the form of particles, comprising i) micronizing obeticholic acid acceptable salt, ester, or amino acid conjugate thereof until at least 90% of the particles have a diameter of less than 25 μm, at least 50% of the particles have a diameter of less than 5 μm, and at least 10% of the particles have a diameter of less than 1 μm, and ii) combining the micronized obeticholic acid particles with at least one pharmaceutically acceptable excipient. In one embodiment, the micronizing is carried out using a jet-mill.

In another aspect the present disclosure provides a method for treating or preventing a disease or condition, comprising administering an effective amount of an obeticholic acid composition of the present disclosure to a patient in need thereof.

In one aspect, the present disclosure provides a method for treating a disease or condition by administering an effective amount of an obeticholic acid composition described herein to a patient in need thereof. In certain embodiments herein the effective amount refers to a titrated dosage administered during a titration period as set forth herein. In other embodiments, the effective amount refers to an adjusted or re-adjusted dosage administered after a titration period as set forth herein.

It is to be understood that the methods described herein refer generally to the obeticholic acid compositions set forth herein. The methods described herein can include any specific formulation provided herein, for example, that provided in Example 11. In one embodiment, the obeticholic acid composition useful in the methods of treating described herein is a composition provided in Example 11. In another embodiment, the obeticholic acid composition useful in the methods of treating described herein is a composition that includes microcrystalline cellulose, sodium starch glycolate, and magnesium stearate as excipients. Such a composition can be provided in a dosage form set forth herein, e.g., an oral dosage form such as a tablet or coated tablet. Thus, in certain instances, the obeticholic acid composition useful in the methods is a tablet or coated tablet for oral administration. In one embodiment, the oral dosage form of the obeticholic acid composition includes a film coating that includes one or more excipients selected from polyvinyl alcohol (part hydrolyzed), titanium dioxide, macrogol (polyethylene glycol 3350), talc, and iron oxide.

In one embodiment, the disease or condition is an FXR mediated disease or condition. Examples of the FXR mediated diseases or conditions include, but not limited to, liver diseases such as a cholestatic liver disease such as primary biliary cirrhosis (PBC) also known as primary biliary cholangitis (PBC), primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, and liver fibrosis. Examples of FXR mediated diseases also include portal hypertension, bile acid diarrhea, hyperlipidemia, high LDL-cholesterol, high HDL-cholesterol, high triglycerides, and cardiovascular disease.

In another aspect, the present disclosure provides methods of treating or preventing a disease or condition described herein by administering an obeticholic acid composition described herein (e.g., obeticholic acid or a pharmaceutically acceptable salt, ester, or amino acid conjugate thereof, where the obeticholic acid or a pharmaceutically acceptable salt, ester, or amino acid conjugate thereof is in the form of particles, and wherein at least 50% of the particles have a diameter of 200 μm or less).

In still another aspect, the present disclosure provides a method of treating primary biliary cirrhosis (PBC) by administering an obeticholic acid composition described herein (e.g., obeticholic acid or a pharmaceutically acceptable salt, ester, or amino acid conjugate thereof, where the obeticholic acid or a pharmaceutically acceptable salt, ester, or amino acid conjugate thereof is in the form of particles, and wherein at least 50% of the particles have a diameter of 200 μm or less), optionally in a titration period. In some examples, the method comprise administering a starting dose in a titration period. The starting dose, adjusted dose, and titration period are as described below.

The PBC can be advanced stage PBC. "Advanced stage PBC" refers to PBC characterized by one or more of the following: Baseline total bilirubin>upper liming of normal (ULN); Baseline total ALP>5×ULN; Baseline transient elastography (TE)>10.7 kPa; Cirrhosis based on an initial or baseline biopsy result or patient having an Ishak score 6 (cirrhosis) or Ludwig/Scheuer PBC Stage 4; or Medical history of ascites, hepatic cirrhosis, jaundice, portal hypertension, portal hypertensive gastropathy or varices esophageal.

Further provided herein are methods of treating primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, or liver fibrosis in a patient in need thereof by administering an effective amount of an obeticholic acid composition described above. In another embodiment, the method is a method of treating NAFLD by administering an effective amount of an obeticholic acid composition described above. In still another embodiment, the method is a method of treating PSC by administering an effective amount of an obeticholic acid composition described above. In yet another embodiment, the method is a method of treating fibrosis (e.g., progressive or liver fibrosis) by administering an effective amount of an obeticholic acid composition described above. In yet another embodiment, the method is a method of treating cirrhosis by administering an effective amount of an obeticholic acid composition described above.

NAFLD is a medical condition that is characterized by the buildup of fat (called fatty infiltration) in the liver. NAFLD is one of the most common causes of chronic liver disease, and encompasses a spectrum of conditions associated with lipid deposition in hepatocytes. It ranges from steatosis (simple fatty liver), to nonalcoholic steatohepatitis (NASH), to advanced fibrosis and cirrhosis. The disease is mostly silent and is often discovered through incidentally elevated liver enzyme levels. NAFLD is strongly associated with obesity and insulin resistance and is currently considered by many as the hepatic component of the metabolic syndrome.

Nonalcoholic steatohepatitis (NASH) is a condition that causes inflammation and accumulation of fat and fibrous (scar) tissue in the liver. Liver enzyme levels in the blood may be more elevated than the mild elevations seen with nonalcoholic fatty liver (NAFL). Although similar conditions can occur in people who abuse alcohol, NASH occurs in those who drink little to no alcohol. NASH affects 2 to 5 percent of Americans, and is most frequently seen in people with one of more of the following conditions: obesity, diabetes, hyperlipidemia, insulin resistance, uses of certain medications, and exposure to toxins. NASH is an increasingly common cause of chronic liver disease worldwide and is associated with increased liver-related mortality and hepatocellular carcinoma, even in the absence of cirrhosis. NASH progresses to cirrhosis in 15-20% of affected individuals and is now one of the leading indications for liver transplantation in the United States. At present there are no approved therapies for NASH.

In one embodiment, the method is a method of treating NASH by administering an obeticholic acid composition described herein, optionally in a titration period as described herein. The NASH patient can be a high risk NASH patient. A "high risk NASH patient" refers to characterization by one or more of: NAS≥4; baseline fibrosis stage 2 or 3; or baseline fibrosis stage 1 with a comorbidity (type 2 diabetes, BMI≥30 kg/m2 or ALT≥60 U/L).

In one embodiment, the disease or condition is hyperlipidemia. In one embodiment, the disease or condition is a cholestatic liver disease. In one embodiment, the disease or condition is PBC. In another embodiment, the disease or condition is a cardiovascular disease. In another embodiment, the cardiovascular disease is atherosclerosis, hypercholesteremia, or hypertriglyceridemia.

The present disclosure also provides a method for treating or preventing NAFLD or NASH. In one embodiment, the present disclosure provides a method for treating or preventing NAFLD or NASH that is associated with hyperlipidemia. In one embodiment, the present disclosure provides a method for treating or preventing NASH. In one embodiment, the present disclosure provides a method for treating or preventing NASH that is associated with hyperlipidemia.

In another aspect, the present disclosure also provides a method for decreasing liver enzymes, comprising administering a therapeutically effective amount of the composition of the present disclosure to a subject in need thereof. In one embodiment, the subject is not suffering from a cholestatic condition. In another embodiment, the subject is suffering from a cholestatic condition. In one embodiment, the liver enzyme is alkaline phosphatase, 7-glutamyl transpeptidase (GGT), and/or 5' nucleotidase.

In certain instances, the methods described herein also include assessing, monitoring, measuring, or otherwise detecting liver function. Assessing, monitoring, measuring, or otherwise detecting liver function can be performed before, during, or after a titration period described herein, or in other instances, performed during the course of any treatment described herein. Liver function can be determined by, for example, assessing, monitoring, measuring, or otherwise detecting a level of one or more liver biomarkers compared to a control. In certain instances the control is a baseline taken from the patient before beginning treatment. In other instances the control is preestablished baseline considered as a normal value.

Values for measure or detection of liver function biomarkers and controls can be expressed as a comparison to Upper Limit of Normal (ULN).

Liver biomarkers can be used to ascertain, quantify the efficacy of the course of treatment with an obeticholic acid composition described herein. In other instances, liver biomarkers described herein can be used to ascertain, quantify liver function during the course of treatment with an obeticholic acid composition described herein. Liver biomarkers can also be used to predict whether a patient or patient population will be susceptible to treatment with an obeticholic acid composition described herein. In one embodiment, the liver biomarkers include assessing, monitoring, measuring or otherwise detecting an amount or level of aspartate transaminase (AST), alanine transaminase (ALT), alkaline phosphatase (ALP), bilirubin, glycine conjugated obeticholic acid, taurine conjugated obeticholic acid, a bile acid, a bile acid glycine conjugate, or a bile acid taurine conjugate. For example, the liver biomarker assessed, monitored, measured, or detected can be ALP.

The ALP level can be a measure of ULN. In one embodiment, a patient before treatment can have an ALP level of at least 1.1×ULN to at least 20×ULN; at least 1.1×ULN to at least 15×ULN; at least 1.1×ULN to at least 12×ULN; at least 1.1×ULN to at least 10×ULN; at least 1.1×ULN to at least 8×ULN; at least 1.1×ULN to at least 6×ULN; at least 1.1×ULN to at least 5×ULN; at least 1.1×ULN to at least 4×ULN; at least 1.1×ULN to at least 3×ULN; or at least 1.1×ULN to at least 2×ULN.

A patient before a treatment described herein can have an ALP level of about 1.5×ULN to about 20×ULN; about 1.5×ULN to about 15×ULN; about 1.5×ULN to about 10 ULN; about 1.5×ULN to about 5×ULN; or about 1.5×ULN to about 3×ULN. A patient before treatment can have an ALP level before a treatment described herein of about 1.5×, 2×, 3×, 4×, 5×, 8×, 10×, 15×, or 20×ULN.

A patient before treatment can have an ALP level before a treatment described herein of greater than about 1.5×, 2×, 3×, 4×, 5×, 8×, 10×, 15×, or 20×ULN. In one embodiment, a patient has an ALP level of about 1.5×ULN. In one embodiment, a patient has an ALP level of about 2×ULN. In one embodiment, a patient has a ALP level of about 5×ULN. In one embodiment, a patient has an ALP level of about 10×ULN. In one embodiment, a patient has a bilirubin level of about 15×ULN. In one embodiment, a patient has an ALP level greater than about 1.5×ULN. In one embodiment, a patient has an ALP level greater than about 2×ULN. In one embodiment, a patient has a ALP level greater than about 5×ULN. In one embodiment, a patient has an ALP level greater than about 10×ULN. In one embodiment, a patient has a bilirubin level greater than about 15×ULN.

In another example, the liver biomarker assessed, monitored, measured, or detected can be bilirubin. The bilirubin level can be a measure of ULN. In one embodiment, a patient before treatment can have a bilirubin level of at least 1.1×ULN to at least 20×ULN; at least 1.1×ULN to at least 15×ULN; at least 1.1×ULN to at least 12×ULN; at least 1.1×ULN to at least 10×ULN; at least 1.1×ULN to at least 8×ULN; at least 1.1×ULN to at least 6×ULN; at least 1.1×ULN to at least 5×ULN; at least 1.1×ULN to at least 4×ULN; at least 1.1×ULN to at least 3×ULN; or at least 1.1×ULN to at least 2×ULN.

A patient before a treatment described herein can have a bilirubin level of about 1.5×ULN to about 20×ULN; about 1.5×ULN to about 15×ULN; about 1.5×ULN to about 10 ULN; about 1.5×ULN to about 5×ULN; or about 1.5×ULN to about 3×ULN. In another example a patient before a treatment described herein can have a bilirubin level of about 2×ULN to about 20×ULN; about 2×ULN to about 15×ULN; about 2×ULN to about 10 ULN; about 2×ULN to about 5×ULN; or about 2×ULN to about 3×ULN. In another example a patient before a treatment described herein can have a bilirubin level of greater than about 2×ULN to greater than about 20×ULN; greater than about 2×ULN to greater than about 15×ULN; greater than about 2×ULN to greater than about 10 ULN; greater than about 2×ULN to greater than about 5×ULN; or greater than about 2×ULN to greater than about 3×ULN.

A patient before treatment can have a bilirubin level before a treatment described herein of about 1.5×, 2×, 3×, 4×, 5×, 8×, 10×, 15×, or 20×ULN. A patient before treatment can have a bilirubin level before a treatment described herein of greater than about 1.5×, 2×, 3×, 4×, 5×, 8×, 10×, 15×, or 20×ULN. In one embodiment, a patient has a bilirubin level greater than about 2×ULN. In one embodiment, a patient has a bilirubin level greater than about 5×ULN. In one embodiment, a patient has a bilirubin level greater than about 10×ULN. In one embodiment, a patient has a bilirubin level greater than about 15×ULN. In one embodiment, a patient has a bilirubin level less than about 2×ULN. In one embodiment, a patient has a bilirubin level less than about 5×ULN. In one embodiment, a patient has a bilirubin level less than about 10×ULN. In one embodiment, a patient has a bilirubin level less than about 15×ULN.

In some instances it can be useful to assess, monitor, measure, or detect ALP and bilirubin to assess, monitor, measure, or otherwise detect liver function or changes in liver function during treatment with an obeticholic acid composition described herein. In certain instances, a patient has an ALP level as provided above (e.g., about 1.5×ULN to about 10×ULN) and a bilirubin level as provided above (e.g., less than about 5×ULN). In one embodiment, the patient has an ALP level between about 1.5×ULN to about 10×ULN and a bilirubin level less than about 2×ULN.

Treatment with a obeticholic acid composition described herein can reduce the levels of ALP and/or bilirubin in a patient described herein. For example, treatment of a disease or condition described herein (e.g., PBC) with an obeticholic acid composition described herein can reduce the level of ALP by 2, 4, 5, 6, 8, 9, 10, 12, 15, 18, 20, 21, 22, 23, 24, 25, 26, 27, 28, 29, 30, 35, 40, 45, 50, 55, 60, 65, 70, 75, 80, 85, 88, 90, 92, 94, 96, 97, 98, 99, 99.2, 99.4, 99.6, 99.7, 99.8, 99.9, or 100%. In another example, the level of ALP can be reduced by at least 100%, at least 125%, at least 150%, at least 175%, at least 200%, at least 225%, at least 250% or at least 300%.

In another example, the level of ALP can be reduced by about 5% to about 50%; about 10% to about 55%; about 10% to about 45%; about 10% to about 40%; about 10% to about 33%, about 10% to about 30%; about 15% to about 30%; about 15% to about 25%; about 20% to about 50%, about 20% to about 40%; about 20% to about 35%; about 20% to about 30%; 20% to about 27%; or about 20% to about 27%. In another example, the level of ALP can be reduced by at least 50%. The level of ALP can be reduced by at least 40%. The level of ALP can be reduced by at least 35%. The level of ALP can be reduced by at least 30%. The level of ALP can be reduced by at least 27%. The level of ALP can be reduced by at least 25%. The level of ALP can be reduced by at least 20%.

The reduction of ALP levels can be represented by the fold change over ULN. For example, treatment with an obeticholic acid described herein can reduce the ALP level of a patient described herein to less than about 5×ULN; less than about 4×ULN, less than about 3×ULN, less than about 2×ULN, less than about 1.7×ULN, less than about 1.5× ULN, less than about 1.25×ULN, or less than about ULN.

In another example, the ALP level is reduced by at least 1, 2, 3, 4, 5, 6, 7, 8, 9, 10, 15, 20, 25, 30, 40, or 50 fold compared to a baseline value. For example, the ALP level after treatment with an obeticholic acid composition described herein can be reduced by 1, 1.2, 1.4, 1.6, 1.8, or 2 fold, including intervening values therein, compared to a baseline value. In another example, the ALP level can be reduced by 2, 2.2, 2.4, 2.6, 2.8, or 3 fold, including intervening values therein, compared to a baseline value. In another example, the ALP level can be reduced 3, 4, or 5 fold, including intervening values therein, compared to a baseline value. In another example, the ALP level can be reduced 5, 7, 9, or 10 fold, including intervening values therein, compared to a baseline value. In another example, the ALP level can be reduced 10, 12, 15, or 20 fold, including intervening values therein, compared to a baseline value.

Treatment of a disease or condition described herein (e.g., PBC) with an obeticholic acid composition described herein can reduce the level of bilirubin by 2, 4, 5, 6, 8, 9, 10, 12, 15, 18, 20, 21, 22, 23, 24, 25, 26, 27, 28, 29, 30, 35, 4-, 45, 50, 55, 60, 65, 70, 75, 80, 85, 88, 90, 92, 94, 96, 97, 98, 99, 99.2, 99.4, 99.6, 99.7, 99.8, 99.9, or 100%. In another example, the level of bilirubin can be reduced by at least 100%, at least 125%, at least 150%, at least 175%, at least 200%, at least 225%, at least 250% or at least 300%.

In another example, the level of bilirubin can be reduced by about 5% to about 50%; about 10% to about 55%; about 10% to about 45%; about 10% to about 40%; about 10% to about 33%, about 10% to about 30%; about 15% to about 30%; about 15% to about 25%; about 20% to about 50%, about 20% to about 40%; about 20% to about 35%; about 20% to about 30%; 20% to about 27%; or about 20% to about 27%. In another example, the level of bilirubin can be reduced by at least 50%. The level of bilirubin can be reduced by at least 40%. The level of bilirubin can be reduced by at least 35%. The level of bilirubin can be reduced by at least 30%. The level of bilirubin can be reduced by at least 27%. The level of bilirubin can be reduced by at least 25%. The level of bilirubin can be reduced by at least 20%.

The reduction of bilirubin levels can be represented by the fold change over ULN. For example, treatment with an obeticholic acid described herein can reduce the bilirubin level of a patient described herein to less than about 5×ULN; less than about 4×ULN, less than about 3×ULN, less than about 2×ULN, less than about 1.7×ULN, less than about 1.5×ULN, less than about 1.25×ULN, or less than about ULN.

In another example, the bilirubin level is reduced by at least 1, 2, 3, 4, 5, 6, 7, 8, 9, 10, 15, 20, 25, 30, 40, or 50 fold compared to a baseline value. For example, the bilirubin level after treatment with an obeticholic acid composition described herein can be reduced by 1, 1.2, 1.4, 1.6, 1.8, or 2 fold, including intervening values therein, compared to a baseline value. In another example, the bilirubin level can be reduced by 2, 2.2, 2.4, 2.6, 2.8, or 3 fold, including intervening values therein, compared to a baseline value. In another example, the bilirubin level can be reduced 3, 4, or 5 fold, including intervening values therein, compared to a baseline value. In another example, the bilirubin level can be reduced 5, 7, 9, or 10 fold, including intervening values therein, compared to a baseline value. In another example, the bilirubin level can be reduced 10, 12, 15, or 20 fold, including intervening values therein, compared to a baseline value.

In another embodiment, one or more biomarkers can stratify a patient population undergoing or who will undergo treatment with an obeticholic acid composition described herein. For example, a PBC patient can be stratified for the risk of hepatocellular carcinoma (HCC).

In yet another embodiment, liver biomarkers useful for detection can include metabolites and bile acids. For example, assessing, monitoring, measuring, or otherwise detecting levels of glycine and taurine conjugates of obeticholic acid can be useful for measuring efficacy of a treatment regimen described herein. For example, assessing, monitoring, measuring, or otherwise detecting levels or detecting plasma levels of bile acids including cholic acid, chenodeoxycholic acid, deoxycholic acid, lithocholic acid, and urosodeoxycholic acid, including glycine and taurine conjugates thereof, and optionally comparing the levels to a control, can be useful for measuring efficacy of a treatment regimen described herein.

In still other embodiments, calculating an AST to platelet index (APRI) can be useful for assessing, monitoring, measuring, or otherwise detecting liver function (including changes thereof). The obeticholic acid compositions described herein can reduce the APRI of a patient described herein. In certain instances, monitoring or measuring the APRI can be used to determine efficacy of treatment with an obeticholic acid composition described herein. In some embodiments, a reduction in APRI is observed in a patient (e.g., a PBC or NASH patient) after administration of an obeticholic acid composition described herein. For example, the APRI may be reduced by about 5% to about 50% in patients treated with obeticholic acid relative to baseline levels measured before dose administration. The reduction may be up to about 5%, 10%, 15%, 20%, 25%, 30%, 35%, 40%, 45% or 50%.

Further provided herein is a method for treating PBC in a patient in need thereof by administering a starting dose of an obeticholic acid composition described herein in a titration period. The method includes assessing liver function of the patient before, during, and after said titration period by either calculating an APRI score for said patient; or by measuring the level of one or more liver biomarker selected from ALP, bilirubin, AST, ALT, glycine conjugated obeticholic acid, taurine conjugated obeticholic acid, a bile acid, a bile acid glycine conjugate, or a bile acid taurine conjugate, where a reduced APRI score compared to a control or a reduced level of the one or more liver biomarkers compared to a control indicates non-impaired liver function. The method further includes assessing tolerance of the patient to the starting dose by grading the severity of one or more adverse effects, if present, and administering an adjusted dose of the obeticholic acid composition, where the adjusted dose includes an amount equal to or greater than an amount of the starting dose. The starting dose, adjusted dose, and titration period are as described below. For example, the starting dose can be about 5 to about 50 mg (e.g., 5 mg) and the adjusted dose can be about 5 to about 50 mg (e.g., 5 mg, 10 mg, or 25 mg) and the titration period can be a time of about 1 to about 6 months, e.g., 1 month, 2 months, 3 months, 4 months, 5 months, or 6 months.

Also provided herein are methods to reduce or eliminate rejection failure of a liver transplant by administering an effective amount of an obeticholic acid composition described above. In certain instances administration of an obeticholic acid composition described herein reduces expression or levels of ALP and/or bilirubin. In one embodiment, administration of an obeticholic acid composition described herein reduces ALP and bilirubin levels, thereby reducing transplant complications or rejection. In another embodiment, administration of an effective amount of an obeticholic acid composition described herein increases post-transplantation survival rate of a liver transplantee.

In one aspect, obeticholic acid may mediate its action primarily via FXR agonism, wherein FGF-19 released from gut enterocytes (in response to FXR agonist) into portal circulation down regulates endogenous bile acid synthesis in the liver. The present disclosure comprehends a method of measuring FXR agonist activity by, for example, measuring release of FGF-19 into the bloodstream or circulation of a patient administered with OCA. Levels of FGF-19 may be measured by methods known in the art, such as those described herein.

Obeticholic acid administration may lead to a significant and a dose-dependent increase in the levels of FGF-19 and in some embodiments, a decrease in the levels of endogenous bile acids and C4 (a bile acid precursor). In some embodiments, a significant increase in FGF-19 levels may be observed from baseline to month 3, month 6 and month 12 after dose administration. In some examples, the FGF-19 levels may increase from about 5% to about 200%. In specific embodiments, the levels may increase by about 5%, 10%, 15%, 20%, 25%, 30%, 35%, 40%, 45%, 50%, 55%, 60%, 65%, 70%, 75%, 80%, 85%, 90%, 95% or 100%.

In some embodiments, the plasma levels of FGF-19, a marker of FXR activation, are determined using a qualified method and a validated method using an enzyme-linked immunosorbent assay (ELISA) method. The plasma concentrations of FGF-19 may be quantitated at predose and after administration of dose.

In some examples, a monoclonal antibody specific for FGF-19 is pre-coated onto a microplate. Standards, quality controls and samples are pipetted into the wells and any FGF-19 present is bound by the immobilized antibody. After washing away any unbound substances, an enzyme-linked polyclonal antibody specific for FGF-19 is added to the wells. Following a wash to remove any unbound antibody-enzyme reagent, a substrate solution is added to the wells and color develops in the proportion to the amount of FGF-19 bound in the initial step. The color development is stopped and the intensity of the color is measured. The calibration range of the method is 15.625 pg/ml to 1000 pg/ml for FGF-19 using a 100 µl aliquot of standard curve, quality control and sample. In some embodiments, no minimum required dilution is used. In other embodiments, samples may be subjected to a 3× minimum required dilution.

Also provided herein are methods to reduce or eliminate rejection failure of a liver transplant by administering an effective amount of an obeticholic acid composition described above. In certain instances, administration of an obeticholic acid composition described herein reduces expression or levels of ALP and/or bilirubin. In one embodiment, administration of an obeticholic acid composition described herein reduces ALP and bilirubin levels, thereby reducing transplant complications or rejection. In another embodiment, administration of an effective amount of an obeticholic acid composition described herein increases post-transplantation survival rate of a liver transplantee.

In another aspect of the disclosure is a method of treating a solid-tumor cancer by administering an effective amount of an obeticholic acid composition as described herein. In another aspect, such methods include treating hepatocellular carcinoma (HCC), colorectal cancer, gastric cancer, liver cancer, breast cancer, renal cancer, or pancreatic cancer by administering an obeticholic acid composition as described herein. In one embodiment is a method of treating HCC by administering an effective amount of an obeticholic acid composition as described herein. In one embodiment is a method of treating colorectal cancer by administering an effective amount of an obeticholic acid composition as described herein. In another embodiment is a method of treating gastric cancer by administering an effective amount of an obeticholic acid composition as described herein. In another embodiment is a method of treating liver cancer by administering an effective amount of an obeticholic acid composition as described herein. In still another embodiment is a method of treating renal cancer by administering an effective amount of an obeticholic acid composition as described herein. In still another embodiment is a method of treating pancreatic cancer by administering an effective amount of an obeticholic acid composition as described herein. It is understood that the treatment of a cancer described herein can be performed by administering an effective amount of an obeticholic acid composition described herein in combination with one or more anticancer agents, such as those described herein. In some embodiments, the effective amount administered is a starting dose as described herein.

Still further provided herein are methods of treating an autoimmune disease in a patient in need thereof by administering an effective amount of an obeticholic acid composition as described herein. In one instance, the autoimmune disease is selected from multiple sclerosis, rheumatoid arthritis, and type I diabetes. In one embodiment is a method of treating multiple sclerosis by administering an effective amount of an obeticholic acid composition as described herein. In another embodiment is a method of treating rheumatoid arthritis by administering an effective amount of an obeticholic acid composition as described herein. In still another embodiment is a method of treating type I diabetes by administering an effective amount of an obeticholic acid composition as described herein. In certain instances, the treatment of the autoimmune disease includes further administering another active agent useful for the treatment, such as without limitation, non-steroidal anti-inflammatory agents (NSAIDs) such as ibuprofen, naproxen, corticosteroids, disease-modifying anti-rheumatic drugs such as methotrexate (Trexall, Otrexup, Rasuvo), leflunomide (Arava), hydroxychloroquine (Plaquenil) and sulfasalazine (Azulfidine), biologic agents such as abatacept (Orencia), adalimumab (Humira), anakinra (Kineret), certolizumab (Cimzia), etanercept (Enbrel), golimumab (Simponi), infliximab (Remicade), rituximab (Rituxan), tocilizumab (Actemra) and tofacitinib (Xeljanz), interferons, such as interferon alpha, interferon beta, interferon gamma, and PEGylated versions thereof, glatiramer acetate (also known in the art as Copaxone), dimethyl fumarate (also known in the art as Tecfidera), fingolimod (also known in the art as Gilenya), teriflunomide (also known in the art as Aubagio), natalizumab (also known in the art as Tysabri), alemtuzumab (also known in the art as Lemtrada), and mitoxantrone. For example, an obeticholic acid composition described herein can be administered in combination with metformin, insulin, insulin mimetic, or any other known anti-diabetic or anti-glycemic agent for treatment of diabetes. In some embodiments, the effective amount administered is a starting dose as described herein.

In another aspect, the present disclosure also provides a method for inhibiting or reversing fibrosis, comprising administering a therapeutically effective amount of the composition of the present disclosure to a subject in need thereof. In one embodiment, the subject is not suffering from a cholestatic condition. In another embodiment, the subject is suffering from a cholestatic condition.

In one embodiment, the subject is not suffering from a cholestatic condition associated with a disease or condition selected from the group consisting of cancers, such as, e.g., cancers as described herein, including primary liver and biliary cancer, metastatic cancer, sepsis, chronic total parenteral nutrition, cystic fibrosis, and granulomatous liver disease. In embodiments, the fibrosis to be inhibited occurs in an organ where FXR is expressed.

In one embodiment, a cholestatic condition is defined as having an abnormally elevated serum level of alkaline phosphatase, 7-glutamyl transpeptidase (GGT), and/or 5' nucleotidase. In another embodiment, a cholestatic condition is further defined as presenting with at least one clinical symptom. In one embodiment, the symptom is itching (pruritus). In another embodiment, a cholestatic condition is selected from the group consisting of primary biliary cirrhosis (PBC), primary sclerosing cholangitis (PBS), biliary atresia, drug-induced cholestasis, hereditary cholestasis, and intrahepatic cholestasis of pregnancy.

In one embodiment, the fibrosis is selected from the group consisting of liver fibrosis, kidney fibrosis, and intestinal fibrosis.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In another embodiment, the subject has intestinal fibrosis associated with a disease selected from the group consisting of Crohn's disease, ulcerative colitis, post-radiation colitis, and microscopic colitis.

In another embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

In another aspect, the present disclosure also provides a method for treating or preventing all forms of conditions related to elevated lipid levels. In one embodiment, the condition is hyperlipidemia where it is associated with a condition selected from resistant primary biliary cirrhosis; primary biliary cirrhosis where there is associated liver function test elevation and hyperlipidemia, primary sclerosing cholangitis, non-alcohol-induced steatohepatitis; and chronic liver disease associated with hepatitis B, C or alcohol. In another embodiment, the present disclosure provides a method for treating or preventing hyperlipidemia, where the hyperlipidemia is primary hyperlipidemia with or without a genetic component, or hyperlipidemia associated with coronary artery disease, cerebrovascular arterial disease, peripheral vascular disease, aortic aneurisms, or carotid atherosclerosis.

In one aspect, the present disclosure provides a method for treating or preventing primary sclerosing cholangitis for similar biochemical abnormalities, as well as chronic hepatitis caused by hepatitis B, C or by alcohol. In one aspect, the present disclosure provides a method for treating or preventing other arterial disorders associated with hyperlipidemia. In one aspect, the present disclosure provides a method for treating or preventing hypertriglyceridemia.

Therapies with FXR agonists may produce various side effects, one of which is pruritus. Pruritus or itch is defined as an unpleasant sensation of the skin that provokes the urge to scratch. It is a characteristic feature of many skin diseases and an unusual sign of some systemic diseases. Pruritus may be localized or generalized and can occur as an acute or chronic condition. Itching lasting more than 6 weeks is termed chronic pruritus. Itching can be intractable and incapacitating, as well as a diagnostic and therapeutic challenge.

One of the advantages of the compositions of the present disclosure includes a decrease in the incidence and/or severity of pruritus in subjects treated with the compositions and according to the methods of the present disclosure.

In one embodiment, the incidence of pruritus decreases by at least 5%, 10%, 15%, 20%, 25%, 30%, 35%, 40%, 45%, or 50% in subjects treated with the compositions of the present disclosure. In a further embodiment, the incidence of pruritus decreases by at least 20%, 25%, 30%, 35%, 40%, 45%, or 50% in subjects treated with the compositions of the present disclosure. In a further embodiment, the incidence of pruritus decreases by at least 5%, 10%, 15%, 20%, 25%, 30%, 35%, 40%, 45%, or 50% in subjects treated with the compositions of the present disclosure during the first one month, two months, three months, four months, five months, or six months after the beginning of the treatment. In a further embodiment, the incidence of pruritus decreases by at least 20%, 25%, 30%, 35%, 40%, 45%, or 50% in subjects treated with the compositions of the present disclosure during the first one month, two months, three months, four months, five months, or six months after the beginning of the treatment.

In one embodiment, the severity of the pruritus decreases by at least 5%, 10%, 15%, 20%, 25%, 30%, 35%, 40%, 45%, or 50% in subjects treated with the compositions of the present disclosure. In a further embodiment, the severity of pruritus decreases by at least 20%, 25%, 30%, 35%, 40%, 45%, or 50% in subjects treated with the compositions of the present disclosure. In a further embodiment, the severity of pruritus decreases by at least 5%, 10%, 15%, 20%, 25%, 30%, 35%, 40%, 45%, or 50% in subjects treated with the compositions of the present disclosure during the first one month, two months, three months, four months, five months, or six months after the beginning of the treatment. In a further embodiment, the severity of pruritus decreases by at least 20%, 25%, 30%, 35%, 40%, 45%, or 50% in subjects treated with the compositions of the present disclosure during the first one month, two months, three months, four months, five months, or six months after the beginning of the treatment.

Obeticholic acid compositions described herein can be administered to a patient in an amount of between about: 1 mg to about 50 mg; 1 to about 40 mg; 1 to about 30 mg; 1 to about 25 mg; 1 to about 20 mg; 1 mg to about 10 mg; or 1 mg to about 5 mg. In one embodiment, the obeticholic acid composition can be administered to a patient in an amount of about: 5 to about 50 mg; 5 to about 40 mg; 5 to about 30 mg; 5 to about 25 mg; 5 to about 20 mg; or 5 to about 10 mg. In other instances, the obeticholic acid composition can be administered in an amount of about 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 mg. In still other instances, the obeticholic acid composition described herein can be administered at an amount of about 5 mg, 10 mg, 15 mg, 25 mg, or 50 mg. For example, an effective amount of a obeticholic acid composition described herein can be about 5 mg, 10 mg, 25 mg, or 50 mg. In another example, the amount of a starting dose of an obeticholic acid composition described herein can be about 5 mg, 10 mg, 25 mg, or 50 mg. In another example, the amount of an adjusted dose or re-adjusted dose of an obeticholic acid composition described herein can be about 5 mg, 10 mg, 25 mg, or 50 mg. It is to be understood the amount of an obeticholic acid composition described herein as administered to a patient described herein refers to the amount of obeticholic acid in the composition.

The amount of an obeticholic acid composition as provided above can refer to an effective amount as described herein. In certain embodiments, an effective amount of the obeticholic acid composition administered to a patient described herein can be 5 mg. In another embodiment, an effective amount of the obeticholic acid composition administered to a patient described herein can be 10 mg. In still another embodiment, an effective amount of the obeticholic acid composition administered to a patient described herein can be 25 mg. In yet another embodiment, an effective amount of the obeticholic acid composition administered to a patient described herein can be 50 mg.

The amount of an obeticholic acid composition as provided above can optionally refer to a starting dose administered during a titration period as described herein. In certain embodiments, a starting dose of the obeticholic acid composition administered to a patient described herein can be 5 mg. In another embodiment, a starting dose of the obeticholic acid composition administered to a patient described herein can be 10 mg. In still another embodiment, a starting dose of the obeticholic acid composition administered to a patient described herein can be 25 mg. In yet another embodiment, a starting dose of the obeticholic acid composition administered to a patient described herein can be 50 mg.

The amount of an obeticholic acid composition as provided above can refer to an adjusted dose administered after a titration period as described herein. In certain embodiments, an adjusted dose of the obeticholic acid composition administered to a patient described herein can be 5 mg. In another embodiment, an adjusted dose of the obeticholic acid composition administered to a patient described herein can be 10 mg. In still another embodiment, an adjusted dose of the obeticholic acid composition administered to a patient described herein can be 25 mg. In yet another embodiment, an adjusted dose of the obeticholic acid composition administered to a patient described herein can be 50 mg.

The amount of an obeticholic acid composition as provided above can refer to a re-adjusted dose administered after a titration period as described herein. In certain embodiments, a re-adjusted dose of the obeticholic acid composition administered to a patient described herein can be 5 mg. In another embodiment, a re-adjusted dose of the obeticholic acid composition administered to a patient described herein can be 10 mg. In still another embodiment, a re-adjusted dose of the obeticholic acid composition administered to a patient described herein can be 25 mg. In yet another embodiment, a re-adjusted dose of the obeticholic acid composition administered to a patient described herein can be 50 mg.

While it is possible to administer obeticholic acid directly without any formulation, obeticholic acid is usually administered in the form of pharmaceutical formulations comprising a pharmaceutically acceptable excipient and obeticholic acid. These formulations can be administered by a variety of routes including oral, buccal, rectal, intranasal, transdermal, subcutaneous, intravenous, intramuscular, and intranasal. Oral formulation of obeticholic acid are described further herein under the section entitled "Oral Formulation and Administration".

In one embodiment, obeticholic acid can be administered transdermally. In order to administer transdermally, a transdermal delivery device ("patch") is needed. Such transdermal patches may be used to provide continuous or discontinuous infusion of a compound of the present disclosure in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, obeticholic acid or obeticholic acid particles, in the required amount in an appropriate solvent with one or a combination of ingredients enumerated herein, as required, followed by filtered sterilization. Generally, dispersions are prepared by incorporating the obeticholic acid into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the obeticholic acid or obeticholic acid particles, plus any additional desired ingredient from a previously sterile-filtered solution thereof.

It can be useful to orally administer an obeticholic acid composition described herein. Oral compositions generally include an inert diluent or an edible pharmaceutically acceptable carrier. They can be enclosed in gelatin capsules or compressed into tablets. For the purpose of oral therapeutic administration, the active compound, obeticholic acid or obeticholic acid particles, can be incorporated with excipients and used in the form of tablets, troches, or capsules. Oral compositions can also be prepared using a fluid carrier for use as a mouthwash, wherein the obeticholic acid or obeticholic acid particles in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as sodium starch glycolate, starch or lactose, a diluent such as microcrystalline cellulose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the obeticholic acid or obeticholic acid particles is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the obeticholic acid or obeticholic acid particles is formulated into ointments, salves, gels, or creams as generally known in the art.

The obeticholic acid or obeticholic acid particles can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of obeticholic acid or obeticholic acid particles calculated to produce the desired therapeutic effect in association with the required pharmaceutical carrier. The specification for the dosage unit forms of the disclosure are dictated by and directly dependent on the unique characteristics of the obeticholic acid or obeticholic acid particles and the particular therapeutic effect to be achieved.

In one embodiment of the present disclosure, there is provided a pharmaceutical formulation comprising at least obeticholic acid as described above in a formulation adapted for buccal and/or sublingual, or nasal administration. This embodiment provides administration of obeticholic acid in a manner that avoids gastric complications, such as first pass metabolism by the gastric system and/or through the liver. This administration route may also reduce adsorption times, providing more rapid onset of therapeutic benefit. The compounds of the present disclosure may provide particularly favorable solubility profiles to facilitate sublingual/buccal formulations. Such formulations typically require relatively high concentrations of active ingredients to deliver sufficient amounts of active ingredients to the limited surface area of the sublingual/buccal mucosa for the relatively short durations the formulation is in contact with the surface area, to allow the absorption of the active ingredient. Thus, the very high activity of obeticholic acid, combined with its high solubility, facilitates its suitability for sublingual/buccal formulation.

Obeticholic acid is preferably formulated in a unit dosage form, each dosage containing from about 0.05 mg to about 1500 mg. In another embodiment, the formulation comprises about 0.05 mg to about 100 mg. In yet another embodiment, the formulation comprises about 1 mg to about 100 mg. In another embodiment, the formulation comprises about 0.05 mg to about 50 mg. In yet another embodiment, the formulation comprises about 0.05 mg to about 30 mg. In another embodiment, the formulation comprises about 0.05 mg to about 20 mg. In yet another embodiment, the formulation comprises about 0.5 mg to about 30 mg. In another embodiment, the formulation comprises about 0.5 mg to about 25 mg. In yet another embodiment, the formulation comprises about 1 mg to about 25 mg. In another embodiment, the formulation comprises about 4 mg to about 26 mg. In another embodiment, the formulation comprises about 5 mg to about 25 mg. In yet another embodiment, the formulation comprises about 0.05 mg to about 2 mg. In another embodiment, the formulation comprises about 1 mg to about 2 mg. In one embodiment, the formulation comprises about 1.2 mg to about 1.8 mg. In one embodiment, the formulation comprises about 1.3 mg to about 1.7 mg. In one embodiment, the formulation comprises about 1.5 mg. In one embodiment, the formulation comprises about 0.05 mg to about 0.5 mg. In another embodiment, the formulation comprises about 0.08 mg to about 0.8 mg. In yet another embodiment, the formulation comprises about 0.1 mg to about 0.5 mg. In another embodiment, the formulation comprises about 0.25 mg.

Obeticholic acid is generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. In one embodiment, the formulation comprises about 0.05 mg to about 1500 mg. In another embodiment, the formulation comprises about 0.05 mg to about 100 mg. In yet another embodiment, the formulation comprises about 1 mg to about 100 mg. In another embodiment, the formulation comprises about 0.05 mg to about 50 mg. In another embodiment, the formulation comprises about 0.05 mg to about 30 mg. In yet another embodiment, the formulation comprises about 0.05 mg to about 20 mg. In yet another embodiment, the formulation comprises about 0.05 mg to about 10 mg.

In one embodiment, the formulation comprises about 3 mg to about 30 mg. In another embodiment, the formulation comprises about 0.05 mg to about 25 mg. In another embodiment, the formulation comprises about 4 mg to about 25 mg. In another embodiment, the formulation comprises about 5 mg to about 25 mg. In another embodiment, the formulation comprises about 5 mg to about 10 mg. In one embodiment, the formulation comprises about 1 mg to about 2 mg. In one embodiment, the formulation comprises about 1.2 mg to about 1.8 mg. In one embodiment, the formulation comprises about 1.3 mg to about 1.7 mg. In one embodiment, the formulation comprises about 0.05 mg to about 0.5 mg. In another embodiment, the formulation comprises about 0.08 mg to about 0.8 mg. In yet another embodiment, the formulation comprises about 0.1 mg to about 0.5 mg. In another embodiment, the formulation comprises about 25 mg. In another embodiment, the formulation comprises about 10 mg. In one embodiment, the formulation comprises about 5 mg. In another embodiment, the formulation comprises about 0.25 mg. However, it will be understood that the amount of obeticholic acid actually administered will be determined by a physician, in the light of the relevant circumstances, including the condition to be treated, the chosen route of administration, the form of obeticholic acid administered, the age, weight, and response of the individual patient, and the severity of the patient's symptoms, and therefore the above dosage ranges are not intended to limit the scope of the disclosure in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The tablet of the present disclosure can comprise an intra-granular portion and an extra-granular portion. The intra-granular portion can contain obeticholic acid, or a pharmaceutically acceptable salt, ester, or amino acid conjugate thereof, and one or more pharmaceutical excipients. The extra-granular portion can contain obeticholic acid, or a pharmaceutically acceptable salt, ester, or amino acid conjugate thereof, and one or more pharmaceutical excipients. In one embodiment, the intra-granular portion and the extra-granular portion of the tablet contain obeticholic acid, or a pharmaceutically acceptable salt, ester, or amino acid conjugate thereof, and one or more pharmaceutical excipients. In another embodiment, the intra-granular portion contains obeticholic acid, or a pharmaceutically acceptable salt, ester, or amino acid conjugate thereof and/or the extra-granular portion does not contain obeticholic acid, or a pharmaceutically acceptable salt, ester, or amino acid conjugate thereof.

The presence of microcrystalline cellulose in the intra-granular portion and/or the extra-granular portion of a tablet comprising obeticholic acid or a pharmaceutically acceptable salt, ester, or amino acid conjugate thereof, can affect the properties of the tablet. In one embodiment, when microcrystalline cellulose is added to only the intra-granular portion of the tablet, tablets of moderate hardness can be produced. In another embodiment, when microcrystalline cellulose is added to only the intra-granular portion of the tablet, tablets of tolerable hardness may be produced. In another embodiment, addition of microcrystalline cellulose to both the intra-granular and extra-granular portions can provide tablets having superior tablet hardness and an improved dissolution profile. In one embodiment, microcrystalline cellulose is added to the intra-granular portion of the tablet. In another embodiment, microcrystalline cellulose is added to both the intra-granular portion and extra-granular portion of the tablet.

When the microcrystalline cellulose is present in the intra-granular portion it can be present in a ratio of microcrystalline cellulose to obeticholic acid, or a pharmaceutically acceptable salt, ester, or amino acid conjugate thereof, between about 20:1 to about 1:5. In one embodiment, the ratio of microcrystalline cellulose to obeticholic acid, or a pharmaceutically acceptable salt, ester, or amino acid conjugate thereof, may be, e.g., between about 19:1 to about 1:5, between about 19:1 to about 1:4, between about 19:1 to about 1:3, between about 19:1 to about 1:2, between about 18:1 to about 1:5, between about 18:1 to about 1:4, between about 18:1 to about 1:3, between about 18:1 to about 1:2, between about 17:1 to about 1:5, between about 17:1 to about 1:4, between about 17:1 to about 1:3, between about 17:1 to about 1:2, between about 16:1 to about 1:5, between about 16:1 to about 1:4, between about 16:1 to about 1:3, between about 16:1 to about 1:2, between about 15:1 to about 1:5, between about 15:1 to about 1:4, between about 15:1 to about 1:3, between about 15:1 to about 1:2, between about 14:1 to about 1:5, between about 14:1 to about 1:4, between about 14:1 to about 1:3, between about 14:1 to about 1:2, between about 13:1 to about 1:5, between about 13:1 to about 1:4, between about 13:1 to about 1:3, between about 13:1 to about 1:2, between about 12:1 to about 1:5, between about 12:1 to about 1:4, between about 12:1 to about 1:3, between about 12:1 to about 1:2, between about 11:1 to about 1:5, between about 11:1 to about 1:4, between about 11:1 to about 1:3, or between about 11:1 to about 1:2. In another embodiment, the ratio of microcrystalline cellulose to obeticholic acid, or a pharmaceutically acceptable salt, ester, or amino acid conjugate thereof, is between about 10:1 to about 1:5, between about 10:1 to about 1:4, between about 10:1 to about 1:3, or between about 10:1 to about 1:2. In another embodiment, the ratio of microcrystalline cellulose to obeticholic acid, or a pharmaceutically acceptable salt, ester, or amino acid conjugate thereof, is between about 9:1 to about 1:4, between about 9:1 to about 1:3, between about 9:1 to about 1:2, or between about 9:1 to about 1:1. In yet another embodiment, the ratio of microcrystalline cellulose to obeticholic acid, or a pharmaceutically acceptable salt, ester, or amino acid conjugate thereof, is between about 8:1 to about 1:3, between about 8:1 to about 1:2, or between about 8:1 to about 1:1. In another embodiment, the ratio of microcrystalline cellulose to obeticholic acid, or a pharmaceutically acceptable salt, ester, or amino acid conjugate thereof, is between about 7:1 to about 1:2 or between about 7:1 to about 1:1. In yet another embodiment, the ratio of microcrystalline cellulose to obeticholic acid, or a pharmaceutically acceptable salt, ester, or amino acid conjugate thereof, is between about 6:1 to about 1:1. In other embodiments, the ratio of microcrystalline cellulose to obeticholic acid, or a pharmaceutically acceptable salt, ester, or amino acid conjugate thereof, is between about 20:1 to about 1:1, between about 19:1 to about 1:1, between about 18:1 to about 1:1, between about 17:1 to about 1:1, between about 16:1 to about 1:1, between about 15:1 to about 1:1, between about 14:1 to about 1:1, between about 13:1 to about 1:1, between about 12:1 to about 1:1, or between about 11:1 to about 1:1. In another embodiments, the ratio of microcrystalline cellulose to obeticholic acid, or a pharmaceutically acceptable salt, ester, or amino acid conjugate thereof, is between about 20:1 to about 2:1, between about 20:1 to about 3:1, between about 20:1 to about 4:1, between about 20:1 to about 5:1, between about 20:1 to about 6:1, between about 20:1 to about 7:1, between about 20:1 to about 8:1, between about 20:1 to about 9:1, between about 20:1 to about 10:1, between about 20:1 to about 11:1, between about 19:1 to about 2:1, between about 19:1 to about 3:1, between about 19:1 to about 4:1, between about 19:1 to about 5:1, between about 19:1 to about 6:1, between about 19:1 to about 7:1, between about 19:1 to about 8:1, between about 19:1 to about 9:1, between about 19:1 to about 10:1, between about 19:1 to about 11:1, between about 18:1 to about 2:1, between about 18:1 to about 3:1, between about 18:1 to about 4:1, between about 18:1 to about 5:1, between about 18:1 to about 6:1, between about 18:1 to about 7:1, between about 18:1 to about 8:1, between about 18:1 to about 9:1, between about 18:1 to about 10:1, between about 18:1 to about 11:1, between about 17:1 to about 2:1, between about 17:1 to about 3:1, between about 17:1 to about 4:1, between about 17:1 to about 5:1, between about 17:1 to about 6:1, between about 17:1 to about 7:1, between about 17:1 to about 8:1, between about 17:1 to about 9:1, between about 17:1 to about 10:1, between about 17:1 to about 11:1, between about 16:1 to about 2:1, between about 16:1 to about 3:1, between about 16:1 to about 4:1, between about 16:1 to about 5:1, between about 16:1 to about 6:1, between about 16:1 to about 7:1, between about 16:1 to about 8:1, between about 16:1 to about 9:1, between about 16:1 to about 10:1, between about 16:1 to about 11:1, between about 15:1 to about 2:1, between about 15:1 to about 3:1, between about 15:1 to about 4:1, between about 15:1 to about 5:1, between about 15:1 to about 6:1, between about 15:1 to about 7:1, between about 15:1 to about 8:1, between about 15:1 to about 9:1, between about 15:1 to about 10:1, between about 15:1 to about 11:1, between about 14:1 to about 2:1, between about 14:1 to about 3:1, between about 14:1 to about 4:1, between about 14:1 to about 5:1, between about 14:1 to about 6:1, between about 14:1 to about 7:1, between about 14:1 to about 8:1, between about 14:1 to about 9:1, between about 14:1 to about 10:1, between about 14:1 to about 11:1, between about 13:1 to about 2:1, between about 13:1 to about 3:1, between about 13:1 to about 4:1, between about 13:1 to about 5:1, between about 13:1 to about 6:1, between about 13:1 to about 7:1, between about 13:1 to about 8:1, between about 13:1 to about 9:1, between about 13:1 to about 10:1, between about 13:1 to about 11:1, between about 12:1 to about 2:1, between about 12:1 to about 3:1, between about 12:1 to about 4:1, between about 12:1 to about 5:1, between about 12:1 to about 6:1, between about 12:1 to about 7:1, between about 12:1 to about 8:1, between about 12:1 to about 9:1, between about 12:1 to about 10:1, between about 12:1 to about 11:1, between about 11:1 to about 2:1, between about 11:1 to about 3:1, between about 11:1 to about 4:1, between about 11:1 to about 5:1, between about 11:1 to about 6:1, between about 11:1 to about 7:1, between about 11:1 to about 8:1, or between about 11:1 to about 9:1, or between about 11:1 to about 10:1. Preferably, the ratio of microcrystalline cellulose to obeticholic acid, or a pharmaceutically acceptable salt, ester, or amino acid conjugate thereof, may be between about 20:1 to about 5:1, between about 16:1 to about 6:1, or between about 16:1 to about 11:1, or any of the above-mentioned ratio ranges between about 20:1 to about 5:1. In another embodiment, the ratio of microcrystalline cellulose to obeticholic acid, or a pharmaceutically acceptable salt, ester, or amino acid conjugate thereof, is about 16:1. In yet another embodiment, the ratio of microcrystalline cellulose to obeticholic acid, or a pharmaceutically acceptable salt, ester, or amino acid conjugate thereof, is about 11:1. In another embodiment, the ratio of microcrystalline cellulose to obeticholic acid, or a pharmaceutically acceptable salt, ester, or amino acid conjugate thereof, is about 6:1. In yet another embodiment, the ratio of microcrystalline cellulose to obeticholic acid, or a pharmaceutically acceptable salt, ester, or amino acid conjugate thereof, is between about 10:1 to about 1:1. In another embodiment, the ratio of microcrystalline cellulose to obeticholic acid, or a pharmaceutically acceptable salt, ester, or amino acid conjugate thereof, is between about 5:1 to about 1:1. In yet another embodiment, the ratio of microcrystalline cellulose to obeticholic acid, or a pharmaceutically acceptable salt, ester, or amino acid conjugate thereof, is between about 3:1 to about 1:1. In another embodiment, the ratio of microcrystalline cellulose to obeticholic acid, or a pharmaceutically acceptable salt, ester, or amino acid conjugate thereof, is between about 2:1 to about 1:1. In another embodiment, the ratio of microcrystalline cellulose to obeticholic acid, or a pharmaceutically acceptable salt, ester, or amino acid conjugate thereof, is between about 4:1 to about 2:1. In yet another embodiment, the ratio of microcrystalline cellulose to obeticholic acid, or a pharmaceutically acceptable salt, ester, or amino acid conjugate thereof, is between about 3:1 to about 2:1. In another embodiment, the ratio of microcrystalline cellulose to obeticholic acid, or a pharmaceutically acceptable salt, ester, or amino acid conjugate thereof, is about 4:1. In another embodiment, the ratio of microcrystalline cellulose to obeticholic acid, or a pharmaceutically acceptable salt, ester, or amino acid conjugate thereof, is about 3:1. In yet another embodiment, the ratio of microcrystalline cellulose to obeticholic acid, or a pharmaceutically acceptable salt, ester, or amino acid conjugate thereof, is about 2:1. In another embodiment, the ratio of microcrystalline cellulose to obeticholic acid, or a pharmaceutically acceptable salt, ester, or amino acid conjugate thereof, is about 1:1.

The tablet hardness of an obeticholic acid containing tablet can be between about 6 kilopascals (kP) to about 14 kP. In one embodiment, the tablet hardness is between about 7 kP to about 12 kP. In another embodiment, the tablet hardness is between about 8 kP to about 12 kP. In yet another, the tablet hardness is between about 8 kP to about 11 kP. In another embodiment, the tablet hardness is between about 9 kP to about 11 kP. In yet another embodiment, the tablet hardness is between about 10 kP to about 11 kP.

In one embodiment, the tablets of the present disclosure comprising obeticholic acid or a pharmaceutically acceptable salt, ester, or amino acid conjugate thereof, microcrystalline cellulose and optionally one or more additional pharmaceutical excipients in the intra-granular portion, and one or more pharmaceutical excipients in the extra-granular portion possess increased hardness. In one embodiment, the tablets of the present disclosure comprising obeticholic acid or a pharmaceutically acceptable salt, ester, or amino acid conjugate thereof, microcrystalline cellulose and optionally one or more additional pharmaceutical excipients in the intra-granular portion, and microcrystalline cellulose and optionally one or more additional pharmaceutical excipients in the extra-granular portion possess increased hardness. In particular, the tablets of the present disclosure comprising microcrystalline cellulose in both the intra-granular portion and extra-granular portion possess increased hardness, for example, as compared with tablets comprising microcrystalline cellulose in only the intra-granular portion. In one embodiment, the hardness is increased at least about 5%, at least about 10%, at least about 20%, at least about 30%, at least about 40%, at least about 50%, at least about 60%, or at least about 70%, for example, as compared with tablets comprising microcrystalline cellulose in only the intra-granular portion. In one embodiment, the hardness is increased at least about 20%, at least about 30%, at least about 40%, or at least about 50%, for example, as compared with tablets comprising microcrystalline cellulose in only the intra-granular portion. In another embodiment, the hardness is increased between about 5% and about 45%, between about 10% and about 40%, between about 15% and about 35%, between about 20% and about 30%, between about 25% and about 35%, between about 25% and about 40%, between about 25% and about 50%, or between about 30% and about 50%, for example, as compared with tablets comprising microcrystalline cellulose in only the intra-granular portion.

In one embodiment, the tablets of the present disclosure comprising obeticholic acid or a pharmaceutically acceptable salt, ester, or amino acid conjugate thereof, microcrystalline cellulose and optionally one or more additional pharmaceutical excipients in the intra-granular portion, and one or more pharmaceutical excipients in the extra-granular portion possess increased hardness. In another embodiment, the tablets of the present disclosure comprising obeticholic acid or a pharmaceutically acceptable salt, ester, or amino acid conjugate thereof, microcrystalline cellulose, and optionally one or more additional pharmaceutical excipients in the intra-granular portion, and microcrystalline cellulose and optionally one or more additional pharmaceutical excipients in the extra-granular portion possess improved dissolution of obeticholic acid or a pharmaceutically acceptable salt, ester, or amino acid conjugate thereof. In particular, the tablets of the present disclosure comprising microcrystalline cellulose in both the intra-granular portion and extra-granular portion possess improved dissolution of obeticholic acid or a pharmaceutically acceptable salt, ester, or amino acid conjugate thereof, for example, as compared with tablets comprising microcrystalline cellulose in only the intra-granular portion. For example, obeticholic acid or a pharmaceutically acceptable salt, ester, or amino acid conjugate thereof in the tablets of the present disclosure dissolves (e.g., in a Disodium Hydrogen Phosphate Buffer) at a rate that is at least 2%, 3%, 4%, 5%, 6%, 7%, 8%, 9%, 10%, 15%, 20%, 30%, 40%, 50%, 80%, or 100% faster than, for example, as compared with the dissolution rate tablets comprising microcrystalline cellulose in only the intra-granular portion.

For example, about 55% to about 95% of obeticholic acid or a pharmaceutically acceptable salt, ester, or amino acid conjugate thereof in the tablet of the present disclosure is dissolved within about 15 minutes, or about 65% to about 95% is dissolved within about 30 minutes, or about 80% to about 95% is dissolved within about 45 minutes, or about 87% to about 97% is dissolved within about 60 minutes, or about 87% to about 99% is dissolved within about 75 minutes. For example, about 60% to about 84% of obeticholic acid or a pharmaceutically acceptable salt, ester, or amino acid conjugate thereof in the tablet of the present disclosure is dissolved within about 15 minutes, or about 75% to about 91% is dissolved within about 30 minutes, or about 85% to about 93% is dissolved within about 45 minutes, or about 90% to about 96% is dissolved within about 60 minutes, or about 90% to about 97% is dissolved within about 75 minutes. For example, about 62% to about 83% of obeticholic acid or a pharmaceutically acceptable salt, ester, or amino acid conjugate thereof in the tablet of the present disclosure is dissolved within about 15 minutes, or about 80% to about 90% is dissolved within about 30 minutes, or about 87% to about 94% is dissolved within about 45 minutes, or about 92% to about 96% is dissolved within about 60 minutes, or about 91% to about 97% is dissolved within about 75 minutes. For example, about 60% to about 84% obeticholic acid or a pharmaceutically acceptable salt, ester, or amino acid conjugate thereof in the tablet of the present disclosure is dissolved within about 15 minutes, or about 70% to about 90% is dissolved within about 30 minutes, or about 85% to about 92% is dissolved within about 45 minutes, or about 89% to about 96% is dissolved within about 60 minutes, or about 90% to about 96% is dissolved within about 75 minutes. For example, at least about 60% obeticholic acid or a pharmaceutically acceptable salt, ester, or amino acid conjugate thereof in the tablet of the present disclosure is dissolved within about 15 minutes, or at least about 90% is dissolved within about 60 minutes. For example, obeticholic acid or a pharmaceutically acceptable salt, ester, or amino acid conjugate thereof in the tablet of the present disclosure has an in vitro dissolution profile of about 51% dissolved within about 15 minutes, or about 66% dissolved within about 30 minutes, or about 79% dissolved within about 45 minutes, or about 85% dissolved within about 60 minutes.

Obeticholic acid tablets can be manufactured via a manufacturing process comprising dry granulation by roller compaction followed by tablet compression and coating. The process steps used to manufacture OCA tablets include: pre-blending, dry granulation, final blending, compression, coating, and packaging.

Obeticholic acid drug substance and one or more pharmaceutical excipients (i.e., microcrystalline cellulose, sodium starch glycolate, and/or magnesium stearate) are added and further optionally blended to produce a premix. In one embodiment, OCA and microcrystalline cellulose is blended to produce a premix. In one embodiment, the premix is blended, passed through a screen and then again blended. In another embodiment, the one or more pharmaceutical excipients are added in small portions and blended between each addition. In one embodiment, the one or more pharmaceutical excipients are added sequentially. In another embodiment, the one or more pharmaceutical excipients are added together.

The premix is then granulated and optionally milled to reduce particle size. In one embodiment, the premix is roller compacted. In another embodiment, the premix is further milled. The premix can be milled using various methods. In one embodiment, the premix is milled using a comil. In another embodiment, the premix is milled using a comil followed by an oscillating bar screen mill.

Once the premix is granulated, a final blending of the obeticholic acid tablet formulation is performed. In the final blending, one or more pharmaceutical excipients (i.e., microcrystalline cellulose, sodium starch glycolate, and/or magnesium stearate) are added to provide a final blend which is further optionally blended. In one embodiment, microcrystalline cellulose is added during the final blending. In one embodiment, the one or more pharmaceutical excipients are added sequentially. In another embodiment, the one or more pharmaceutical excipients are added together.

The final blend is then compressed to form the tablet. The compression parameters can be adjusted to produce tablets of the desired weight, hardness, thickness, and friability. The tablet press speed and feeder speed can also be adjusted to help reduce tablet weight variation. The obeticholic acid tablets are then coated with a coating material (i.e., Opadry® II white, Opadry® II green, or Opadry® II yellow) using a coating solution.

Obeticholic acid compositions described herein can be administered in accordance with a dosing regimen. A dosing regimen refers to continual and intermittent administration of a obeticholic acid composition described herein at one or more of the amounts described herein. Thus, in certain instances, a dosing regimen can include administration of a obeticholic acid composition described herein continually for any number of days, weeks, months, or years as set forth herein. In other instances, a dosing regimen can include administration of a obeticholic acid composition described herein intermittently, where, for example, the composition is administered for one period of time followed by a rest period or off period where the obeticholic acid composition is not administered.

Obeticholic acid compositions useful in the methods of treating described herein include administration of such compositions daily (QD), every other day (Q2D), once a week (QW), twice a week (BID), three times a week (TIW), once a month (QM), or twice a month (Q2M). In one embodiment, a obeticholic acid composition described herein is administered QD. Thus, an effective amount of an obeticholic acid composition described herein can be administered QD to treat a disease or condition described herein. A starting dose described herein can be administered QD during the course of a titration period described herein to treat a disease or condition described herein. An adjusted dose described herein can be administered QD to treat a disease or condition described herein.

In another embodiment, an obeticholic acid composition described herein is administered Q2D. An effective amount of an obeticholic acid composition described herein can be administered Q2D to treat a disease or condition described herein. A starting dose described herein can be administered Q2D during the course of a titration period described herein to treat a disease or condition described herein. An adjusted dose described herein can be administered Q2D to treat a disease or condition described herein.

In another embodiment, an obeticholic acid composition is described herein administered QW. An effective amount of an obeticholic acid composition described herein can be administered QW to treat a disease or condition described herein. A starting dose described herein can be administered QW during the course of a titration period described herein to treat a disease or condition described herein. An adjusted dose described herein can be administered QW to treat a disease or condition described herein.

In another embodiment, an obeticholic acid composition is described herein administered BID. An effective amount of an obeticholic acid composition described herein can be administered BID to treat a disease or condition described herein. A starting dose described herein can be administered BID during the course of a titration period described herein to treat a disease or condition described herein. An adjusted dose described herein can be administered BID to treat a disease or condition described herein.

In another embodiment, an obeticholic acid composition is described herein administered TIW. An effective amount of an obeticholic acid composition described herein can be administered TIW to treat a disease or condition described herein. A starting dose described herein can be administered TIW during the course of a titration period described herein to treat a disease or condition described herein. An adjusted dose described herein can be administered TIW to treat a disease or condition described herein.

In another embodiment, an obeticholic acid composition is described herein administered QM. An effective amount of an obeticholic acid composition described herein can be administered QM to treat a disease or condition described herein. A starting dose described herein can be administered QM during the course of a titration period described herein to treat a disease or condition described herein. An adjusted dose described herein can be administered QM to treat a disease or condition described herein.

In another embodiment, an obeticholic acid composition is described herein administered Q2M. An effective amount of an obeticholic acid composition described herein can be administered Q2M to treat a disease or condition described herein. A starting dose described herein can be administered Q2M during the course of a titration period described herein to treat a disease or condition described herein. An adjusted dose described herein can be administered Q2M to treat a disease or condition described herein.

The embodiments described above include administration at an amount described above. For example, an obeticholic acid composition described herein can be administered in a frequency provided above in an amount of 5 mg, 10 mg, 25 mg, or 50 mg.

Dosing regimens of the obeticholic acid compositions described herein useful for treating diseases and conditions described herein can include a titration period. A titration period typically includes a lower dosage of an obeticholic acid composition described herein for a period of time. In certain instances, and without being bound by any particular theory, administration using a titration period described herein can decrease or eliminate the onset of adverse effects. In other instances, and without being bound by any particular theory, administration using a titration period described herein can permit increased dosages of obeticholic acid compositions described herein to an individual over the course of a treatment.

A titration period can be a period of time of about: 1 month to about 24 months; 1 month to about 21 months; 1 month to about 18 months; 1 month to about 15 months; 1 month to about 12 months; 1 month to about 9 months; 1 month to about 6 months; or 1 month to about 3 months. In another embodiment, a titration period includes a time of about: 3 months to about 24 months; 3 months to about 21 months; 3 months to about 18 months; 3 months to about 15 months; 3 months to about 12 months; 3 or months to about 6 months. In still another embodiment, a titration period includes a time of about: 6 months to about 24 months; 6 months to about 21 months; 6 months to about 18 months; 6 months to about 15 months; or 6 months to about 12 months. In yet another embodiment, a titration period includes a time of about: 2 months to about 4 months; 2 months to about 7 months; 2 months to about 8 months; 4 months to about 8 months; 5 months to about 7 months; or 5 months to about 8 months. For example, a titration period can be about 1 to about 6 months. In another example, a titration period can be about 3 to about 6 months.

A titration period can include a time of about 1, 2, 3, 4, 5, 6, 7, 8, 9, 10, 11, 12, 13, 14, 15, 16, 17, 18, 19, 20, 21, 22, 23, or 24 months. In certain embodiments, a titration period includes a time of about 1, 2, 3, 4, 5, 6, 7, 8, 9, 10, 11, or 12 months. In another embodiment, the titration period includes a time of about 1, 2, 3, 4, 5, 6, 7, 8, or 9 months. In another embodiment, the titration period includes a time of about 1, 2, 3, 4, 5, or 6 months. In another embodiment, the titration period includes a time of about 1, 2, or 3 months. For example, a titration period can be about 1 month. In another example a titration period can be about 2 months. In another example a titration period can be about 3 months. In still another example a titration period can be about 4 months. In yet another example a titration period can be about 5 months. In another example a titration period can be about 6 months. In one example a titration period is 3 months or 6 months. In another example a titration period can be about 7 months. In another example a titration period can be about 8 months. In another example a titration period can be about 9 months.

As provided above, the amounts of a obeticholic acid composition described herein, optionally administered in a titration period can be reduced compared to an adjusted amount as described herein. Accordingly, provided herein are treatment regimens that include administering obeticholic acid compositions described herein for the treatment of a disease or condition described herein (e.g., PBC) wherein the starting dose administered during a titration period described above is lower than the amount of an adjusted dose administered after a titration period. Still further provided herein are treatment regimens that include administering obeticholic acid compositions described herein for the treatment of a disease or condition described herein (e.g., PBC) where the starting dose administered during a titration period described above is lower than the amount of an adjusted dose administered after a titration period and where the frequency of administration (e.g., QD, Q2D, or QW) for the adjusted dose is greater than the frequency of administration of the starting dose. Still further provided herein are treatment regimens that include administering obeticholic acid compositions described herein for the treatment of a disease or condition described herein (e.g., PBC) where the starting dose administered during a titration period described above is lower than the amount of an adjusted dose administered after a titration period and where the frequency of administration (e.g., QD, Q2D, or QW) for the adjusted dose is less than the frequency of administration of the starting dose. Increases in the adjusted dose (or any re-adjusted dose) can be performed after the patient's liver function is assessed, monitored, or measured as described herein, where the liver function is considered not-impaired.

In embodiments, the adjusted dose can be increased compared to the starting dose when the level of ALP is about equal to or is not reduced compared to a control as described herein. In embodiments, the adjusted can be increased compared to the starting dose when the level of bilirubin is about equal to or is not reduced compared to a control as described herein. In embodiments, the adjusted dose can be increased compared to the starting dose when the level of ALP and bilirubin are about equal to or are not reduced compared to a control as described herein. In certain instances, the adjusted dose can be increased compared to the starting dose where a patient described herein tolerates the starting dose amount. In certain embodiments, the starting dose can be 5 mg. In certain embodiments, the starting dose is 10 mg. In certain embodiments, the starting dose is 5 mg and the adjusted dose is greater than 5 mg (e.g., about 6 mg to about 50 mg). In one embodiment, the starting dose is 5 mg and the adjusted dose is 10 mg.

Also provided herein are treatment regimens that include administering obeticholic acid compositions described herein for the treatment of a disease or condition described herein (e.g., PBC) where the starting dose administered during a titration period described above is equal to the amount of an adjusted dose administered after a titration period. Further provided herein are treatment regimens that include administering obeticholic acid compositions described herein for the treatment of a disease or condition described herein (e.g., PBC) where the starting dose administered during a titration period described above is equal to the amount of an adjusted dose administered after a titration period and where the frequency of administration (e.g., QD, Q2D, or QW) for the starting dose is the same as the adjusted dose. Still further provided herein are treatment regimens that include administering obeticholic acid compositions described herein for the treatment of a disease or condition described herein (e.g. PBC) where the starting dose administered during a titration period described above is equal to the amount of an adjusted dose administered after a titration period and where the frequency of administration (e.g., QD, Q2D, or QW) for the adjusted dose is greater than the frequency of administration of the starting dose. Still further provided herein are treatment regimens that include administering obeticholic acid compositions described herein for the treatment of a disease or condition described herein (e.g., PBC) where the starting dose administered during a titration period described above is equal to the amount of an adjusted dose administered after a titration period and where the frequency of administration (e.g., QD, Q2D, or QW) for the adjusted dose is less than the frequency of administration of the starting dose. The adjusted dose (or any re-adjusted dose) can be equal to the starting dose where the patient's liver function is assessed, monitored, or measured as described herein, where the liver function is considered not-impaired.

In embodiments, the adjusted dose can be equal to the starting dose when the level of ALP is reduced compared to a control as described herein. In embodiments, the adjusted dose can be equal to the starting dose when the level of bilirubin is reduced compared to a control as described herein. In embodiments, the adjusted dose can be equal to the starting dose when the level of ALP and bilirubin are reduced compared to a control as described herein. In certain instances, the adjusted dose can be equal to the starting dose where a patient described herein tolerates or poorly tolerates (e.g., has onset of adverse effects described herein) the starting dose amount. In certain embodiments, the starting dose can be 5 mg. In certain embodiments, the starting dose is 10 mg. In certain embodiments, the starting dose is 5 mg and the adjusted dose is 5 mg. In one embodiment, the starting dose is 10 mg and the adjusted dose is 10 mg.

Further provided herein are treatment regimens that optionally include a starting dose and an adjusted dose as provided in the regimens above, where the adjusted dose is further reduced during the course of treatment. In certain instances, the adjusted dose is reduced to a new re-adjusted dose having a decreased amount of an obeticholic acid composition described herein. In other instances the adjusted dose is reduced to a new re-adjusted dose having the same amount of an obeticholic acid composition described herein but a decreased frequency of administration (e.g., from QD to Q2D or QW). In still other instances, the adjusted dose is modified such that the re-adjusted dose includes a decreased amount of an obeticholic acid composition described herein and is administered at a decreased frequency compared to the adjusted dose.

The obeticholic acid composition described herein can be administered for any number of days, weeks, months, or years, including indefinitely, provided that the dosage remains efficacious for the patient and the patient tolerates the dosage (e.g., an adjusted or re-adjusted dose as described herein). In certain instances, an obeticholic acid composition described herein is administered to a patient described herein until loss of efficacy, or until development of unacceptable toxicity or undesired adverse effects, such as, for example, those described herein. Daily dosing of an obeticholic acid composition described herein can be dependent upon patient tolerance to the dosage, composition, or frequency of administration. For example, daily dosing can be administered to a patient described herein where the patient tolerates a daily dosage amount (e.g., 5 mg, 10 mg, 25 mg, or 50 mg). Alternatively or additionally, the daily dosing can be modified to increase or reduce the amount of an obeticholic acid composition described herein as provided above where the patient is tolerant or is intolerant to the dose, respectively. In certain embodiments, modification of the adjusted dose (or any re-adjusted dose) can be performed after the patient's liver function is assessed, monitored, or measured as described herein. In certain instances, the adjusted dose (or re-adjusted dose) is increased or maintained (e.g., equivalent to a starting dose) where the liver function is not-impaired. In other instances, the adjusted dose (or re-adjusted dose) is decreased or maintained (e.g., equivalent to a starting dose) where the patient's liver function is impaired.

The amount of an obeticholic acid described herein administered to a patient described herein can be modified as a result of intolerability or development of one or more adverse effects such as those described herein. For example, in one instance the amount of an obeticholic acid composition described herein administered to a patient can be changed from a QD dosage to a Q2D dosage. In certain embodiments, the dosage of an obeticholic acid described herein is modified from a QD to Q2D dosage upon development of an adverse effect described herein (e.g., severe pruritus). In one example, administration of an obeticholic acid composition described herein at 5 mg QD can be modified to a 5 mg Q2D dosage. Such a modification can reduce or eliminate undesired adverse effects while maintaining the desired efficacy. In another example, administration of an obeticholic acid composition described herein at 10 mg QD can be reduced to 5 mg QD. It should be understood that exemplary dosing regimens described herein can be combined. For example, a reduced dosage of an obeticholic acid composition described herein from 10 mg to 5 mg QD could be further reduced to a 5 mg Q2D dosage where undesired adverse effects remain. In still another example, dosing of the obeticholic acid composition can be temporarily suspended (e.g., an off period) for about 1, 2, 3, 4, 5, 6, 7, 8, 9, 10, 11, 12, 13, or 14 days, or 1, 2, 3, or 4 weeks.

In one exemplary dosing regimen, a PBC patient is administered an obeticholic acid composition described herein where: the starting dose of the obeticholic acid composition described herein is administered QD to a patient described herein at an amount of 5 mg and the obeticholic acid composition is administered QD to the patient in an adjusted dose of 5 mg. The exemplary dosing regimen can include a titration period of about 1 to about 6 months.

In another exemplary dosing regimen, a PBC patient is administered an obeticholic acid composition described herein where: the starting dose of the obeticholic acid composition described herein is administered QD to a patient described herein at an amount of 5 mg in a titration period of about 3 months or about 6 months and the obeticholic acid composition is administered QD to the patient in an adjusted dose of 5 mg.

In still another exemplary dosing regimen, a PBC patient is administered an obeticholic acid composition described herein where: the starting dose of the obeticholic acid composition described herein is administered QD to a patient in a titration period of about 3 months or about 6 months and the obeticholic acid composition is administered QD to the patient in an adjusted dose of 10 mg.

In another exemplary dosing regimen, a PBC patient is administered an obeticholic acid composition described herein where: the starting dose of the obeticholic acid composition described herein is administered QD to a patient in a titration period of about 3 months or about 6 months and the obeticholic acid composition is administered QD to the patient in an adjusted dose of 5 mg, where the adjusted dose is modified to a 5 mg Q2D re-adjusted dose upon development of an adverse effect (e.g., pruritus or severe pruritus).

In still another exemplary dosing regimen, a PBC patient is administered a obeticholic acid composition described herein, where the starting dose of the obeticholic acid composition described herein is administered QD to a patient in a titration period of about 3 months or about 6 months and the obeticholic acid composition is administered QD to the patient in an adjusted dose of 10 mg, where the adjusted dose is subsequently modified to a 5 mg QD re-adjusted dose upon development of an adverse effect (e.g., pruritus or severe pruritus).

The amount of an obeticholic acid composition described herein administered to a patient can be determined by the existence of any preexisting conditions in the patient. For example, where a patient described herein has or has had hepatic impairment, the dosage of the obeticholic acid composition described herein can be modified. In certain instances, the hepatic impairment is a Child-Pugh Class B or Class C hepatic impairment. In one embodiment, the hepatic impairment is Child-Pugh Class C. In such instances, the amount of an obeticholic acid composition described herein can be administered in a decreased amount during and after a titration period when compared to administration of the same obeticholic acid composition to a patient who does not have hepatic impairment.

In one example dosing regimen, a patient having hepatic impairment is administered an obeticholic acid composition described herein at an amount of about 1 mg to about 5 mg, where the composition is administered at least once weekly (QW). In one instance, the obeticholic acid composition described herein is administered at an amount of about 5 mg once weekly to a patient diagnosed with hepatic impairment (e.g., Child-Pugh Class B or C).

For example, the dosing regimen can include administering an obeticholic acid composition described herein to a patient having hepatic impairment, where the obeticholic acid composition is administered at a starting dose of 5 mg QW for a titration period of 3 or 6 months and administered at an adjusted dose of 5 mg QW. The patient's liver function can be assessed, monitored, or measured as described herein. Where the patient's liver function is not impaired, the adjusted dose can be increased to a re-adjusted dose of 5 mg administered BIW or 5 mg QD.

In certain instances a patient can develop liver impairment during the course of administration. It is understood, using the disclosure provided herein, that the adjusted dose can be decreased in amount or frequency to avoid progression of liver impairment.

Further provided herein is a method of treating PBC in a patient in need thereof by administering an effective amount of a obeticholic acid composition described herein QD, where the effective amount is either a 5 mg or 10 mg dose. In another aspect is a method of treating PBC in a patient in need thereof by administering a starting dose of 5 mg QD of an obeticholic acid composition described herein for at least 3 months; evaluating the tolerance of the patient, the patient's liver function as described herein, and/or the efficacy of treatment, where patient tolerance, liver function, and/or lowered efficacy indicate end of a titration period and administration of an adjusted dose of 10 mg QD. In one embodiment, the patient tolerance, liver function, and/or lowered efficacy indicate end of a titration period and administration of an adjusted dose of 5 mg QD.

In embodiments described herein, an obeticholic acid composition described herein can be metabolized to a obeticholic acid conjugate, such as for example, a glycine, taurine, or sarcosine conjugate of obeticholic acid. Such metabolites can be useful in treating a disease or condition provided herein. In certain instances, production of conjugates can be assessed, monitored, measured, or detected, as described herein during the course of a treatment. In some embodiments, increased levels of obeticholic acid conjugates can result in adjusted dosages of an obeticholic acid composition described herein.

Also provided herein are methods of treating a disease or condition described herein where the treatment further includes administration of one or more active agents and combinations thereof. For example, ursodeoxycholic acid (UDCA) is commonly administered for treatment of PBC, yet a majority of patients administered UDCA alone have either an inadequate response or no response to the treatment. In such instances, there is a need for new medicaments or additional medicaments for the treatment of PBC. The obeticholic acid compositions described herein can be administered as described herein (e.g., according to one or more dosing regimens provided above) in combination with UDCA. In some instances, the UDCA is administered at an amount of about 10 to 15 mg/kg/day. In another instance, the UDCA is administered at an amount of about 300, 600, 900, or 1200 mg/day. Administration of UDCA can include a rest or off period of 1, 2, 3, or 4 weeks. In one example, an obeticholic acid composition described herein is administered as described herein in combination with UDCA, where the UDCA is administered at an amount provided above or in accordance with a package insert. The term package insert refers to instructions customarily included in commercial packages of medicaments approved by the FDA or a similar regulatory agency of a country other than the USA, which contains information about, for example, the usage, dosage, administration, contraindications, and/or warnings concerning the use of such medicaments.

In another example, the active agent is a peroxisome proliferator-activated receptor alpha (PPARα) agonist, a peroxisome proliferator-activated receptor delta (PPARδ) agonist, a dual PPARα/δ agonist, a dual PPARα/γ agonist, or pan-PPAR agonist, an HMG CoA reductase inhibitor, a GLP1 agonist, insulin, insulin mimetic, metformin, a GTP4 agonist, an HST2 inhibitor, a DPP-IV inhibitor, an SGLT2 inhibitor or a hydroxysteroid dehydrogenase (HSD) inhibitor, such as an 11β-HSD1 inhibitor, an ASK1 inhibitor, an ACC1 inhibitor, a NOX1 and/or NOX4 inhibitor, an inhibitor or antagonist of one or more chemokine receptors, such as, for example, CCR2 and CCR5.

In instances where an obeticholic acid composition described herein is useful for the treatment of a cancer described herein, such compositions can be co-administered with one or more cancer agents.

The anti-cancer agent useful in methods of treating solid-tumor cancers provided herein can include any known class of anti-cancer agents such as, for example, radiation therapy, operations, alkylating agents, antimetabolites, anthracyclines, campothecins, vinca alkaloids, taxanes or platinums, as well as other antineoplastic agents known in the art. Such anti-cancer agent and antineoplastic agent classifications are known in the art and used in accordance with their plain and ordinary meaning.

Exemplary anti-cancer agents include but are not limited to: ABRAXANE; abiraterone; ace-11; aclarubicin; acivicin; acodazole hydrochloride; acronine; actinomycin; acylfulvene; adecypenol; adozelesin; adriamycin; aldesleukin; all trans-retinoic acid (ATRA); altretamine; ambamustine; ambomycin; ametantrone acetate; amidox; amifostine; aminoglutethimide; aminolevulinic acid; amrubicin; amsacrine; anagrelide; anastrozole; andrographolide; antarelix; anthramycin; aphidicolin glycinate; apurinic acid; ara-CDP-DL-PTBA; arginine deaminase; ARRY-162; ARRY-300; ARRY-142266; AS703026; asparaginase; asperlin; asulacrine; atamestane; atrimustine; AVASTIN; axinastatin 1; axinastatin 2; axinastatin 3; azasetron; azatoxin; azatyrosine; azacitidine; AZD8330; azetepa; azotomycin; balanol; batimastat; BAY 11-7082; BAY 43-9006; BAY 869766; bendamustine; benzochlorins; benzodepa; benzoylstaurosporine; beta-alethine; betaclamycin B; betulinic acid; b-FGF inhibitor; bicalutamide; bisantrene; bisaziridinylspermine; bisnafide; bisnafide dimesylate; bistratene A; bisantrene hydrochloride; bleomycin; bleomycin sulfate; busulfan; bizelesin; breflate; bortezomib; brequinar sodium; bropirimine; budotitane; buthionine sulfoximine; bryostatin; cactinomycin; calusterone; calcipotriol; calphostin C; camptothecin derivatives; capecitabine; carboxamide-amino-triazole; carboxyamidotriazole; CaRest M3; CARN 700; caracemide; carbetimer; carboplatin; carmustine; carubicin hydrochloride; carzelesin; castanospermine; cecropin B; cedefingol; celecoxib; cetrorelix; chlorins; chloroquinoxaline sulfonamide; cicaprost; chlorambucil; Chlorofusin; cirolemycin; cisplatin; CI-1040; cis-porphyrin; cladribine; clomifene analogues; clotrimazole; collismycin A; collismycin B; combretastatin A4; combretastatin analogue; conagenin; crambescidin 816; crisnatol; crisnatol mesylate; cryptophycin 8; cryptophycin A derivatives; curacin A; cyclopentanthraquinones; cycloplatam; cypemycin; cyclophosphamide; cytarabine; cytarabine ocfosfate; cytolytic factor; cytostatin; dacarbazine; dactinomycin; daunorubicin; daunorubicin hydrochloride; decarbazine; dacliximab; dasatinib; decitabine; dehydrodidemnin B; deslorelin; dexamethasone; dexifosfamide; dexrazoxane; dexverapamil; dexormaplatin; dezaguanine; dezaguanine mesylate; diaziquone; didemnin B; didox; diethylnorspermine; dihydro 5 azacytidine; dihydrotaxol; 9-dioxamycin; diphenyl spiromustine; docosanol; dolasetron; docetaxel; doxorubicin; doxorubicin hydrochloride; doxifluridine; droloxifene; droloxifene citrate; dromostanolone propionate; dronabinol; duazomycin; duocarmycin SA; ebselen; ecomustine; edelfosine; edrecolomab; edatrexate; eflornithine hydrochloride; eflornithine; elemene; emitefur; elsamitrucin; enloplatin; enpromate; epipropidine; epirubicin; epirubicin hydrochloride; episteride; erbulozole; eribulin; esorubicin hydrochloride; estramustine; estramustine phosphate sodium; etanidazole; etoposide; etoposide phosphate; etoprine; exemestane; fadrozole; fadrozole hydrochloride; fazarabine; fenretinide; filgrastim; finasteride; flavopiridol; flezelastine; fluasterone; floxuridine; fludarabine phosphate; fludarabine; fluorodaunorubicin hydrochloride; forfenimex; formestane; fluorouracil; floxouridine; flurocitabine; fosquidone; fostriecin sodium; fostriecin; fotemustine; gadolinium texaphyrin; gallium nitrate; galocitabine; ganirelix; gelatinase inhibitors; gemcitabine; geldanamycin; gossyphol; GDC-0973; GSK1120212/trametinib; herceptin; hydroxyurea; hepsulfam; heregulin; hexamethylene bisacetamide; hypericin; ibandronic acid; ibrutinib; idarubicin; idarubicin hydrochloride; ifosfamide; canfosfamide; ilmofosine; iproplatin; idoxifene; idramantone; ilmofosine; ilomastat; imidazoacridones; imatinib (e.g., GLEEVEC); imiquimod; iniparib (BSI 201); iobenguane; iododoxorubicin; ipomeanol; irinotecan; irinotecan hydrochloride; irsogladine; isobengazole; isohomohalicondrin B; itasetron; iimofosine; interleukin IL-2 (including recombinant interleukin II; or rIL.sub.2); interferon alfa-2a; interferon alfa-2b; interferon alfa-n1; interferon alfa-n3; interferon beta-1a; interferon gamma-1b; jasplakinolide; kahalalide F; lamellarin N triacetate; lanreotide; leinamycin; lenograstim; lentinan sulfate; leptolstatin; letrozole; leuprorelin; levamisole; lenalidomide; lenvatinib; liarozole; lissoclinamide 7; lobaplatin; lombricine; lometrexol; lonidamine; losoxantrone; lovastatin; loxoribine; lurtotecan; lutetium texaphyrin; lysofylline; lanreotide acetate; lapatinib; letrozole; leucovorin; leuprolide acetate; liarozole hydrochloride; lometrexol sodium; lomustine; losoxantrone hydrochloride; pomalidomide; LY294002; maitansine; mannostatin A; marimastat; masoprocol; maspin; matrilysin inhibitors; menogaril; merbarone; meterelin; methioninase; metoclopramide; MIF inhibitor; mifepristone; miltefosine; mirimostim; mitoguazone; mitolactol; mitonafide; mitoxantrone; mofarotene; molgramostim; mopidamol; mycaperoxide B; myriaporone; maytansine; mechlorethamine hydrochloride; megestrol acetate; melengestrol acetate; melphalan; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nafarelin; nagrestip; napavin; naphterpin; nartograstim; nedaplatin; nemorubicin; neridronic acid; nilutamide; nisamycin; nitric oxide modulators; nitroxide antioxidant; nitrullyn; nocodazole; nogalamycin; oblimersen (GENASENSE); octreotide; okicenone; olaparib (LYNPARZA); oligonucleotides; onapristone; ondansetron; oracin; oral cytokine inducer; ormaplatin; oxisuran; oxaloplatin; osaterone; oxaliplatin; oxaunomycin; palauamine; palmitoylrhizoxin; pamidronic acid; panaxytriol; panomifene; parabactin; PARP (polyADP ribose polymerase) inhibitors; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; porfiromycin; prednisone; prostaglandin J2; pyrazoloacridine; paclitaxel; PD035901; PD184352; PD318026; PD98059; peliomycin; pentamustine; peplomycin sulfate; PKC412; pipobroman; piposulfan; piroxantrone hydrochloride; plicamycin; plomestane; podophyllotoxin; polyphenol E; porfimer sodium; porfiromycin; prednimustine; procarbazine; procarbazine hydrochloride; puromycin; puromycin hydrochloride; pyrazofurin; raltitrexed; ramosetron; retelliptine demethylated; rhizoxin; rituximab; Ru retinamide; rogletimide; rohitukine; romurtide; roquinimex; rubiginone B1; ruboxyl; riboprine; romidepsin; rucaparib; safingol; safingol hydrochloride; saintopin; sarcophytol A; sargramostim; semustine; sizofiran; sobuzoxane; sodium borocaptate; sodium phenylacetate; solverol; sonermin; sorafenib; sunitinib; sparfosic acid; spicamycin D; spiromustine; splenopentin; spongistatin 1; Spongistatin 2; Spongistatin 3; Spongistatin 4; Spongistatin 5; Spongistatin 6; Spongistatin 7; Spongistatin 8; and Spongistatin 9; squalamine; stipiamide; stromelysin inhibitors; sulfinosine; suradista; suramin; swainsonine; SB239063; selumetinib/AZD6244; simtrazene; SP600125; sparfosate sodium; sparsomycin; spirogermanium hydrochloride; spiroplatin; streptonigrin; streptozocin; sulofenur; tallimustine; tamoxifen methiodide; talazoparib (BMN 673); tauromustine; tazarotene; tecogalan sodium; tegafur; tellurapyrylium; temoporfin; temozolomide; teniposide; tetrachlorodecaoxide; tetrazomine; thaliblastine; thiocoraline; thrombopoietin; thymalfasin; thymopoietin receptor agonist; thymotrinan; tirapazamine; titanocene bichloride; topsentin; toremifene; tretinoin; triacetyluridine; triciribine; trimetrexate; triptorelin; tropisetron; turosteride; tyrphostins; talisomycin; TAK-733; taxotere; tegafur; teloxantrone hydrochloride; teroxirone; testolactone; thiamiprine; thioguanine; thiotepa; tiazofurin; tirapazamine; toremifene citrate; trastuzumab; trestolone acetate; triciribine phosphate; trimetrexate; trimetrexate glucuronate; triptorelin; tubulozole hydrochloride; tumor necrosis factor-related apoptosis-inducing ligand (TRAIL); UBC inhibitors; ubenimex; U0126; uracil mustard; uredepa; vapreotide; variolin B; velaresol; veliparib (ABT-888); veramine; verteporfin; vinorelbine; vinxaltine; vitaxin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; wortmannin; XL518; zanoterone; zeniplatin; zilascorb; zinostatin stimalamer; zinostatin; and zorubicin hydrochloride.

Other exemplary anti-cancer agents include Erbulozole (e.g., R-55104); Dolastatin 10 (e.g., DLS-10 and NSC-376128); Mivobulin isethionate (e.g., CI-980); NSC- 639829; Discodermolide (e.g., NVP-XX-A-296); ABT-751 (Abbott; e.g., E-7010); Altorhyrtin A; Altorhyrtin C; Cemadotin hydrochloride (e.g., LU-103793 and NSC-D-669356); CEP 9722; Epothilone A; Epothilone B; Epothilone C; Epothilone D; Epothilone E; Epothilone F; Epothilone B N-oxide; Epothilone AN-oxide; 16-aza-epothilone B; 21-aminoepothilone B; 21-hydroxyepothilone D; 26-fluoroepothilone; Auristatin PE (e.g., NSC-654663); Soblidotin (e.g., TZT-1027); LS-4559-P (Pharmacia; e.g., LS-4577); LS-4578 (Pharmacia; e.g., LS-477-P); LS-4477 (Pharmacia); LS-4559 (Pharmacia); RPR-112378 (Aventis); DZ-3358 (Daiichi); FR-182877 (Fujisawa; e.g., WS-9265B); GS-164 (Takeda); GS-198 (Takeda); KAR-2 (Hungarian Academy of Sciences); BSF-223651 (BASF; e.g., ILX-651 and LU-223651); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (e.g., LY-355703); AC-7739 (Ajinomoto; e.g., AVE-8063A and CS-39.HCl); AC-7700 (Ajinomoto; e.g., AVE-8062; AVE-8062A; CS-39-L-Ser.HCl; and RPR-258062A); Vitilevuamide; Tubulysin A; Canadensol; CA-170 (Curis, Inc.); Centaureidin (e.g., NSC-106969); T-138067 (Tularik; e.g., T-67; TL-138067 and TI-138067); COBRA-1 (Parker Hughes Institute; e.g., DDE-261 and WHI-261); H10 (Kansas State University); H16 (Kansas State University); Oncocidin A1 (e.g., BTO-956 and DIME); DDE-313 (Parker Hughes Institute); Fijianolide B; Laulimalide; SPA-2 (Parker Hughes Institute); SPA-1 (Parker Hughes Institute; e.g., SPIKET-P); 3-IAABU (Cytoskeleton/Mt. Sinai School of Medicine; e.g., MF-569); Narcosine (e.g., NSC-5366); Nascapine; D-24851 (Asta Medica); A-105972 (Abbott); Hemiasterlin; 3-BAABU (Cytoskeleton/Mt. Sinai School of Medicine; e.g., MF-191); TMPN (Arizona State University); Vanadocene acetylacetonate; T-138026 (Tularik); Monsatrol; lnanocine (e.g., NSC-698666); 3-IAABE (Cytoskeleton/Mt. Sinai School of Medicine); A-204197 (Abbott); T-607 (Tularik; e.g., T-900607); RPR-115781 (Aventis); Eleutherobins (e.g., Desmethyleleutherobin; Desaetyleleutherobin; lsoeleutherobin A; and Z-Eleutherobin); Caribaeoside; Caribaeolin; Halichondrin B; D-64131 (Asta Medica); D-68144 (Asta Medica); Diazonamide A; A-293620 (Abbott); NPI-2350 (Nereus); Taccalonolide A; TUB-245 (Aventis); A-259754 (Abbott); Diozostatin; (−)-Phenylahistin (e.g., NSCL-96F037); D-62638 (Asta Medica); D-62636 (Asta Medica); Myoseverin B; D-43411 (Zentaris; e.g., D-81862); A-289099 (Abbott); A-318315 (Abbott); HTI-286 (e.g., SPA-110; trifluoroacetate salt) (Wyeth); D-82317 (Zentaris); D-82318 (Zentaris); SC-12983 (NCI); Resverastatin phosphate sodium; BPR-OY-007 (National Health Research Institutes); and SSR-250411 (Sanofi)); goserelin; leuprolide; triptolide; homoharringtonine; topotecan; itraconazole; deoxyadenosine; sertraline; pitavastatin; clofazimine; 5-nonyloxytryptamine; vemurafenib; dabrafenib; gefitinib (IRESSA); erlotinib (TARCEVA); cetuximab (ERBITUX); lapatinib (TYKERB); panitumumab (VECTIBIX); vandetanib (CAPRELSA); afatinib/BIBW2992; CI-1033/canertinib; neratinib/HKI-272; CP-724714; TAK-285; AST-1306; ARRY334543; ARRY-380; AG-1478; dacomitinib/ PF299804; OSI-420/desmethyl erlotinib; AZD8931; AEE726; pelitinib/EKB-569; CUDC-101; WZ8040; WZ4002; WZ3146; AG-490; XL647; PD153035; 5-azathioprine; 5-aza-2'-deoxycytidine; 17-N-Allylamino-17-Demethoxygeldanamycin (17-AAG); 20-epi-1,25 dihydroxyvitamin D3; 5 ethynyluracil; and BMS-599626.

In one aspect is a method for treating patients with colorectal cancer (optionally refractory) by administering an obeticholic acid composition described herein in combination with capecitabine and/or PLX4032 (Plexxikon).

In another aspect is a method for treating colorectal cancer (optionally refractory) by administering an obeticholic acid composition described herein in combination with capecitabine, xeloda, and/or CPT-11.

In another aspect is a method for treating colorectal cancer (optionally refractory) by administering an obeticholic acid composition described herein in combination with capecitabine, xeloda, and/or CPT-11.

In another aspect is a method for treating patients with colorectal cancer (optionally refractory) or patients with unresectable or metastatic colorectal carcinoma by administering an obeticholic acid composition described herein in combination with capecitabine and irinotecan.

In another aspect is a method for treating patients with unresectable or metastatic hepatocellular carcinoma by administering an obeticholic acid composition described herein in combination with interferon alpha or capecitabin.

In another aspect is a method for treating patients with pancreatic cancer by administering an obeticholic acid composition described herein in combination with gemcitabine.

Patients described herein include a patients having a disease or condition described herein. A patient can be described or referred to by the condition treated. For example, a patient having PBC can be referred to herein as a PBC patient. A patient described herein can have a preexisting condition (e.g., a condition other than the disease or condition treated by the obeticholic acid composition described herein that existed at the time of first administration). In one instance a patient described herein has hepatic impairment. In another instance a patient described herein has renal impairment. In yet another instance the patient is an elderly/geriatric patient or a pregnant patient. In another instance the patient is an pediatric patient.

In some embodiments, administration of an obeticholic acid composition described herein together with certain contra-active agents can result in (1) decreased efficacy of the obeticholic acid composition and/or (2) development of toxicity or adverse effects described herein. For example, administration of an obeticholic acid composition described herein with blood clotting and anti-coagulation agents can result in decreased International Normalized Ratio (INR). In certain instances, coagulation and anti-coagulation agents can be administered in combination with an obeticholic acid composition described herein by monitoring fluctuations of the INR of the patient and adjusting dosages as understood in the art to maintain proper INR.

In another example, administration of an obeticholic acid composition described herein in combination with a bile acid binding resin (e.g., cholestyramine, colestipol, or colesevelam) can result in decreased efficacy of the obeticholic acid composition at a lower dosage of the composition (e.g., 1 to 5 mg). In certain embodiments, a bile acid binding resin is administered in combination with an obeticholic acid composition described herein at least about 4 to 6 hours before or after the dosage of the obeticholic acid composition.

In one embodiment, the compositions described herein reduce adverse effects associated with other formulations (e.g., larger particle sized obeticholic acid). For example, an obeticholic acid composition described herein when administered to a patient described herein for a condition or disease described herein can reduce one or more adverse effects selected from Hepatic encephalopathy, ascites, variceal bleeding, skin eruptions, prurigo, pruritus (including generalized, eye, anal, vulvovaginal and rash), fatigue, asthenia, abdominal pain (including upper and lower pain and tenderness), abdominal discomfort, gastrointestinal pain, dizziness, urticaria (including cholinergic), rashes (including macular, popular, maculo-papular, and heat rashes), arthralgia, oropharyngeal pain, cough, constipation, edemal peripheral, palpitations, pyrexia, eczema, and procedural pain. In certain instances, the one or more adverse effects that are reduced include pruritus. It was discovered, inter alia, that titration of an obeticholic acid composition described herein can reduce the incidence of or mean time until onset of severe pruritus.

In another embodiment, the obeticholic acid compositions described herein include reduced levels of impurities commonly found in the synthesis of obeticholic acid. 6α-ethylursodeoxycholic acid (6-EUDCA), 3α-hydroxy-6α-ethyl-7-keto-5β-cholan-24-oic acid, 6β-ethylchenodeoxycholic acid; 3α,7α-dihydroxy-6β-ethyl-5β-cholan-24-oic acid, 3α,7α-dihydroxy-6-ethyliden-5β-cholan-24-oic acid, Chenodeoxycholic acid (CDCA); 3α,7α-dihydroxy-5β-cholan-24-oic acid, Dimer of OCA, 3α-(3α,7α-dihydroxy-6α-ethyl-5β-cholan-24-oyloxy)-7α-hydroxy-6α-ethyl-5β-cholan-24-oic acid, or 3α-O-Acetyl-6α-ethylchenodeoxycholic acid; 3α-O-acetyl-7α-hydroxy-6α-ethyl-5β-cholan-24-oic acid.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The disclosure having now been described by way of written description, those of skill in the art will recognize that the disclosure can be practiced in a variety of embodiments and that the foregoing description and examples below are for purposes of illustration and not limitation of the claims that follow.

SELECTED EMBODIMENTS

Embodiment 1

A method of treating primary biliary cirrhosis (PBC) in a patient in need thereof, the method comprising administering a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less.

Embodiment 2

A method of treating primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, or liver fibrosis in a patient in need thereof, the method comprising administering a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less.

Embodiment 3

The method of embodiment 2, wherein the method comprises treating NASH.

Embodiment 4

A method of treating a solid-tumor cancer in a patient in need thereof, the method comprising administering an effective amount of a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less.

Embodiment 5

The method of embodiment 1, 2 or 4, wherein the effective amount comprises a starting dose.

Embodiment 6

The method of embodiment 5, wherein the starting dose is administered in a titration period.

Embodiment 7

The method of any one of embodiments 4 to 6, wherein the cancer comprises hepatocellular carcinoma (HCC), colorectal cancer, gastric cancer, liver cancer, kidney cancer, or pancreatic cancer.

Embodiment 8

A method of treating an autoimmune disease in a patient in need thereof, the method comprising administering an effective amount of a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less.

Embodiment 9

The method of embodiment 7, wherein the effective amount comprises a starting dose.

Embodiment 10

The method of embodiment 8, wherein the starting dose is administered in a titration period.

Embodiment 11

The method of embodiment 7 or 8, wherein the autoimmune disease is selected from the group consisting of: PBC, multiple sclerosis, rheumatoid arthritis, and type-I diabetes.

Embodiment 12

The method of any one of embodiments 1-2, 6 or 9, wherein the titration period comprises 1 to 6 months.

Embodiment 13

The method of embodiment 11, wherein the titration period is 3 months.

Embodiment 14

The method of embodiment 11, wherein the titration period is 6 months.

Embodiment 15

The method of any one of embodiments 12 to 15, wherein the starting dose is administered to the patient once daily.

Embodiment 16

The method of any one of embodiments 11 to 14, wherein the starting dose is administered to the patient once daily.

Embodiment 17

The method of any one of embodiments 11 to 14, wherein the starting dose is administered to the patient once weekly.

Embodiment 18

The method of any one of embodiments 11 to 14, wherein the starting dose is administered to the patient once every other day.

Embodiment 19

The method of any one of embodiments 11 to 17, wherein the starting dose comprises about 1 mg to 50 mg.

Embodiment 20

The method of any one of embodiments 11 to 17, wherein the starting dose comprises about 1 mg to 25 mg.

Embodiment 21

The method of any one of embodiments 11 to 17, wherein the starting dose comprises about 1 mg to 10 mg.

Embodiment 22

The method of any one of embodiments 11 to 17, wherein the starting dose comprises about 1 mg to 5 mg.

Embodiment 23

The method of any one of embodiments 11 to 17, wherein the starting dose comprises about 5 mg.

Embodiment 24

The method of any one of embodiments 11 to 17, wherein the starting dose comprises about 10 mg.

Embodiment 25

The method of any one of embodiments 11 to 17, wherein the starting dose comprises about 25 mg.

Embodiment 26

The method of any one of embodiments 11 to 17, wherein the starting dose comprises about 50 mg.

Embodiment 27

The method of any one of embodiments 1 to 26, further comprising assessing or monitoring liver function before, during, or after the titration period.

Embodiment 28

The method of embodiment 27, wherein the assessing or monitoring comprises measuring a level of one or more liver biomarkers compared to a control.

Embodiment 29

The method of embodiment 28, wherein the liver biomarker is selected from the group consisting of: AST, ALT, alkaline phosphatase (ALP), bilirubin, glycine conjugated obeticholic acid, taurine conjugated obeticholic acid, a bile acid, a bile acid glycine conjugate, or a bile acid taurine conjugate.

Embodiment 30

The method of embodiment 29, comprising detecting a level of ALP in the patient.

Embodiment 31

The method of embodiment 29 or 30, comprising detecting a level of bilirubin in the patient.

Embodiment 32

The method of any one of embodiments 27 to 31, further comprising calculating a AST to platelet ratio (APRI) for the patient.

Embodiment 33

The method of any one of embodiments 12 to 32, wherein the obeticholic acid composition is administered to the patient as an adjusted dose after the titration period.

Embodiment 34

The method of embodiment 33, wherein the adjusted dose is equal to the titrated dose.

Embodiment 35

The method of embodiment 33, wherein the adjusted dose is equal to the starting dose when the level of ALP is reduced compared to a control.

Embodiment 36

The method of embodiment 33, wherein the adjusted dose is greater than the titrated dose.

Embodiment 37

The method of any one of embodiments 33 to 36, wherein the adjusted dose is administered more frequently than the titrated dose.

Embodiment 38

The method of any one of embodiments 33 to 36, wherein the adjusted dose is administered less frequently than the titrated dose.

Embodiment 39

The method of any one of embodiments 33 to 38, wherein the adjusted dose of the obeticholic acid composition is administered to the patient once daily.

Embodiment 40

The method of any one of embodiments 33 to 38, wherein the adjusted dose of the obeticholic acid composition is administered to the patient once daily.

Embodiment 41

The method of any one of embodiments 33 to 38, wherein the adjusted dose of the obeticholic acid composition is administered to the patient once daily.

Embodiment 42

The method of any one of embodiments 33 to 38, wherein the adjusted dose of the obeticholic acid composition is administered to the patient once weekly.

Embodiment 43

The method of any one of embodiments 33 to 38, wherein the adjusted dose of the obeticholic acid composition is administered to the patient once every other day.

Embodiment 44

The method of any one of embodiments 33 to 38, wherein the adjusted dose of the obeticholic acid composition is administered to the patient twice a week.

Embodiment 45

The method of any one of embodiments 33 to 44, wherein the adjusted dose comprises about 1 mg to 50 mg.

Embodiment 46

The method of any one of embodiments 33 to 44, wherein the adjusted dose comprises about 1 mg to 25 mg.

Embodiment 47

The method of any one of embodiments 33 to 44, wherein the adjusted dose comprises about 1 mg to 10 mg.

Embodiment 48

The method of any one of embodiments 33 to 44, wherein the adjusted dose comprises about 1 mg to 5 mg.

Embodiment 49

The method of any one of embodiments 33 to 44, wherein the adjusted dose comprises about 5 mg.

Embodiment 50

The method of any one of embodiments 33 to 44, wherein the adjusted dose comprises about 10 mg.

Embodiment 51

The method of any one of embodiments 33 to 44, wherein the adjusted dose comprises about 25 mg.

Embodiment 52

The method of any one of embodiments 33 to 44, wherein the adjusted dose comprises about 50 mg.

Embodiment 53

The method of any one of embodiments 1 to 52, wherein the method further comprises administering one or more active agents, or combinations thereof.

Embodiment 54

The method of embodiment 53, wherein the active agent is ursodeoxycholic acid (UDCA).

Embodiment 55

The method of embodiment 53, wherein the active agent is a peroxisome proliferator-activated receptor alpha (PPARα) agonist, a peroxisome proliferator-activated receptor delta (PPARδ) agonist, a dual PPARα/δ agonist, a dual PPARα/γ agonist, or pan-PPAR agonist, an HMG CoA reductase inhibitor, a GLP1 agonist, insulin, insulin mimetic, metformin, a GTP4 agonist, an HST2 inhibitor, a DPP-IV inhibitor, an SGLT2 inhibitor or a hydroxysteroid dehydrogenase (HSD) inhibitor, such as an 11β-HSD1 inhibitor, an ASK1 inhibitor, an ACC1 inhibitor, a NOX1 and/or NOX4 inhibitor, an inhibitor or antagonist of one or more chemokine receptors, such as, for example, CCR2 and CCR5.

Embodiment 56

The method of any one of embodiments 1 to 55, wherein the obeticholic acid composition is administered as a first line therapy for the treatment of PBC.

Embodiment 57

The method of any one of embodiments 1 to 56, wherein the patient is has renal impairment or hepatic impairment.

Embodiment 58

A method for treating primary biliary cirrhosis (PBC) in a patient in need thereof, the method comprising:
administering a starting dose of a composition comprising obeticholic acid, or a pharmaceutically acceptable salt, ester, or amino acid conjugate thereof, in a titration period, wherein obeticholic acid or a pharmaceutically acceptable salt, ester, or amino acid conjugate thereof is in the form of particles, and wherein at least 50% of the particles have a diameter of 200 μm or less;

assessing liver function of the patient before, during, and after the titration period by: calculating an AST to platelet ratio (APRI) score for the patient; or measuring the level of one or more liver biomarker selected from ALP, bilirubin, AST, ALT, glycine conjugated obeticholic acid, taurine conjugated obeticholic acid, a bile acid, a bile acid glycine conjugate, or a bile acid taurine conjugate;

wherein a reduced APRI score compared to a control or a reduced level of the one or more liver biomarkers compared to a control indicates non-impaired liver function;

assessing tolerance of the patient to the starting dose by grading the severity of one or more adverse effects, if present; and administering an adjusted dose of the obeticholic acid composition, wherein the adjusted dose comprises an amount equal to or greater than an amount of the starting dose.

Embodiment 59

The method of embodiment 58, wherein the adjusted dose is administered at an amount equal to an amount of the starting dose.

Embodiment 60

The method of embodiment 58, wherein the adjusted dose is administered at an amount greater than an amount of the starting dose.

Embodiment 61

The method of embodiment 58, wherein the adjusted dose of the obeticholic acid composition is administered at the same frequency as the starting dose.

Embodiment 62

The method of embodiment 58, wherein the adjusted dose of the obeticholic acid composition is administered at a decreased frequency than the starting dose.

Embodiment 63

The method of embodiment 58, wherein the effective amount of the obeticholic acid composition is administered at an increased frequency than the starting dose.

Embodiment 64

The method of any one of embodiments 58 to 63, wherein the starting dose is 5 mg.

Embodiment 65

The method of any one of embodiments 58 to 64, wherein the starting dose is administered QD.

Embodiment 66

The method of any one of embodiments 58 to 64, wherein the adjusted dose is 5 mg.

Embodiment 67

The method of any one of embodiments 58 to 64, wherein the adjusted dose is 10 mg.

Embodiment 68

The method of any one of embodiments 58 to 67, wherein the adjusted dose is administered QD or Q2D.

Embodiment 69

The method of any one of embodiments 58 to 68, further comprising assessing the patient for tolerance to the adjusted dose.

Embodiment 70

The method of embodiment 69, wherein the adjusted dose is modified to a re-adjusted dose when the patient.

Embodiment 71

The method of embodiment 70, wherein the re-adjusted dose comprises an equal amount compared to the adjusted dose and administration at a reduced frequency.

Embodiment 72

The method of embodiment 71, wherein the re-adjusted dose comprises a reduced amount compared to the adjusted dose and administration at an equal frequency.

Embodiment 73

The method of embodiment 58, wherein the patient has hepatic impairment.

Embodiment 74

The method of embodiment 73, wherein the starting dose is administered QW.

Embodiment 75

The method of embodiment 74, wherein the starting dose is 5 mg.

Embodiment 75

The method of any one of embodiments 58 to 75, wherein the adjusted dose is equivalent to the starting dose when the level of ALP is reduced compared to a control.

Embodiment 76

The method of any one of embodiments 58 to 75, wherein the adjusted dose comprises an amount equal to the starting dose and wherein the adjusted dose is administered at a greater frequency than the starting dose.

Embodiment 77

A composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for use in treating primary biliary cirrhosis (PBC) in a patient in need thereof.

Embodiment 78

A composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for use in treating primary biliary cirrhosis (PBC) in a patient in need thereof.

Embodiment 79

A composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for use in treating primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, or liver fibrosis in a patient in need thereof in a patient in need thereof.

Embodiment 80

The composition of embodiment 79, for use in treating NASH.

Embodiment 81

A composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for use in treating a solid-tumor cancer in a patient in need thereof.

Embodiment 82

The composition of embodiments 77, 79 or 81, wherein said composition further comprises said obeticholic acid composition as a starting dose.

Embodiment 83

The composition of embodiment 82, wherein said starting dose is prepared to be administered in a titration period.

Embodiment 84

The composition of any one of embodiments 81 to 83, for use in treating hepatocellular carcinoma (HCC), colorectal cancer, gastric cancer, liver cancer, kidney cancer, or pancreatic cancer.

Embodiment 85

A composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for use in treating an autoimmune disease in a patient in need thereof.

Embodiment 86

The composition of embodiment 85, wherein said composition further comprises said obeticholic acid composition as a starting dose.

Embodiment 87

The composition of embodiment 86, wherein said starting dose is prepared to be administered in a titration period.

Embodiment 88

The composition of embodiment 85 or 86, for use in treating multiple sclerosis, rheumatoid arthritis, or type-I diabetes.

Embodiment 89

The composition of any one of embodiments 78-79, 83 or 87, wherein said titration period comprises 1 to 6 months.

Embodiment 90

The composition of embodiment 89, wherein said titration period is 3 months.

Embodiment 91

The composition of embodiment 89, wherein said titration period is 6 months.

Embodiment 92

The composition of any one of embodiments 89 to 91, wherein said starting dose is prepared to be administered to said patient once daily.

Embodiment 93

The composition of any one of embodiments 89 to 92, wherein said starting dose is prepared to be administered to said patient once daily.

Embodiment 94

The composition of any one of embodiments 89 to 92, wherein said starting dose is prepared to be administered to said patient once weekly.

Embodiment 95

The composition of any one of embodiments 89 to 92, wherein said starting dose is prepared to be administered to said patient once every other day.

Embodiment 96

The composition of any one of embodiments 89 to 95, wherein said starting dose comprises about 1 mg to 50 mg.

Embodiment 97

The composition of any one of embodiments 89 to 95, wherein said starting dose comprises about 1 mg to 25 mg.

Embodiment 98

The composition of any one of embodiments 89 to 95, wherein said starting dose comprises about 1 mg to 10 mg.

Embodiment 99

The composition of any one of embodiments 89 to 95, wherein said starting dose comprises about 1 mg to 5 mg.

Embodiment 100

The composition of any one of embodiments 89 to 95, wherein said starting dose comprises about 5 mg.

Embodiment 101

The composition of any one of embodiments 89 to 95, wherein said starting dose comprises about 10 mg.

Embodiment 102

The composition of any one of embodiments 89 to 95, wherein said starting dose comprises about 25 mg.

Embodiment 103

The composition of any one of embodiments 89 to 95, wherein said starting dose comprises about 50 mg.

Embodiment 104

The composition of any one of embodiments 78 to 103, wherein said patient liver function assessed or monitored before, during, or after said titration period.

Embodiment 105

The composition of embodiment 104, wherein said assessing or monitoring comprises measuring a level of one or more liver biomarkers compared to a control.

Embodiment 106

The composition of embodiment 105, wherein said liver biomarker is selected from the group consisting of: AST, ALT, alkaline phosphatase (ALP), bilirubin, glycine conjugated obeticholic acid, taurine conjugated obeticholic acid, a bile acid, a bile acid glycine conjugate, or a bile acid taurine conjugate.

Embodiment 107

The composition of embodiment 106, wherein said liver biomarker is ALP.

Embodiment 108

The composition of embodiment 106 or 107, wherein said liver biomarker is bilirubin.

Embodiment 109

The composition of any one of embodiments 104 to 108, further comprising calculating an AST to platelet ratio (APRI) for said patient.

Embodiment 110

The composition of any one of embodiments 89 to 109, wherein said obeticholic acid composition is prepared to be administered to said patient as an adjusted dose after said titration period.

Embodiment 111

The composition of embodiment 110, wherein said adjusted dose is equal to said titrated dose.

Embodiment 112

The composition of embodiment 110, wherein said adjusted dose is equal to said starting dose when a level of ALP is reduced compared to a control.

Embodiment 113

The composition of embodiment 110, wherein said adjusted dose is greater than said titrated dose.

Embodiment 114

The composition of any one of embodiments 110 to 113, wherein said adjusted dose is prepared to be administered more frequently than said titrated dose.

Embodiment 115

The composition of any one of embodiments 110 to 113, wherein said adjusted dose is prepared to be administered less frequently than said titrated dose.

Embodiment 116

The composition of any one of embodiments 110 to 115, wherein said adjusted dose of said obeticholic acid composition is prepared to be administered to said patient once daily.

Embodiment 117

The composition of any one of embodiments 110 to 115, wherein said adjusted dose of said obeticholic acid composition is prepared to be administered to said patient once daily.

Embodiment 118

The composition of any one of embodiments 110 to 115, wherein said adjusted dose of said obeticholic acid composition is prepared to be administered to said patient once daily.

Embodiment 119

The composition of any one of embodiments 110 to 115, wherein said adjusted dose of said obeticholic acid composition is prepared to be administered to said patient once weekly.

Embodiment 120

The composition of any one of embodiments 110 to 115, wherein said adjusted dose of said obeticholic acid composition is prepared to be administered to said patient once every other day.

Embodiment 121

The composition of any one of embodiments 110 to 115, wherein said adjusted dose of said obeticholic acid composition is prepared to be administered to said patient twice a week.

Embodiment 122

The composition of any one of embodiments 110 to 121, wherein said adjusted dose comprises about 1 mg to 50 mg.

Embodiment 123

The composition of any one of embodiments 110 to 121, wherein said adjusted dose comprises about 1 mg to 25 mg.

Embodiment 124

The composition of any one of embodiments 110 to 121, wherein said adjusted dose comprises about 1 mg to 10 mg.

Embodiment 125

The composition of any one of embodiments 110 to 121, wherein said adjusted dose comprises about 1 mg to 5 mg.

Embodiment 126

The composition of any one of embodiments 110 to 121, wherein said adjusted dose comprises about 5 mg.

Embodiment 127

The composition of any one of embodiments 110 to 121, wherein said adjusted dose comprises about 10 mg.

Embodiment 128

The composition of any one of embodiments 110 to 121, wherein said adjusted dose comprises about 25 mg.

Embodiment 129

The composition of any one of embodiments 110 to 121, wherein said adjusted dose comprises about 50 mg.

Embodiment 130

The composition of any one of embodiments 78 to 129, wherein said obeticholic acid composition is prepared to be co-administered one or more active agents, or combinations thereof.

Embodiment 131

The composition of embodiment 130, wherein said active agent is ursodeoxycholic acid (UDCA).

Embodiment 132

The composition of embodiment 130, wherein the active agent is a peroxisome proliferator-activated receptor alpha (PPARα) agonist, a peroxisome proliferator-activated receptor delta (PPARδ) agonist, a dual PPARα/δ agonist, a dual PPARα/γ agonist, or pan-PPAR agonist, an HMG CoA reductase inhibitor, a GLP1 agonist, insulin, insulin mimetic, metformin, a GTP4 agonist, an HST2 inhibitor, a DPP-IV inhibitor, an SGLT2 inhibitor or a hydroxysteroid dehydrogenase (HSD) inhibitor, such as an 11β-HSD1 inhibitor, an ASK1 inhibitor, an ACC1 inhibitor, a NOX1 and/or NOX4 inhibitor, an inhibitor or antagonist of one or more chemokine receptors, such as, for example, CCR2 and CCR5.

Embodiment 133

The composition of any one of embodiments 78 to 132, wherein said obeticholic acid composition is prepared to be administered as a first line therapy for the treatment of PBC.

Embodiment 134

The composition of any one of embodiments 78 to 133, wherein said patient is has renal impairment or hepatic impairment.

Embodiment 135

A composition comprising a starting dose of obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less for use in treating primary biliary cirrhosis (PBC) in a patient in need thereof wherein the composition is prepared to be administered in a titration period wherein the liver function of the patient is assessed before, during, and after said titration period by calculating an AST to platelet ratio (APRI) score for said patient or by measuring the level of one or more liver biomarker selected from ALP, bilirubin, AST, ALT, glycine conjugated obeticholic acid, taurine conjugated obeticholic acid, a bile acid, a bile acid glycine conjugate, or a bile acid taurine conjugate, wherein a reduced APRI score compared to a control or a reduced level of said one or more liver biomarkers compared to a control indicates non-impaired liver function; and the tolerance of the patient to said starting dose is assessed by grading the severity of one or more adverse effects, if present; and the obeticholic acid composition is prepared to be administered as an adjusted dose, wherein said adjusted dose comprises an amount equal to or greater than an amount of said starting dose.

Embodiment 136

The composition of embodiment 135, wherein said adjusted dose is prepared to be administered at an amount equal to an amount of said starting dose.

Embodiment 137

The composition of embodiment 135, wherein said adjusted dose is prepared to be administered at an amount greater than an amount of said starting dose.

Embodiment 138

The composition of embodiment 135, wherein said adjusted dose of said obeticholic acid composition is prepared to be administered at the same frequency as said starting dose.

Embodiment 139

The composition of embodiment 135, wherein said adjusted dose of said obeticholic acid composition is prepared to be administered at a decreased frequency than said starting dose.

Embodiment 140

The composition of embodiment 135, wherein said effective amount of said obeticholic acid composition is prepared to be administered at an increased frequency than said starting dose.

Embodiment 141

The composition of any one of embodiments 135 to 140, wherein said starting dose is 5 mg.

Embodiment 142

The composition of any one of embodiments 135 to 141, wherein said starting dose is prepared to be administered QD.

Embodiment 143

The composition of any one of embodiments 135 to 141, wherein said adjusted dose is 5 mg.

Embodiment 144

The composition of any one of embodiments 135 to 141, wherein said adjusted dose is 10 mg.

Embodiment 145

The composition of any one of embodiments 135 to 144, wherein said adjusted dose is prepared to be administered QD or Q2D.

Embodiment 146

The composition of any one of embodiments 135 to 145, wherein said patient is assessed for tolerance to said adjusted dose.

Embodiment 147

The composition of embodiment 146, wherein said adjusted dose is modified to a re-adjusted dose.

Embodiment 148

The composition of embodiment 147, wherein said re-adjusted dose comprises an equal amount compared to said adjusted dose and is prepared to be administrated at a reduced frequency.

Embodiment 149

The composition of embodiment 148, wherein said re-adjusted dose comprises a reduced amount compared to said adjusted dose and is prepared to be administrated at an equal frequency.

Embodiment 150

The composition of embodiment 135, wherein said patient has hepatic impairment.

Embodiment 151

The composition of embodiment 150, wherein said starting dose is prepared to be administered QW.

Embodiment 152

The composition of embodiment 151, wherein said starting dose is 5 mg.

Embodiment 153

The composition of any one of embodiments 135 to 152, wherein said adjusted dose is equivalent to said starting dose when said level of ALP is reduced compared to a control.

Embodiment 154

The composition of any one of embodiments 135 to 152, wherein said adjusted dose comprises an amount equal to said starting dose and wherein said adjusted dose is prepared to be administrated at a greater frequency than said starting dose.

Embodiment 155

Use of a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 µm or less, for the manufacture of a medicament for use in treating primary biliary cirrhosis (PBC) in a patient in need thereof.

Embodiment 156

Use of a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 µm or less, for the manufacture of a medicament for use in treating primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, or liver fibrosis in a patient in need thereof in a patient in need thereof.

Embodiment 157

The use of embodiment 156, for use in treating NASH.

Embodiment 158

Use of a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for the manufacture of a medicament for use in treating a solid-tumor cancer in a patient in need thereof.

Embodiment 159

The use of embodiments 155, 156 or 158, wherein said composition further comprises said obeticholic acid composition as a starting dose.

Embodiment 160

The use of embodiment 159, wherein said starting dose is prepared to be administered in a titration period.

Embodiment 161

The use of any one of embodiments 158 to 160, wherein said cancer is hepatocellular carcinoma (HCC), colorectal cancer, gastric cancer, liver cancer, kidney cancer, or pancreatic cancer.

Embodiment 162

Use of a composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less, for the manufacture of a medicament for use in treating an autoimmune disease in a patient in need thereof.

Embodiment 163

The use of embodiment 162, wherein said obeticholic acid composition is prepared to be administered as a starting dose.

Embodiment 164

The use of embodiment 163, wherein said starting dose is prepared to be administered in a titration period.

Embodiment 165

The use of embodiment 162 or 163, wherein said autoimmune disease is multiple sclerosis, rheumatoid arthritis, or type-I diabetes.

Embodiment 166

The use of any one of embodiments 155-156, 160 or 164, wherein said titration period comprises 1 to 6 months.

Embodiment 167

The use of embodiment 166, wherein said titration period is 3 months.

Embodiment 168

The use of embodiment 166, wherein said titration period is 6 months.

Embodiment 169

The use of any one of embodiments 166 to 168, wherein said starting dose is prepared to be administered to said patient once daily.

Embodiment 170

The use of any one of embodiments 166 to 169, wherein said starting dose is prepared to be administered to said patient once daily.

Embodiment 171

The use of any one of embodiments 166 to 169, wherein said starting dose is prepared to be administered to said patient once weekly.

Embodiment 172

The use of any one of embodiments 166 to 169, wherein said starting dose is prepared to be administered to said patient once every other day.

Embodiment 173

The use of any one of embodiments 166 to 172, wherein said starting dose comprises about 1 mg to 50 mg.

Embodiment 174

The use of any one of embodiments 166 to 172, wherein said starting dose comprises about 1 mg to 25 mg.

Embodiment 175

The use of any one of embodiments 166 to 172, wherein said starting dose comprises about 1 mg to 10 mg.

Embodiment 176

The use of any one of embodiments 166 to 172, wherein said starting dose comprises about 1 mg to 5 mg.

Embodiment 177

The use of any one of embodiments 166 to 172, wherein said starting dose comprises about 5 mg.

Embodiment 178

The use of any one of embodiments 166 to 172, wherein said starting dose comprises about 10 mg.

Embodiment 179

The use of any one of embodiments 166 to 172, wherein said starting dose comprises about 25 mg.

Embodiment 180

The use of any one of embodiments 166 to 172, wherein said starting dose comprises about 50 mg.

Embodiment 181

The use of any one of embodiments 155 to 180, wherein liver function of said patient is assessed or monitored before, during, or after said titration period.

Embodiment 182

The use of embodiment 181, wherein said assessing or monitoring comprises measuring a level of one or more liver biomarkers compared to a control.

Embodiment 183

The use of embodiment 182, wherein said liver biomarker is selected from the group consisting of: AST, ALT, alkaline phosphatase (ALP), bilirubin, glycine conjugated obeticholic acid, taurine conjugated obeticholic acid, a bile acid, a bile acid glycine conjugate, or a bile acid taurine conjugate.

Embodiment 184

The use of embodiment 183, wherein said liver biomarker is ALP.

Embodiment 185

The use of embodiment 183 or 184, wherein said liver biomarker is bilirubin.

Embodiment 186

The use of any one of embodiments 181 to 185, further comprising calculating an AST to platelet ratio (APRI) for said patient.

Embodiment 187

The use of any one of embodiments 166 to 186, wherein said obeticholic acid composition is prepared to be administered to said patient as an adjusted dose after said titration period.

Embodiment 188

The use of embodiment 187, wherein said adjusted dose is equal to said titrated dose.

Embodiment 189

The use of embodiment 187, wherein said adjusted dose is equal to said starting dose when a level of ALP is reduced compared to a control.

Embodiment 190

The use of embodiment 187, wherein said adjusted dose is greater than said titrated dose.

Embodiment 191

The use of any one of embodiments 187 to 190, wherein said adjusted dose is prepared to be administered more frequently than said titrated dose.

Embodiment 192

The use of any one of embodiments 187 to 190, wherein said adjusted dose is prepared to be administered less frequently than said titrated dose.

Embodiment 193

The use of any one of embodiments 187 to 192, wherein said adjusted dose of said obeticholic acid composition is prepared to be administered to said patient once daily.

Embodiment 194

The use of any one of embodiments 187 to 192, wherein said adjusted dose of said obeticholic acid composition is prepared to be administered to said patient once daily.

Embodiment 195

The use of any one of embodiments 187 to 192, wherein said adjusted dose of said obeticholic acid composition is prepared to be administered to said patient once daily.

Embodiment 196

The use of any one of embodiments 187 to 192, wherein said adjusted dose of said obeticholic acid composition is prepared to be administered to said patient once weekly.

Embodiment 197

The use of any one of embodiments 187 to 192, wherein said adjusted dose of said obeticholic acid composition is prepared to be administered to said patient once every other day.

Embodiment 198

The use of any one of embodiments 187 to 192, wherein said adjusted dose of said obeticholic acid composition is prepared to be administered to said patient twice a week.

Embodiment 199

The use of any one of embodiments 187 to 198, wherein said adjusted dose comprises about 1 mg to 50 mg.

Embodiment 200

The use of any one of embodiments 187 to 198, wherein said adjusted dose comprises about 1 mg to 25 mg.

Embodiment 201

The use of any one of embodiments 187 to 198, wherein said adjusted dose comprises about 1 mg to 10 mg.

Embodiment 202

The use of any one of embodiments 187 to 198, wherein said adjusted dose comprises about 1 mg to 5 mg.

Embodiment 203

The use of any one of embodiments 187 to 198, wherein said adjusted dose comprises about 5 mg.

Embodiment 204

The use of any one of embodiments 187 to 198, wherein said adjusted dose comprises about 10 mg.

Embodiment 205

The use of any one of embodiments 187 to 198, wherein said adjusted dose comprises about 25 mg.

Embodiment 206

The use of any one of embodiments 187 to 198, wherein said adjusted dose comprises about 50 mg.

Embodiment 207

The use of any one of embodiments 155 to 206, wherein said obeticholic acid composition is prepared to be administered in combination with one or more active agents, or combinations thereof.

Embodiment 208

The use of embodiment 207, wherein said active agent is ursodeoxycholic acid (UDCA).

Embodiment 209

The use of embodiment 207, wherein the active agent is a peroxisome proliferator-activated receptor alpha (PPARα) agonist, a peroxisome proliferator-activated receptor delta (PPARδ) agonist, a dual PPARα/δ agonist, a dual PPARα/γ agonist, or pan-PPAR agonist, an HMG CoA reductase inhibitor, a GLP1 agonist, insulin, insulin mimetic, metformin, a GTP4 agonist, an HST2 inhibitor, a DPP-IV inhibitor, an SGLT2 inhibitor or a hydroxysteroid dehydrogenase (HSD) inhibitor, such as an 11β-HSD1 inhibitor, an ASK1 inhibitor, an ACC1 inhibitor, a NOX1 and/or NOX4 inhibitor, an inhibitor or antagonist of one or more chemokine receptors, such as, for example, CCR2 and CCR5.

Embodiment 210

The use of any one of embodiments 155 to 209, wherein said obeticholic acid composition is prepared to be administered as a first line therapy for the treatment of PBC.

Embodiment 211

The use of any one of embodiments 155 to 210, wherein said patient is has renal impairment or hepatic impairment.

Embodiment 212

The use of a composition comprising a starting dose of obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less for use in treating primary biliary cirrhosis (PBC) in a patient in need thereof wherein the composition is prepared to be administered in a titration period wherein:
the liver function of the patient is assessed before, during, and after said titration period by calculating an AST to platelet ratio (APRI) score for said patient or by measuring the level of one or more liver biomarker selected from ALP, bilirubin, AST, ALT, glycine conjugated obeticholic acid, taurine conjugated obeticholic acid, a bile acid, a bile acid glycine conjugate, or a bile acid taurine conjugate, wherein a reduced APRI score compared to a control or a reduced level of said one or more liver biomarkers compared to a control indicates non-impaired liver function; and
the tolerance of the patient to said starting dose is assessed by grading the severity of one or more adverse effects, if present; and the obeticholic acid composition is prepared to be administered as an adjusted dose, wherein said adjusted dose comprises an amount equal to or greater than an amount of said starting dose.

Embodiment 213

The use of embodiment 212, wherein said adjusted dose is prepared to be administered at an amount equal to an amount of said starting dose.

Embodiment 214

The use of embodiment 212, wherein said adjusted dose is prepared to be administered at an amount greater than an amount of said starting dose.

Embodiment 215

The use of embodiment 212, wherein said adjusted dose of said obeticholic acid composition is prepared to be administered at the same frequency as said starting dose.

Embodiment 216

The use of embodiment 212, wherein said adjusted dose of said obeticholic acid composition is prepared to be administered at a decreased frequency than said starting dose.

Embodiment 217

The use of embodiment 212, wherein said effective amount of said obeticholic acid composition is prepared to be administered at an increased frequency than said starting dose.

Embodiment 218

The use of any one of embodiments 212 to 217, wherein said starting dose is 5 mg.

Embodiment 219

The use of any one of embodiments 212 to 218, wherein said starting dose is prepared to be administered QD.

Embodiment 220

The use of any one of embodiments 212 to 218, wherein said adjusted dose is 5 mg.

Embodiment 221

The use of any one of embodiments 212 to 218, wherein said adjusted dose is 10 mg.

Embodiment 222

The use of any one of embodiments 212 to 221, wherein said adjusted dose is prepared to be administered QD or Q2D.

Embodiment 223

The use of any one of embodiments 212 to 222, wherein said patient is assessed for tolerance to said adjusted dose.

Embodiment 224

The use of embodiment 223, wherein said adjusted dose is modified to a re-adjusted dose.

Embodiment 225

The use of embodiment 224, wherein said re-adjusted dose comprises an equal amount compared to said adjusted dose and is prepared to be administrated at a reduced frequency.

Embodiment 226

The use of embodiment 225, wherein said re-adjusted dose comprises a reduced amount compared to said adjusted dose and is prepared to be administrated at an equal frequency.

Embodiment 227

The use of embodiment 212, wherein said patient has hepatic impairment.

Embodiment 228

The use of embodiment 227, wherein said starting dose is prepared to be administered QW.

Embodiment 229

The use of embodiment 228, wherein said starting dose is 5 mg.

Embodiment 230

The use of any one of embodiments 212 to 229, wherein said adjusted dose is equivalent to said starting dose when said level of ALP is reduced compared to a control.

Embodiment 231

The use of any one of embodiments 212 to 229, wherein said adjusted dose comprises an amount equal to said starting dose and wherein said adjusted dose is prepared to be administered at a greater frequency than said starting dose.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended. It is to be further understood that resort may be had to various other embodiments, modifications, and equivalents thereof which may suggest themselves to those skilled in the art without departing from the spirit of the present disclosure and/or scope of the appended claims.

Example 1: Particle Size Analysis 5 mg tablet and 10 mg tablet formulations of obeticholic acid (OCA or INT-747) demonstrated a slow dissolution release profile. Particle size of agglomeration was identified as playing a primary role in the release rate and dissolution and variability in the blend uniformity and content uniformity of the tablet formulations. In order to obtain an appropriate particle size distribution (PSD), milling of obeticholic acid was investigated. The particle size of the formulations was reduced using comilling and jet milling to improve its dissolution release profile. Particle size analysis was performed using a dry dispersion method and analyzed by laser diffraction using Sympatec equipment.

Particle size distribution was assessed using a dry dispersion method analyzed by laser diffraction using a Sympatec Laser Helos/KF-Magic F71000 with Rodos Dispersing Unit. The OCA sample (0.5 g sample) was tested as a dry powder. The parameters for the validated particle size analysis method are described below:

Apparatus: Sympatec Laser Helos/KF-Magic F71000 with Rodos Dispersing Unit, Vibri sampling unit with Sniffer rotation, Nilfisk exhaustion or equivalent.

Deionization apparatus: Sartorius or equivalent.

Measuring range: R3: 0.5/0.9 to 175 μm.

Dispersing principle: Dry.

Pressure: 1.0 bar.

Feed rate: 80%.

Feed height: 2 mm.

Sniffer rotation: 20%.

Trigger conditions: Time base: 100 ms; Start: Ka.28≥1%; Stop: 1 s c.opt≤1%.

Comilling. The use of a comil with different screen sizes was evaluated. Three comil screens were utilized: 1.14 mm, 0.61 mm, and 0.46 mm. The milled active pharmaceutical ingredient (API) was evaluated for appearance, particle size distribution as well as process yield. The process yield was difficult to determine accurately, but as expected, a larger amount of milled drug product was recovered from the larger screen sizes. The particle size distribution of unmilled and comilled obeticholic acid is shown below in Table 1.

TABLE 1

Particle size distribution of unmilled and comilled obeticholic acid.

| Sample Description | $D_{10}$ | $D_{25}$ | $D_{50}$ | $D_{75}$ | $D_{90}$ | $D_{95}$ |
|---|---|---|---|---|---|---|
| Unmilled API (no comil) | 4.8 | 105.1 | 218.6 | 335.7 | 427.6 | 472.6 |
| Unmilled API (no comil) | 3.3 | 36.4 | 167.7 | 273.7 | 355.6 | 398.2 |
| Comilled with 0.46 mm screen | 5.7 | 122.9 | 217.5 | 283.0 | 335.1 | 360.3 |
| Comilled with 0.61 mm screen | 4.1 | 102.2 | 263.1 | 351.0 | 410.9 | 447.9 |
| Comilled with 0.61 mm screen | 5.5 | 106.6 | 223.2 | 320.8 | 393.8 | 429.8 |
| Comilled with 1.14 mm screen | 7.9 | 73.9 | 239.3 | 340.8 | 412.0 | 452.7 |

After the comil, the material visually appeared to have a lower particle size and be more uniform in size when compared to unmilled (API). However, the measured particle size distribution of the material by dry dispersion described above did not show a difference between the comilled and the unmilled OCA. The PSD data demonstrate a more robust milling technique is required to significantly reduce the particle size of the material.

Jet milling using Hosokawa AFG 100 jet mill

Jet milling studies were performed using a Hosokawa AFG 100 jet mill. The results showed a significant reduction in the particle size distribution (PSD). Jet milling was carried out with various classifier speeds to determine the optimum set of jet mill parameters. The jet mill parameters used in the Hosokawa AFG 100 jet mill are provided below:

Hosokawa AFG 100 jet mill parameters:
Pressure in the mill: −0.2~−0.3 mm Aq.
Nozzle diameter/number: 1.9 Φmm×3
Consumption of compressed air: 0.7 Nm3/min
Classification Parameters
Rotor rotation speed: 4000 rpm
Current rating of motor: 4.2 Amp
Current operating: 2.4 Amp
Rotor seal pressure: 0.1 MPa (1 bar)
Bearing seal pressure: 0.1 MPa (1 bar)
Rotor type: SUS
Powder Collector
Filter material/length/number: Gore/2 ft/4

The particle size distribution of unmilled and jet milled OCA (API) is shown below in Table 2.

TABLE 2

Particle size distribution of unmilled and jet milled obeticholic acid.

| Sample Description | $D_{10}$ | $D_{16}$ | $D_{50}$ | $D_{84}$ | $D_{90}$ | $D_{99}$ |
|---|---|---|---|---|---|---|
| Unmilled API | 4.8 | — | 218.6 | — | 427.6 | — |
| Jet mill, classifier speed 2000 rpm | 1.7 | 2.3 | 10.9 | 57.2 | 69.3 | 97.9 |
| Jet mill, classifier speed 5000 rpm | 1.3 | 1.7 | 4.2 | 15.2 | 18.9 | 55.8 |
| Jet mill, classifier speed 10000 rpm | 1.1 | 1.4 | 2.7 | 4.7 | 5.6 | 9.0 |
| Jet mill, classifier speed 4000 rpm | 1.3 | 1.6 | 3.8 | 17.0 | 21.7 | 36.0 |

The results above show that jet milling at high classifier speeds (i.e., 4000 rpm, 5000 rpm and 10,000 rpm) showed a significant reduction in the PSD.

Jet milling using spiral jet mill. Jet milling studies were performed using a spiral jet mill. The results showed a significant reduction in the particle size distribution (PSD). Jet milling was carried out with various a range of parameters to determine the optimal settings. The jet mill parameters used in the spiral jet mill are provided below:

Spiral jet mill parameters controlling the final PSD are:
Feed rate: Product amount fed into the milling chamber per unit time
Pressure: Fluid pressure through the nozzle section which influences the speed at which the particles collide

TABLE 3

Milling Parameters Used During Development at JetPharma

| Lot Number | Batch Size | Feed Rate | Nitrogen Pressure | PSD |
|---|---|---|---|---|
| JP1307001 | 10.0 kg | Evaluated range: 200-400 g/30" Target range: 300 ± 10 g/30" | Evaluated range: 2.0-4.0 bar Target range: 3.0 ± 0.2 bar | $X_{10}$: 1 μm $X_{50}$: 5 μm $X_{90}$: 20 μm |

TABLE 3-continued

Milling Parameters Used During Development at JetPharma

| Lot Number | Batch Size | Feed Rate | Nitrogen Pressure | PSD |
|---|---|---|---|---|
| JP1408001 | 5.6 kg | Evaluated range: 200-400 g/30" Target range: 290 ± 10 g/30" | Evaluated range: 2.0-4.0 bar Target range: 3.2 ± 0.2 bar | $X_{10}$: 1 μm $X_{50}$: 5 μm $X_{90}$: 19 μm |
| JP1408002 | 4.8 kg | Evaluated range: 200-400 g/30" Target range: 290 ± 10 g/30" | Evaluated range: 2.0-4.0 bar Target range: 3.2 ± 0.2 bar | $X_{10}$: 1 μm $X_{50}$: 4 μm $X_{90}$: 14 μm |
| JP1408003 | 6.3 kg | Evaluated range: 200-400 g/30" Target range: 290 ± 10 g/30" | Evaluated range: 2.0-4.0 bar Target range: 3.2 ± 0.2 bar | $X_{10}$: 1 μm $X_{50}$: 4 μm $X_{90}$: 15 μm |

The impact of jet-milling on API particle size and surface area is detailed in Table 4-1 and Table 4-2, respectively. Surface area was tested per a BET (Brunauer, Emmett, and Teller theory). The BET method for analyzing surface area is based on adsorption of gas on a surface. The amount of gas adsorbed at a given pressure allows a determination of the surface area.

Figure 2:
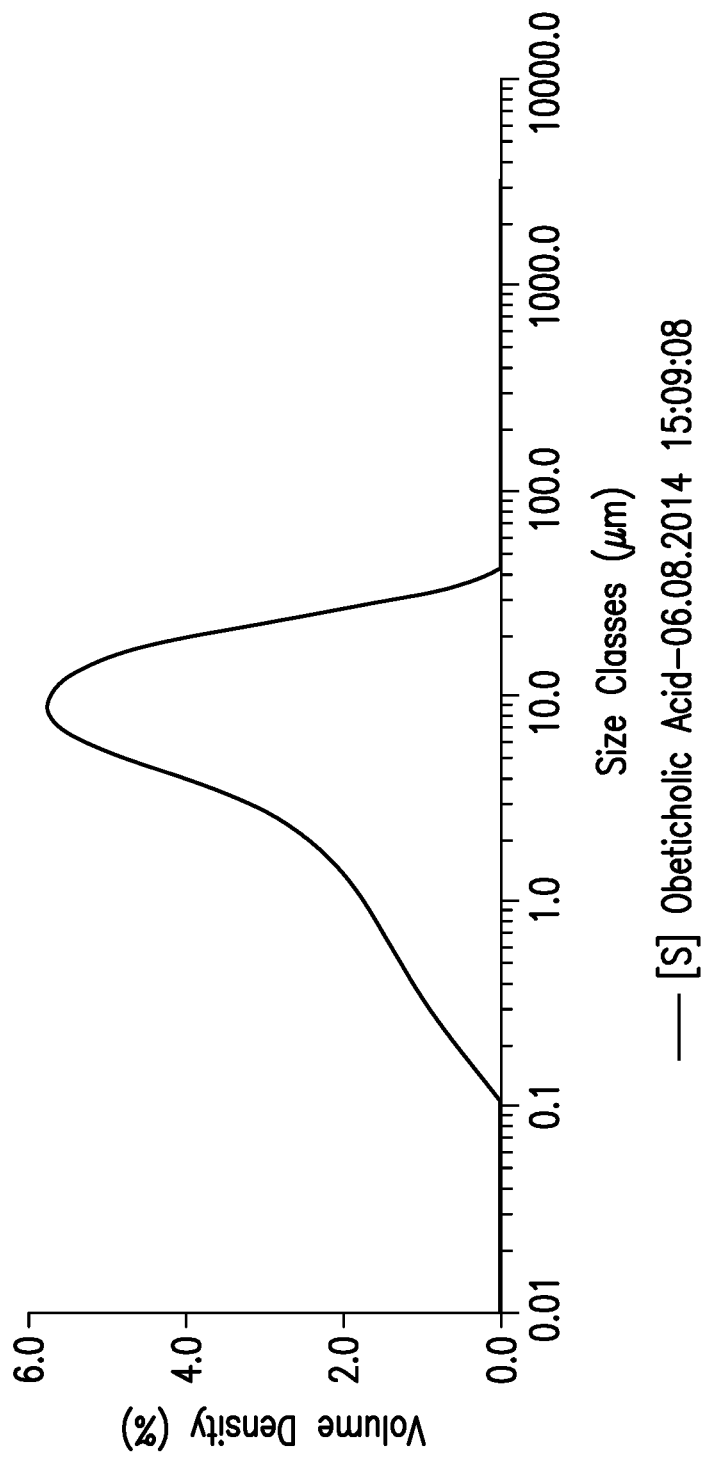
FIG. 2 is a particle size distribution histogram of obeticholic acid after jet-milling.

As can be observed from Table 2, the API particle size distribution after jet-milling undergoes a dramatic shift towards much smaller, more uniformly-sized particles within a tighter distribution, while surface area increases approximately 3-fold. FIG. 1 and FIG. 2 illustrate the typical particle size distribution of unmilled and jet-milled API, respectively.

TABLE 4-1

Impact of jet-milling (micronization) on particle size distribution of OCA drug substance
Particle Size Distribution of Unmicronized and Micronized OCA Drug Substance

| | OCA Example # | | | | | |
|---|---|---|---|---|---|---|
| | 1 | | 2 | | 3 | |
| | Before | After | Before | After | Before | After |
| $D_v$ (10) | 2.6 | 0.7 | 1.8 | 0.6 | 5.3 | 0.7 |
| $D_v$ (50) | 26 | 6.1 | 19 | 4.4 | 39 | 4.9 |
| $D_v$ (90) | 162 | 18.8 | 231 | 17.8 | 221 | 14.1 |
| $D_v$ (99) | 419 | 30.8 | 509 | 34.6 | 513 | 25.9 |

TABLE 4-2

Impact of jet-milling (micronization) on surface area of OCA drug substance
Surface Area of Unmicronized and Micronized OCA Drug Substance

| | OCA Example # | | | | | |
|---|---|---|---|---|---|---|
| | 1 | | 2 | | 3 | |
| | Before | After | Before | After | Before | After |
| Surface Area (m²/kg) | 1557 | 3178 | 1854 | 3848 | 809 | 3412 |

Example 2: Improved Manufacturing Process of Obeticholic Acid (OCA) Tablets

The manufacturing process of 5 mg and 10 mg obeticholic acid (OCA) tablets uses dry granulation by roller compaction followed by tablet compression and coating. The process steps used to manufacture OCA tablets include: pre-blending; dry granulation, final blending, compression, coating, and packaging. The equipment used to manufacture OCA tablets are shown in Table 5.

TABLE 5

Equipment Used to Manufacture OCA Tablets

| Process Step | Equipment |
| --- | --- |
| Sieving | 0.5 mm and 1.0 mm aperture sieve |
| Pre-blending | Drum and Bin blender, appropriately sized drum and bin |
| Roller compaction | Roller compactor, Alexanderwerk PP150 (or WP120) or equivalent fitted with upper and lower mill screens |
| Final blending | Bin blender, appropriately sized bin |
| Compression | Rotary tablet press, Kilian T300 or equivalent |
| Coating | Perforated pan coater, Manesty Accelacota 150 or equivalent 48-inch coating pan |

Microcrystalline cellulose was added to the intra-granular portion of the tablet mixture which produced tablets of moderate hardness. Modification to the manufacturing process to add microcrystalline cellulose to both the intra-granular and extra-granular portions of the tablet for both the 5 mg and 10 mg tablet generated more robust tablets (harder tablets). The compression challenges observed were overcome by redistributing a portion of microcrystalline cellulose in the 5 mg and 10 mg OCA formulation blends. This change in the manufacturing process impacted the quality attributes, specifically the dissolution profile, of the OCA tablets.

OCA drug substance and excipients were added in specific quantities and order during pre- and final blending. Prior to manufacture, the materials were dispensed in the appropriate portions as shown in Table 6. Microcrystalline cellulose (MCC) and sodium starch glycolate (SSG) were sieved with a 1.0 mm aperture sieve before use. Magnesium stearate was sieved using a 0.5 mm aperture sieve immediately before use.

TABLE 6

Material Dispensing Summary for OCA Tablets

| Component | Quantity for 5 mg OCA Tablet Formulation (kg) | Quantity for 10 mg OCA Tablet Formulation (kg) | Quantity for 25 mg OCA Tablet Formulation (kg) |
| --- | --- | --- | --- |
| Intra-granular (Pre Blending) | | | |
| OCA drug substance | $2.5^a$ | $5.0^a$ | $12.5^a$ |
| MCC-for-Premix | 7.5 | 10.0 | 25.0 |
| MCC-for-Rinse | 7.5 | 10.0 | 12.5 |
| MCC-1 | $25.5^a$ | $33.0^a$ | $41.0^a$ |
| SSG-1 | 4.0 | 4.0 | 4.0 |
| Silicon dioxide-1 | — | — | 1.0 |
| Magnesium stearate-1 | 0.5 | 0.5 | 0.5 |
| Extra-granular (Final Blending) | | | |
| MCC-2 | $50.0^b$ | $35.0^b$ | — |
| SSG-2 | $2.0^b$ | $2.0^b$ | $2.0^b$ |
| Silicon dioxide-2 | — | — | $1.0^b$ |
| Magnesium stearate-2 | $0.5^b$ | $0.5^b$ | $0.5^b$ |
| Coating | | | |
| Opadry ® II Yellow 85F32351 | $6.0^c$ | $6.0^c$ | $6.0^c$ |
| Purified water$^d$ | 24.0 | 24.0 | 24.0 |
| Total | 104.0 | 104.0 | 104.0 |

MCC = Microcrystalline cellulose;
SSG = Sodium starch glycolate;
$^a$OCA drug substance amount assumes the drug substance content is 100%; actual amount added is adjusted for based on the potency of the drug substance lot used; the amount of microcrystalline cellulose is correspondingly decreased.
$^b$The amounts of extra-granular excipients are adjusted based on the yield of the process through roller compaction. The dispensing summary presented assumes a 100% yield through roller compaction.
$^c$The amount of coating material prepared during the process is 150% of target. Excess coating material is discarded.
$^d$Water is removed during processing.

Preblending Process. To an appropriately sized blender drum was added OCA and a microcrystalline cellulose (MCC) for premix (MCC-for-Premix: a portion of the total MCC added to the tablet formulation) to produce OCA premix. The resulting mixture was blended 90 to 120 revolutions (approximately for 3 minutes at a blender speed of about 30 rpm) and discharged. For the 5 mg tablets, OCA was pre-mixed with approximately 3 parts MCC (to 1 part OCA). For the 10 mg tablets, OCA was pre-mixed with approximately 2 parts MCC (to 1 part OCA).

After unloading the API/MCC premix (OCA premix) from the drum, the drum was rinsed with a further portion of MCC (MCC-for-Rinse: same amount as used for the premix), to recover any API retained on the drum surfaces to provide the MCC-rinse portion. A blend time of 3 minutes (i.e., about 90 to 120 revolutions) was used for this rinse process, i.e., MCC-rinse process. The API/MCC premix and MCC drum rinse (MCC-rinse portion) were passed through a 1.0 mm aperture sieve on addition to the larger drum used for the Pre-RC (roller compaction) blending process (i.e., 150 liter drum for 5 mg tablets and 70 liter drum for 10 mg tablets). The sieve removed any soft agglomerates of OCA, and ensured good blend uniformity was achieved before roller compaction.

An appropriately sized bin was then charged with the following components: approximately ¼ (one-fourth) of MCC-1, ½ (half) of OCA Premix, MCC drum rinse (MCC Rinse), ½ of OCA Premix, and ¼ of MCC-1 in the order specified. The resulting mixture was then blended for 300 to 360 revolutions (about 20 minutes for 5 mg tablets, about 10 minutes for 10 mg tablets) in a Pharmatech MB400 drum blender or a Tumblemix drum blender or V-blender. The SSG-1 and the remaining ½ of MCC-1 was added to the bin and the mixture was then blended for 300 to 360 revolutions (about 10 to 20 minutes). Magnesium stearate-1 was then added to the bin via a 0.5 mm aperture sieve and the mixture was blended for 70 to 90 revolutions (about 3 minutes). For the 25 mg tablet, silicon dioxide was added via a 0.5 mm aperture sieve together with SSG-1 and the remaining ½ of MCC-1 to the bin and the mixture was then blended for 300 to 360 revolutions (about 10 to 20 minutes). The blender revolutions for the various preblending steps provide homogeneity of the pre-blend formulation.

Dry granulation. The pre-blend was transferred from the bin blender to the roller compactor hopper. The pre-blend was roller compacted to provide flakes which were milled into granules through an in-line dual screen milling system. The granules were then collected in a suitable container. Roller compaction parameters used in the commercial production are shown in Table 7. This process provided the roller compacted active granules (intra-granular portion) for use in the final blending step. Roll pressure (compaction force), roll gap, and screen size (lower mill) are meaningful process parameters in the roller compaction process. The roll pressure, roll gap, and screen size provided granules with consistent physical characteristics and particle-size distribution.

TABLE 7

Roller Compactor Settings Used for Commercial Production

| Attribute | Setting |
| --- | --- |
| Roll pressure (bar) | 40 to 48 |
| Roll gap (mm) | 2.5 to 4.0 |
| Upper mill screen size (mm) | 2.0 |
| Lower mill screen size (mm) | 0.8 |

Final Blending. The final blending of the OCA tablet formulation was performed in 2 steps. First, an appropriately sized bin was charged with the roller-compacted active granules (intra-granular portion), extra-granular sodium starch glycolate-2 (SSG-2) and extra-granular MCC-2, and the resulting mixture was blended for 450 to 540 revolutions. For the 25 mg tablet, silicon dioxide was added via a 0.5 aperture sieve together with SSG-2 and extra-granular MCC-2. Magnesium stearate-2 was then added to the bin and the mixture was blended for 70 to 90 revolutions. Blender revolution is a meaningful process parameter in the final blending process providing a final blend with acceptable homogeneity.

Compression Process. The final blend prepared in the blending process was used to supply the rotary tablet press fitted with the appropriate OCA tablet tooling. OCA tablet tooling is specific to the tablet strength. During equipment start-up, the tablet press was set up by adjusting compression parameters to produce tablets that meet the in-process control targets for tablet weight, hardness, thickness, and friability. Tablet press speed (about 70 rpm) and feeder speed (about 30 rpm to about 40 rpm) were set to achieve satisfactory tablet weight variation. The tablet press depth of fill was set to achieve the target tablet weight. The main compression pressure (rollers) was set to achieve the target hardness and thickness (compression force of about 8 kN). A small amount of pre-compression force (about 0.5 kN) was applied before the main compression to expel air from the blend to ensure satisfactory tablet friability. Adjustments were made throughout the compression operation to continuously meet the in-process control targets. After the tablets were ejected from the press, they were passed through a tablet deduster and metal detector prior to collection in tablet containers.

In-process control testing for appearance, tablet weight, hardness, thickness, friability, and disintegration time is conducted at specific internals throughout the tablet compression process and are provided in Table 8. Press speed and compression are meaningful process parameters in the tablet compression process. The specified press speed provided tablets with the target tablet weight. Compression, including both pre- and main compression, provided tablets that met the tablet hardness, thickness and firability limits. In addition, the provided tablets showed fast disintegration time.

TABLE 8

In-Process Tests for Compression Step

| In-process Test | 5 mg OCA Tablets | 10 mg OCA Tablet | 25 mg OCA Tablet |
| --- | --- | --- | --- |
| | | Acceptance Criteria | |
| Appearance | White, round tablets with 5 debossed on one side and INT on the other side | White, triangular tablets with 10 debossed on one side and INT on the other side | White, oval tablets with 25 debossed on one side and INT on the other side |
| Weight of 20 tablets | 3.92 g to 4.08 g (Target 4.00 g) | | |
| Individual weight of 20 tablets | 200 mg, NMT 2 individual tablets deviate from mean by more than 7.5% and none by more than 15% | | |
| Hardness (mean) | 7 kP to 13 kP (target 10 kP) | 8 kP to 14 kP (target 11 kP) | 9 kP to 15 kP (target 12 kP) |
| Thickness (mean) | 3.5 mm to 4.1 mm (target: 3.8 mm) | 4.0 mm to 4.6 mm (target: 4.3 mm) | 4.3 mm to 4.9 mm (target: 4.6 mm) |
| Friability (6.5 g/100 rotations) | NMT 0.5% | | |
| Disintegration time (6 tablets) | NMT 2 min | | |

NMT = not more than

Tablet Coating. The 5 mg and 10 mg OCA tablets were coated with a non-functional immediate release coating material. Tablet cores were coated with Opadry® II coating material using a perforated pan coater and a 48-inch pan. A 20% w/w coating solution was prepared by mixing Opadry® II with purified water. An excess of coating solution was prepared to ensure sufficient coating material is available for the coating process.

The tablet cores were loaded into the pan of the perforated pan coater (i.e., O'Hara Labcoat MX coating machine and 1×Schlick Model 930/7-1 S35 with 1.2 mm nozzle spray gun) and the coating process was initiated. The pan rotation speed (about 12 rpm) was monitored and maintained in the appropriate range to ensure the tablet cores flowed consistently throughout the coating process. Pan speed is a meaningful process parameter, as this can affect tablet appearance (too high a pan speed can damage the tablets). Tablet bed temperature is a meaningful process parameter, as this can affect tablet water content and protects the tablets from over-wetting (which causes tablet appearance defects). Exhaust air temperature is linked to tablet bed temperature and is a meaningful process parameter if tablet bed temperature is not recorded.

The supply air temperature of about 60 to 72° C. and an exhaust air temperature of about 45 to 55° C. was used to maintain tablet bed temperature at about 45 to 48° C. Supply and exhaust air temperatures were monitored throughout the coating step to maintain the bed temperature range of about 45 to 48° C. After the desired 4% weight gain was achieved, the pan speed and supply air temperature were reduced (to about 4 rpm and 45° C.) to ensure dry tablets. The heater was then turned off and tablets were further cooled while jogging the pan. Tablet weight gain (target 4% gain) and appearance were checked periodically during the tablet coating process as in-process controls. The in-process tests conducted during the coating process are shown below in Table 9.

TABLE 9

In-Process Tests for Coating Process

| In-process Test | 5 mg OCA Tablets | 10 mg OCA Tablets Acceptance Criteria | 25 mg OCA Tablets |
|---|---|---|---|
| Appearance | Off-white to yellow, round tablets with 5 debossed on one side and INT on the other side | Off-white to yellow, triangular tablets with 10 debossed on one side and INT on the other side | Off-white to yellow, oval tablets with 25 debossed on one side and INT on the other side |
| Tablet weight gain | 3.0% to 5.0% | 3.0% to 5.0% | 3.0% to 5.0% |

Packaging. Tablets were packaged in the commercial primary packaging configuration using a standard automated bottling operation. The primary packaging configuration utilized a white high-density polyethylene bottle (40 cc) and child resistant cap with an induction seal. The commercial bottle will contain 30 OCA tablets. Tablet quantity, induction seal, cap torque, print quality, and appearance control testing was conducted at specific intervals throughout the packaging process. Induction sealing is a meaningful process parameter in the packaging process providing a completely sealed bottle. The in-process testing parameters for the packaging process is provided in Table 10 below.

TABLE 10

In-Process Tests for Packaging Process

| In-process Test | Acceptance Criteria |
|---|---|
| Tablet quantity | Correct tablet fill quantity (30 count) |
| Induction seal integrity | Totally sealed bottle |
| Cap torque test | 15 lb/in$^2$ to 25 lb/in$^2$ |
| Print quality | Print is present and correct |
| Appearance (AQL inspection) | Satisfactory |

AQL = Acceptable quality limit

Example 3: Dissolution Testing of Obeticholic Acid Film-Coated Tablets

Unmilled 5 mg tablet and 10 mg tablet formulations of OCA were observed to release the drug slowly. The formulation of the 5 mg and 10 mg tablets are shown below in Table 11.

TABLE 11

5 mg, 10 mg, and 25 mg film-coated tablets formulations

| Material | mg/tablet | | |
|---|---|---|---|
| | 5 mg | 10 mg | 25 mg |
| Intragranular | | | |
| OCA Drug Substance [a] | 5.0 | 10.0 | 25.0 |
| Microcrystalline Cellulose [a] | 81.0 | 106.0 | 157.0 |
| Sodium Starch Glycolate | 8.0 | 8.0 | 8.0 |
| Colloidal Silicon Dioxide | — | — | 2.0 |
| Magnesium Stearate | 1.0 | 1.0 | 1.0 |
| Granule Mass | 95.0 | 125.0 | 193.0 |
| Ratio of Microcrystalline Cellulose to OCA | about 16:1 | about 11:1 | about 6:1 |
| Extragranular | | | |
| Microcrystalline Cellulose | 100.0 | 70.0 | — |
| Sodium Starch Glycolate | 4.0 | 4.0 | 4.0 |
| Colloidal Silicon Dioxide | — | — | 2.0 |
| Magnesium Stearate | 1.0 | 1.0 | 1.0 |
| Final Blend/Tablet Core | 200.0 | 200.0 | 200.0 |
| Tablet Coating | | | |
| Opadry II Coating Material | 8.0 | 8.0 | 8.0 |
| Coated Tablet | 208.0 | 208.0 | 208.0 |

[a] OCA quantity presented assumes drug substance is anhydrous and 100% pure; actual amount is adjusted based on potency of the drug substance lot used, and amount of microcrystalline cellulose is correspondingly decreased.

Upon testing, the tablets containing unmilled OCA demonstrated a slow dissolution release profile. For the dissolution method, both RI and Corona detectors were initially evaluated for analysis of the dissolution media. Considering the need to quantify OCA (INT-747) at levels as low as 10% of a 5 mg strength tablet dissolved in the dissolution media (1 µg/mL), the Corona CAD detector was chosen for the dissolution tests because it has a better sensitivity to OCA than the RI detector.

Tablet dissolution for both the 5 mg and 10 mg tablets was conducted in 900 mL of 50 mM Disodium Hydrogen Phosphate Buffer ($Na_2HPO_4$), pH 6.8 at 37° C. using USP II paddle apparatus at a paddle speed of 75 rpm. Samples were assayed undiluted by filtering through a 0.2 µm PVDF syringe filter using a gradient RP-HPLC method with CAD detection. This method utilized an Agilent Zorbax SB-C18 4.6 mm×150 mm, 3.5 µm HPLC column. A 50 µL sample was separated by a 20 minute gradient program, at a temperature of 40° C. and a flow rate of 1.5 mL per minute. Two mobile phases were used in the program; one consisted of a degassed Acidified Water pH 3.0/Acetonitrile (45:55) mixture and the other degassed Acetonitrile. The OCA drug substance eluted with an approximate retention time of 10 minutes.

The dissolution methodology is summarized below in Table 12.

TABLE 12

Parameters for the obeticholic acid 5 mg and 10 mg tablet dissolution method.

| Parameter | Value |
|---|---|
| Apparatus | USP Apparatus II (paddles) |
| Dissolution Media | 50 mM sodium phosphate dibasic buffer, pH 6.8 |
| Dissolution Volume | 900 mL |
| Rotation Speed | 75 rpm |
| Temperature | 37° C. ± 0.5° C. |

TABLE 12-continued

Parameters for the obeticholic acid 5 mg and 10 mg tablet dissolution method.

| Parameter | Value |
| --- | --- |
| Sample Volume | 10 mL with medium replacement |
| Sample Pull Times | 10, 15, 30, 45, 60 minutes |
| Sample Analysis | HPLC/Corona CAD |

Abbreviations:
HPLC = high performance liquid chromatography;
rpm = revolutions per minute;
USP = United States Pharmacopeia;
CAD = charged aerosol detector Obeticholic acid was comilled with a 0.61 mm screen or jet-milled as described above to reduce the particle size of the material. Jet-milling (i.e., micronization) resulted in material that had a smaller, more uniform particle size and increased surface area, leading to faster drug release from tablets containing jet-milled OCA. The dissolution release rate of tablets containing comilled and jet-milled OCA is shown below in Table 13.

TABLE 13

Dissolution release rates of comilled and jet-milled OCA

| Dissolution time (min) | 5 mg tablets containing comilled OCA Dissolution rate (%) | 10 mg tablets containing comilled OCA Dissolution rate (%) | 5 mg tablets containing Jet-milled OCA Dissolution rate (%) |
| --- | --- | --- | --- |
| 15 | 42 | 51 | 83 |
| 30 | 57 | 66 | 89 |
| 45 | 68 | 79 | 91 |
| 60 | 77 | 85 | 94 |
| 75 | 89 | 92 | 95 |

Table 13 shows that reduction in particle size of the OCA drug product improves elution properties.

Figure 3:
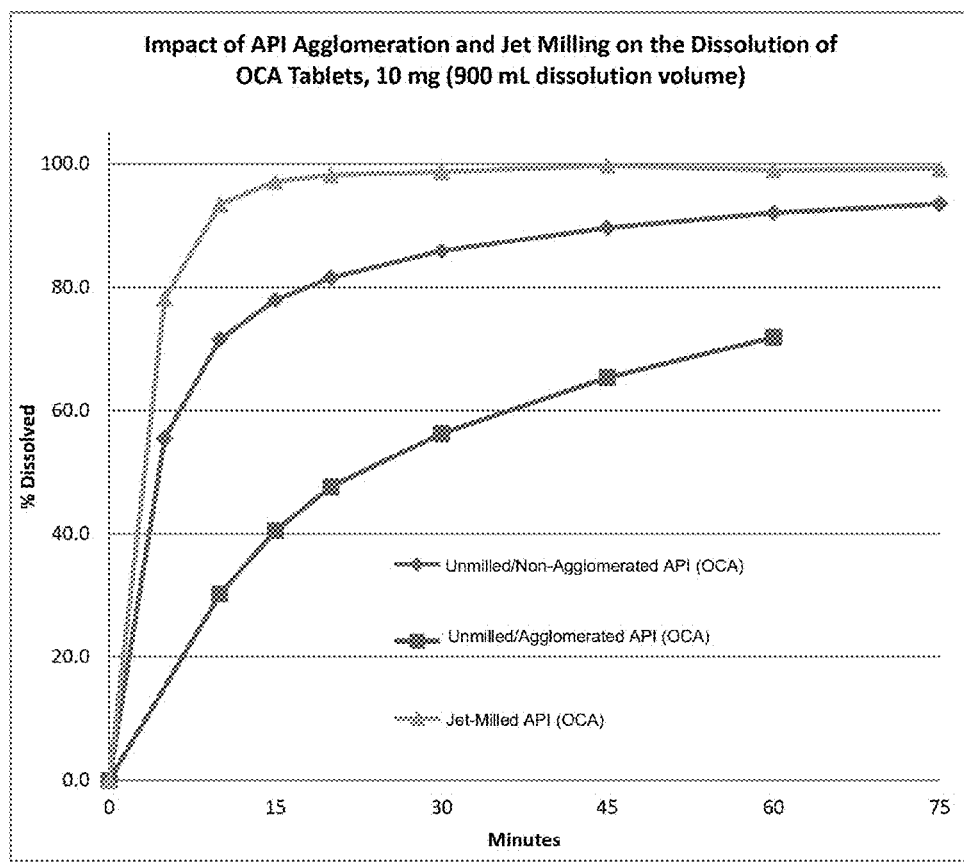
FIG. 3 is a graph showing the dissolution profile of 10 mg tablets containing unmilled/non-agglomerated, unmilled/agglomerated, or jet-milled obeticholic acid.
Figure 4:
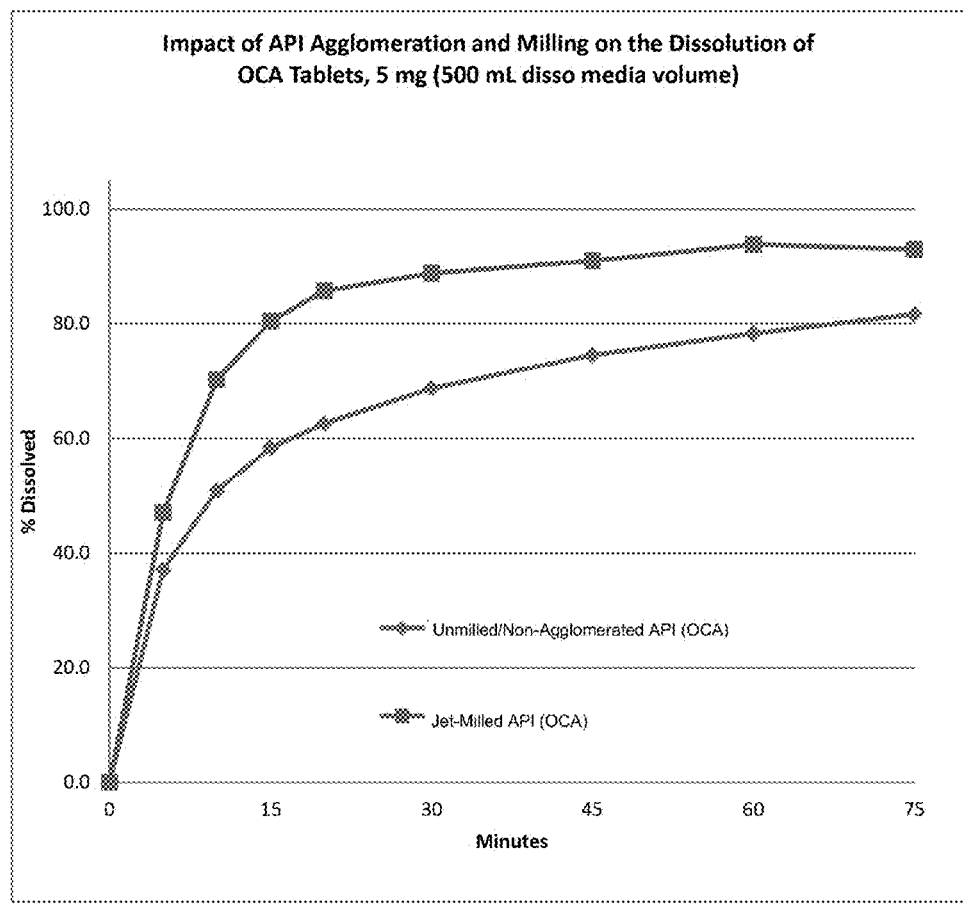
FIG. 4 is a graph showing the dissolution profile of 5 mg tablets containing unmilled or jet-milled obeticholic acid.

As shown in FIG. 3 and FIG. 4, the particle size distribution of the OCA impacted the drug dissolution rate, even in media where OCA is freely soluble (pH 6.8). It is therefore possible that differences in particle size could impact OCA bioavailability if dissolution becomes rate-limiting for absorption. For this reason, the particle size distribution of the active is considered a critical process parameter.

The dissolution profiles of 10 mg tablets containing either unmilled (a batch of unmilled OCA with smaller particle size; $D_{50}$>about 100 µM), unmilled/agglomerated, or jet-milled OCA is compared in FIG. 3.

Drug release was compared for 5 mg tablets containing unmilled (agglomerated) and jet-milled OCA. The difference in release profiles was more dramatic for the 5 mg tablets than the 10 mg tablets. This is likely due to coning effects in the smaller dissolution volume of 500 mL which may have contributed to the slower/incomplete dissolution due to the non-favorable hydrodynamics in the test vessel. The dissolution profiles of 5 mg tablets containing either unmilled/agglomerated, or jet-milled OCA is compared in FIG. 4.

Example 4: Content Uniformity Testing of Obeticholic Acid Tablets

The content uniformity of 5 mg and 10 mg tablets containing comilled OCA and jet-milled OCA was evaluated by RP-HPLC. The results are shown below in Table 14.

TABLE 14

Content uniformity of 5 mg and 10 mg tablets of unmilled, comilled and jet-milled OCA

| | 5 mg tablets containing comilled OCA | 10 mg tablets containing comilled OCA | 5 mg tablets containing jet-milled OCA |
| --- | --- | --- | --- |
| Content Uniformity (%) | 104 (AV = 18, 89.0%-110.6%) | 104 (AV = 14, 97.4%-111.5%) | 105.2 (AV = 8, 101.4%-109.2%) |

The results in Table 14 show the content uniformity data for tablets containing comilled and jet-milled OCA. Tablets containing comilled OCA showed a higher variability in content uniformity. The smaller particle size of the jet-milled material provides better content uniformity of the OCA tablets.

Example 5: Stability Studies of 5 mg and 25 mg Obeticholic Acid Tablets

The stability of 5 mg and 25 mg tablets were tested in accelerated stability studies. The stability test was conducted at 40° C. and 75 relative humidity (RH) for 6 months. The formulation of the 5 mg and 25 mg tablets are shown above in Table 11.

5 mg and 25 mg OCA tablets were placed on stability at the 40° C./75% RH storage conditions. Samples stored at the accelerated condition were pulled from storage at 1, 2, 3, and 6 months for assessment of stability. The tests performed for stability evaluations include appearance, assay for OCA by HPLC, and related substances by HPLC Corona.

Obeticholic acid and formulations of obeticholic acid were tested for stability. An unknown impurity at relative retention time (RRT) 1.75 was observed during stability studies of the tablets containing different batches of the 5 mg and 25 mg tablet formulation. The stability test using uncoated tablets showed an increase of a new impurity at about 0.05% with the test conducted at 25° C., 60% RH for 4 weeks, and about 0.2% with the test conducted at 40° C., 75% RH for 4 weeks. A study was conducted to identify the structure of the impurity, clarify the origin for the generation of the impurity, and adopt measures to ensure that quality was not compromised during storage of the tablet. The structure of OCA and the identified structure of the impurity are respectively shown below:

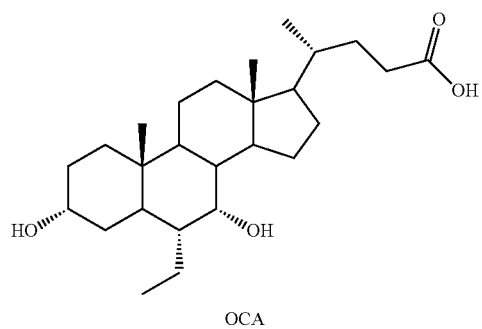

OCA

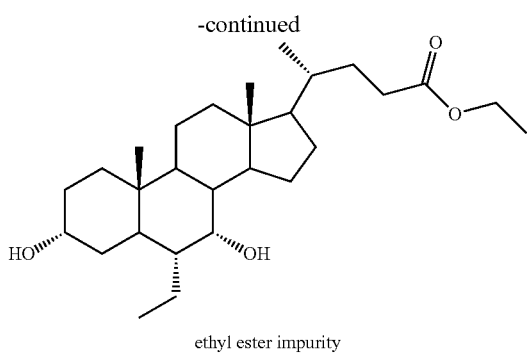

ethyl ester impurity

An analysis was conducted with LC/HRMS using LTQ-Orbitrap Discovery. The LC/HRMS Test conditions used are outlined in Table 15 below:

TABLE 15

LC/HRMS conditions for identifying impurities found in OCA after stability testing

| Equipment: | [HPLC] | Shimadzu prominence (LC-20A series) |
| | [MS] | Thermo Fisher Scientific LTQ Orbitrap Discovery |
| Ionization method: | ESI | (negative and positive mode) |
| HPLC conditions: | [Column] | Phenomenex, Kinetex C-18, 2.6 μm, 4.6 mm I.D. × 100 mm |
| | [Mobile phase] | A: AcOH aqueous solution*[1] containing 15% MeOH B: MeCN containing 15% MeOH |

| Gradient conditions. | |
| --- | --- |
| Time (min.) | B (%). |
| 0.0 → 25.0 | 40 → 65 |
| 25.0 → 35.0 | 65 → 95 |
| 35.0 → 50.0 | 95 |
| 50.0 → 50.1 | 95 → 40 |
| 50.1 → 60.0 | 40 |
| 60.1 | stop |

| | [Measurement time] | 60 min |
| | [Detection] | Total Ion Current Chromatogram (TICC) |
| | [Flow rate] | 1.0 mL/min. |
| | [Column temperature] | Approximately 40° C. |
| | [Sample drug product solvent] | Mobile phase B |
| | [Injection] | 5 μl |
| Sample*[2] | | OCA drug product (product stored for 4 weeks at 60° C.) solution (OCA concentration 500 μg/mL) *[3] Drug product placebo solution (prepared in the same way as (1)) Impurity 1-5 and OCA mixed solution (5 μg/mL each) OCA powder (5000 rpm) OCA unground product OCA drug product (stored at 50° C., 85% RH for 4 weeks) solution |

Figure 7A:
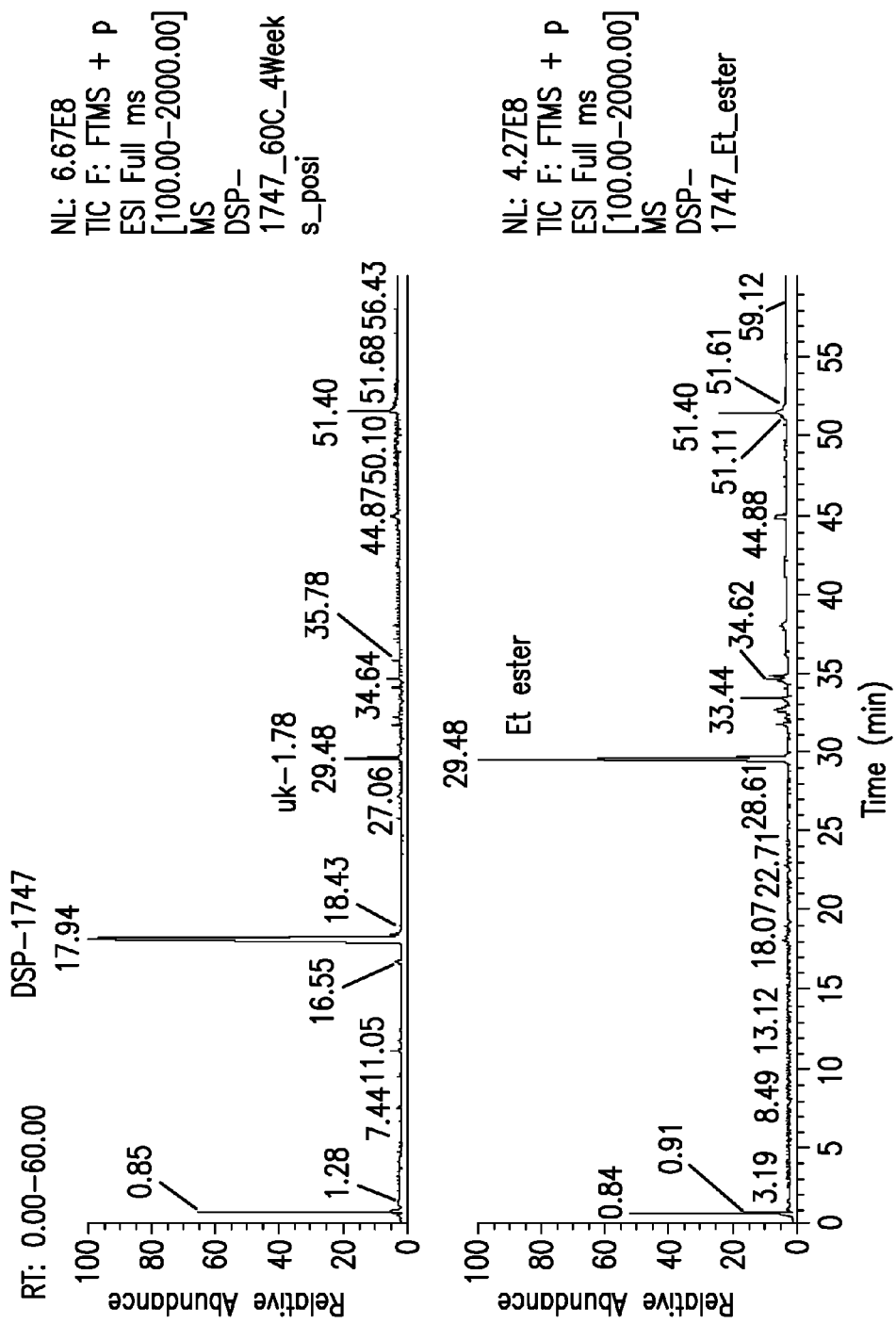
FIG. 7A shows the LC/HRMS spectrum in the positive mode of a sample of obeticholic acid OCA and the synthesized ethyl ester of obeticholic acid OCA.

Based on the results, it was determined that the impurity is an ethyl ester of obeticholic acid (OCA). Subsequently, an authentic sample of the ethyl ester was synthesized by dissolving obeticholic acid in ethanol, adding concentrated sulfuric acid and heating the mixture. The retention time and mass spectrometry of the authentic sample matched those of the impurity and thus the structure of the impurity was confirmed as an ethyl ester of obeticholic acid (FIG. 7A and FIG. 7B). Comparison of the retention time and the mass spectrum of the ethy ester impurity and authentic sample is shown in FIG. 7A and FIG. 7B.

Bottom row: TICC of ethyl ester (positive mode)

The structure of the ethyl ester impurity (shown above) was determined through mass spectrometry analysis combined with analysis of OCA fragmentation, and was confirmed by mass spectrometry analysis of synthesized OCA ethyl ester (the above authentic sample having the same retention time as the ethyl ester impurity).

Since the ethyl ester impurity can be formed in the presence of ethanol, the formulation was examined to determine if any excipient could be a possible source of the ethanol. It was found that sodium starch glycolate from two different manufacturers, sodium starch glycolate (Glycolys®) from Roquette Pharma containing no more than 6% ethanol and sodium starch glycolate (Explotab®) from JRS Pharma containing no more than 3% ethanol, were used to make the tablet formulations. A comparison of accelerated stability data at 40° C./75% RH of batches are shown below in Table 16.

TABLE 16

OCA Ethyl Ester Impurity (RRT 1.75) Content in Accelerated (40° C./75% RH) Stability Studies

| Lot Number (Manufacturer) | Time 0 | 1 Month | 3 Months | 6 Months |
| --- | --- | --- | --- | --- |
| DNSY, 5 mg Patheon (Explotab ®) | ND | ND | ND | ND |
| DNSZ, 25 mg Patheon (Explotab ®) | ND | ND | ND | ND |
| PDS0048-03, 5 mg Piramal (Glycolys ®) | ND | NT | 0.35% | 0.44% |
| PDS0048-10, 25 mg Piramal (Glycolys ®) | ND | NT | 0.17% | 0.25% |

ND = Not detected;
NT = Not tested

The results in Table 16 show that the ethyl ester impurity is not observed after 6 months in samples containing low ethanol sodium starch glycolate (i.e., Explotab®). However, the ethyl ester impurity in samples containing high ethanol sodium starch glycolate (i.e., Glycolys®) was observed as early as three months into the stability study. This data indicates that the ethanol content of the sodium starch glycolate is critical to the stability of the OCA formulation.

Stability Testing of Film Coated Tablets. Furthermore, in the film coated tablet stability test an increase in a specific impurity was confirmed at a rate of approximately 0.09% with the test conducted at 40° C., 75% RH for 4 weeks. Given that the generation of this impurity only occurred in film coated tablets, it was surmised that the impurity was a reactant with a film coating component. Also, based on the structure of ethyl ester impurity it is known that the carboxylic acid of OCA reacted easily with alcohol. Of the film coating components, it was possible that 2 components, polyvinyl alcohol (PVA) and polyethylene glycol (PEG) 4000 could be the cause of the impurity.

Subsequently, when a blending combination change test was conducted the specific impurity was generated and it was discovered that PEG4000 was the cause. Therefore, it was estimated that the structure of this impurity was an ester produced by a reaction between a PEG4000 hydroxyl group and the OCA carboxylic acid. The structure of OCA and PEG ester impurity are shown below:

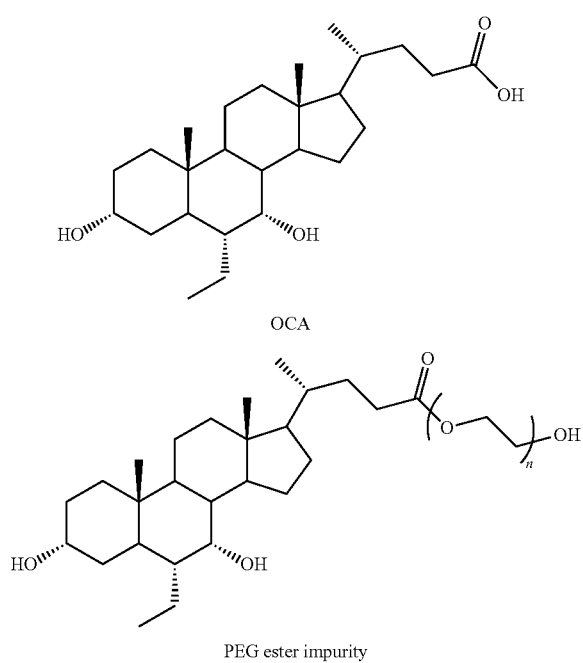

PEG ester impurity

Figure 8A:
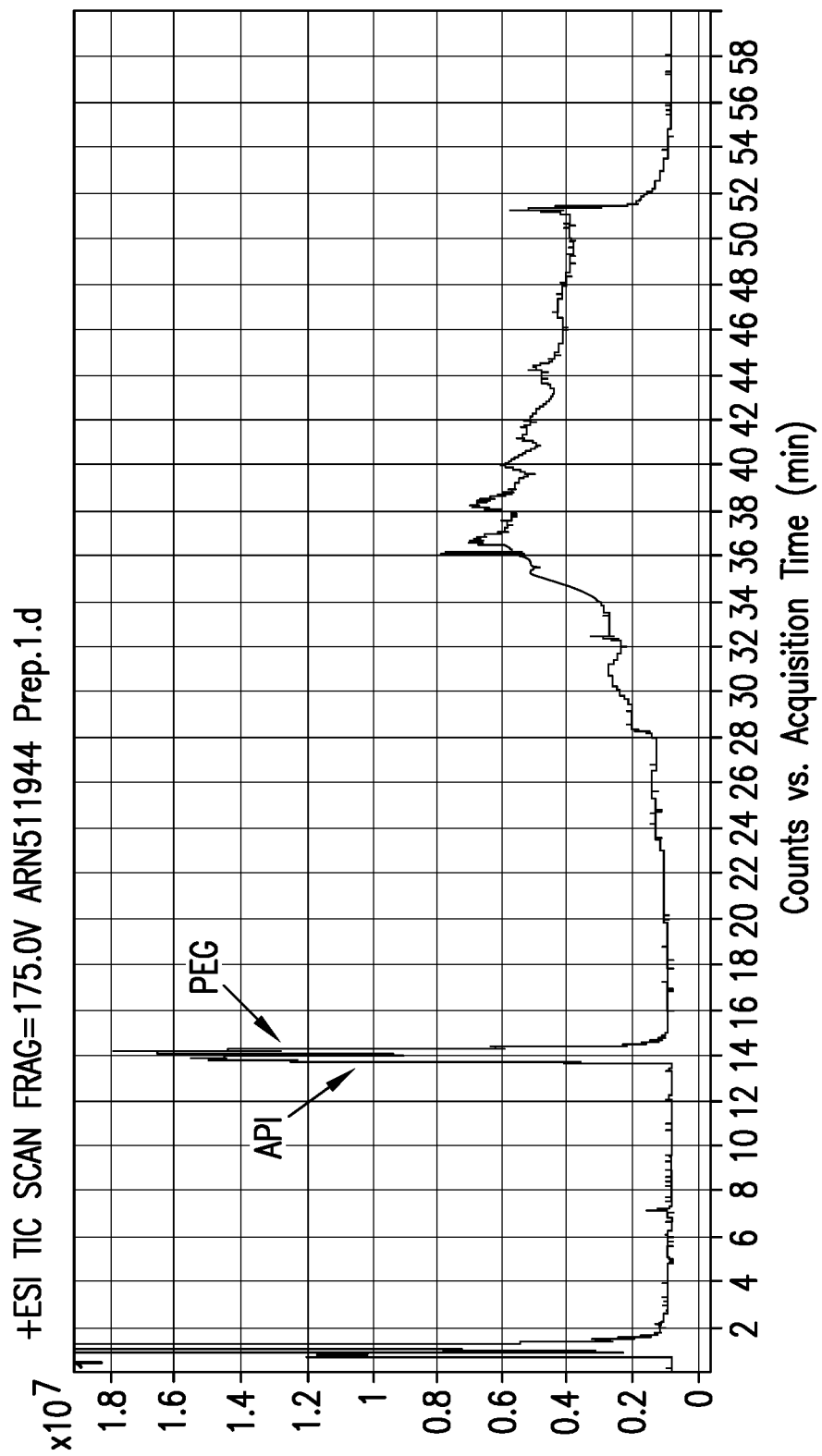
FIG. 8A shows the total ion count (TIC) chromatogram in the positive ion mode acquired on Q-TOF LC/MS of a sample of obeticholic acid OCA containing the PEG impurity.
Figure 8B:
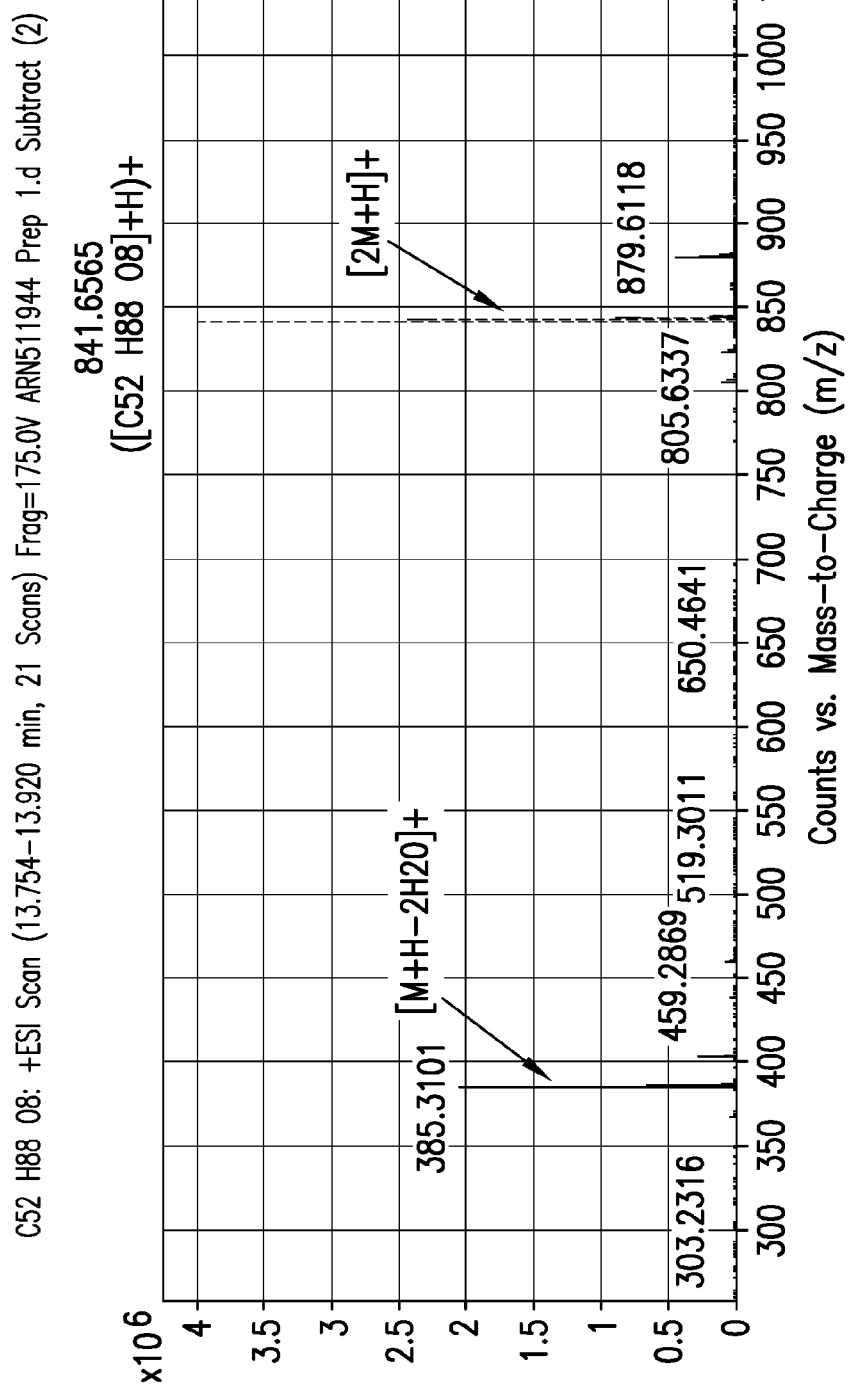
FIG. 8B shows the mass spectra in the positive mode acquired on Q-TOF LC/MS of a sample of obeticholic acid OCA containing the PEG impurity.
Figure 8C:
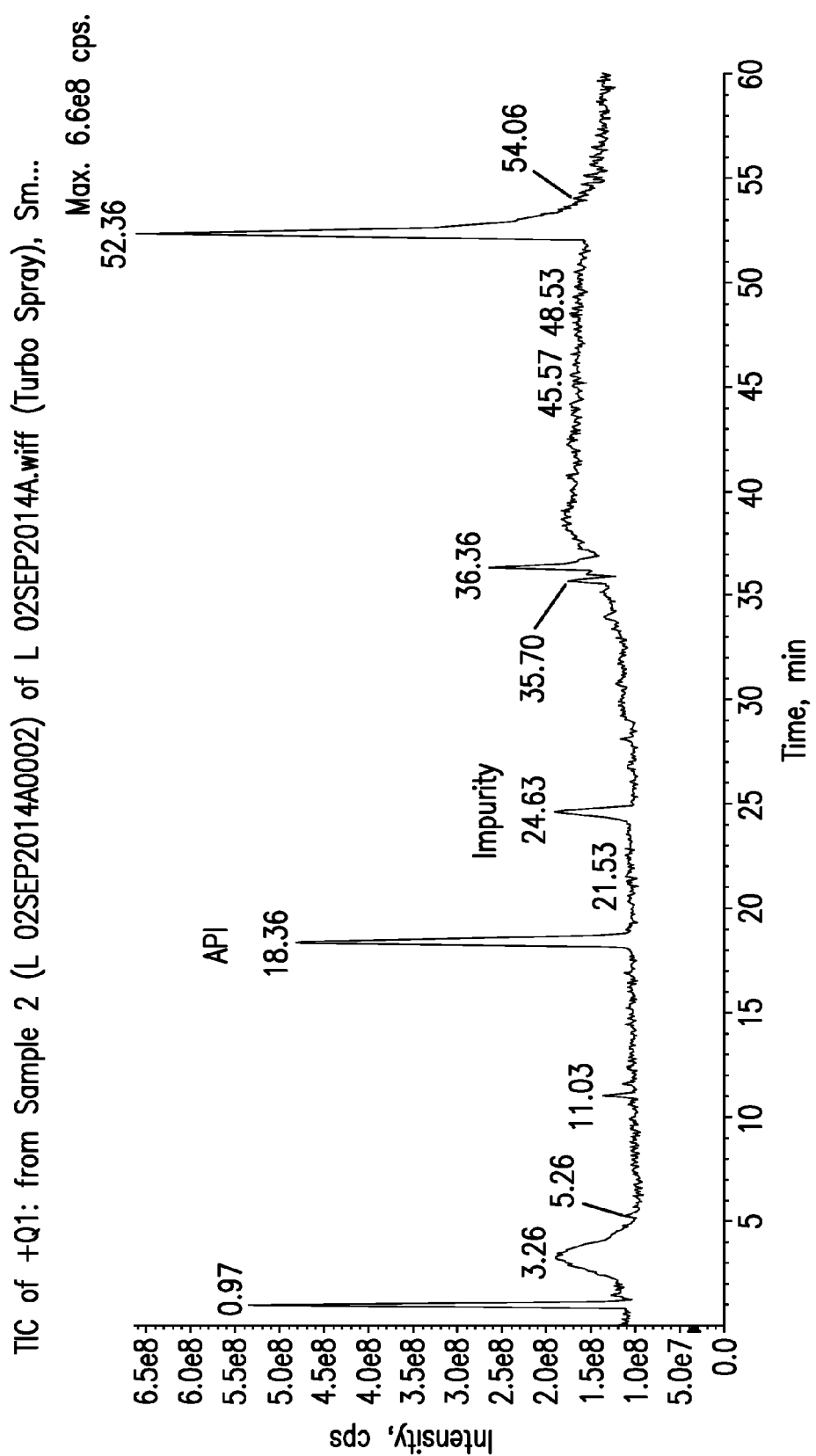
FIG. 8C shows the total ion count (TIC) chromatogram acquired on triple quad (QQQ) mass spectrometer of a sample of obeticholic acid OCA containing the PEG impurity.
Figure 9:
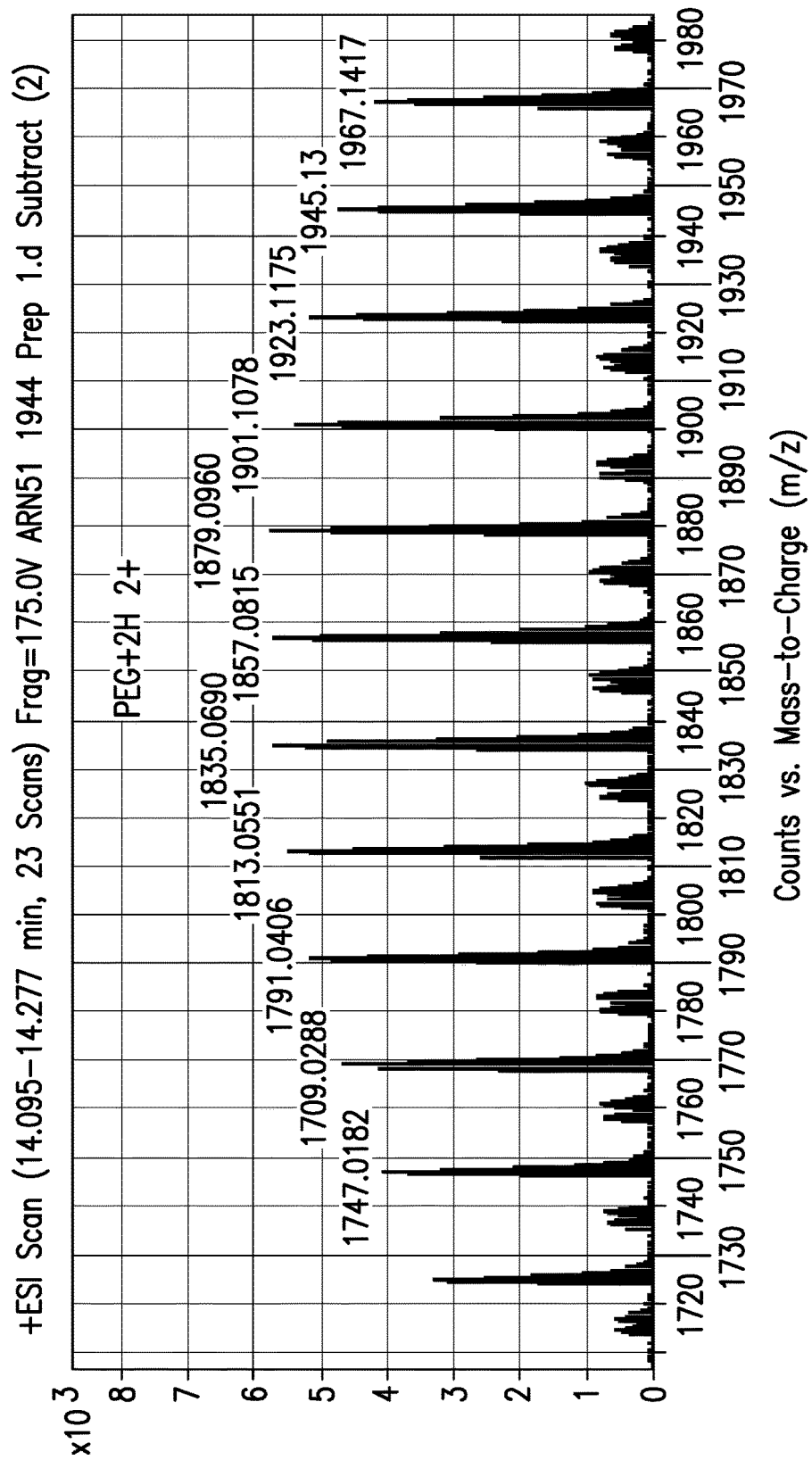
FIG. 9 shows an enlarged spectrum of the co-eluting peaks containing obeticholic acid OCA and the PEG impurity displaying spacing characteristics of PEG.

High resolution mass spectrometry (HRMS) was conducted to confirm the structure. The mean molecular weight of PEG ester impurity was expected to exceed 4000. micrO-TOF-QII (Bruker Daltonics) was used to measure high molecular weight compounds. When measured with the APCI technique in positive mode, an m/z was obtained that supported the structure of PEG ester impurity shown above. (FIGS. 8A, 8B, and 8C). Enlargement of the mass spectrum of a sample containing the specific impurity showed peak spacing characteristic of PEG (FIG. 9).

The LC/HRMS Test conditions used are outlined in Table 17 below:

TABLE 17

LC/HRMS test conditions for the identification of the impurity found in film coated OCA tablets after stability testing.

| Equipment: | [HPLC] | Agilent 1200 |
| | [MS] | micrOTOF-QII (Bruker Daltonics) |
| Ionization method: | APCI | positive mode |
| HPLC conditions: | [Column] | Phenomenex, Kinetex C-18, 2.6 µm, 4.6 mm I.D. × 100 mm |
| | [Mobile phase] | A: AcOH aqueous solution*[2] containing 15% MeOH<br>B: MeCN containing 15% MeOH |

| Gradient conditions. | |
| --- | --- |
| Time (min.) | B (%). |
| 0.0 → 25.0 | 40 → 65 |
| 25.0 → 35.0 | 65 → 95 |
| 35.0 → 50.0 | 95 |
| 50.0 → 50.1 | 95 → 40 |
| 50.1 → 60.0 | 40 |
| 60.1 | stop. |

| [Measurement time] | 60 min |
| [Detection] | Total Ion Current Chromatogram (TICC) |

TABLE 17-continued

LC/HRMS test conditions for the identification of the impurity found in film coated OCA tablets after stability testing.

| | [Flow rate] | 1.0 mL/min. |
| | [Column temperature] | Approximately 40° C. |
| | [Sample drug product solvent] | Mobile phase B |
| | [Injection] | 5 µl |
| Sample | | OCA film coated tablet (product stored for 4 weeks at 60° C.) extract solution*[3] |

*[2] pH 3.0
*[3] The 500 µl sample prepared was concentrated to dryness under a stream of nitrogen, dissolved in 50 µl of mobile phase B and used as the sample (OCA concentration: 5 mg/mL).

The extract from the film coated tablets was measured using the APCI technique in positive mode. Analysis of the retention time, the mass spectra, and the m/z value confirmed the structure of PEG ester impurity (shown above and in FIGS. 8A, 8B, and 8C).

Example 6: Solubility Studies of OCA in Various Buffers and Biological Media

Solubility Studies of OCA in Various Buffers. A study was performed to screen different media of various pH over the pH range 1.2-10.0, incorporating the physiological pH range (1.2-6.8) for immediate release tablets. The solubility of OCA was measured at 37° C. in various buffers from pH 1.2 to 10.0. The equilibrium solubility results for OCA in various aqueous buffer solutions are presented in Table 18 below.

TABLE 18

Equilibrium solubility and recovery for OCA at 37° C. in various buffers from pH 1.2 to 10.0

| pH, Media (Buffer) | Solubility (mg/mL) | % Recovery | USP Solubility Rating |
| --- | --- | --- | --- |
| pH 1.2 Hydrochloric acid | N/A | <1 | Practically insoluble |
| pH 2.0 Hydrochloric acid | N/A | <1 | Practically insoluble |
| pH 3.0 Acid Phthalate | N/A | <1 | Practically insoluble |
| pH 4.1 Acetate | 0.003 | <1 | Slightly soluble |
| pH 5.1 Acetate | 0.023 | 5 | Sparingly soluble |
| pH 6.0 Phosphate | 0.050 | 10 | Soluble |
| pH 6.8 Phosphate[a] | 0.220 | 94 | Freely soluble |
| pH 7.0 Phosphate | 0.462 | 92 | Freely soluble |
| pH 8.0 Phosphate | 0.486 | 97 | Freely soluble |
| pH 9.0 Alkaline Borate | 0.462 | 92[b] | Freely soluble |
| pH 10.0 Alkaline Borate | 0.056 | 11[b] | Soluble |

[a] Dissolution media (50 mM sodium phosphate dibasic buffer, pH 6.8)
[b] Basic decomposition of drug substance suspected.

OCA is a weak acid ($pK_a=4.82$) and exhibits a pH-solubility profile consistent with that of a weak acid. As expected, the solubility of the free acid form is highest when deprotonated and lowest when protonated.

OCA drug substance was observed to precipitate out of solution in those acidic buffers in the pH range 1.2 to 3.0. Solutions at pH 4.1 to 6.0 also had some precipitation resulting in a cloudy solution. Solutions at pH 6.8 to 10 produced clear solutions. The recovery of OCA steadily diminishes at pH higher than 8.0, indicating basic decomposition of the drug substance.

The nominal concentration for dissolved 5 mg and 10 mg tablets in the typical dissolution volume of 900 mL is approximately 0.006 & 0.01 mg/mL, respectively. Above pH 6.8 the solubility is well above 0.01 mg/mL, the minimum concentration required to dissolve a 5 mg or 10 mg tablet in 900 mL of dissolution medium (i.e., sink conditions).

Figure 5:
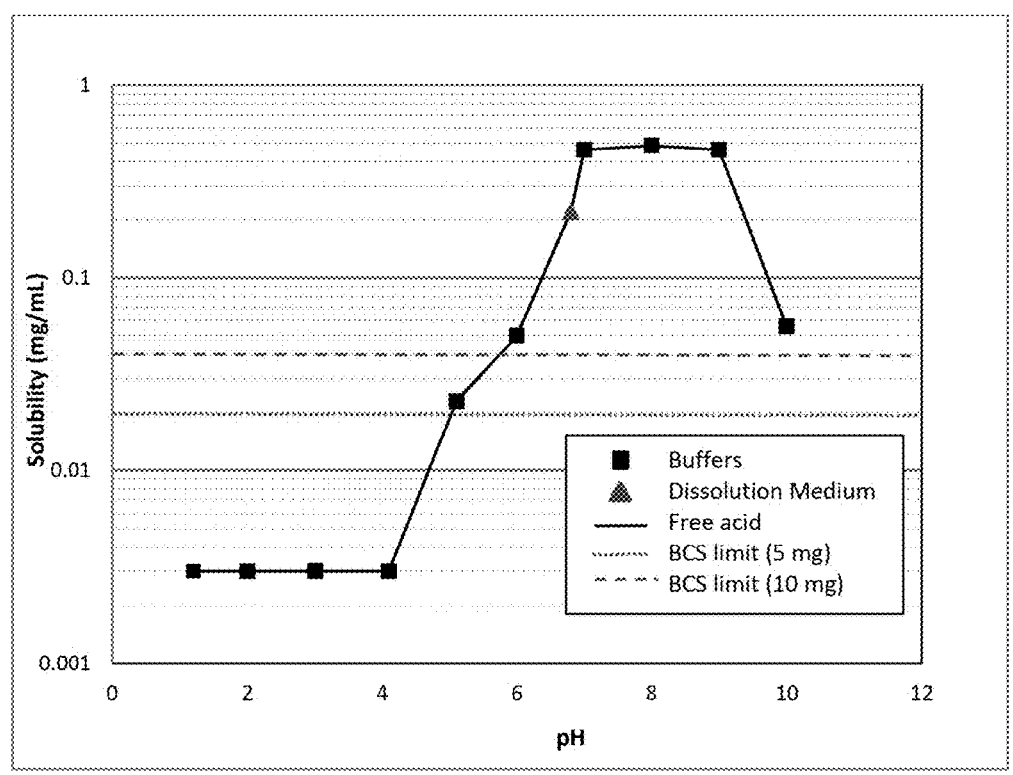
FIG. 5 is a graph showing solubility of obeticholic acid in various buffers at 37° C. over a pH range of about 1.2 to about 12. The dashed and dotted lines represent the Biopharmaceutical Classification System (BCS) limit for 5 mg and 10 mg doses, respectively (5 and 10 mg/250 mL)

As demonstrated in FIG. 5, solubility of OCA increases as a function of increasing pH, plateauing just above approximately pH 7. The dramatic increase in solubility observed between approximately pH 4 and pH 7 indicates that this pH region is less-than-ideal for use in the dissolution media. However, given that OCA is freely soluble at pH 6.8 and that this pH is physiologically relevant to the site of absorption, it was selected for use in diligent pursuit of a discriminating and relevant dissolution method.

Solubility Studies of OCA in Biological Media. A solubility study was performed in physiologically relevant dissolution media at 37° C. and pH of 1.2, 4.5, and 6.8 along with fasted state simulated gastric fluid (FaSSGF, pH 1.2), fed state simulated intestinal fluid (FeSSIF, pH 5.0) and fasted state simulated intestinal fluid (FaSSIF, pH 6.5). The solubility results for OCA in physiologically relevant buffers are presented in Table 19.

TABLE 19

Solubility of OCA in biologically relevant media at 37° C.

| pH (Medium) | Solubility (mg/mL) | USP Solubility Rating |
|---|---|---|
| 1.2 (0.1N HCl) | <LOQ | Practically insoluble |
| 1.2 (FaSSGF)[a] | <LOQ | Practically insoluble |
| 4.5 | <LOQ | Practically insoluble |
| 5.0 (FeSSIF)[b] | 0.82 | Freely soluble |
| 6.5 (FaSSIF)[c] | 0.64 | Freely soluble |
| 6.8[d] | 0.22 | Freely soluble |
| 6.8 with surfactant[e] | 0.59 | Freely soluble |

Figure 6:
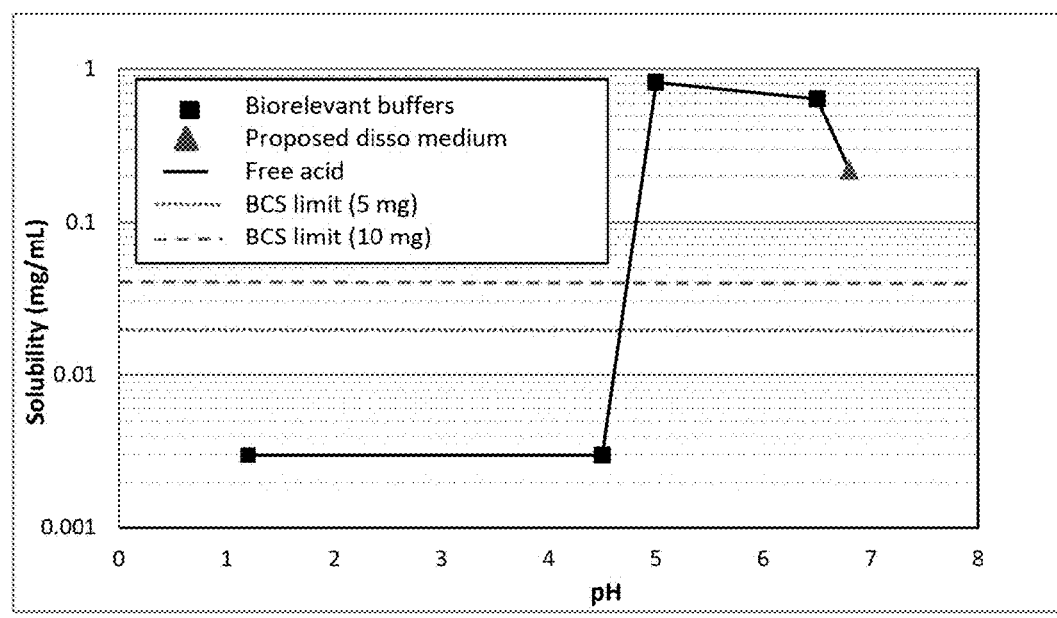
FIG. 6 is a graph showing obeticholic acid solubility in various biologically relevant buffers over a pH range of about 1.2 to about 12. The dashed and dotted lines represent the Biopharmaceutical Classification System (BCS) high-solubility limit for 5 mg and 10 mg doses, respectively (5 and 10 mg/250 mL).

[a]FaSSGF is de-ionized water containing sodium taurocholate (80 μM) and NaCl (34.2 mM), pH 1.6.
[b]FeSSIF is de-ionized water containing sodium taurocholate (15 mM) and lecithin (3.75 mM) with an osmolarity of 635 ± 10 mOsmol, pH 5.0.
[c]FaSSIF is de-ionized water containing sodium taurocholate (3 mM) and lecithin (0.75 mM) with an osmolarity of 270 ± 10 mOsmol, pH 6.5.
[d]Proposed dissolution medium; 0.5 mM sodium phosphate dibasic, pH 6.8.
[e]Surfactant is polysorbate 80 (Tween 80 ®)
Abbreviation:
USP = United States Pharmacopeia As shown in Table 19 and FIG. 6, from a Biopharmaceutical Classification System (BCS) perspective, OCA is poorly soluble below pH 4.5 and highly soluble above pH 5.0 in biologically relevant media. This provides further support and justification for selecting pH 6.8 phosphate buffer as the dissolution medium. A 35-fold increase in OCA solubility is evident at pH 5.0 in the presence of the taurocholate bile acid and lecithin emulsifier vs. pH 5.1 acetate buffer alone. This is likely due to the formation of highly soluble micelles in the presence of the amphipathic surfactant lecithin. One would expect similar solubility enhancement in vivo, as taurocholic acid and lecithin are typically present in the gastric and intestinal milieu.

Example 7

This example describes a study of two doses of OCA (10 mg and 50 mg) vs. placebo for a period of 12 weeks (85 days). The study was completed by 48 patients and PK data are available for 34 patients. All patients returned to the study site for 4 visits (Day 15, Day 29, Day 57, and Day 85) for evaluations of efficacy, safety, tolerability, and compliance with investigational product.

Key Inclusion criteria:
Age>18 years,
Both male and female had to use one effective method of contraception,
Proven or likely PBC demonstrated by patient presenting with at least 2 of the 3 diagnostic criteria
History of increased ALP
Positive AMA
Liver biopsy consistent with PBC
Screening ALP value between 1.5 and 10×ULN.
Key Exclusion Criteria
1. The following drugs were contraindicated: ursodeoxycholic acid (UDCA), colchicine, methotrexate, azathioprine, or systemic corticosteroids
2. Conjugated bilirubin>2×ULN; ALT or AST>5×ULN and serum creatinine>133 μmol/L (1.5 mg/dL)
3. History or presence of hepatic decompensation
4. History of presence of concomitant liver diseases such as Hepatitis B or C; HIV; primary sclerosing cholangitis, alcoholic liver disease, definite autoimmune liver disease or biopsy proven nonalcoholic steatohepatitis (NASH).

The percent change (%) in serum ALP from Baseline to End of Study (EOS) was monitored. The baseline value was the mean of the pretreatment screening and day 0 evaluations. The EOS value was Day 85/ET or the last observed ALP value on treatment.

Absolute changes in serum ALP levels were monitored from Baseline to Day 15, Day 29, Day 57, Day 85/ET and Follow-Up (Day 99). The percentage of patients was calculated who met the definition of PBC responder criteria applying the Paris I, Toronto I, Toronto II, Toronto III, Toronto IV, Mayo II, and Barcelona disease prognostic risk criteria at Day 85/ET. Each patient was tested for absolute and percent change in serum aspartate aminotransferase (AST), alanine aminotransferase (ALT), gamma-glutamyl transferase (GGT), and conjugated (direct) bilirubin values from Baseline to Day 15, Day 29, Day 57, Day 85/ET and Follow-Up (Day 99). Efficacy results are shown in Table 20 below.

TABLE 20

Percent Change in ALP from Baseline - ITT population.

| Percent Change | Placebo (n = 23) | OCA 10 mg (n = 20) | OCA 50 mg (n = 16) |
|---|---|---|---|
| Mean (SD) | 0.4 (15.3) | −44.5 (24.4) | −37.6 (21.0) |
| Median | −0.8 | −53.9 | −37.2 |
| p-value[a,b] | NA | <0.0001 | <0.0001 |

Reductions in GGT and ALT and AST. GGT levels decreased, relative to placebo, at all-time points from day 15 to Day 85/ET in both the OCA 10 mg and OCA 50 mg groups. In the ITT Population, the mean (SD) GGT levels decreased from 653 (370) U/L at baseline to 184 (203) U/L at Day 85/ET in the OCA 10 mg group, and from 455 (418) U/L at baseline to 202 (300) U/L at day 85/ET in the OCA 50 mg group. Placebo GGT levels were 466 (321) U/L at Baseline and 502 (383) U/L at Day 85/ET.

ALT levels decreased, relative to placebo, from baseline to Day 85/ET in both OCA 10 mg and OCA 50 mg groups. The mean (SD) ALT levels decreased from 86 (44) U/L at baseline to 54 (41) U/L at Day 85/ET in the OCA 10 mg group, and similarly decreased from 71 (38) U/L at baseline to 49 (29) U/L at Day 85/ET in the OCA 50 mg group. There was no change in the levels of ALT in the placebo group from baseline to Day 85/ET.

The mean (SD) AST levels at Day 85/ET were 54 (40) U/L and 56 (28) U/L in OCA 10 mg and OCA 50 mg groups compared to baseline levels of 67 (33) U/L and 66 (29) U/L, respectively. There was no change in the levels of AST in the placebo group from Baseline to Day 85/ET.

Changes in serum lipids were observed across all treatment groups including placebo, but the magnitude of HDL-C change was greater in the OCA treatment groups. Mean HDL-C levels decreased from 1.73 (0.45) mmol/L at baseline to 1.57 (0.46) mmol/L at the end of treatment (ET) in the OCA 10 mg arm. In the OCA 50 mg arm, the mean (SD) HDL-C decreased from 1.95 (0.55) mmol/L at baseline to 1.86 (0.56) mmol/L at ET. In the placebo arm the mean HDL-C decreased from 1.84 (0.52) mmol/L at baseline to 1.70 (0.44) mmol/L at ET. The effect of HDL-C lowering is not as prominent in the OCA 50 mg treatment group, perhaps due to a 44% dropout rate which occurred early in treatment (<1 month). At Day 85/ET, a mean change in LDL-C of −0.08 (0.43) mmol/L was observed in the placebo group compared to mean changes of +0.10 (0.58) mmol/L and +0.23 (0.52) mmol/L in the OCA 10 mg and OCA 50 mg groups, respectively.

Patients with early stage PBC demonstrated ALP reductions with OCA 10 mg and 50 mg monotherapy, which were greater than placebo (on average approximately 40% for each OCA dose vs. minimal change in placebo). The adverse events reported were consistent with the known safety profile of the drug, with pruritus and headache being the most frequent AEs reported. Fatigue was reported infrequently.

TABLE 21

ALP Levels (U/L) at Baseline and Day 85/ET: ITT Population (N = 59).

| | Placebo (n = 23) | OCA 10 mg (n = 20) | OCA 50 mg (n = 16) |
|---|---|---|---|
| Baseline | | | |
| Mean (SD) | 408.4 (223.0) | 461.6 (298.7) | 431.1 (177.2) |
| Median | 320.5 | 366.3 | 379.0 |
| Day 85/ET | | | |
| Mean (SD) | 420.1 (253.5) | 228.1 (117.0) | 269.8 (158.9) |
| Median | 288.0 | 196.5 | 197.5 |
| Change from Baseline to Day 85/ET, Mean (SD) | 11.7 (63.0) | −233.5 (212.3) | −161.3 (129.7) |

Example 8

This example describes a study conducted using an international, multi-center, randomized, double-blind, placebo-controlled, multi-dose, parallel group to determine efficacy and safety of obeticholic acid (OCA) in combination with ursodeoxycholic acid (UDCA) in subjects with primary biliary cirrhosis.

Key Inclusion Criteria
Male or female age 18-75 years and on a stable dose of UDCA for at least 6 months prior to screening
Screening ALP level between 1.5× upper limit of normal (ULN) and 10×ULN
Proven or likely PBC, as demonstrated by the subject presenting with at least 2 of the following 3 diagnostic factors:
History of increased ALP levels for at least 6 months prior to Day 0
Positive antimitochondrial antibody (AMA) titer (>1:40 titer on immunofluorescence or M2 positive by enzyme-linked immunosorbent assay) or PBC-specific antinuclear antibodies (antinuclear dot and nuclear rim positive)
Liver biopsy consistent with PBC
Key Exclusion Criteria
Use of colchicine, methotrexate, azathioprine, or systemic corticosteroids
Screening conjugated (direct) bilirubin>2×ULN; ALT or AST>5×ULN; serum creatinine>1.5 mg/dL (133 μmol/L)
History or presence of hepatic decompensation (e.g., variceal bleeds, encephalopathy, or poorly controlled ascites)
History or presence of other concomitant liver diseases or human immunodeficiency virus (HIV) or other viral hepatitis infection
Clinically significant medical condition, and gastrointestinal conditions affecting drug ADME The percent change (%) in serum ALP from Baseline to End of Study (EOS) was tested where [EOS=Day 85 or last observed ALP value on treatment]

Also observed were the absolute and percent changes in serum ALP levels from Baseline to Day 15, Day 29, Day 57, Day 85/ET and Follow-Up (Day 99). Patients were examined for the absolute and percent change in serum gamma-glutamyl transferase (GGT), alanine aminotransferase (ALT), and aspartate aminotransferase (AST) values from Baseline to Day 15, Day 29, Day 57, Day 85/ET and Follow-Up (Day 99). Patients were examined for absolute and percent changes in serum albumin and conjugated (direct) bilirubin values from Baseline to Day 15, Day 29, Day 57, Day 85/ET and Follow-Up (Day 99). Patients' Enhanced liver fibrosis (ELF) score and change in levels of its components, hyaluronic acid, aminoterminal peptide of pro-collagen III, and tissue inhibitor of matrix metalloproteinase-1 from Baseline to Day 85/ET were performed. The absolute and percent changes in levels of C-reactive protein, non-esterified fatty acid, tumor necrosis factor alpha, tumor necrosis factor beta, tumor growth factor beta, bile acids, glutathione, immunoglobulin M, and osteopontin from Baseline to Day 85/ET were taken.

Bile acid analysis: Absolute and percent changes in the levels of total bile acids and OCA plasma concentrations, and their conjugates, from Baseline to Day 85/ET.

The absolute and percent change in fibroblast growth factor-19 (FGF-19) levels from Baseline to Day 85/ET were taken.

Figure 10:
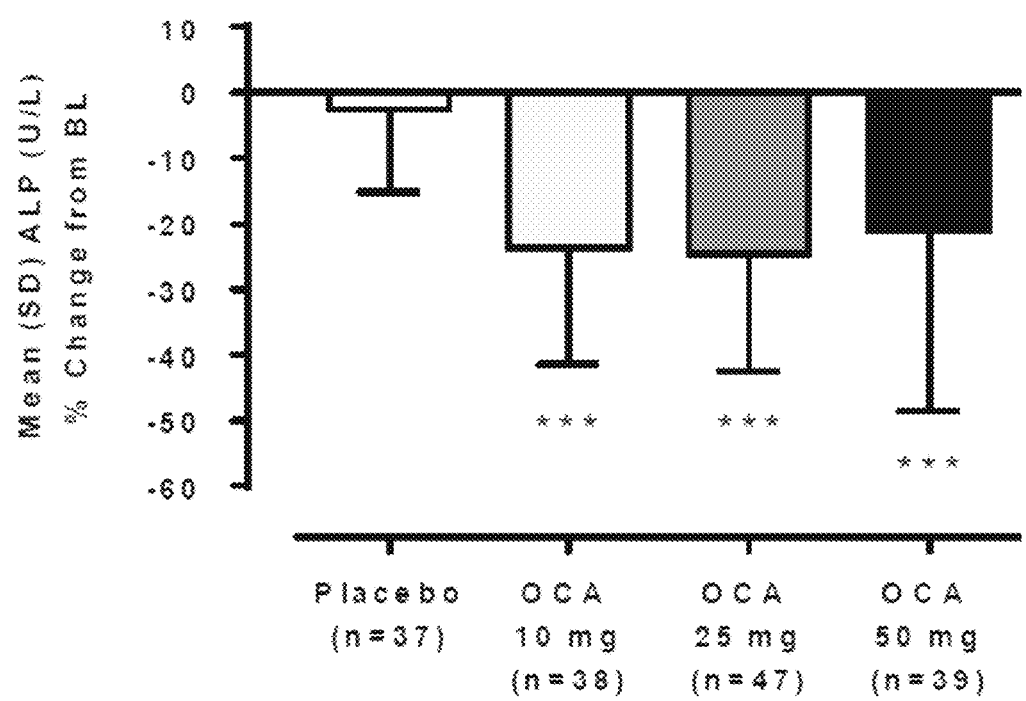
FIG. 10 illustrates the percent Change in ALP levels from Baseline to EOS: mITT Population (N=161).

Overall, 165 subjects (100%) received at least 1 dose of investigational product (ITT and Safety Populations) and 136 subjects comprised the Completer Population. One hundred sixty-one subjects (98%) were included for the analysis of the mITT Population as measured by the percent change in ALP from Baseline to EOS; the mITT Population for sensitivity analysis of the primary endpoint included 163 subjects. It should be noted that the mITT population was defined for the primary analysis as all patients randomized who received at least one dose of study medication and had at least one post-baseline ALP evaluation which was taken at most seven days after their last dose of study medication. (See FIG. 10). The mITT Population for the sensitivity analysis included ALP assessments obtained up to 15 days after the last investigational product use (unlike 7 days for primary endpoint). The number of subjects was balanced across all groups in all analysis populations with the exception of the Completer Population due to the higher proportion of discontinuations with OCA 50 mg.

TABLE 22

ALP (U/L) at Baseline to Day 85/ET: ITT Population (N = 165) and Completer Population (N = 136).

|  | Placebo | OCA 10 mg | OCA 25 mg | OCA 50 mg |
|---|---|---|---|---|
| ITT Population Baseline | (n = 38) | (n = 38) | (n = 48) | (n = 41) |
| Mean (SD) | 275.2 (102.7) | 294.4 (149.4) | 290.0 (123.6) | 289.5 (106.2) |
| Median | 249.5 | 234.8 | 255.8 | 262.5 |
| Day 85/ET |  |  |  |  |
| Mean (SD) | 270.7 (118.7) | 219.0 (113.5) | 225.0 (169.1) | 227.9 (115.9) |
| Median | 234.5 | 177.5 | 187.5 | 197.0 |
| Mean (SD) Change | −4.6 (34.9) | −75.4 (81.5) | −65.0 (91.3) | −62.9 (101.9) |
| Median Change | −6.3 | −47.5 | −69.3 | −56.5 |
| Mean (SD) Percent Change | −2.6 (12.4) | −23.3 (17.1) | −24.0 (18.8) | −20.0 (27.4) |
| Median Percent Change | −3.2 | −21.0 | −27.8 | −22.7 |
| P-value | NA | <0.0001 | <0.0001 | <0.0001 |
| Completer Population Baseline | (n = 37) | (n = 32) | (n = 42) | (n = 25) |
| Mean (SD) | 276.4 (103.8) | 298.6 (159.5) | 274.9 (80.2) | 279.3 (110.5) |
| Median | 250.0 | 234.8 | 255.8 | 236.5 |
| Day 85/ET |  |  |  |  |
| Mean (SD) | 272.1 (120.0) | 212.3 (120.2) | 199.0 (59.8) | 179.1 (63.6) |
| Median | 235.0 | 175.0 | 187.5 | 158.5 |
| Mean (SD) Change | −4.3 (35.3) | −86.3 (83.7) | −76.0 (48.8) | −101.8 (85.5) |
| Median Change | −6.0 | −61.3 | −71.3 | −76.0 |
| Mean (SD) Percent Change | −2.5 (12.6) | −26.7 (16.0) | −26.6 (14.7) | −32.5 (20.1) |
| Median Percent Change | −3.1 | −23.5 | −28.2 | −33.9 |

Example 9

This example describes a randomized, double-blind, placebo-controlled, parallel-group, 12-month trial evaluating OCA in patients with PBC as a monotherapy. The study was performed using a randomized, double-blind, placebo-controlled, parallel-group, in patients with PBC who either: (1) were on ursodeoxycholic acid (UDCA) for at least 12 months (and on stable dose for ≥3 months), or (2) were unable to tolerate UDCA, and did not receive UDCA for 3 months prior to Day 0.

Where all eligibility criteria (see below) were met, participants were stratified into one of four groups, i.e., two factors each with two sub-categories (specified in parentheses):

pre-treatment ALP≥3.0×ULN and/or aspartate aminotransferase (AST)≥2.0×ULN and/or TB ULN; ('no' for all three conditions, 'yes' to at least one of the three conditions)

intolerance to UDCA; ('no' hence UDCA usage for at least 12 months, with a stable dose for at least 3 months, prior to study start with the assumption of continued stable usage of UDCA throughout the study; 'yes' hence no UDCA usage for at least 3 months prior to study start with the assumption of continued non-usage of UDCA throughout the study).

Key Inclusion Criteria

Definite or probable PBC diagnosis as demonstrated by the presence of 2 of the following 3 diagnostic factors:

History of elevated ALP levels for at least 6 months

Positive anti-mitochondrial antibody (AMA) titer or if AMA negative or in low titer (<1:80) PBC specific antibodies (anti-GP210 and/or anti-SP100 and/or antibodies against the major M2 components [PDC-E2, 2-oxo-glutaric acid dehydrogenase complex])

Liver biopsy consistent with PBC

At least 1 of the following qualifying biochemistry values:

ALP≥1.67×ULN or

Total bilirubin>ULN but <2×ULN

Age≥18 years

Taking UDCA for at least 12 months (stable dose for ≥3 months) prior to Day 0, or unable to tolerate UDCA (no UDCA for ≥3 months) prior to Day 0.

Contraception: Female patients had to be postmenopausal, surgically sterile, or if premenopausal, had to use ≥1 effective (≤1% failure rate) method of contraception during the trial and for 30 days after the EOT Visit.

Key exclusion criteria

Any hepatic decompensation

Portal hypertension, cirrhosis and complications of cirrhosis/portal hypertension History of liver transplantation, current placement on a liver transplant list or current Model for End Stage Liver Disease (MELD) score≥15

Cirrhosis with complications, including history or presence of: spontaneous bacterial peritonitis, hepatocellular carcinoma, bilirubin>2×ULN Hepatorenal syndrome (type I or II) or Screening serum creatinine>2 mg/dL (178 μmol/L)

Competing etiology for liver disease (e.g., hepatitis C, active hepatitis B, nonalcoholic steatohepatitis (NASH), alcoholic liver disease (ALD), autoimmune hepatitis, primary sclerosing cholangitis, Gilbert's Syndrome)

Severe pruritus (Intense or widespread and interfering with activities of daily living) or pruritus requiring treatment with bile acid sequestrants, rifampicin within 2 months of day 0

On prohibited medications (such as fenofibrates, budesonide, corticosteroids, valproate, isoniazid etc.); please see the list of prohibited medications in protocol review.

Patients who had previously participated in a clinical trial of OCA were not allowed to participate Prolonged QT interval, pregnancy or lactation.

If female: known pregnancy, or had a positive urine pregnancy test (confirmed by a positive serum pregnancy test), or lactating Known history of human immunodeficiency virus infection Presence of any other disease or condition that was interfering with the absorption, distribution, metabolism, or excretion of drugs including bile salt metabolism in the intestine. Patients with inflammatory bowel disease or who had undergone gastric bypass procedures were excluded (gastric lap band was acceptable).

Medical conditions that could cause non-hepatic increases in ALP (e.g., Paget's disease)

One goal of the study was to demonstrate the efficacy of OCA, relative to placebo, based on its effects on ALP and TB. Other objectives included assessing safety, histological, bile acid, and biomarker (i.e., not including ALP and TB) parameters.

ALP and TB composite response criteria were measured; a patient was designated as a responder if all three of the following conditions were met:

A value of ALP<1.67×ULN

ALP reduction from baseline≥15%

A value of TB<ULN

The absolute and percent change from Baseline in ALP, gamma-glutamyl transferase (GGT), alanine aminotransferase (ALT), AST, total bilirubin, conjugated (direct) bilirubin, albumin, prothrombin time and international normalized ratio (INR) at all-time points was measured. The percentage of patients with a decrease in ALP of ≥10%, ≥15%, ≥20%, and ≥40% from Baseline or ≤ULN at month 12 was measured. The percentage of patients achieving the following biochemical response criteria was also measured:

ALP≤3×ULN and AST≤2×ULN and bilirubin≤ULN ((Corpechot 2008); Paris I)

ALP≤1.5×ULN and AST≤1.5×ULN and bilirubin ULN ((Corpechot≤2011), Paris II)

ALP≤1.67×ULN and bilirubin≤ULN ((Momah 2012), Mayo II)

ALP≤1.76×ULN ((Kumagi 2010b), Toronto II)

Normal bilirubin (values ULN) and/or normal albumin (values lower limit of normal [LLN]; (Kuiper 2009) [Rotterdam criteria])

The absolute change from Baseline for enhanced liver fibrosis (ELF) and hepatic stiffness (at select sites) as assessments of end stage liver failure. The absolute and percent change from Baseline on: C-reactive protein (CRP), tumor necrosis factor-alpha (TNF-α), tumor necrosis factor-beta (TGF-β), fibroblast growth factor-19 (FGF-19) levels, interleukin-6 (IL-6), and CK-18 was measured. The absolute and percent change from Baseline on PBC-40 domains was measured.

Absolute and percent change from Baseline on PBC autoantibodies (IgA, IgG, IgM) and interleukins (IL-12 [p40], IL-23) were measured.

Measuring the plasma OCA concentrations including OCA (unconjugated), conjugates (glyco-OCA and tauro-OCA), and total OCA (the sum of OCA unconjugated, glyco-OCA, and tauro-OCA).

Measuring the absolute change from Baseline for total bile acids, endogenous bile acids, and individual total and unconjugated bile acids (UDCA, deoxycholic acid, cholic acid and lithocholic acid), glyco-conjugate, and tauro-conjugate; proportion of each of the individual bile acids to total bile acids Bile acid sequestrant (BAS) concomitant exposure. The primary analysis set used for all efficacy analyses, along with the summarization of disposition along with demographics and baseline characteristics, was the Intent-to-Treat' (ITT) analysis set. This analysis set included all randomized patients who received at least one dose of blinded study drug. When utilizing this analysis set, patients were analyzed according to the treatment group that they were randomized to regardless of the actual treatment received. It should be noted that all but one randomized patient received at least one dose of blinded study drug.

For sensitivity analysis purposes, all efficacy analyses were repeated utilizing a 'Completer' analysis set. This analysis set was comprised of all ITT patients who participated through the end of the double-blind period (i.e., through the Month 12 visit). When utilizing this analysis set, patients were analyzed according to the treatment group that they were randomized to, regardless of the actual treatment received.

For additional sensitivity analysis purposes, all efficacy analyses were again repeated utilizing an 'Efficacy Evaluable' (EE) analysis set. This analysis set was comprised of all 'Completer' patients who did not have any major protocol deviations that would potentially affect the efficacy of the study drug. This analysis set definition was finalized in a blinded manner prior to database lock.

For population pharmacokinetic (PK) analysis purposes, the PK analysis set was utilized, which consisted of all patients who had at least 1 confirmed fasted analyzable sample at and who did not have any major protocol deviations that could potentially affect exposure levels.

To control the overall study-wise type I error rate, a step-down/closed sequential testing procedure was pre-specified to adjust for the multiple comparisons of the two OCA dose groups individually to placebo on the primary study endpoint alone. Starting with the 10 mg OCA comparison to placebo on the primary endpoint, the step-down could only be carried to the OCA Titration comparison to placebo (on the primary endpoint), if and only if the 10 mg OCA comparison to placebo was found to be statistically significant (i.e., p-value less than 0.05). If the 10 mg OCA comparison to placebo was not statistically significant (i.e., p-value greater than or equal to 0.05), then the hypothesis test for the OCA Titration comparison to placebo on the primary endpoint would be deemed as exploratory.

This pre-specified multiplicity adjustment procedure was narrow in scope in that it only pertained to the individual OCA dose comparisons with placebo on the primary endpoint alone. Hence even if both OCA dose comparisons were found to be statistically significant, then any other hypothesis test would still be deemed as exploratory in nature.

A Cochran-Mantel-Haenszel (CMH) test which adjusted for both randomization stratification variables as described above, was used for pre-specified analysis. In tandem with the CMH test, a Breslow-Day test was also conducted, to test for the homogeneity of the treatment effect across the 5 different randomization strata.

The PK population was used to summarize OCA and bile acid concentrations. The change from Baseline concentrations within each treatment group was compared using a paired t-test. Descriptive statistics of OCA plasma concentrations and the extent of BAS concomitant exposure were provided by treatment group. Initial evaluation of the effects of BAS on OCA, total bile acid concentrations, and ALP was performed using a correlation analysis.

It can be observed from Table 23 that both OCA treatment groups showed a superior difference in the proportion/percentage of patients achieving response at Month 12 when individually compared to placebo using the CMH test. The corresponding Breslow-Day test result shows that the treatment effects were homogeneous across the different randomization strata. This analysis was repeated utilizing the Completer and EE analysis sets and the conclusions were consistent. The ultra-worse-case imputation strategy, implemented by the FDA statistical reviewer as described above, did not impact the study conclusions. In regards to ALP or TB values at Month 12, there were no patients who were designated as outliers (i.e., by having studentized residual values greater than three), and there was no impact on study conclusions between corrected laboratory values (as presented) and original (i.e., uncorrected) laboratory values. All of the previously presented analyses were re-conducted utilizing a baseline value that was the median of all pre-first dose measurements, and, separately, a traditional baseline definition (both approaches as described above); there was no impact on study conclusions with either approach. Considering the pre-specified step-down/closed sequential testing procedure as previously described, formal hypothesis testing is stopped at this point. Any subsequent inferential statistic reported below should be considered exploratory

TABLE 23

Proportion of Patients who Achieved Response

| Statistics | 10 mg OCA (N = 73) | OCA Titration (N = 70) | Placebo (N = 73) |
|---|---|---|---|
| Response at Month 6 - n (|%) [1] | 37 (50.7%) | 24 (34.3%) | 5 (6.9%) |
| Corresponding 95% Wald CI | 39.2%, 62.2% | 23.2%, 45.4% | 1.1%, 12.6% |
| Response at Month 12 - n (%) [1] | 34 (46.6%) | 32 (45.7%) | 7 (9.6%) |
| Corresponding 95% Wald CI | 36.5%, 59.4% | 34.0%, 57.4% | 2.8%, 16.3% |
| CMH Test p-value [2] | <0.0001 | <0.0001 | |
| Corresponding Breslow-Day Test p-value | 0.9072 | 0.5045 | |

It can be observed from Table 24 that both OCA treatment arms reduced ALP relative to placebo. It should be noted that the continuous descriptive statistics pertaining to the baseline absolute change from baseline 12 and percentage change from baseline utilized only the available data at those time points (i.e., no missing data were imputed). The categorical descriptive statistics (i.e., frequencies and corresponding proportions) utilized the worse-case (i.e., non-response) imputation strategy.

Patients from the OCA Titration and OCA 10 mg groups, respectively, achieved an ALP reduction from Baseline≥40% compared with 1 (1%) placebo patient. The numbers of patients normalizing ALP values i.e., 118 U/L in females and 124 U/L males are as follows: 1 (1%) patient from OCA titration group, 5 (7%) patients from the OCA 10 mg group, and zero placebo-treated patients.

It can be seen that ALP concentration levels are reduced in both OCA treatment groups, and during the first three months; these reduced levels remain stable during the long-term safety and efficacy (LTSE) period, signifying durability of response.

TABLE 24

Total Bilirubin (TB) Summary.

| Time Point/Statistics | 10 mg OCA (N = 73) | OCA Titration (N = 70) | Placebo (N = 73) |
|---|---|---|---|
| Baseline ALP Concentration (U/L) | | | |
| N | 73 | 70 | 73 |
| Mean (SD) | 316.3 (103.88) | 325.9 (116.24) | 327.5 (115.01) |
| Median | 271.3 | 281.3 | 311.9 |
| Min, Max | 207, 620 | 187, 811 | 144, 746 |
| Month 12 ALP Concentration (U/L) | | | |
| N | 63 | 64 | 70 |
| Mean (SD) | 191.2 (61.38) | 219.5 (99.76) | 321.3 (142.88) |
| Median | 181.7 | 196.6 | 270.5 |
| Min, Max | 95, 444 | 116, 690 | 149, 733 |
| Absolute Change from Baseline to Month 12 (U/L) | | | |
| N | 63 | 64 | 70 |
| Mean (SD) | −117.1 (72.84) | −103.5 (87.03) | −7.7 (87.96) |
| Median | −99.0 | −85.5 | −15.8 |
| Min, Max | −346, 0.3 | −402, 127 | −208, 308 |
| Percentage Change from Baseline to Month 12 (%) | | | |
| N | 63 | 64 | 70 |
| Mean (SD) | −36.4 (14.88) | −30.5 (18.97) | −2.5 (23.82) |
| Median | −38.3 | −31.5 | −4.7 |

TABLE 24-continued

Total Bilirubin (TB) Summary.

| Time Point/Statistics | 10 mg OCA (N = 73) | OCA Titration (N = 70) | Placebo (N = 73) |
|---|---|---|---|
| Min, Max | −72, 0.1 | −74, 23 | −45, 80 |
| Decrease in ALP ≥ 10% at Month 12 - n (%) | 61 (83.6%) | 55 (78.6%) | 29 (39.7%) |
| Decrease in ALP ≥ 15% at Month 12 - n (%) | 57 (78.1%) | 54 (77.1%) | 21 (28.8%) |
| Decrease in ALP ≥ 20% at Month 12 - n (%) | 54 (74.0%) | 49 (70.0%) | 17 (23.3%) |
| Decrease in ALP ≥ 40% at Month 12 - n (%) | 25 (34.3%) | 21 (30.0%) | 1 (1.4%) |
| Baseline ALP Concentration (×ULN) | | | |
| N | 73 | 70 | 73 |
| Mean (SD) | 2.658 (0.878) | 2.747 (0.9851) | 2.760 (0.9732) |
| Median | 2.293 | 2.378 | 2.607 |
| Min, Max | 1.68, 5.23 | 1.58, 6.86 | 1.22, 6.31 |
| Month 12 ALP Concentration (×ULN) | | | |
| N | 63 | 64 | 70 |
| Mean (SD) | 1.606 (0.5161) | 1.851 (0.8449) | 2.705 (1.1987) |
| Median | 1.527 | 1.661 | 2.286 |
| Min, Max | 0.80, 3.75 | 0.98, 5.84 | 1.26, 6.19 |
| ALP < 1.0 × ULN at Month 12 - n (%) | 5 (6.9%) | 1 (1.4%) | 0 |
| ALP < 1.67 × ULN at Month 12 - n (%) | 48 (54.8%) | 33 (47.1%) | 12 (16.4%) |

Figure 11:
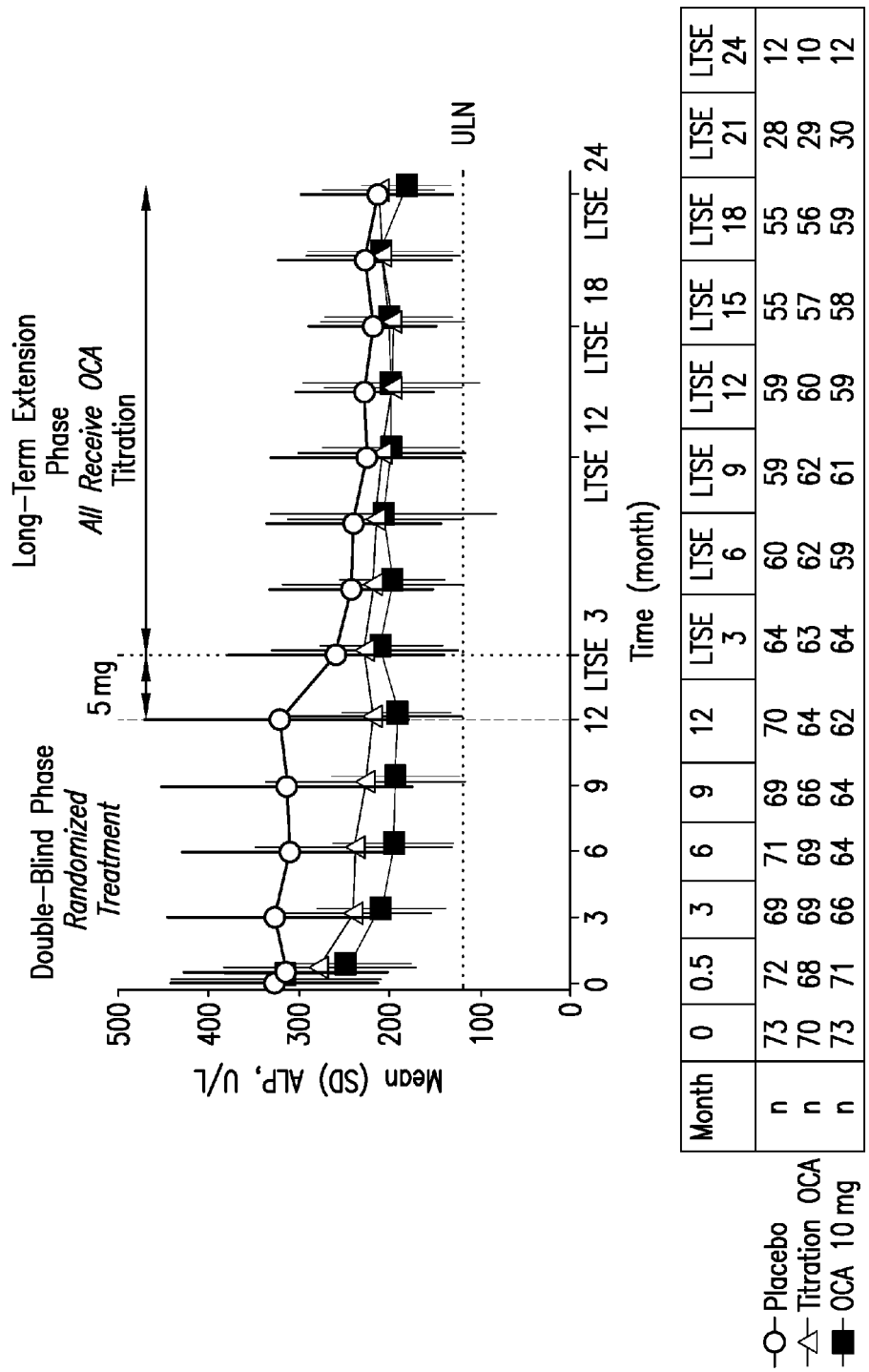
FIG. 11 illustrates ALP Concentration (U/L) over duration of treatment.

After completing the treatment period, 193 out of the 216 ITT patients (64 on 10 mg OCA, 63 on OCA Titration, and 66 Placebo patients) continued on open-label OCA treatment during the LTSE period (note: that all placebo patients were switched to OCA 5 mg and then all patients were switched to OCA 10 mg). FIG. 11 presents ALP concentrations over time, organized by originally randomized treatment group.

Figure 12:
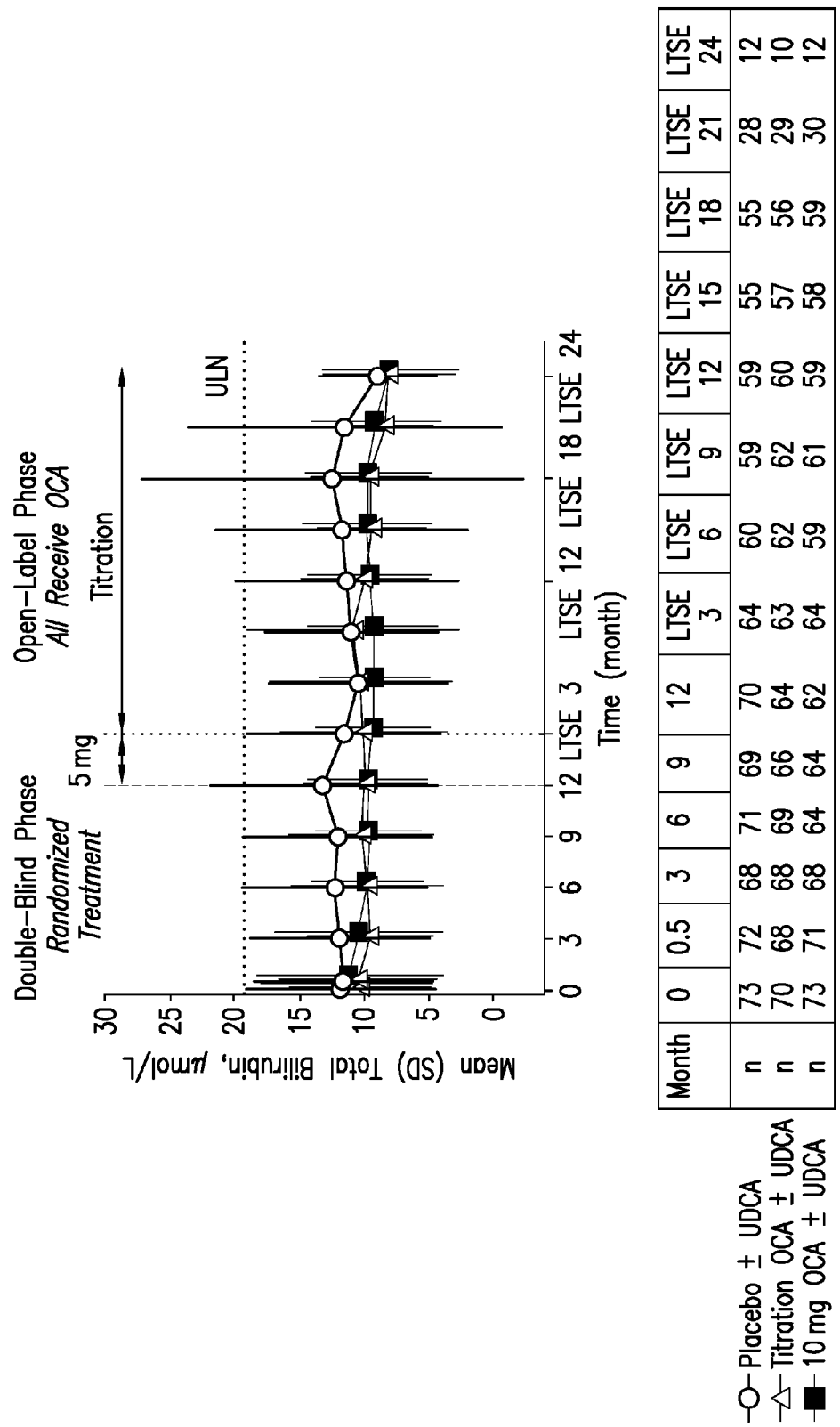
FIG. 12 illustrates TB Concentration (μmol/L) over duration of treatment.

It can be observed from Table above that reductions from baseline in TB were greater in both OCA treatment groups than in the placebo group. It should be noted that the continuous descriptive statistics pertaining to the baseline, absolute change from baseline and percentage change from baseline values utilized only the available data at those time points (i.e., no missing data was imputed). The categorical descriptive statistics (i.e., frequencies and corresponding proportions) utilized the worse-case imputation strategy. FIG. 12 illustrates TB concentrations over time, organized by originally randomized treatment group for the 193 ITT patients continuing on open-label OCA treatment during the LTSE period.

Dose Titration: A total of 69 of 70 ITT patients from the OCA titration group completed month 6. Of these, 36 (52%) remained at 5 mg for the duration of the treatment period and 33 (48%) who did not meet the primary composite endpoint at Month 6, but, because they tolerated the investigational product, were titrated to 10 mg. Thirteen (39%) of the patients who up-titrated met the composite endpoint suggesting that a benefit can be gained with titration of OCA from 5 mg to 10 mg in those patients who did not respond to the 5 mg dose.

Because for some patients, a response can be achieved with OCA 5 mg, initiating treatment on OCA 5 mg and titrating subsequently to 10 mg if needed and if tolerated appears to be a reasonable dosing strategy. For patients who do not achieve an optimal response within 6 months of treatment with OCA 5 mg, additional benefit may be gained by titrating to OCA 10 mg.

Effect of Bile Acid Sequestrants (BAS) Exposure on Efficacy. For patients receiving BAS, OCA 5 mg and 10 mg trough concentrations were slightly lower compared to those patients who did not receive BAS. The decreased trough concentrations resulted in a modest attenuation in efficacy in patients receiving OCA 5 mg (despite instruction to dose BS at least 4 hours apart from OCA), but did not appear to affect efficacy in patients receiving OCA 10 mg.

ALP and total bilirubin, were evaluated in relation to age at baseline, age at time of diagnosis, and years since diagnosis. The effect of OCA was consistent independent of age at diagnosis, duration of PBC, or years since diagnosis. In general, the subgroups were consistent with the observed effect in the overall ITT population. Greater improvements were observed in OCA-treated subjects, compared with placebo subjects.

It can be observed from Table 25 that both OCA treatment groups showed a difference in the proportion/percentage of patients achieving response when individually compared to placebo. This analysis was repeated utilizing the Completer and EE analysis sets and the conclusions were consistent. The ultra-worse-case imputation strategy, implemented by the FDA statistical reviewer as described above, did not impact the results. All of the previously presented analyses were re-conducted utilizing a baseline value that was the median of all pre-first dose measurements, and, separately, a traditional baseline definition (both approaches as described above); there was no impact on the results with either approach.

TABLE 25

| Statistics | 10 mg OCA (N = 60) | OCA Titration (N = 60) | Placebo (N = 61) |
|---|---|---|---|
| Response at Month 6 - n (%) [1] | 25 (41.7%) | 21 (35.0%) | 1 (1.6%) |
| Corresponding 95% Wald CI | 29.2%, 54.1% | 22.9%, 47.1% | 0.0%, 4.8% |
| Baseline ALP ≥ 2.0 × ULN - n (%) | 42 (70.0%) | 47 (78.3%) | 46 (75.4%) |
| ALP < 2.0 × ULN at Month 6 - n (%) [2] | 30 (71.4%) | 24 (51.1%) | 8 (17.4%) |
| Decrease in ALP ≥ 40% at Month 6 - n (%) [2] | 10 (23.8%) | 13 (27.7%) | 0 |
| ALP < 2.0 × ULN and Decrease ≥ 40% at Month 6 - n (%) [2] | 9 (21.4%) | 11 (23.4%) | 0 |
| Baseline ALP ≥ 1.67 × ULN but < 2.0 × ULN - n (%) | 18 (30.0%) | 13 (21.7%) | 15 (24.6%) |
| ALP < 1.67 × ULN at Month 6 - n (%) [3] | 17 (94.4%) | 10 (76.9%) | 3 (20.0%) |
| Decrease in ALP ≥ 15% at Month 6 - n (%) [3] | 16 (88.9%) | 11 (84.6%) | 1 (6.7%) |
| ALP < 1.67 × ULN and Decrease ≥ 15% at Month 6 - n (%) [3] | 16 (88.9%) | 10 (76.9%) | 1 (6.7%) |
| Response at Month 12 - n (%) [1] | 26 (43.3%) | 23 (38.3%) | 3 (4.9%) |
| Corresponding 95% Wald CI | 30.8%, 55.9% | 26.0%, 50.6% | 0.0%, 10.3% |
| Baseline ALP ≥ 2.0 × ULN - n (%) | 42 (70.0%) | 47 (78.3%) | 46 (75.4%) |
| ALP < 2.0 × ULN at Month 12 - n (%) [2] | 29 (69.1%) | 28 (59.6%) | 9 (19.6%) |
| Decrease in ALP ≥ 40% at Month 12 - n (%) [2] | 13 (31.0%) | 16 (34.0%) | 1 (2.2%) |
| ALP < 2.0 × ULN and Decrease ≥ 40% at Month 12 - n (%) [2] | 12 (28.6%) | 13 (27.7%) | 1 (2.2%) |
| Baseline ALP ≥ 1.67 × ULN but < 2.0 × ULN - n (%) | 18 (30.0%) | 13 (21.7%) | 15 (24.6%) |
| ALP < 1.67 × ULN at Month 12 - n (%) [3] | 16 (88.9%) | 11 (84.6%) | 6 (40.0%) |
| Decrease in ALP ≥ 15% at Month 12 - n (%) [3] | 14 (77.8%) | 10 (76.9%) | 2 (13.3%) |
| ALP < 1.67 × ULN and Decrease ≥ 15% at Month 12 - n (%) [3] | 14 (77.8%) | 10 (76.9%) | 2 (13.3%) |

Treatment with OCA (10 mg) in a cohort of subjects with early stage PBC who were enrolled with incomplete biochemical response to UDCA resulted in statistically significant improvement from baseline in alkaline phosphatase for the pre-specified endpoint of reduction of ALP to <1.67× ULN and 15%, relative to placebo. The percentage of patients achieving response was statistically significantly different than placebo [34 of 73 (46.6%) in the OCA 10 mg arm, 32 of 70 (45.7%) in the titration arm and 7 of 73 (9.6%) in the placebo arm]. The effect of OCA on achieving a reduction in ALP was independent of age at diagnosis, duration of PBC, and baseline ALP.

Secondary analysis showed that patients from the OCA Titration and OCA 10 mg groups achieved an ALP reduction from Baseline≥40% compared with 1 (1%) placebo patient. The numbers of patients normalizing ALP values i.e., 118 U/L in females and 124 U/L males are as follows: 1 (1%) patient from OCA titration group, 5 (7%) patients from the OCA 10 mg group, and zero placebo-treated patients.

Example 10

This example describes clinical pharmacology and dosing of obeticholic acid (OCA—including obeticholic acid compositions described herein). The starting dosage of OCA is 5 mg orally once daily in adult patients who have failed to achieve an adequate reduction in alkaline phosphatase on a stable dose of UDCA for an adequate duration or who were intolerant to UDCA. OCA can be supplied as an oral tablet containing obeticholic acid in a formulation as described herein.

If an adequate reduction in alkaline phosphatase has not been achieved after 3 months of OCA 5 mg once daily, and the patient is tolerating the drug, the dose of OCA can be increased to 10 mg once daily.

For patients experiencing intolerability due to pruritus, one of the following modifications was considered:
Reduce the dosage to:
5 mg every other day, for patients intolerant to 5 mg once daily or
5 mg once daily, for patients intolerant to 10 mg once daily Alternative dosing schedules, such as dosing every other day, every third day or every seventh day.
Interruption of dosing for up to 2 weeks followed by restarting at a reduced dose or on an alternative dosing schedule.
hepatic decompensation.
Addition of an antihistamine or a bile acid sequestrants.
OCA may be taken with or without food. Food does not have a clinically relevant effect on the PK of 10 mg OCA.
Bile acid binding resins may be taken at least 4 hours before or 4 hours after (or at as great an interval as possible) OCA. Bile acid binding resins such as cholestyramine, colestipol, or colesevelam affect bile acid absorption and may reduce the absorption, systemic exposure, and efficacy of OCA.

No dose adjustment is believed to be needed when OCA is used in patients with serum creatinine clearance>50 mL/min/1.73 $m^2$. No data are available as to how severe impairment would impact the systemic exposure to OCA and its conjugates.

Dose adjustment may be needed in patients with hepatic impairment. Dose adjustment may not be needed in patients with mild hepatic impairment (Child-Pugh Class A). In some examples, the starting dosage is 5 mg once weekly for patients with moderate or severe hepatic impairment (Child-Pugh Class B or C). If an adequate reduction in alkaline phosphatase has not been achieved after 3 months of OCA 5 mg once weekly, and the patient is tolerating the drug, the OCA dose should be increased to 5 mg twice weekly and then to 5 mg every day depending on response and tolerability.

Obeticholic acid is absorbed with peak plasma concentrations (Cmax) occurring at a median time (tmax) of approximately 2 hours. Co-administration with food does not alter the extent of absorption of obeticholic acid. Following multiple-dose administration of 5, 10, and 25 mg once daily for 14 days, systemic exposures of obeticholic acid increase dose proportionally. Exposures to glyco-obeticholic acid and tauro-obeticholic acid, and total obeticholic acid increase more than proportionally with dose.

Following multiple oral doses of OCA 10 mg once daily, peak plasma concentrations (Cmax) of OCA occurring at a median time (Tmax) of approximately 1.5 hours. Median $T_{max}$ for glyco-OCA and tauro-OCA is 10 hours.

Distribution. Human plasma protein binding of obeticholic acid and its conjugates is greater than 99%. The volume of distribution of OCA is 613 L. The volume of distributions of glycol- and tauro-obeticholic acid has not been determined.

Elimination and Metabolism. Obeticholic acid is conjugated with glycine or taurine in the liver and secreted into bile. These glycine and taurine conjugates of obeticholic acid are absorbed in the small intestine leading to enterohepatic recirculation. The conjugates can be deconjugated in the ileum and colon by intestinal microbiota, leading to the conversion to obeticholic acid that can be reabsorbed or excreted in feces, the principal route of elimination.

After daily administration of obeticholic acid, there is accumulation of the glycine and taurine conjugates of obeticholic acid which have in vitro pharmacological activities similar to the parent drug, obeticholic acid. The metabolite-to-parent ratios of the glycine and taurine conjugates of obeticholic acid were 13.8 and 12.3, respectively, after daily administration. An additional third obeticholic acid metabolite, 3-glucuronide is formed but is considered to have minimal pharmacologic activity.

Excretion. After administration of radiolabeled obeticholic acid, greater than 85% is excreted in feces. Urinary excretion is less than 3%.

Figure 13:
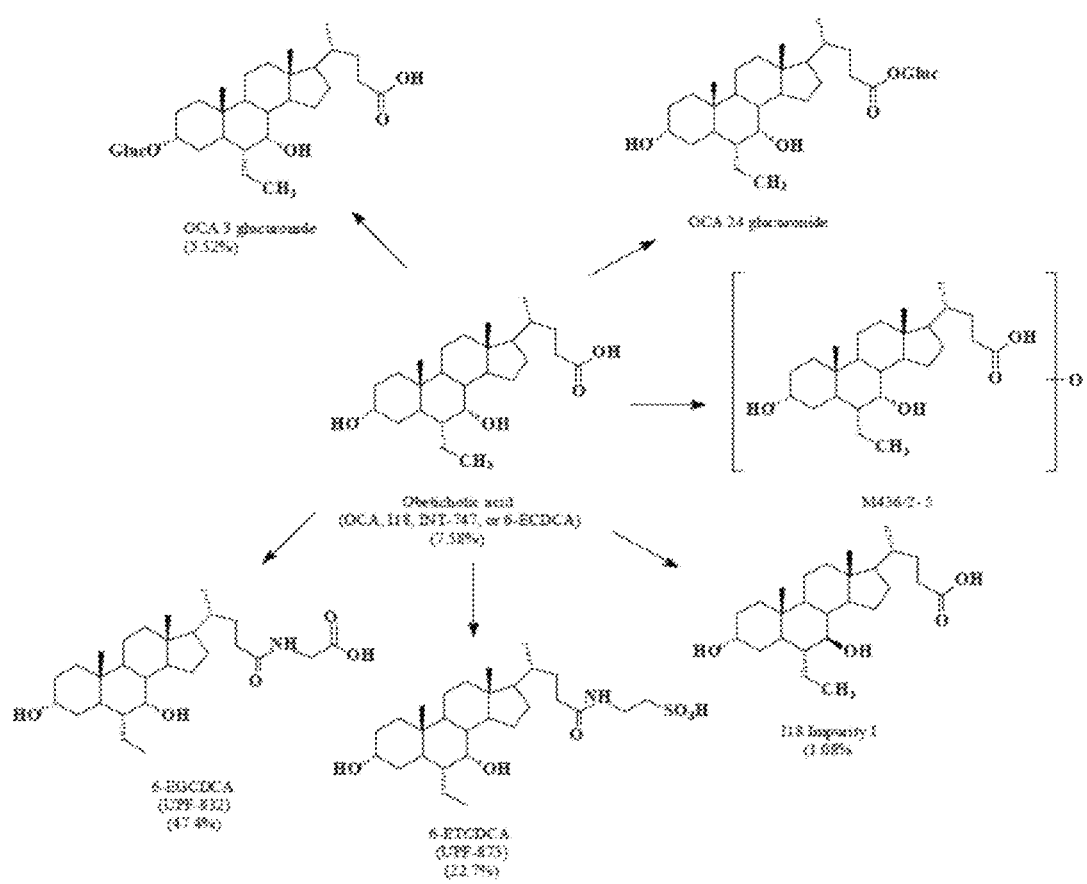
FIG. 13 illustrates proposed metabolic pathways of OCA in human plasma.

The proposed human metabolic pathways are shown in FIG. 13.

Following an oral administration of 25 mg [$^{14}$C]-OCA, about 87% of the dose is excreted in feces through biliary secretion. Less than 3% of the dose is excreted in the urine with no detection of OCA.

The effective half-life of OCA is about 24 hours.

Gender, age, and race had no impact on the pharmacokinetics of OCA based on the population-PK analysis. Population PK analysis dataset consisted of 301 female and 505 male subjects, age ranging from 18 to 71 years and had 10 Asian, 233 Black, 554 White and 9 Other subjects.

In vitro studies: Obeticholic acid is not an inhibitor of CYP2C8 and did not cause a significant change in the expression of CYP2B6, CYP2C8, CYP2D6, MRP2, MRP3, MRP4, MATE1, and OATP2B1. Obeticholic acid showed either no or weak effects on these metabolizing enzymes and transporters.

Concomitant administration of 20 mg omeprazole once daily with obeticholic acid 10 mg once daily resulted in a less than 1.2-fold increase in obeticholic acid exposure.

Treatment with obeticholic acid 10 mg or obeticholic acid titration (5 mg to 10 mg) resulted in clinically meaningful and statistically significant increases (p<0.0001) relative to placebo, in the number of patients achieving the primary composite endpoint at all study time points (see Table 26). Responses occurred as early as 2 weeks and were dose dependent (obeticholic acid 5 mg compared with obeticholic acid 10 mg at 6 months, p=0.04).

TABLE 26

Percentage of Patients Achieving Response.[A]

| | Obeticholic acid ± UDCA [B] | | |
|---|---|---|---|
| | Obeticholic acid Titration [C] (N = 70) | Obeticholic acid 10 mg (N = 73) | Placebo ± UDCA [B] (N = 73) |
| Month 6 | | | |
| Dose | 5 mg | 10 mg | |
| Responders, n (%) | 24 (34) | 37 (51) | 5 (7) |
| p-value [D] | <0.0001 | <0.0001 | NA |
| Month 12 | | | |
| Dose | 5 mg or 10 mg | 10 mg | |
| Responders, n (%) | 32 (46) | 34 (47) | 7 (10) |
| p-value [D] | <0.0001 | <0.0001 | NA |

NA = not applicable
[A] Percentage of Subjects Achieving an ALP less than 1.67 × ULN and Total Bilirubin less than or equal to the ULN and an ALP decrease of 15% or greater. Missing values were considered a non-response.
[B] The majority of patients received treatment in combination with UDCA and a small number of patients unable to tolerate UDCA received obeticholic acid as monotherapy.
[C] Subjects randomized to obeticholic acid titration received obeticholic acid 5 mg for the initial 6-month period. At Month 6, patients who did not achieve the composite endpoint and did not have evidence of tolerability issues were titrated from 5 mg to 10 mg for the final 6 months of the double-blind phase.
[D] p-values for comparing obeticholic acid versus placebo are obtained using CMH General Association test stratified by double-blind Baseline UDCA usage (yes/no) and double-blind Baseline total bilirubin (less than or equal to the ULN/greater than the ULN).

Figure 14A:
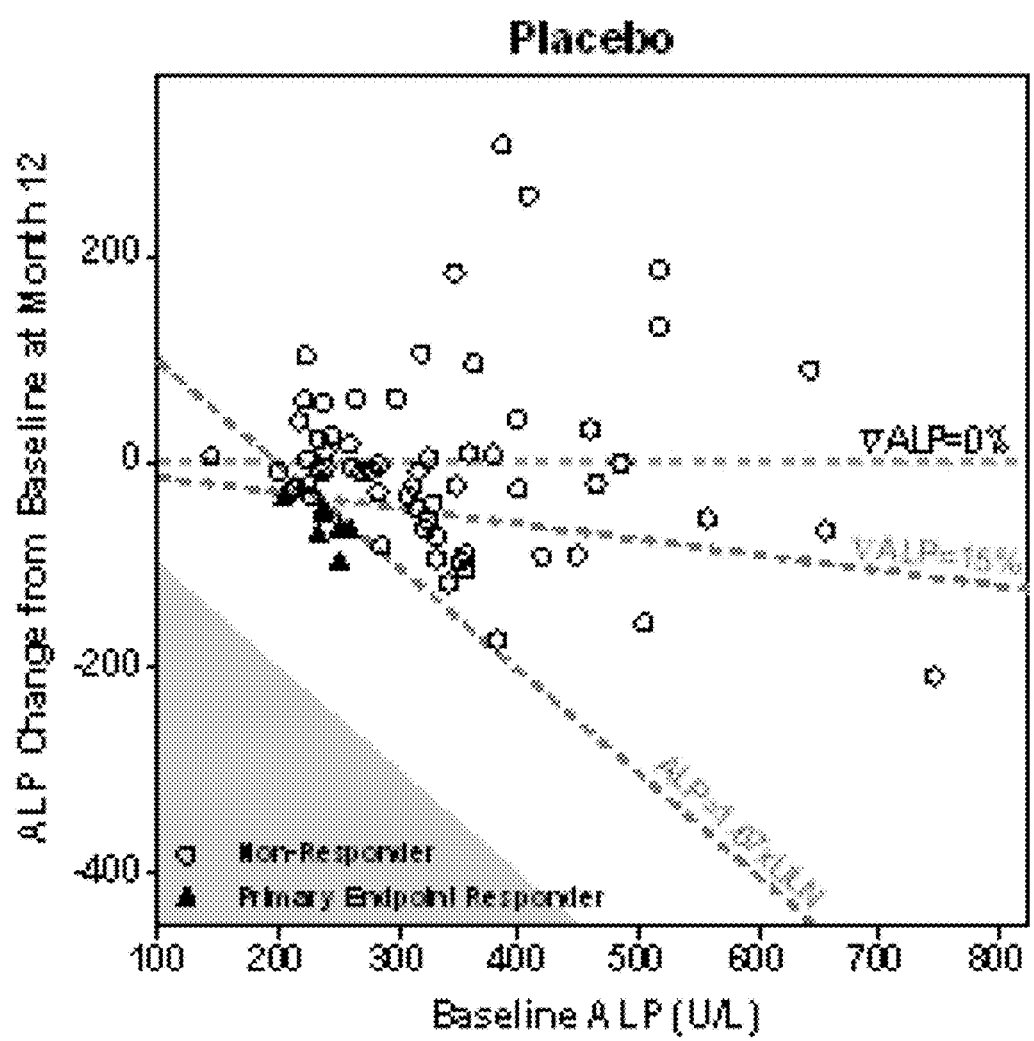
FIG. 14 illustrates Observed Individual Patient-Level Change in ALP from Baseline at Month for responders and non-responders by treatment group (Placebo (FIG. 14A), for OCA titration (FIG. 14B) and for OCA 10 mg (FIG. 14C)).
Figure 14B:
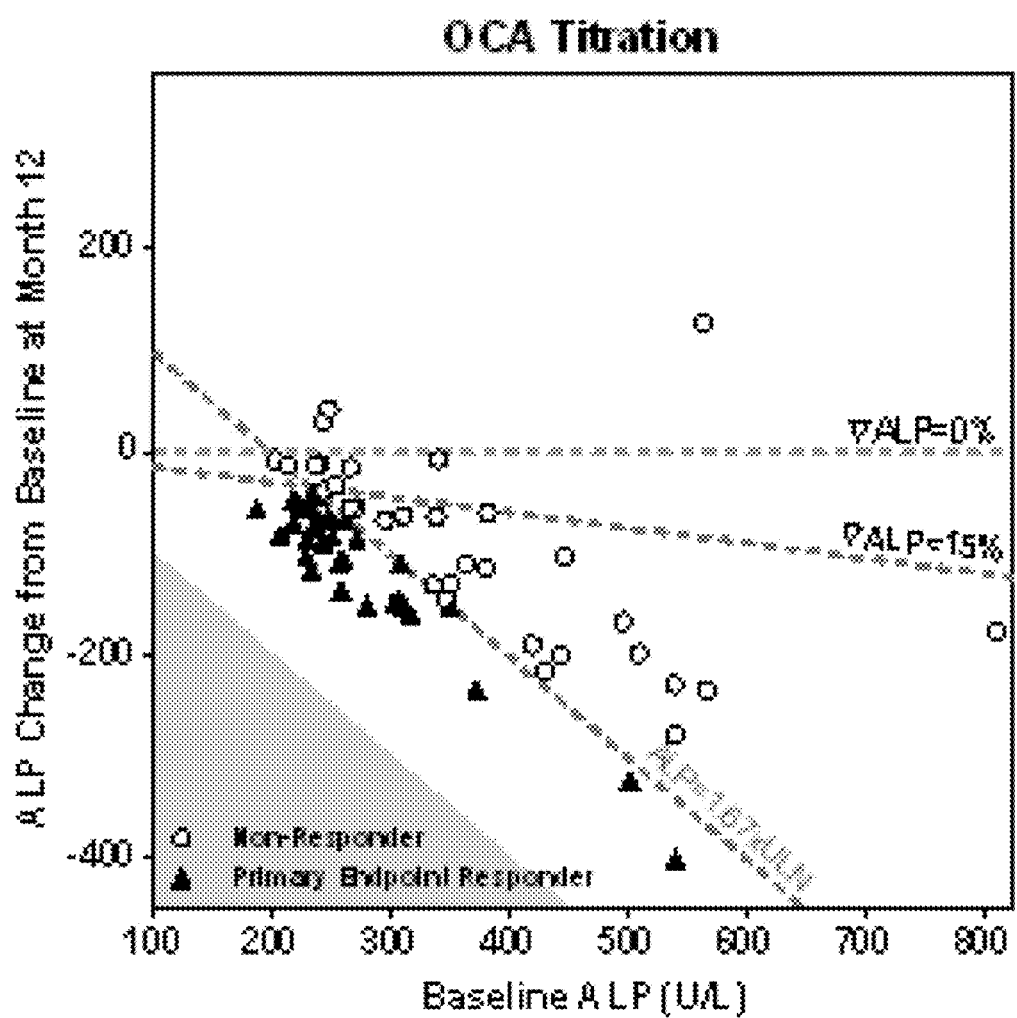
Figure 14C:
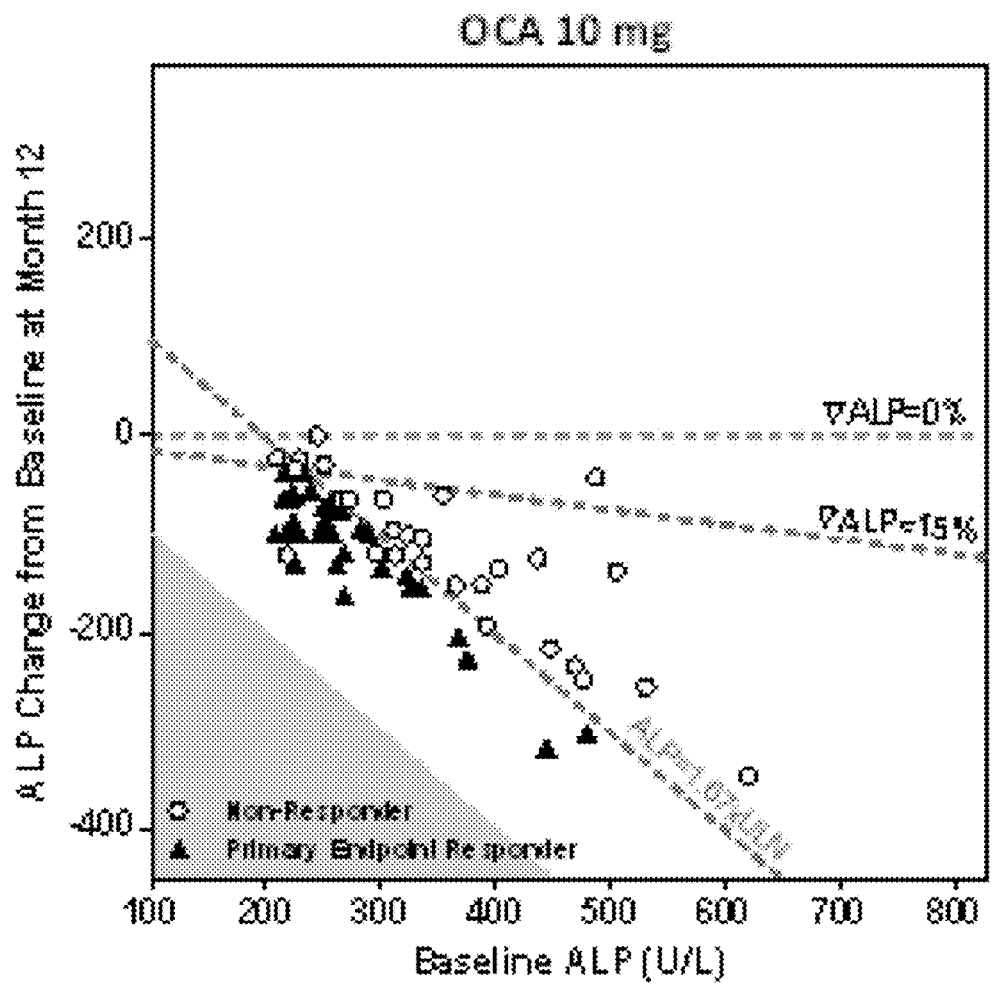

In one example, 77% of patients on both titration and 10 mg obeticholic acid achieved a reduction of at least 15% in ALP at 12 months compared to 29% of patients on placebo (see FIG. 14A, FIG. 14B, FIG. 14C). In addition, 36% of patients treated with placebo experienced an increase in ALP associated with worsening of disease compared to 5% of patients on titration obeticholic acid and 2% on 10 mg obeticholic acid.

Figure 15A:
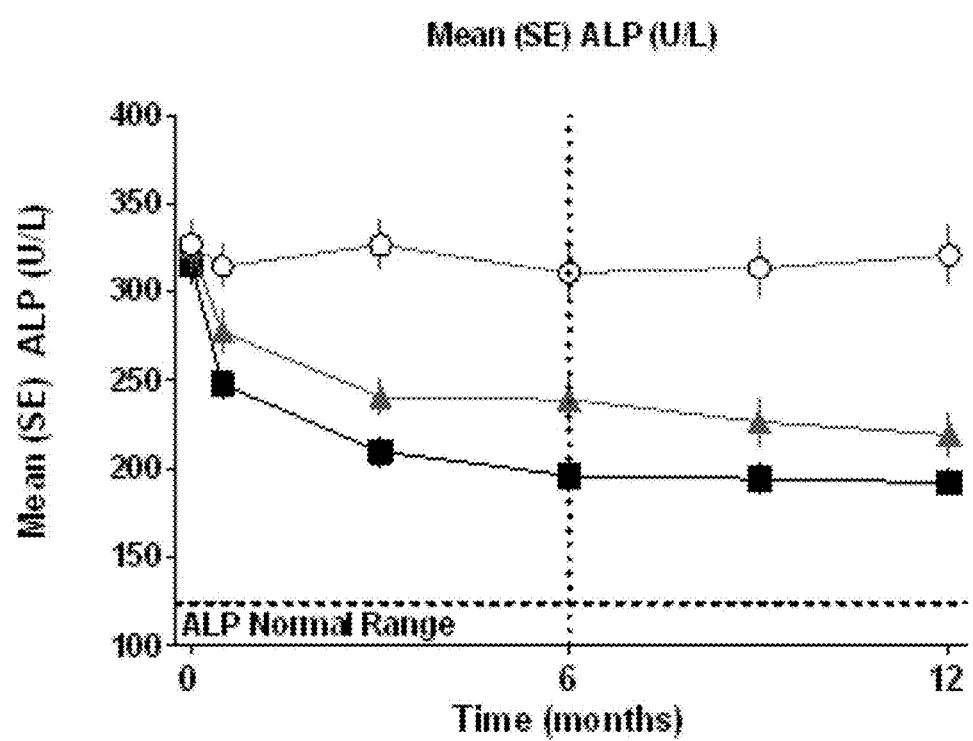
FIG. 15A illustrates mean ALP over time and FIG. 15B illustrates mean total bilirubin (TB) over time.
Figure 15B:
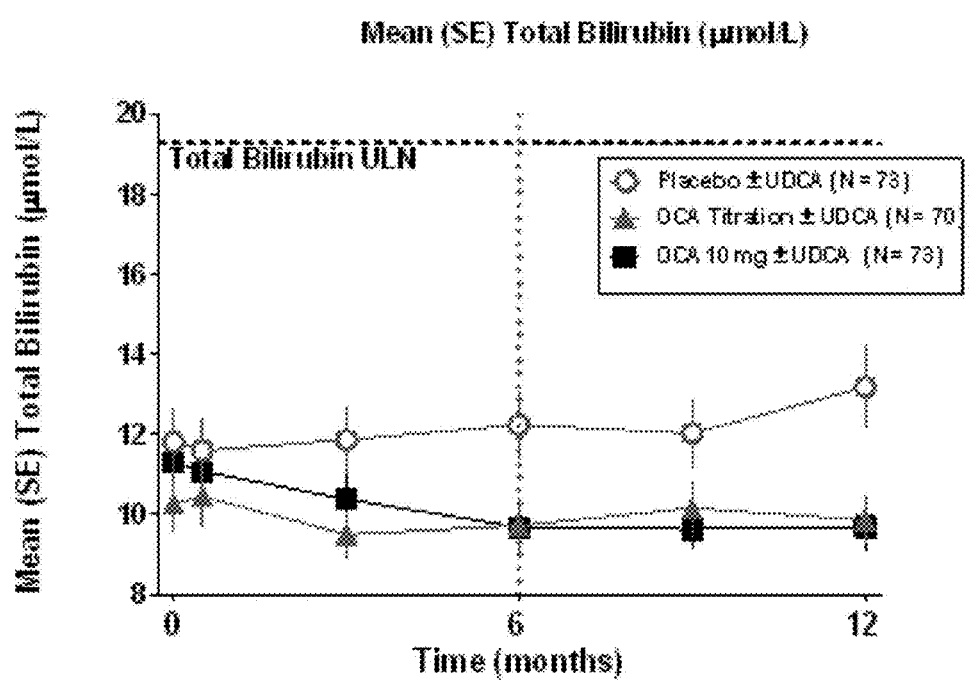

Treatment with obeticholic acid also resulted in clinically meaningful and statistically significant improvements versus placebo (p<0.0001) in ALP levels as early as 2 weeks and at all timepoints thereafter (see FIG. 15A, FIG. 15B). During the double-blind, 12 month period, bilirubin levels increased in the placebo patients and remained stable in patients taking obeticholic acid.

Patients randomized to the obeticholic acid titration group received obeticholic acid 5 mg for the initial 6-month period. At Month 6, patients who did not yet meet the criteria for the composite endpoint and did not have evidence of tolerability issues were titrated from obeticholic acid 5 mg to obeticholic acid 10 mg for the final 6 months of the double-blind phase. SE=standard error.

The above dosing regimen including a 5 mg QD starting dose, followed by up-titration to 10 mg QD at 3 months was based on response and tolerability for the overall population. Based on the dose dependent increase in incidences of pruritus and better tolerability profile with time with a lower starting dose, 5 mg QD (once daily) is an effective starting dose for the general population.

The increase in dose from 5 mg to 10 mg QD resulted in additional responders from month 6 to month 12. There were also 19% patients (out of patients on 5 mg QD dosing) who were responders (as per the primary composite endpoint criteria), but became non-responders, possibly due to disease progression, with continued dosing of 5 mg QD. These patients also benefit from up-titration to 10 mg QD.

Figure 16:
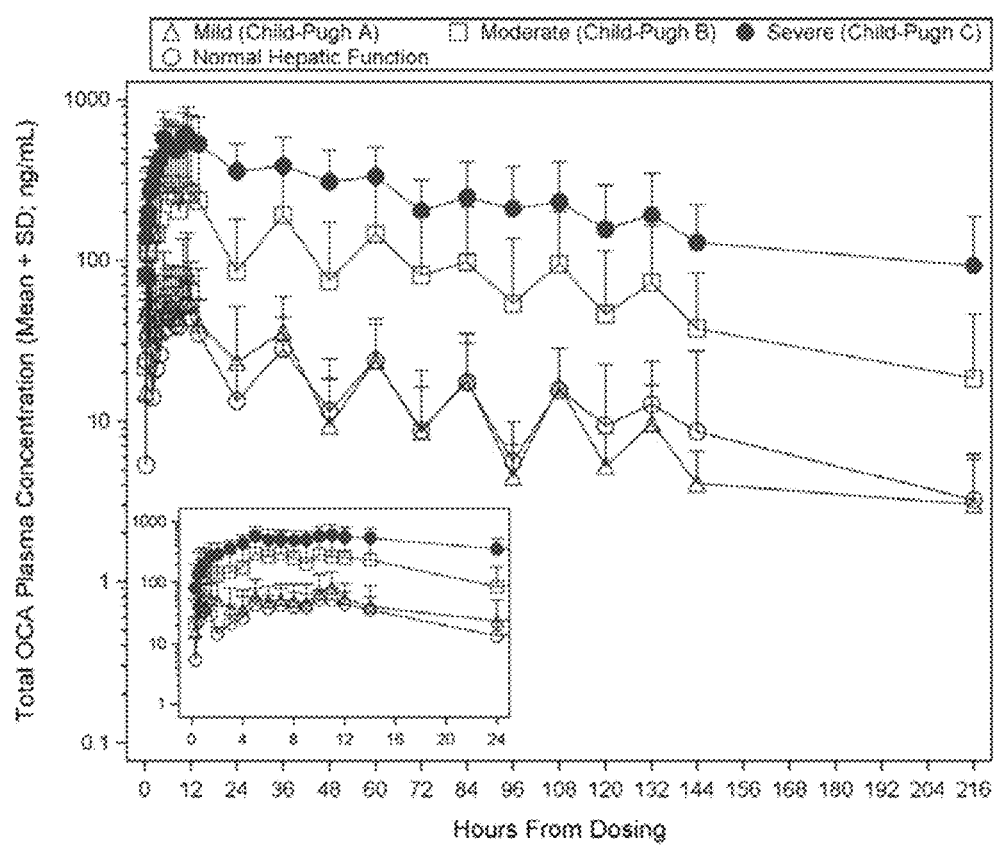
FIG. 16 illustrates the mean plasma concentration-time profile (Semi-log) of total OCA following a single oral dose of 10 mg OCA (inset shows expanded view of first 24 hours).
Figure 17A:
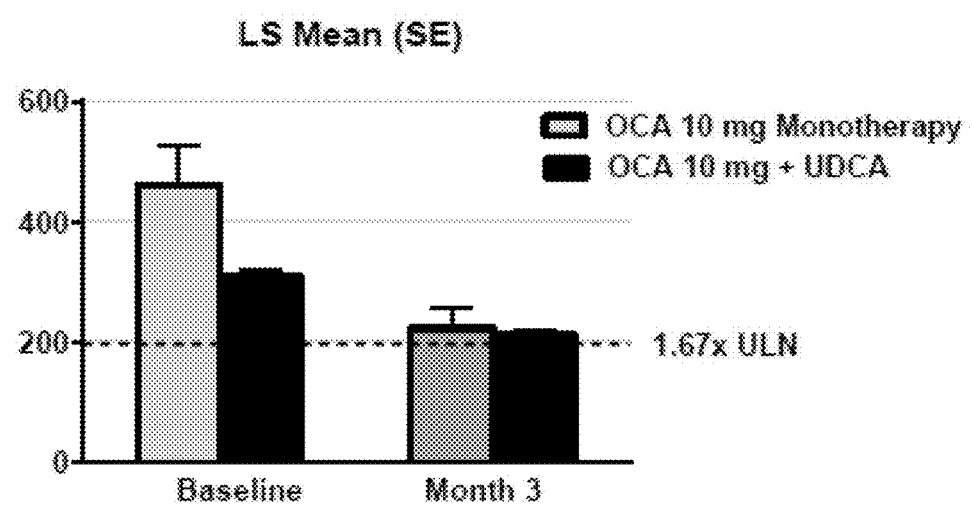
FIG. 17A illustrates ALP levels and FIG. 17B illustrates change in ALP from baseline with OCA monotherapy and combination therapy with UDCA, based on pooled data from study 747-201, study 747-202 and Phase 3 study 747-301.
Figure 17B:
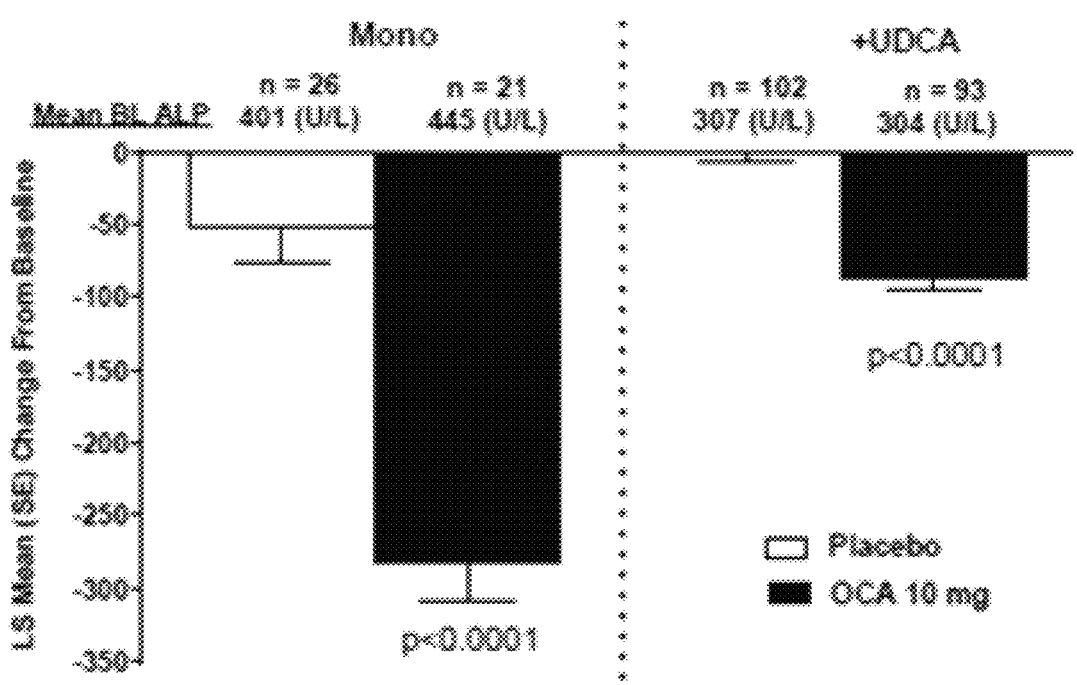
Figure 24A:
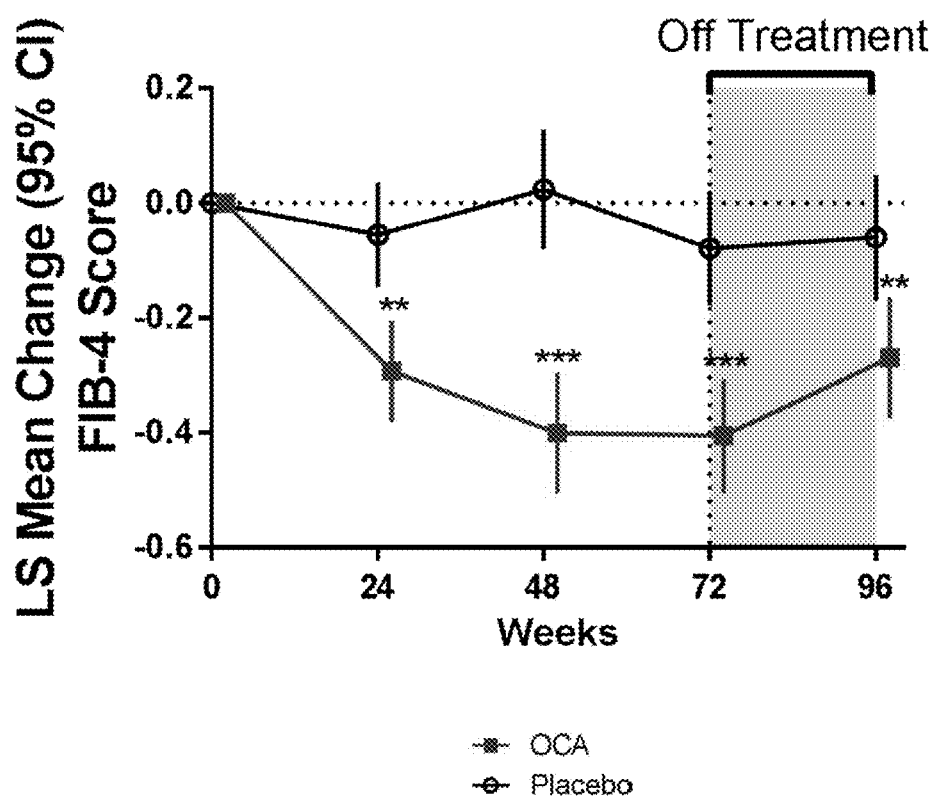
FIG. 24A, FIG. 24B, and FIG. 24C illustrate changes in FIB-4 Score, APRI Score, and NFS during the course of treating NASH using the obeticholic acid compositions described herein, respectively. $*p<0.05$, $p<0.01$, $*p<0.0001$; P-values were calculated using ANCOVA models, regressing change from baseline at each post-baseline visit on treatment group and baseline value of the outcome.
Figure 24B:
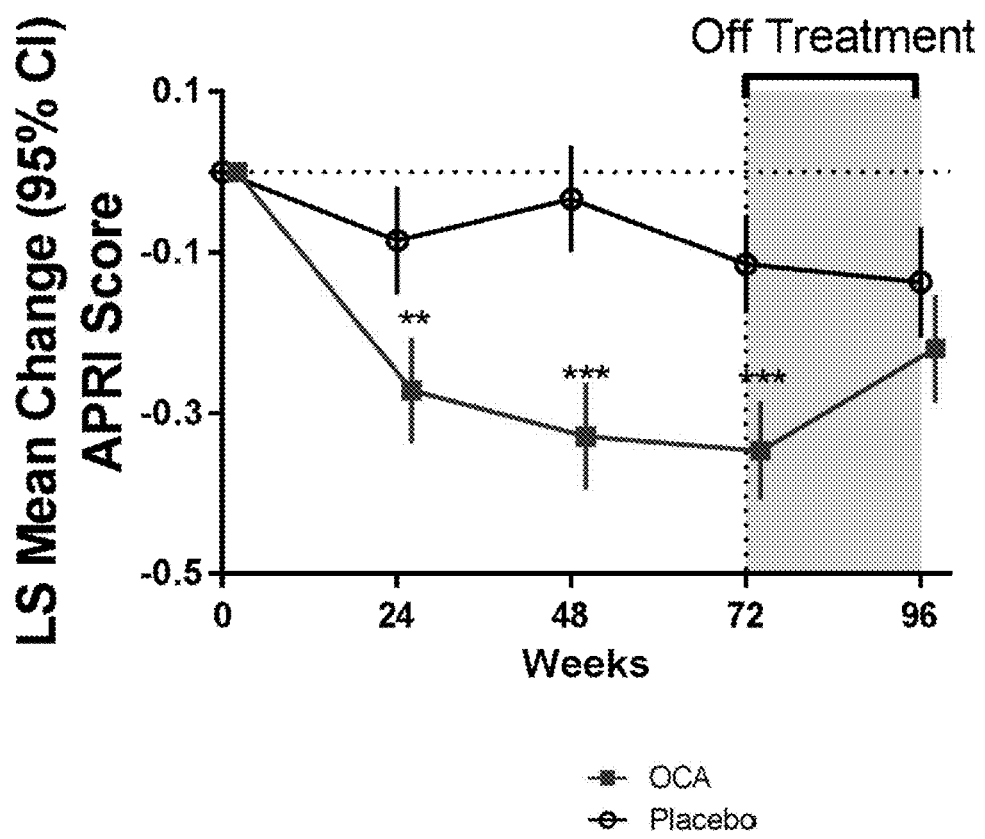
Figure 24C:
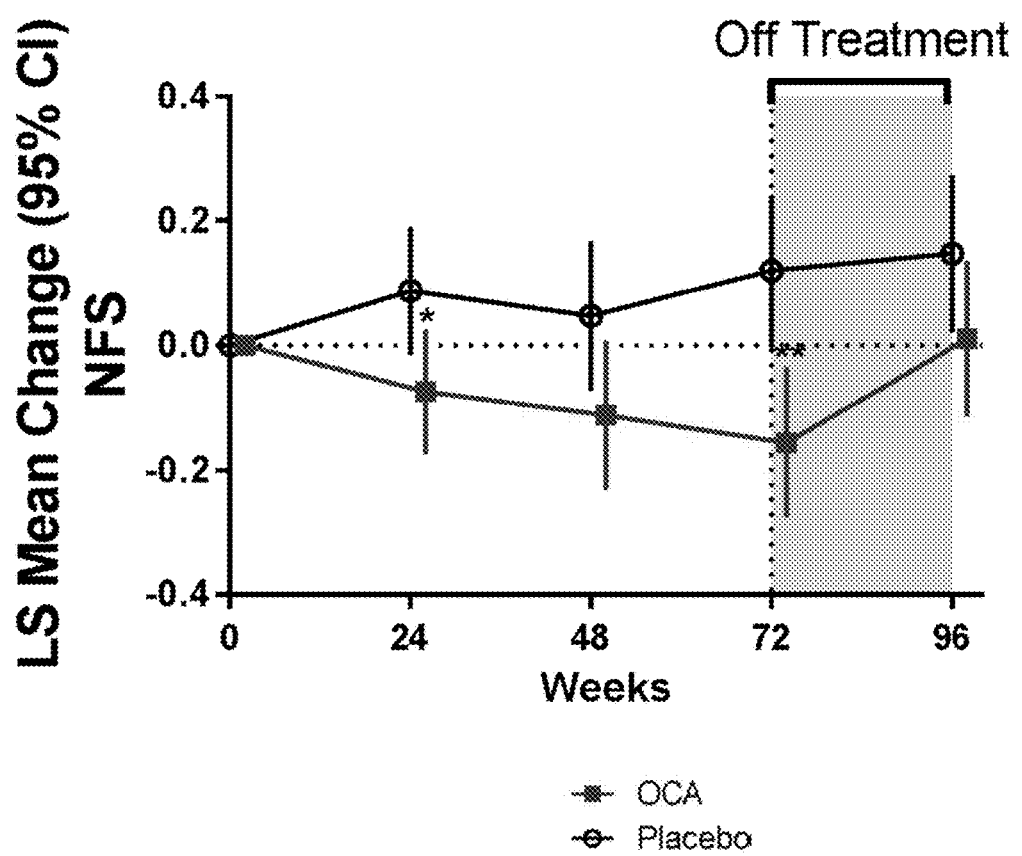
Figures 27A, 27B, 27C, 27D, 27E, 27F:
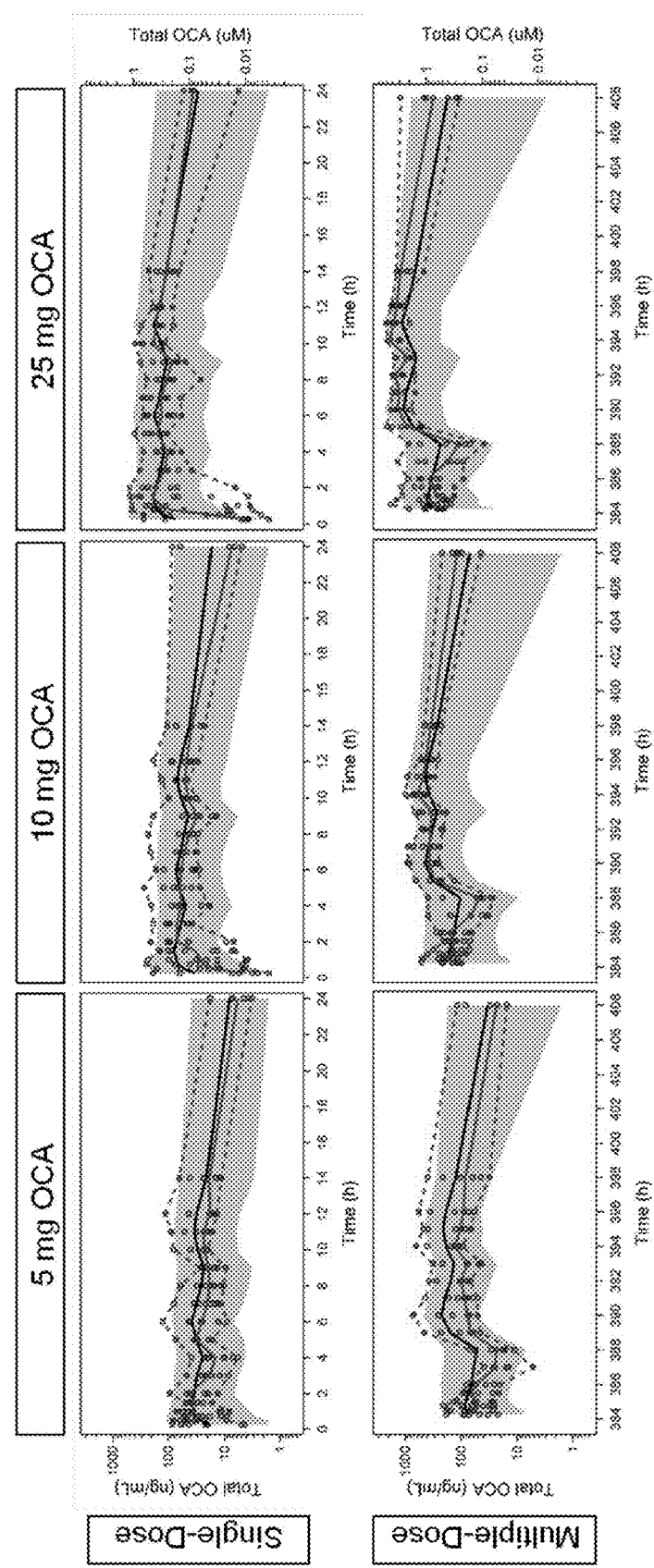
FIGS. 27A-F show External Validation of Model in Subjects with Normal Hepatic Function where
Figures 28A, 28B, 28C, 28D, 28E, 28F:
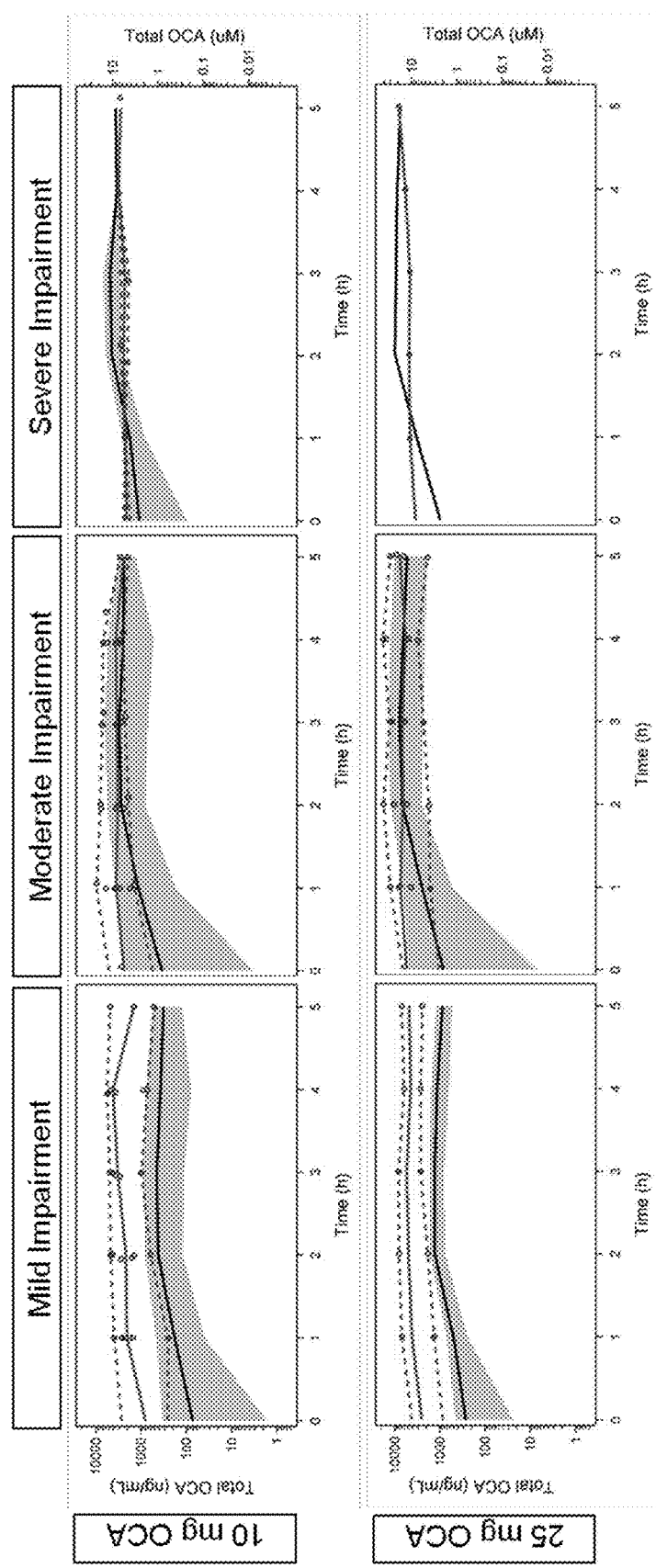
FIGS. 28A-F show External Validation of Model in Patients with Impaired Hepatic Function where

In the dedicated hepatic impairment study with a single dose of 10 mg, the systemic exposure (AUC0-9 days) to total OCA was 1.1-, 4.2-, and 17.3-fold in subjects with mild, moderate and severe hepatic impairment, respectively, when compared to normal healthy volunteers. The mean total OCA concentration-time profiles in this study are shown in FIG. 16 and the mean PK parameters (Cmax and AUCt) for total OCA in plasma for normal healthy volunteers and subjects with various categories of hepatic impairment are quantified in Table 27.

TABLE 27

Mean (SD) PK parameters of plasma total OCA.

| Parameters | Normal Hepatic Function (N = 8) | Mild (N = 8) | Moderate (N = 8) | Severe (N = 8) |
|---|---|---|---|---|
| Cmax (ng/mL) | 68.3 (27.6) | 107 (65.1) | 348 (377) | 674 (281) |
| AUC0-t (hr*ng/mL) | 2480 (1810) | 2770 (2060) | 15700 (19100) | 41000 (21900) |

There was no apparent association of change of unbound free fraction percentage (% Fu) of OCA and tauro-OCA with the increased degree of hepatic impairment. Mean % Fu of glyco-OCA increased in patients with severe hepatic impairment.

Example 11

Obeticholic acid (OCA) is a farnesoid X receptor (FXR) agonist and as shown, inter alia, useful for the treatment of primary biliary cholangitis/cirrhosis (PBC), nonalcoholic steatohepatitis (NASH), and other liver diseases. OCA is the 6α-ethyl derivative of chenodeoxycholic acid (CDCA). Patients with cirrhosis have systemic bile acid exposure higher than those in healthy subjects (×18) while hepatic bile acid exposure is only ~2× higher. Thus systemic OCA exposure may not be reflective of OCA concentrations in the liver or intestine, the primary sites of action.

Plasma levels of OCA and its conjugates were measured in healthy subjects and cirrhotic patients with varying degrees of hepatic impairment. A physiologic pharmacokinetic model for OCA was developed to quantitatively describe the absorption, distribution, metabolism, and excretion of OCA in patients with and without hepatic impairment. The model was based on a published multi-compartment PK model for CDCA, and consisted of systemic, hepatobiliary, and intestinal systems. The model was used to simulate the pathophysiological abnormalities caused by cirrhosis including decreased hepatic uptake, portal-systemic shunting, decreased liver volume, and differences in amino acid conjugation.

There was good agreement between predicted and observed increases in systemic OCA exposure after a single 10 mg dose in subjects with mild (×1.4), moderate (×8), and severe (×13) hepatic impairment relative to healthy subjects. The predicted increases in liver exposure for subjects with mild, moderate, and severe hepatic impairment were increased only 1.1-, 1.5-, and 1.7-fold, relative to healthy participants. Hepatic exposure of OCA, the primary site of pharmacological activity, is increased marginally (~2-fold) in patients with cirrhosis.

Bile acids are the natural endogenous ligand for the farnesoid X receptor (FXR) which is a nuclear receptor with high expression levels in the liver and intestine. Nuclear receptors constitute a family of ligand-activated transcription factors which can either activate or repress target genes, including those involved in bile acid homeostasis. FXR activation appears to lead to decreased bile acid synthesis via CYP7A1 suppression, decreased conjugated bile acid uptake, and increased excretion from the hepatocytes via induction of transporters. Obeticholic acid (OCA, 6-ethyl chenodeoxycholic acid) is a FXR agonist. OCA is a modification of chenodeoxycholic acid (CDCA), the most potent endogenous agonist of FXR and differs from CDCA by the addition of an ethyl group at the 6 carbon position. The addition of this ethyl group to CDCA confers approximately 100-fold greater potency compared to CDCA.

PBC is a rare chronic autoimmune disease characterized by T-cell mediated destruction of the intrahepatic bile ducts, decreased bile secretion, bile acid retention in the liver, inflammation, fibrosis, cirrhosis, and liver failure, followed by either liver transplantation or death. NASH is a chronic liver disease often associated with type 2 diabetes or metabolic syndrome which is defined by presence of hepatic steatosis, inflammation, and cytological ballooning with eventual varying degrees of fibrosis and possible cirrhosis leading to liver transplantation, hepatocellular carcinoma or death. In general, chronic injury to the liver can lead to the formation of regenerative nodules and fibrous bands in the liver that form after an extended process of fibrosis. Cirrhosis causes the interface between the sinusoids and the hepatocytes to fill with fibrotic tissue leading to increased resistance to hepatic blood flow causing portal hypertension and its associated complications. Previous reports have shown that patients with cirrhosis have systemic bile acid exposure markedly higher than those in healthy subjects (18-fold higher) while hepatic bile acid exposure was only ~2-fold higher.

There are 4 primary mechanisms of hepatic impairment that are related to the pharmacokinetics of endogenous bile acids and OCA: reduced hepatic uptake (caused in part by capillarization of the sinusoids), portal systemic shunting (both hepatic and extrahepatic), decreased functional liver volume, and increased taurine conjugation. Mild liver disease may be associated with little or no change in the hepatic uptake of bile acids but severe cirrhosis and/or jaundice causes large decreases in the extraction ratio that affects all bile acids similarly. Healthy control subjects have hepatic uptakes of bile acids of at least 70%. In contrast, values in cirrhotic patients were reduced over a wide range of values with some less than 10%.

Portosystemic shunting appears to occur secondary to the development of portal hypertension. With ongoing liver injury, resultant fibrogenesis and the occurrence of nodular regeneration, intrahepatic resistance increases. When coupled with increased splanchnic blood flow into the liver that occurs as a result of splanchnic vasodilation in cirrhotics, portal pressures can become elevated and blood is shunted through collateral vessels, away from the liver. Portosystemic shunting can occur via either diversion of blood through newly developed veins or via anastomoses ("shunts") formed between existing portal and hepatic veins and is associated with higher systemic bile acid concentrations. Relative to normal controls, the portal blood flow was 91%, 64%, and 55%, for Child-Pugh scores-A, -B, and -C, respectively. In response to the decreased portal blood flow to the liver, the hepatic arterial blood flow increased by 41%, 63%, and 92% for Child Pugh-A, -B, and -C, relative to normal controls. This increase in arterial blood flow in response to decreased portal blood flow is termed hepatic arterial buffer response and allows for relatively constant blood flow to the liver regardless of portosystemic shunting. The SimCYP library for cirrhotic subjects uses a decrease of 89%, 71%, and 61% in functional liver size relative to control subjects in subjects with Child-Pugh Score-A, -B, and -C, respectively, based on meta-analyses (SimCYP simulator Version 11; Simcyp Limited, Sheffield, UK).

Bile acids are metabolized in the liver, primarily by conjugation (N-acylamidation) to the amino acids glycine or taurine. In healthy humans, a normal adult ratio of glycine to taurine bile acid conjugation ("G/T ratio") is 3:1 with a range of 1:1 to 5:1. Dietary intake of taurine increases the proportion of bile acids conjugated with taurine. In contrast, oral ingestion of glycine does not change the G/T ratio. The G/T ratio in healthy and disease states appears to be governed by the liver as opposed to intestinal control via preferential deconjugation of glycine conjugated bile acids by bacteria or preferential conjugate uptake into the enterocytes. It has been reported in the literature that the G/T ratio is decreased in patients with cirrhosis.

A physiologic pharmacokinetic model exists describing the metabolism and enterohepatic circulation of CDCA. The CDCA model included 9 spaces based on anatomical and physiological considerations (systemic circulation, portal circulation, sinusoidal circulation, liver, bile duct, gallbladder, duodenum-jejunum, ileum, and colon) with each space possessing a compartment of either CDCA, glycine-conjugated CDCA (glyco-CDCA), or taurine-conjugated CDCA (tauro-CDCA). The model included transfer coefficients describing fluid flow, biotransformation of chemical entities, and transport across membranes.

Without being bound by any particular theory, due to the similar structure of CDCA, OCA was considered to have comparable pharmacokinetic properties when compared to CDCA. This examples describes development of a physiologic PK model to quantitatively describe the absorption, distribution, metabolism, and excretion of OCA. In addition, the model was used to define the effects of hepatic impairment to predict the systemic and liver exposure to OCA in subjects with various degrees of liver impairment relative to healthy subjects with normal liver function. The model was developed based on 3 studies in healthy volunteers and 2 studies in patients with varying degrees of hepatic impairment (N=399).

All participants in each of the studies were over 18 years of age and provided informed consent for willing participation. The studies were conducted in accordance with the Declaration of Helsinki (Seoul 2008 Revision) and adhered to guidelines for Good Clinical Practices and were approved by all relevant ethics committees.

Data from was used to develop the model in healthy subjects (n=160) and then adjust for hepatic impairment (n=32) using the data from the above Examples. After development, the model was validated with data sourced from healthy subjects and cirrhotic patients.

The data used in model development included subject identifiers, time of dosing and sample collection, plasma drug concentrations (OCA, glyco-OCA, and tauro-OCA), dose amount, disease status (e.g., Child-Pugh score), and meal consumption information. Study participants received standardized meals at specified times during inpatient observation. Gallbladder contraction was assumed to last 90 minutes after the start of a meal. Drug concentrations below the limit of quantification (BLQ) were imputed to half of the lower limit of quantification (LLOQ). Observed and BLQ concentrations of OCA, glyco-OCA, and tauro-OCA associated with samples drawn prior to the first dose were excluded from the analyses. As the glyco- and tauro-conjugates are nearly equipotent relative to OCA on FXR, total OCA concentrations were calculated as the sum of OCA, glyco-OCA, and tauro-OCA.

Concentrations of OCA (420.6 g/mol), glyco-OCA (477.7 g/mol), and tauro-OCA (527.8 g/mol) were measured from human plasma samples using high performance liquid chromatography tandem mass spectrometry (LC-MS/MS) (Shimadzu 10AVP HPLC System, Kyoto, Japan; AB MDX Sciex API-4000 LC-MS/MS System, Framingham, Mass.). The LLOQ for OCA, glyco-OCA, and tauro-OCA was 0.594 nM, 0.523 nM, and 0.474 nM, respectively.

The PK model developed for CDCA used 27 compartments consisting of 9 spaces with anatomical and physiological considerations, each requiring three compartments to accommodate CDCA, glyco-CDCA, and tauro-CDCA. Division of each space into 3 compartments was necessary because while flow rates (e.g., blood flow) were independent of chemical structure, biotransformation rates (e.g., conjugation and deconjugation) and transport rates (e.g., hepatic uptake) differed based on chemical structure. Values for the physiologic compartment volumes and transfer rates used in the model were obtained from the literature. To construct the PK model for OCA, the physiologic PK model for CDCA was structurally modified to accurately reflect the interaction of human physiology and OCA.

A number of structural modifications were made to the base CDCA model in order to adapt it for use with OCA. For simplification, a single space was used to represent the gut (small and large intestines). Since OCA is an exogenous molecule, it was assumed that there was no endogenous synthesis and an absorption compartment with a first-order transfer coefficient ($K_a$) was included to represent the administration and absorption kinetics of an oral OCA dose. Based on steric hindrance by the 6-ethyl group of OCA, no bacterial 7-alpha dehydroxylation biotransformation activity (i.e., CDCA to lithocholic acid) was included in the model. Compartment volumes in the model were fixed to physiological values from the base CDCA model. The OCA model used the physiological flow values for blood, bile and gastrointestinal transit from the original physiologic PK model for CDCA, with the exception of flows from bile duct to gallbladder and from bile duct to gut. The physiological values from the base model led to poor predictions and may not be applicable due to the simplification of the enteral system into a unified gut compartment. The biotransformation and transport rates in the model, being dependent on chemical entity structure, were estimated by fitting the model to the plasma concentration time profiles of OCA, glyco-OCA, and tauro-OCA.

The PK model was first developed using the OCA, glyco-OCA, and tauro-OCA plasma concentration time profiles from healthy volunteers with normal hepatic function. Model parameter estimates related to healthy physiology were then held constant while the PK model was further developed using OCA, glyco-OCA, and tauro-OCA plasma concentration time profiles from patients with hepatic impairment (Child-Pugh scores A, B, and C). Only parameters specific to hepatic impairment were estimated during this process.

Four mechanisms of hepatic impairment were incorporated into the OCA PK model and included (1) reduction of hepatic uptake, (2) portal systemic shunting, (3) decreased functional volume, and (4) preferential conjugation to taurine. These parameters were incorporated in the model in a manner allowing the parameter estimates in subjects with mild, moderate, and severe hepatic impairment to progressively deviate relative to the parameter values estimated in healthy volunteers. These deviations for the portal systemic shunting and decreased functional liver volume mechanisms used physiological values from the Simcyp library for cirrhotic subjects (SimCYP simulator Version 11; Simcyp Limited, Sheffield, UK). The deviations for the reduced hepatic uptake and change in OCA conjugation mechanisms were estimated based on fitting of the plasma drug concentration time profiles from subjects with hepatic impairment. Table 28 lists the model parameters and coding modifications associated with the four mechanisms of hepatic impairment.

TABLE 28

Model Parameters and Coding Modification associated with mechanism of Hepatic Impairment.

| Anatomical/ Physiological Change | Equations |
|---|---|
| Decreased hepatic uptake | $t_{10\text{-}Mild} = t_{10}$ *exp(Effect in Mild hepatic impairment in hepatic uptake of OCA and conjugates) |
| | $t_{10\text{-}Moderate} = t_{10}$ *exp(Effect in Moderate hepatic impairment in hepatic uptake of OCA and conjugates) |
| | $t_{10\text{-}Severe} = t_{10}$ *exp(Effect in Severe hepatic impairment in hepatic uptake of OCA and conjugates) |
| Portal-systemic shunting/ Arterial buffer response | $f_{4\text{-}Mild} = f_4$*1.408 for mild hepatic impairment |
| | $f_{4\text{-}Moderate} = f_4$*1.625 for moderate hepatic impairment |
| | $f_{4\text{-}Severe} = f_4$*1.915 for severe hepatic impairment |
| | $f_{8\text{-}Mild} = f_8$*0.91 for mild hepatic impairment |
| | $f_{8\text{-}Moderate} = f_8$*0.635 for moderate hepatic impairment |
| | $f_{8\text{-}Severe} = f_8$*0.554 for severe hepatic impairment |
| Decreased functional/ anatomical liver volume | $V_{liver\text{-}Mild} = V_{liver\text{-}healthy}$*0.891 for mild hepatic impairment |
| | $V_{liver\text{-}Moderate} = V_{liver\text{-}healthy}$*0.71 for moderate hepatic impairment |
| | $V_{liver\text{-}Severe} = V_{liver\text{-}healthy}$*0.61 for severe hepatic impairment |
| Changes in metabolism/ conjugation | $b_{16\text{-}Mild} = b_{16}$* exp(Effect of Mild hepatic impairment on OCA tauro-conjugation) for mild hepatic impairment |
| | $b_{16\text{-}Moderate} = b_{16}$* exp(Effect of Moderate hepatic impairment on OCA tauro-conjugation) for moderate hepatic impairment |
| | $b_{16\text{-}Severe} = tb_{16}$* exp(Effect of Severe hepatic impairment on OCA tauro-conjugation) for severe hepatic impairment |

For the portal systemic shunting mechanism, the coefficient for portal to sinusoidal flow was progressively decreased as hepatic impairment worsened and was matched by a progressive increase in flow from the portal to systemic circulation of equal magnitude. The latter flow does not occur in healthy individuals. To compensate for reduced blood flow to the liver, the coefficient for hepatic arterial flow from the systemic circulation to the sinusoids was progressively increased with worsening hepatic impairment (i.e., hepatic arterial buffer response).

The biotransformation coefficient for conjugation of taurine to OCA was allowed to change for mild, moderate, and severe hepatic impairment relative to the coefficient in healthy subjects while the coefficient for conjugation to glycine was fixed at the value for healthy individuals.

The OCA physiologic PK model used a population PK approach and consisted of a description of the relationships between plasma drug concentrations and time as well as components for between subject and residual variability. Between subject variability (BSV) was modeled assuming a log-normal distribution as follows:

$$\theta_{in} = \theta_{TVn} \exp(\eta_{in})$$

$$(f_1 \ldots \eta_m) \sim MVN(0, \Omega)$$

Where $\theta_{TVn}$ is the population typical value for the $n^{th}$ PK parameter (e.g., clearance) and $\eta_{in}$ (ETA) is the random BSV on the $n^{th}$ parameter for subject i that jointly follow a multivariate normal distribution (MVN) with a mean of zero and variance of $\Omega$. The BSV model assumes that PK parameters are log-normally distributed. Due to the high level of model complexity, BSV was only incorporated on $K_a$ and the flow rate from gallbladder to gut, both parameters that analysis showed had substantial impact on the plasma concentration time profiles. Residual variability was assumed to have additive and proportional components:

$$y_{ij} = \hat{y}_{ij} \times (1 + \varepsilon_{ij}) + \varepsilon_{2ij}$$

Where $y_{ij}$ and $\hat{y}_{ij}$ represent the $j^{th}$ observed and predicted plasma drug concentration for the $i^{th}$ subject and $\varepsilon$ is the random residual variability. Each $\varepsilon$ is normally distributed with a mean of zero and a variance of $\sigma^2$. Distinct residual variability components were estimated for OCA, glyco-OCA, and tauro-OCA.

Model development was guided by feedback from various diagnostic plots including: observed OCA, glyco-OCA, and tauro-OCA versus population prediction (PRED) or individual prediction (IPRED) with a line of unity and trend line, conditional weighted residuals (CWRES) of OCA, glyco-OCA, and tauro-OCA versus PRED or time, and prediction-corrected visual predictive checks (pcVPC; 200 iterations).

A simulation with 200 replicates was performed based on subjects in the phase 1 hepatic impairment study using the OCA physiologic PK model. Dosing and meal consumption history were used to simulate rich 0 to 216 hour concentration-time profiles of OCA, glyco-OCA, and tauro-OCA. Total OCA was calculated for each observation by summing the molar-based concentrations for OCA, glyco-OCA, and tauro-OCA. Total OCA concentrations from the systemic circulation and liver were subjected to non-compartmental analysis to calculate $C_{max}$ and $AUC_{(0-216h)}$.

Phoenix® NLME™ software version 1.3 (Certara Inc., Princeton, N.J.) was used for the physiologic population PK analysis and simulations with Lindstrom-Bates First-order Conditional Estimation (FOCE-LB). Analysis datasets, visualizations, and exploratory analyses were created using R software version 3.1 (The R Foundation) and SAS version 9.4 (SAS Institute Inc., Cary, N.C.). GraphPad Prism software version 6.07 (Graphpad Software Inc., La Jolla, Calif.) was used for the generation of some graphical analyses.

The OCA physiologic PK model was initially developed using 8248 plasma sample concentrations of OCA, glyco-OCA, and tauro-OCA from 160 healthy volunteers administered 10 mg OCA in a cross-over design. Each subject contributed PK samples from both study periods. The healthy volunteer pool had normal hepatic function, was primarily male (59%), mean (SD) age was 37.0 (9.8) years, and mean (SD) weight was 76.4 (11.8) kg. Volunteers were 65.6% white, 32.5% black, 0.6% Asian, and 1.3% other. The percentage of BLQ samples with imputed concentrations was 38.2%, 9.4%, and 24.4% for OCA, glyco-OCA, and tauro-OCA, respectively.

The healthy PK model contained a total of 22 parameters: 7 flow parameters, 4 biotransformation parameters, and 11 transport parameters (Table 29). Many of these were expected to have values specific to exogenous OCA (e.g., hepatic uptake) or did not exist in the base model (e.g., $K_a$ or $K_{out}$) and thus required estimation. Most of the flow parameters were fixed to physiological values from the literature with the exception of bile duct to gallbladder and from bile duct to gut. All structural parameters (Table 29) were well estimated (≤5.5% CV). The BSV for flow from bile duct to gallbladder was 78.1% (19.3% CV) and for the oral absorption of OCA was 195% (2.21% CV). The additive portion of residual variability was ≤1 nM (15-50% CV) and the proportional portion ranged from 72% to 88% (30-70% CV) for OCA and its conjugates. The pcVPC results shown in FIG. 25A, FIG. 25B, FIG. 25C, and FIG. 25D and the goodness of fit plots shown in FIGS. 18A-F and FIGS. 19A-F indicate acceptable model performance.

TABLE 29

Model Parameters in Normal Hepatic Function

| Parameter | Parameter Description | Estimate | CV % | BSV (RSE %) |
|---|---|---|---|---|
| $f_4$ (L/h) | Hepatic arterial flow | 14.4 | Fixed | NA |
| $f_3$ (L/h) | Hepatic portal flow | 39.6 | Fixed | |
| $t_{10}$ (h$^{-1}$) | OCA transport rate from liver to sinusoidal space | 1698 | 1.0 | |
| $t_9$ (h$^{-1}$) | Glyco-OCA transport rate from sinusoidal space to liver | 1210 | 2.0 | |
| $t_{11}$ (h$^{-1}$) | Tauro-OCA transport rate from sinusoidal space to liver | 1615 | 1.9 | |
| $t_{13}$ (h$^{-1}$) | OCA transport rate from sinusoidal space to liver | 1.62 | Fixed | |
| $t_{12}$ (h$^{-1}$) | Glyco-OCA and tauro-OCA transport rate from liver to sinusoidal space | 1.62 | Fixed | |
| $f_{24}$ (L/h) | Flow from bile duct to gut | 7.29 | 4.5 | |
| $f_{22}$ (L/h) | Flow from bile duct to gallbladder | 0.856 | 4.4 | 78.1% (19.3) |
| $f_{23}$ (h$^{-1}$) | Rate of output from gallbladder to gut | 1.2 | Fixed | NA |
| $k_{out}$ (L/h) | Rate of fecal elimination of OCA | 0.612 | 5.5 | |
| $b_{15}$ (h$^{-1}$) | OCA rate of conjugation with glycine | 1.44 | 4.5 | |
| $b_{16}$ (h$^{-1}$) | OCA rate of conjugation with taurine | 0.312 | 1.9 | |
| $b_{36}$ (h$^{-1}$) | Glyco-OCA rate of deconjugation to OCA | 0.0431 | 4.5 | |
| $b_{37}$ (h$^{-1}$) | Tauro-OCA rate of deconjugation to OCA | 0.0200 | 1.8 | |
| $t_{34}$ (h$^{-1}$) | OCA rate of absorption from gut to portal space | 0.857 | 3.4 | |
| $t_{33}$ (h$^{-1}$) | Glyco-OCA rate of absorption from gut to portal space | 0.904 | 1.1 | |
| $t_{35}$ (h$^{-1}$) | Tauro-OCA rate of absorption from gut to portal space | 1.62 | 2.2 | |
| $K_a$ (h$^{-1}$) | OCA first order rate constant of oral absorption | 5.32 | 1.0 | 195% (2.21) |
| $t_{19}$ (h$^{-1}$) | Glyco-OCA transport rate from liver to bile duct | 7.44 | 0.7 | NA |
| $t_{21}$ (h$^{-1}$) | Tauro-OCA transport rate from liver to bile duct | 9.28 | 1.0 | |
| | Proportional Error OCA (%) | 88.0 | 33.9 | NA |
| | Proportional Error Glyco-OCA (%) | 62.6 | 32.7 | |
| | Proportional Error Tauro-OCA (%) | 71.6 | 70.4 | |
| | Additive Error OCA (nM) | 0.546 | 16.5 | |
| | Additive Error Glyco-OCA (nM) | 0.675 | 21.8 | |
| | Additive Error Tauro-OCA (nM) | 0.469 | 50.3 | |

Development of the PK model for the physiological changes associated with hepatic impairment used 928 plasma sample concentrations of OCA, glyco-OCA, and tauro-OCA from 32 subjects-8 subjects each with mild, moderate, severe hepatic impairment and normal hepatic function. Subjects were administered a single 10 mg dose of OCA. The study subjects were primarily male (72%), had a mean (SD) age of 55.0 (5.6) years, and mean (SD) body weight was 81.7 (16.9) kg. Participants were 90.6% white, 3.1% black, 3.1% Asian, and 3.1% other. Mean Child-Pugh Score was 8.0 (2.0) (Child-Pugh Score: Class A/Mild 5-6 points, Class B/Moderate 7-9 points, Class C/Severe 10-15 points). The percentage of BLQ samples with imputed concentrations was 16.8%, 5.4%, and 9.6% for OCA, glyco-OCA, and tauro-OCA, respectively.

The 22 PK parameters from the healthy PK model were held fixed during the development of the model for hepatic impairment. Portal systemic shunting and reduced functional liver volume parameters were fixed to physiological values from the literature while parameters associated with reduced hepatic uptake and changes in OCA conjugation were estimated. Parameter estimates for hepatic uptake and taurine conjugation obtained from the hepatic impairment PK model are presented in Table 30. The structural parameters were well estimated (<25% CV) with the exception of the change in hepatic uptake in OCA and its conjugates in moderate hepatic impairment (44% CV) and the change in OCA conjugation for severe hepatic impairment (109% CV). The BSV for flow from bile duct to gallbladder was 168% (299% CV) and for the oral absorption of OCA was 246% (9.87% CV). The additive portion of residual variability was ≤1 nM (>75% CV) and the proportional portion ranged from 112% to 123% for OCA and its conjugates (>75% CV). This magnitude of variability is consistent with a bile acid analog that undergoes extensive enterohepatic recirculation. The pcVPC results shown in FIGS. 26A-D and the goodness of fit plots indicate acceptable model performance.

TABLE 30

Modified Model Parameters in Impaired Hepatic Function

| Parameter | Estimate | CV % |
|---|---|---|
| Effect in Mild hepatic impairment in hepatic uptake of OCA and conjugates | −0.132 | 9.11 |
| Effect in Moderate hepatic impairment in hepatic uptake of OCA and conjugates | −1.86 | 44.3 |
| Effect in Severe hepatic impairment in hepatic uptake of OCA and conjugates | −2.37 | 24.9 |
| Effect of Mild hepatic impairment on OCA tauro-conjugation | 0.00481 | 0.341 |
| Effect of Moderate hepatic impairment on OCA tauro-conjugation | 1.05 | 15.8 |
| Effect of Severe hepatic impairment on OCA tauro-conjugation | 1.56 | 109 |
| Proportional Error OCA (%) | 122 | 77.1 |
| Proportional Error Glyco-OCA (%) | 112 | 384 |
| Proportional Error Tauro-OCA (%) | 123 | 636 |
| Additive Error OCA (nM) | 0.993 | 77.1 |

TABLE 30-continued

Modified Model Parameters in Impaired Hepatic Function

| Parameter | Estimate | CV % |
|---|---|---|
| Additive Error Glyco-OCA (nM) | 0.273 | 383 |
| Additive Error Tauro-OCA (nM) | 0.532 | 627 |
| BSV | | |
| OCA first order rate constant of oral absorption | 246% | 9.87 |
| Flow from bile duct to gallbladder | 168% | 299 |

The final OCA physiologic PK model, developed for both normal and impaired hepatic function, was validated with external PK data in subjects with normal (single doses of 10 mg and multiple-dosing to steady-state with doses of 5 mg, 10 mg, or 25 mg) and hepatic impairment (cirrhosis and portal hypertension). FIG. 27A to FIG. 27C and FIG. 28A to FIG. 28C show pcVPC-based assessments of the model's ability to accurately predict the plasma total OCA concentration time profiles under these varied conditions. The model predicted the profiles well for subjects with normal hepatic function (FIGS. 20A-F, FIGS. 21A-D) and for subjects with moderate or severe hepatic impairment (FIGS. 22A-F). For mild hepatic impairment, the model tended to underestimate the total OCA concentrations.

Simulations of total OCA in the systemic circulation (plasma) and in the liver after a single 10 mg dose were compared to observed total OCA plasma concentrations from the hepatic impairment clinical study in FIGS. 23A-B. The total OCA exposures are summarized as either the $C_{max}$ or the AUC over the 216-hour sampling period. For both exposure measures, and across all levels of hepatic function, there appeared to be agreement between the exposures observed in the clinical trial and the exposures predicted by the PK model. Simulation data in Table 31 reveals that the systemic AUC of total OCA in subjects with mild, moderate, and severe hepatic impairment increased 1.4-, 8.0-, and 13-fold relative to subjects with normal hepatic function. However, in the liver, the predicted AUC of total OCA in subjects with mild, moderate, and severe hepatic impairment increased only 1.1-, 1.5-, and 1.7-fold relative to subjects with normal hepatic function.

This OCA physiologic PK model, derived from prior bile acid models, provides valuable insights into the absorption, distribution, metabolism, and excretion of the drug. Orally administered OCA is absorbed from the intestines, conjugated with glycine or taurine in the hepatocyte, and the conjugated OCA circulates enterohepatically. Conjugation also results in most of the OCA conjugates being poorly absorbed in the proximal small intestine and reaching the terminal ileum, where bile acids are actively conserved. The predominant pharmacodynamic activity of OCA is thus mediated by its taurine and glycine amidates in the hepatocyte and distal small intestine.

The PK model used a dosing compartment and first-order rate constant ($K_a$) to represent the cumulative processes from oral intake of OCA through entry into the gut. The population mean half-life for this process was 0.13 hours, but the high BSV on $K_a$ indicated that the absorption process varied substantially between subjects. Once in the gut, the model estimated the extent of intestinal absorption for OCA at approximately 56%. This value is likely an underestimation due to consolidation of the various segments of the small and large intestine into a single gut compartment wherein OCA gets absorbed and excreted from the same compartment. The extent of intestinal absorption for glyco-OCA and tauro-OCA was 95% and 99%, respectively. Simulations for healthy subjects using the PK model showed that at steady-state, ~90% of total OCA mass is distributed to the gut and the gallbladder. Approximately 8% of the total OCA mass resides in the liver while ~1% can be found in the plasma of the systemic circulation. In contrast, the simulated total OCA mass increases to ~10% in the systemic circulation in patients with Child-Pugh C hepatic impairment with the liver distribution being approximately equal to healthy subjects (~10%). The simulated gut and gallbladder distribution was 79% in patient with Child-Pugh C hepatic impairment. The low systemic levels of total OCA would in part explain the high variability observed in plasma.

The PK model estimated hepatic uptake, in healthy subjects, at 79%, 73%, and 78% for OCA, glyco-OCA, and tauro-OCA, respectively, are consistent with hepatic uptake values reported for CDCA. Once in the liver, OCA was conjugated to glycine and taurine in a ratio of 4.6:1, consistent with the normal range for endogenous bile acids. Simulations from the PK model showed that the half-life for

TABLE 31

Systemic AUC of total OCA in Patients with mild, moderate, and severe hepatic impairment.

| | | | Liver Impairment | | | Ratio (Liver Impairment/Normal) | | |
|---|---|---|---|---|---|---|---|---|
| Exposure | Metric | Normal | Mild | Moderate | Severe | Mild/Normal | Moderate/normal | Severe/normal |
| Systemic | AUC (ng × h/mL) | 2339 | 3156 | 18785 | 30986 | 1.35 | 8.03 | 13.2 |
| | $C_{avg}$ (ng/mL) | 10.8 | 14.6 | 87 | 143 | 1.35 | 8.03 | 13.2 |
| | $C_{max}$ (ng/mL) | 99.5 | 131 | 634 | 961 | 1.31 | 6.38 | 9.66 |
| Liver | AUC (ng × h/mL) | 47427 | 53032 | 69540 | 82521 | 1.12 | 1.47 | 1.74 |
| | $C_{avg}$ (ng/mL) | 220 | 246 | 322 | 382 | 1.12 | 1.47 | 1.74 |
| | $C_{max}$ (ng/mL) | 2395 | 2665 | 2701 | 2651 | 1.11 | 1.13 | 1.11 |

| Mean Simulated OCA Distribution (% Nanomoles Total OCA) | | |
|---|---|---|
| Systemic Circulation | 1.03 | 10.36 |
| Portal Circulation | 0.77 | 2.33 |
| Sinusoidal Circulation | 0.05 | 0.45 |
| Liver | 7.88 | 10.44 |
| Bile Ducts | 0.14 | 0.13 |
| Gallbladder | 39.94 | 37.74 |
| Gut | 50.20 | 38.56 |

OCA is approximately 4 days indicating a time to steady-state or a post-treatment washout period of about 2 weeks. The estimated OCA half-life is consistent with the half-life values for CDCA reported in the literature.

Simulations using the PK model predicted changes in systemic and liver OCA concentrations associated with changes in the severity of hepatic impairment. Model simulations predicted that for mild, moderate, and severe hepatic impairment, total OCA concentrations in the plasma increase 1.4-, 8.0-, and 13-fold relative to subjects with normal hepatic function while total OCA concentrations in the liver increase 1.1-, 1.5-, and 1.7-fold, respectively. The predicted changes in plasma OCA concentrations were similar to the observed concentration of total endogenous bile acids in subjects with alcoholic cirrhosis. The concentration of total endogenous bile acids measured in the plasma were increased 1.6-, 6.4-, and 13-fold for mild, moderate, and severe hepatic impairment relative to normal hepatic function, respectively. Previously, soluble and tissue-bound hepatic bile acids were measured by Fischer et al. from the livers of end-stage liver disease patients and compared to measurements made from healthy livers (resected for tumors but functionally and histologically normal). It was shown that endogenous bile acid levels in the serum of patients with end-stage liver disease prior to liver transplantation were 18-fold greater than those in healthy subjects; however, in the livers from patients with end-stage liver disease bile acid levels were only approximately 2-fold higher relative to healthy livers. The observed 2-fold increase in the liver exposure of endogenous bile acids is in good agreement with the predicted increase in total OCA exposure in subjects with severe hepatic impairment (1.7-fold; Child-Pugh C). These results suggest that the PK characteristics of OCA are very similar to endogenous bile acids.

There were some differences between the observed and predicted values in the external validation in patients with mild hepatic impairment. The Child-Pugh score is based on total bilirubin, serum albumin, prothrombin time, ascites, and hepatic encephalopathy. While all of these parameters are indicators of prognosis in liver disease, they do not all necessarily reflect substantial changes in PK or flow mechanics in/around the liver. Without being bound by any particular theory, the presence of portal hypertension in the validation cohort for mild impairment may be a reason for a discrepancy between predicted and observed values in patients with mild hepatic impairment.

The OCA physiologic model predicted liver to plasma ratios for OCA concentrations that were similar to the ratios previously observed for endogenous bile acids. These results indicate that the liver to plasma ratio is not consistent between healthy subjects and patients with hepatic impairment. The liver is the primary site of action for the safety and efficacy of OCA; therefore, it is important to account for the differences in systemic and liver exposure when assessing an effective dose. The hepatically-impaired patients treated with OCA experienced plasma OCA exposures >10-fold higher than those experienced by healthy subjects, yet there was no apparent impact on the overall safety profile experienced by these patients. The safety results are consistent with only a modest increase in liver exposure of OCA associated with hepatic impairment. Collectively, the results from these analyses and those from literature for bile acids would suggest that the dose of OCA administered to hepatically-impaired patients should be modestly lower than those for patients with normal hepatic function to achieve similar hepatic exposure.

Example 12

This example describes a clinical, double-blind study examining the effect of daily 25 mg OCA on nonalcoholic steatohepatitis (NASH). OCA lead to biopsy proven improvements in liver fibrosis. Patients with NASH who have elevated NAFLD activity scores (NAS) and fibrosis are at a higher risk of progression to cirrhosis and liver related mortality.

The high risk subgroup was defined as patients with a baseline NAS≥4, baseline fibrosis stage 2 or 3 or baseline fibrosis stage 1 with a comorbidity (type 2 diabetes, BMI≥30 kg/m$^2$ or ALT≥60 U/L) (OCA n=114; Placebo n=112). The Fibrosis-4 (FIB-4), the aspartate transaminase to platelet ratio (APRI), and the NAFLD fibrosis score (NFS) were all examined between baseline through 72 weeks of treatment and for an additional 24 weeks of follow up.

Significant reductions were observed as early as week 24 and persisted through the course of treatment. Patients receiving OCA had significant improvements compared to placebo in all three non-invasive measures of fibrosis at week 72 (FIB-4 OCA-Placebo LS Mean change=−0.33, 95% CI=[−0.47, −0.19], p<0.0001; APRI OCA-Placebo LS Mean change=−0.23, 95% CI=[−0.32, −0.15], p<0.0001; NFS OCA-Placebo LS Mean change=−0.28, 95% CI=[−0.45, −0.10], p<0.01). However, 24 weeks after concluding treatment, all three scores had diminished improvement and trended toward baseline values.

Treatment with OCA lead to significant early and sustained improvements in FIB-4, APRI, and NFS in patients in a subgroup at higher risk for liver related mortality in NASH. However, without OCA, improvement in these non-invasive measures of fibrosis diminished, possibly due to continuing underlying disease pathogenesis.

The invention claimed is:

1. A composition comprising obeticholic acid, or a pharmaceutically acceptable salt, ester, or amino acid conjugate thereof, wherein obeticholic acid or a pharmaceutically acceptable salt, ester, or amino acid conjugate thereof is in the form of particles, and wherein at least 50% of the particles have a diameter of 200 μm or less.

2. The composition of claim 1, wherein at least 50% of the particles have a diameter of 100 μm or less.

3. The composition of claim 2, wherein at least 50% of the particles have a diameter of 50 μm or less.

4. The composition of claim 3, wherein at least 50% of the particles have a diameter of 10 μm or less.

5. The composition of claim 4, wherein at least 50% of the particles have a diameter of 5 μm or less.

6. The composition of claim 1, wherein at least 90% of the particles have a diameter of 200 μm or less.

7. The composition of claim 6, wherein at least 90% of the particles have a diameter of 100 μm or less.

8. The composition of claim 7, wherein at least 90% of the particles have a diameter of 25 μm or less.

9. The composition of claim 1 further comprising at least one pharmaceutically acceptable excipient having an alcohol content of less than about 6% (wt/wt).

10. The composition of claim 9, wherein the at least one pharmaceutical acceptable excipient is sodium starch glycolate.

11. A tablet comprising an intra-granular portion and an extra-granular portion, the intra-granular portion comprising obeticholic acid, or a pharmaceutically acceptable salt, ester, or amino acid conjugate thereof, microcrystalline cellulose, and one or more additional pharmaceutical excipients, and the extra-granular portion comprising one or more pharmaceutical excipients.

12. The tablet of claim 11, wherein the extra-granular portion comprises microcrystalline cellulose.

13. A method for preparing a composition comprising obeticholic acid, or a pharmaceutically acceptable salt, ester, or amino acid conjugate thereof, in the form of particles, wherein at least 50% of the particles have a diameter of 200 µm or less, comprising forming the particles through jet-milling.

14. The tablet of claim 11, wherein obeticholic acid or a pharmaceutically acceptable salt, ester, or amino acid conjugate thereof is jet-milled.

15. The tablet of claim 14, wherein obeticholic acid or a pharmaceutically acceptable salt, ester, or amino acid conjugate thereof is in the form of particles, and wherein at least 50% of the particles have a diameter of 200 µm or less.

16. The composition of claim 1 is in a unit dosage form.

17. The composition of claim 16, wherein the unit dosage form is a tablet.

18. The composition of claim 17, wherein the tablet comprises an intra-granular portion and an extra-granular portion.

19. The composition of claim 18, wherein the intra-granular portion comprises microcrystalline cellulose and obeticholic acid, or a pharmaceutically acceptable salt, ester, or amino acid conjugate thereof in a ratio between about 20:1 to about 1:5.

* * * * *